US007578999B2

(12) United States Patent
Winkler et al.

(10) Patent No.: US 7,578,999 B2
(45) Date of Patent: *Aug. 25, 2009

(54) ANTIBODIES SPECIFIC FOR SCLEROSTIN

(75) Inventors: David G. Winkler, Arlington, MA (US); Jiye Shi, Rochester, NY (US); John Latham, Seattle, WA (US)

(73) Assignee: Celltech R & D, Inc., Bothell, WA (US)

( * ) Notice: Subject to any disclaimer, the term of this patent is extended or adjusted under 35 U.S.C. 154(b) by 223 days.

This patent is subject to a terminal disclaimer.

(21) Appl. No.: 11/399,210

(22) Filed: Apr. 5, 2006

(65) Prior Publication Data

US 2006/0233801 A1      Oct. 19, 2006

Related U.S. Application Data

(63) Continuation of application No. 10/463,190, filed on Jun. 16, 2003, now abandoned.

(51) Int. Cl.
*A61K 39/00* (2006.01)
*A61K 39/395* (2006.01)
*C07K 16/00* (2006.01)
*C07K 16/18* (2006.01)

(52) U.S. Cl. .............. 424/130.1; 424/135.1; 424/139.1; 424/141.1; 424/142.1; 530/387.1; 530/387.3; 530/387.9; 530/388.1; 530/388.15; 530/389.2

(58) Field of Classification Search ....................... None
See application file for complete search history.

(56) References Cited

U.S. PATENT DOCUMENTS

| | | | |
|---|---|---|---|
| 6,395,511 B1 | 5/2002 | Brunkow et al. | |
| 6,495,736 B1 | 12/2002 | Brunkow et al. | |
| 6,803,453 B1 * | 10/2004 | Brunkow et al. | 530/388.23 |
| 7,381,409 B2 * | 6/2008 | Winkler et al. | 424/139.1 |
| 2004/0158045 A1 * | 8/2004 | Brunkow et al. | 530/388.25 |
| 2005/0106683 A1 * | 5/2005 | Winkler et al. | 435/70.21 |
| 2007/0110747 A1 * | 5/2007 | Paszty et al. | 424/145.1 |

FOREIGN PATENT DOCUMENTS

| | | |
|---|---|---|
| WO | WO 00/32773 A | 6/2000 |
| WO | WO 01/92308 A | 12/2001 |
| WO | WO 02/24888 A2 | 4/2002 |
| WO | WO 03/106657 A | 12/2003 |

OTHER PUBLICATIONS

Balemans, W., et al., "Increased Bone Density in Sclerosteosis is Due to the Deficiency of a Novel Secreted Protein (SOST)," Human Molecular Genetics, 10(5):537-543, 2001.
Bradley et al., "Modifying The Mouse: Design and Desire," Bio/Technology (1992) 10:534-539.
Brunkow, M.E. et al. "Bone Dysplasia Sclerosteosis Results from Loss of the Sost Gene Product, A Novel Cystine Knot-Containing Protein," American Journal of Human Genetics, 68(3):577-589, 2001.

Campbell et al., "Totipotency of Multipotentiality of Cultured Cells: Applications and Progress," Theriogenology (1997) 47:63-72.
Hoffman et al., "BMP Signaling Pathways in Cartilage and Bone Formation," Critical Review in Eukaryotic Gene Expression (2001) 11(1-3)23-45.
Lian et al., "Bone Formation: Osteoblast Lineage Cells, Growth Factors, Matrix Proteins, and the Mineralization Process," Primer on the Metabolic Bone Diseases and Disorders of Mineral Metabolism, 4th Edition (1999) 14-29.
Mullins et al., "Transgenesis in the Rat and Larger Mammals," J. Clin. Invest. (1996) 97(7):1557-1560.
Oshima et al., "TGF-β Receptor Type II Deficiency Results in Defects of Yolk Sac Hematopoiesis and Vasculogenesis," Developmental Biology (1996) 179:297-302.
Pittenger et al., "Multilineage Potential of Adult Human Mesenchymal Stem Cells," Science (1999) 284:143-147.
Pockwinse et al., "Expression of Cell Growth and Bone Specific Genes at Single Cell Resolution During Development of Bone Tissue-Like Organization in Primary Osteoblast Cultures," Journal of Cellular Biochemistry (1992) 49:310-323.
Reddi, A. Hari, "Interplay between bone morphogenetic proteins and cognate binding proteins in bone and cartilage development: noggin, chordin and Dan," Arthritis Res. (2000) 3:1-5.
Schmitt et al., "Bone Morphogenetic Proteins: An Update on Basic Biology and Clinical Relevance," Journal of Orthopaedic Research (1999) 17:269-278.
Smith, "TGF β inhibitors, new and unexpected requirements in vertebrate development," TIG (1999) 15(1):3-5.
Cook et al., J. Biol. Chem., 280(48):40177-186 (2005).
Keller et al., Nat. Struct. Mol. Biol., 11(5):481-488 (2004).
Albertsen et al., "A physical map and candidate genes in the BRCA1 region on chromosome 17q12-21," Nature Genetics, 7:472-479 (1994).
Balemans et al., "Localization of the Gene for Sclerosteosis to the van Buchem Disease-Gene Region on Chromosome 17q12-q21," Am. J. Hum. Genet., 64:1661-1669 (1999).

(Continued)

*Primary Examiner*—Elizabeth C. Kemmerer
(74) *Attorney, Agent, or Firm*—Marshall, Gerstein & Borun LLP

(57) ABSTRACT

A novel class or family of TGF-β binding proteins is disclosed. Also disclosed are assays for selecting molecules for increasing bone mineralization and methods for utilizing such molecules. In particular, compositions and methods relating to antibodies that specifically bind to TGF-beta binding proteins are provided. These methods and compositions relate to altering bone mineral density by interfering with the interaction between a TGF-beta binding protein sclerostin and a TGF-beta superfamily member, particularly a bone morphogenic protein. Increasing bone mineral density has uses in diseases and conditions in which low bone mineral density typifies the condition, such as osteopenia, osteoporosis, and bone fractures.

23 Claims, 13 Drawing Sheets

OTHER PUBLICATIONS

Chan et al., "Á new paradigm in the treatment of osteoporosis: Wnt pathway proteins and their antagonists," *Current Opinion in Investigational Drugs*, 8(4):293-298 (2007).

Expert Opinion from Dr. Catalina Lopez-Correa, dated Mar. 6, 2009.

Li et al., "Sclerostin Binds to LRP5/6 and Antagonizes Canonical Wnt Signalling," *Jour. Bio. Chem.*, 280(20); 19883-19887 (2005).

van Bezooijen et al., "Wnt but Not BMP Signaling Is Involving in the Inhibitory Action of Sclerostin on BMP-Stimulated Bone Formation," *J. Bone. Miner. Res.* 22:19-28 (2007).

Written Submission of Eli Lilly & Company, dated Mar. 9, 2009, Opposition to European Patent No. 1133558.

* cited by examiner

Common Cysteine Backbone

```
                     1                                                      50
    human-gremlin.pro  ————————  ————————  ————————  ————————  ————————
   human-cerberus.pro  MHLLLFQLLV LLPLGKTTRH QDGRQNQSSL SPVLLPRNQR ELPTGNHEEA
       human-dan.pro  ————————  ————————  ————————  ————————  ————————
      human-beer.pro  ————————  ————————  ————————  ————————  ————————

51                                                    100
    human-gremlin.pro  ————————  ————————M SRTAYTVGAL LLLLGTLLPA AEGKKKGSQG
   human-cerberus.pro  EEKPDLFVAV PHLVAT.SPA GEGQRQREKM LSRFGRFWKK PEREMHPSRD
       human-dan.pro  ————————  ————————  ————————  ————————  ————————
      human-beer.pro  ————————  ————————  ————————  ————MQLPLA LCLVCLLVHT 101                                                   150
    human-gremlin.pro  AI.PPPDKAQ HNDSEQTQSP QQPGSRNRGR GQGRGTAMPG EEVLESSQEA
   human-cerberus.pro  SDSEPFPPGT QSLIQPID.G MKMEKSPLRE EAKKFWHHFM FRKTPASQGV
       human-dan.pro  ————————  ————————  ———————— MLRVLVGAVL PAMLLAAPPP
      human-beer.pro  AFRVVEGQGW QAFKNDATEI IPELGEYPEP PPELENNKTM NRAENGGRPP 151         ↓          ↓         ↓↓          200
    human-gremlin.pro  LHVTERKYLK RDWCKTQPLK QTIHEEGCNS RTIINRF.CY GQCNSFYIPR
   human-cerberus.pro  ILPIKSHEVH WETCRTVPFS QTITHEGCEK VVVQNNL.CF GKCGSVHFP.
       human-dan.pro  INKLALFPDK SAWCEAKNIT QIVGHSGCEA KSIQNRA.CL GQCFSYSVPN
      human-beer.pro  HHPFETKDVS EYSCRELHFT RYVTDGPCRS AKPVTELVCS GQCGPARLLP 201        ↓           ↓                    250
    human-gremlin.pro  HIRKEEGSFQ SCSF...CKP KKFTTMMVTL NCPELQPPTK K.KRVTRVKQ
   human-cerberus.pro  ..GAAQHSHT SCSH...CLP AKFTTMHLPL NCTELSSVIK V...VMLVEE
       human-dan.pro  TFPQSTESLV HCDS...CMP AQSMWEIVTL ECPGHEEVPR VDKLVEKILH
      human-beer.pro  NAIGRGKWWR PSGPDFRCIP DRYRAQRVQL CPGGEAPRA RKVRLVAS..

↓5↓                                                  300
    human-gremlin.pro  CRC.ISIDLD ————————  ————————  ————————  ————————
   human-cerberus.pro  CQCKVKTEHE DGHILHAGSQ DSFIPGVSA~ ————————  ————————
       human-dan.pro  CSCQACGKEP SHEGLSVYVQ GEDGPGSQPG THPHPHPHPH PGGQTPEPED
      human-beer.pro  CKCKRLTRFH NQSELKDFGT EAARPQKGRK PRPRARSAKA NQAELENAY~

301       314
    human-gremlin.pro  ————————  ————
   human-cerberus.pro  ————————  ————
       human-dan.pro  PPGAPHTEEE GAED
      human-beer.pro  ————————  ————
```

*Fig. 1*

RNA In Situ Hybridization of Mouse Embryo Sections

BMP-5/Beer Dissociation Constant Characterization
.75  1.5  7.5  15  30  60  120 nM BMP-5
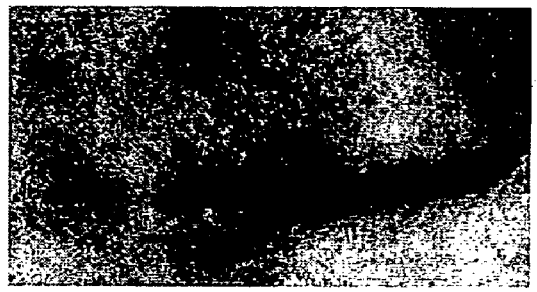
*Anti-FLAG immunoprecipitation
*Anti-BMP-5 western blot
Ionic Disruption of BMP-5/Beer Binding
| NaCl(mM) | 500 | 150 | 150 | BMP-5 western control |
|---|---|---|---|---|
| Beer | + | + | − | |
| BMP-5 | + | + | + | |
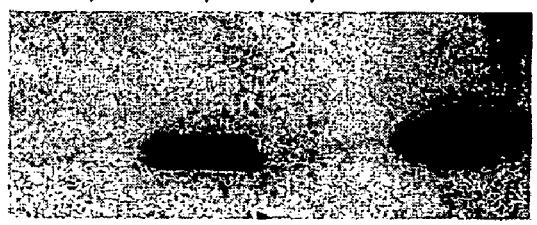
*Anti-FLAG immunoprecipitation
*Anti-BMP-5 western blot
*Fig. 6*

```
                    20              40              60
NOGG_HUMAN  : QHYLHIRPA--RSDNLPLVDLIEHPDPIFDPKEKDLNETLLRSLLGGHYDPGFMATSPP-EDRPG :  62
NOGG_CHICK  : QHYLHIRPA--RSDNLPLVDLIEHPDPIFDPKEKDLNETLLRSLMGGHFDPNFMAMSLP-EDRLG :  62
NOGG_XENLA  : QHYLHIRPA--RSENLPLVDLIEHPDPIYDPKEKDLNETLLRTLMVGHFDPNFMATILP-EERLG :  62
NOGG_FUGRU  : QHYYLLRPI--RSDSLPIVELKEDPGPVFDPKERDLNETELKSVLG-DFDSRFLSVLPPAEDGHA :  62
NOGG_ZEBRA  : QHYYLLRPI--RSDSLPIVELKEDPDPVLDPKERDLNETELRAILGSHFEQNFMSINPP-EDKHA :  62
SOST_HUMAN  : QGWQA-FKNDATEIIP-GLHEMPHP--PPELENNKTMNRAENGGRP-PHHPFETKDV----- :  52
SOST_RAT    : QGWQA-FKNDATEIIP-GLHEMPHP--PPELENNQTMNRAENGGRP-PHHPYDTKDV----- :  52
SOST_MOUSE  : QGWQA-FRNDATEVIP-GLHEMPHP--PPE-NNQTMNRAENGGRP-PHHPYDAKDV----- :  50

80             100             120
NOGG_HUMAN  : GGGGAAGGAEDLAELDQLLRQRPSGAMPSEIKGLEFSEGLAQGKKQRLSKKLRRKLQMWLWSQTF : 127
NOGG_CHICK  : --------VDDLAELDLLLRQRPSGAMPGEIKGLEFYDGLQPGKKHRLSKKLRRKLQMWLWSQTF : 119
NOGG_XENLA  : --------VEDLGELDLLLRQKPSGAMPAEIKGLEFYEGLQS-KKHRLSKKLRRKLQMWLWSQTF : 118
NOGG_FUGRU  : G-------NDELDDFD-AQR--WGGALPKEIRAVDF-DAPQLGKKHKPSKKLKRRLQQWLWAYSF : 116
NOGG_ZEBRA  : G-------QDELNESE-LMKQRPNGIMPKEIKAMEF-DIQ-HGKKHKPSKKLRRRLQLWLWSYTF : 117
SOST_HUMAN  : ---------------------------------------------------------SEYS :  56
SOST_RAT    : ---------------------------------------------------------SEYS :  56
SOST:MOUSE  : ---------------------------------------------------------SEYS :  54

140             160             180
NOGG_HUMAN  : CP-VLYA-WNDLGSRFWPRMVKVGSCFSKRSCSVPEGM---------------VCKPPKSVHL : 173
NOGG_CHICK  : CP-VLYT-WNDLGSRFWPRMVKVGSCYSKRSCSVPEGM---------------VCKPAKSVHL : 165
NOGG_XENLA  : CP-VLYT-WNDLGTRFWPRMVKVGSCYSKRSCSVPEGM---------------VCKAAKSMHL : 164
NOGG_FUGRU  : CP-LAHA-WTDLGSRFWPRFVRAGSCLSKRSCSVPEGM---------------TCKPATSTHL : 162
NOGG_ZEBRA  : CP-VVHT-WDDLGNRFWPRMLKVGSCYNKRSCSVPEGM---------------VCKPPKSSHL : 163
SOST_HUMAN  : CRELHFTRYVTDGPCRSAKPVTELVCS--GQCGPARLLPNAIGRGKWWRPSGPDFRCIPDRYRAQ : 119
SOST_RAT    : CRELHYTRFVTDGPCRSAKPVTELVCS--GQCGPARLLPNAIGRVKWWRPNGPDFRCIPDRYRAQ : 119
SOST_MOUSE  : CRELHYTRFLTDGPCRSAKPVTELVCS--GQCGPARLLPNAIGRVKWWRPNGPDFRCIPDRYRAQ : 117
```

FIG. 10A

```
                              200             220             240             260
NOGG_HUMAN : TVLRWRCQ-RRGGQRCGWIPIQYRIISEQKCSC---------------------------------- : 205
NOGG_CHICK : TILRWRCQ-RRGGQRCTWIPIQYRIIAEQKCSC---------------------------------- : 197
NOGG_XENLA : TILRWRCQ-RRVQQKCAWITIQYPVISEQKCSC---------------------------------- : 196
NOGG_FUGRU : TILRWRCVQRKVGLKCAWIPMQYPVITDQKCSC---------------------------------- : 195
NOGG_ZEBRA : TVLRWRCVQRKGGLKCAWIPVQYPVISEQKCSC---------------------------------- : 196
SOST_HUMAN : RV-QLLCP---GG--EAPRARKVRLVASCKCKRLTRFHNQSELKDFGTEAARPQKGRKPRPRARS   : 178
SOST_RAT   : RV-QLLCP---GG--AAPRSRKVRLVASCKCKRLTRFHNQSELKDFGPETARPQKGRKPRPRARG   : 178
SOST_MOUSE : RV-QLLCP---GG--AAPRSRKVRLVASCKCKRLTRFHNQSELKDFGPETARPQKGRKPRPGARG   : 176

NOGG_HUMAN : -------------   :   -
NOGG_CHICK : -------------   :   -
NOGG_XENLA : -------------   :   -
NOGG_FUGRU : -------------   :   -
NOGG_ZEBRA : -------------   :   -
SOST_HUMAN : AKANQAELENAY    : 190
SOST_RAT   : AKANQAELENAY    : 190
SOST_MOUSE : AKANQAELENAY    : 188
```

*FIG. 10B*

SEQUENCE LISTING

<160> NUMBER OF SEQ ID NOS: 143

<210> SEQ ID NO 1
<211> LENGTH: 2301
<212> TYPE: DNA
<213> ORGANISM: Homo sapien

<400> SEQUENCE: 1
agagcctgtg ctactggaag gtggcgtgcc ctcctctggc tggtaccatg cagctcccac    60

```
tggccctgtg tctcgtctgc ctgctggtac acacagcctt ccgtgtagtg gagggccagg      120
ggtggcaggc gttcaagaat gatgccacgg aaatcatccc cgagctcgga gagtaccccg      180
agcctccacc ggagctggag aacaacaaga ccatgaaccg gcggagaaac ggagggcggc      240
ctccccacca cccctttgag accaaagacg tgtccgagta cagctgccgc gagctgcact      300
tcacccgcta cgtgaccgat gggccgtgcc gcagcgccaa gccggtcacc gagctggtgt      360
gctccggcca gtgcggcccg cgcgcctgc tgcccaacgc catcggccgc ggcaagtggt      420
ggcgacctag tgggcccgac ttccgctgca tccccgaccg ctaccgcgcg cagcgcgtgc      480
agctgctgtg tccggtggt gaggcgccgc gcgcgcgcaa ggtgcgcctg gtggcctcgt      540
gcaagtgcaa gcgcctcacc cgcttccaca ccagtcgga gctcaaggac ttcgggaccg      600
aggccgctcg gccgcagaag ggccggaagc gcgcggcccccg cgcccggagc gccaaagcca      660
accaggccga gctggagaac gcctactaga gcccgcccgc gccccctcccc accggcgggc      720 gccccggccc tgaacccgcg ccccacattt ctgtcctctg cgcgtggttt gattgtttat      780
atttcattgt aaatgcctgc aacccagggc aggggctga accttccag ccctgagga      840 atcccgggcg ccggcaaggc cccctcagc ccgccagctg aggggtccca cggggcaggg      900
gagggaattg agagtcacag acactgagcc acgcagcccc gcctctgggg ccgcctacct      960
ttgctggtcc cacttcagag gaggcagaaa tggaagcatt tcaccgccc tggggtttta     1020 agggagcggt gtgggagtgg gaaagtccag ggactggtta agaaagttgg ataagattcc     1080
cccttgcacc tcgctgccca tcagaaagcc tgaggcgtgc ccagagcaca agactggggg     1140
caactgtaga tgtggtttct agtcctggct ctgccactaa cttgctgtgt aaccttgaac     1200
tacacaattc tccttcggga cctcaatttc cactttgtaa aatgagggtg gaggtgggaa     1260
taggatctcg aggagactat tggcatatga ttccaaggac tccagtgcct tttgaatggg     1320
cagaggtgag agagagagag agaaagagag agaatgaatg cagttgcatt gattcagtgc     1380
caaggtcact tccagaattc agagttgtga tgctctcttc tgacagccaa agatgaaaaa     1440
caaacagaaa aaaaaaagta aagagtctat ttatggctga catatttacg gctgacaaac     1500
tcctggaaga agctatgctg cttcccagcc tggcttcccc ggatgtttgg ctacctccac     1560
ccctccatct caaagaaata acatcatcca ttggggtaga aaaggagagg gtccgagggt     1620
ggtgggaggg atagaaatca catccgcccc aacttcccaa agagcagcat ccctcccccg     1680
acccatagcc atgttttaaa gtcaccttcc gaagagaagt gaaaggttca aggacactgg     1740
ccttgcaggc ccgagggagc agccatcaca aactcacaga ccagcacatc ccttttgaga     1800
caccgccttc tgcccaccac tcacggacac atttctgcct agaaaacagc ttcttactgc     1860
tcttacatgt gatggcatat cttacactaa agaatatta ttgggggaaa aactacaagt     1920
gctgtacata tgctgagaaa ctgcagagca taatagctgc cacccaaaaa tcttttgaa     1980 aatcatttcc agacaacctc ttactttctg tgtagttttt aattgttaaa aaaaaaaagt     2040
tttaaacaga agcacatgac atatgaaagc ctgcaggact ggtcgttttt ttggcaattc     2100
ttccacgtgg gacttgtcca caagaatgaa agtagtggtt tttaaagagt taagttacat     2160
atttattttc tcacttaagt tatttatgca aaagttttc ttgtagagaa tgacaatgtt     2220
aatattgctt tatgaattaa cagtctgttc ttccagagtc cagagacatt gttaataaag     2280
acaatgaatc atgaccgaaa g                                              2301

<210> SEQ ID NO 2
```

<211> LENGTH: 213
<212> TYPE: PRT
<213> ORGANISM: Homo sapien

<400> SEQUENCE: 2

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 3
<211> LENGTH: 2301
<212> TYPE: DNA
<213> ORGANISM: Homo sapien

<400> SEQUENCE: 3
agagcctgtg ctactggaag gtggcgtgcc ctcctctggc tggtaccatg cagctcccac       60
tggccctgtg tctcgtctgc ctgctggtac acacagcctt ccgtgtagtg gagggctagg      120
ggtggcaggc gttcaagaat gatgccacgg aaatcatccc cgagctcgga gagtaccccg      180
agcctccacc ggagctggag aacaacaaga ccatgaaccg ggcggagaac ggagggcggc      240
ctccccacca ccccttttgag accaaagacg tgtccgagta cagctgccgc gagctgcact      300
tcacccgcta cgtgaccgat gggccgtgcc gcagcgccaa gccggtcacc gagctggtgt      360
gctccggcca gtgcggcccg cgcgcctgc tgcccaacgc catcggccgc ggcaagtggt      420
ggcgacctag tgggcccgac ttccgctgca tccccgaccg ctaccgcgcg cagcgcgtgc      480
agctgctgtg tccggtggt gaggcgccgc gcgcgcaa ggtgcgcctg gtggcctcgt      540
gcaagtgcaa gcgcctcacc cgcttccaca accagtcgga gctcaaggac ttcgggaccg      600
aggccgctcg gccgcagaag ggccggaagc cgcggcccg cgcccggagc gccaaagcca      660
accaggccga gctggagaac gcctactaga gcccgcccgc gcccctcccc accggcgggc      720

```
gccccggccc tgaacccgcg ccccacattt ctgtcctctg cgcgtggttt gattgtttat    780
atttcattgt aaatgcctgc aacccagggc aggggctga gaccttccag gccctgagga     840
atcccgggcg ccggcaaggc cccctcagc ccgccagctg aggggtccca cggggcaggg     900
gagggaattg agagtcacag acactgagcc acgcagcccc gcctctgggg ccgcctacct    960
ttgctggtcc cacttcagag gaggcagaaa tggaagcatt tcaccgccc tggggtttta    1020 agggagcggt gtgggagtgg gaaagtccag ggactggtta agaaagttgg ataagattcc    1080
cccttgcacc tcgctgccca tcagaaagcc tgaggcgtgc ccagagcaca agactggggg    1140
caactgtaga tgtggtttct agtcctggct ctgccactaa cttgctgtgt aaccttgaac    1200
tacacaattc tccttcggga cctcaatttc cactttgtaa aatgagggtg gaggtgggaa    1260
taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaagta agagtctat ttatggctga catatttacg gctgacaaac     1500
tcctggaaga agctatgctg cttcccagcc tggcttcccc ggatgtttgg ctacctccac    1560
ccctccatct caaagaaata acatcatcca ttggggtaga aaggagagg gtccgagggt     1620 ggtgggaggg atagaaatca catccgcccc aacttcccaa agagcagcat ccctcccccg    1680
acccatagcc atgttttaaa gtcaccttcc gaagagaagt gaaaggttca aggacactgg    1740
ccttgcaggc ccgagggagc agccatcaca aactcacaga ccagcacatc cctttgaga     1800 caccgccttc tgcccaccac tcacggacac atttctgcct agaaaacagc ttcttactgc    1860
tcttacatgt gatggcatat cttacactaa aagaatatta ttgggggaaa aactacaagt    1920
gctgtacata tgctgagaaa ctgcagagca taatagctgc cacccaaaaa tcttttgaa    1980 aatcatttcc agacaacctc ttactttctg tgtagttttt aattgttaaa aaaaaaagt     2040 tttaaacaga agcacatgac atatgaaagc ctgcaggact ggtcgttttt ttggcaattc    2100
ttccacgtgg gacttgtcca caagaatgaa agtagtggtt tttaaagagt taagttacat    2160
atttattttc tcacttaagt tatttatgca aaagttttc ttgtagagaa tgacaatgtt     2220
aatattgctt tatgaattaa cagtctgttc ttccagagtc cagagacatt gttaataaag    2280
acaatgaatc atgaccgaaa g                                              2301

<210> SEQ ID NO 4
<211> LENGTH: 23
<212> TYPE: PRT
<213> ORGANISM: Homo sapien

<400> SEQUENCE: 4

Met Gln Leu Pro Leu Ala Leu Cys Leu Val Cys Leu Leu Val His Thr
 1               5                  10                  15

Ala Phe Arg Val Val Glu Gly
            20

<210> SEQ ID NO 5
<211> LENGTH: 2301
<212> TYPE: DNA
<213> ORGANISM: Homo sapien

<400> SEQUENCE: 5
agagcctgtg ctactggaag gtggcgtgcc ctcctctggc tggtaccatg cagctcccac     60
```

```
tggccctgtg tctcatctgc ctgctggtac acacagcctt ccgtgtagtg gagggccagg    120
ggtggcaggc gttcaagaat gatgccacgg aaatcatccg cgagctcgga gagtaccccg    180
agcctccacc ggagctggag aacaacaaga ccatgaaccg gcggagaac ggagggcggc     240
ctccccacca cccctttgag accaaagacg tgtccgagta cagctgccgc gagctgcact    300
tcacccgcta cgtgaccgat gggccgtgcc gcagcgccaa gccggtcacc gagctggtgt    360
gctccggcca gtgcggcccg cgcgcgcctgc tgcccaacgc catcggccgc ggcaagtggt   420
ggcgacctag tgggcccgac ttccgctgca tccccgaccg ctaccgcgcg cagcgcgtgc    480
agctgctgtg tccggtggt gaggcgccgc gcgcgcgcaa ggtgcgcctg gtggcctcgt    540
gcaagtgcaa gcgcctcacc cgcttccaca accagtcgga gctcaaggac ttcgggaccg    600
aggccgctcg gccgcagaag ggccggaagc cgcggccccg cgcccggagc gccaaagcca    660
accaggccga gctggagaac gcctactaga gcccgcccgc gcccctcccc accggcgggc    720
gccccggccc tgaacccgcg ccccacattt ctgtcctctg cgcgtggttt gattgtttat    780
atttcattgt aaatgcctgc aacccagggc aggggctga  ccttccag gccctgagga     840
atcccgggcg ccggcaaggc cccctcagc ccgccagctg aggggtccca cggggcaggg    900
gagggaattg agagtcacag acactgagcc acgcagcccc gcctctgggg ccgcctacct    960
ttgctggtcc cacttcagag gaggcagaaa tggaagcatt ttcaccgccc tggggttta    1020
agggagcggt gtgggagtgg gaaagtccag ggactggtta agaaagttgg ataagattcc    1080
cccttgcacc tcgctgccca tcagaaagcc tgaggcgtgc ccagagcaca agactggggg    1140
caactgtaga tgtggtttct agtcctggct ctgccactaa cttgctgtgt aaccttgaac    1200
tacacaattc tccttcggga cctcaatttc cactttgtaa aatgagggtg gaggtgggaa    1260
taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttggggtaga aaaggagagg gtccgagggt    1620
ggtgggaggg atagaaatca catccgcccc aacttcccaa agagcagcat ccctccccg     1680
acccatagcc atgttttaaa gtcaccttcc gaagagaagt gaaaggttca aggacactgg    1740
ccttgcaggc ccgagggagc agccatcaca aactcacaga ccagcacatc cctttttgaga   1800
caccgccttc tgcccaccac tcacggacac atttctgcct agaaaacagc ttcttactgc    1860
tcttacatgt gatggcatat cttacactaa aagaatatta ttgggggaaa aactacaagt    1920
gctgtacata tgctgagaaa ctgcagagca taatagctgc cacccaaaaa tcttttgaa    1980
aatcatttcc agcaacctc ttactttctg tgtagttttt aattgttaaa aaaaaaagt     2040
tttaaacaga agcacatgac atatgaaagc ctgcaggact ggtcgttttt ttggcaattc    2100
ttccacgtgg gacttgtcca caagaatgaa agtagtggtt tttaaagagt taagttacat    2160
atttatttc tcacttaagt tatttatgca aaagttttc ttgtagagaa tgacaatgtt      2220
aatattgctt tatgaattaa cagtctgttc ttccagagtc cagagacatt gttaataaag    2280
acaatgaatc atgaccgaaa g                                             2301
```

<210> SEQ ID NO 6
<211> LENGTH: 213

<212> TYPE: PRT
<213> ORGANISM: Homo sapien

<400> SEQUENCE: 6

```
Met Gln Leu Pro Leu Ala Leu Cys Leu Ile Cys Leu Leu Val His Thr
 1               5                  10                  15

Ala Phe Arg Val Val Glu Gly Gln Gly Trp Gln Ala Phe Lys Asn Asp
                20                  25                  30

Ala Thr Glu Ile Ile Arg Glu Leu Gly Glu Tyr Pro Glu Pro Pro Pro
            35                  40                  45

Glu Leu Glu Asn Asn Lys Thr Met Asn Arg Ala Glu Asn Gly Gly Arg
        50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

<210> SEQ ID NO 7
<211> LENGTH: 2301
<212> TYPE: DNA
<213> ORGANISM: Homo sapien

<400> SEQUENCE: 7

```
agagcctgtg ctactggaag gtggcgtgcc ctcctctggc tggtaccatg cagctcccac    60
tggccctgtg tctcgtctgc ctgctggtac acacagcctt ccgtgtagtg gagggccagg   120
ggtggcaggc gttcaagaat gatgccacgg aaatcatccg cgagctcgga gagtaccccg   180
agcctccacc ggagctggag aacaacaaga ccatgaaccg ggcggagaac ggagggcggc   240
ctccccacca cccctttgag accaaagacg tgtccgagta cagctgccgc gagctgcact   300
tcacccgcta cgtgaccgat gggccgtgcc gcagcgccaa gccggtcacc gagctggtgt   360
gctccggcca gtgcggcccg cgcgcctgc tgcccaacgc catcggccgc ggcaagtggt   420
ggcgacctag tgggcccgac ttccgctgca tccccgaccg ctaccgcgcg cagcgcgtgc   480
agctgctgtg tccggtggt gaggcgccgc gcgcgcgcaa ggtgcgcctg gtggcctcgt   540
gcaagtgcaa gcgcctcacc cgcttccaca accagtcgga gctcaaggac ttcgggaccg   600
aggccgctcg gccgcagaag ggccggaagc cgcggcccg cgcccggagc gccaaagcca   660
accaggccga gctggagaac gcctactaga gcccgcccgc gccctcccc accggcgggc   720
```

```
gccccggccc tgaacccgcg ccccacattt ctgtcctctg cgcgtggttt gattgtttat    780
atttcattgt aaatgcctgc aacccagggc aggggctga  gaccttccag gccctgagga    840
atcccgggcg ccggcaaggc ccccctcagc ccgccagctg aggggtccca cggggcaggg    900
gagggaattg agagtcacag acactgagcc acgcagcccc gcctctgggg ccgcctacct    960
ttgctggtcc cacttcagag gaggcagaaa tggaagcatt tcaccgccc  tggggtttta   1020
agggagcggt gtgggagtgg gaaagtccag ggactggtta agaaagttgg ataagattcc   1080
cccttgcacc tcgctgccca tcagaaagcc tgaggcgtgc ccagagcaca agactggggg   1140
caactgtaga tgtggtttct agtcctggct ctgccactaa cttgctgtgt aaccttgaac   1200
tacacaattc tccttcggga cctcaatttc cactttgtaa aatgagggtg gaggtgggaa   1260
taggatctcg aggagactat tggcatatga ttccaaggac tccagtgcct tttgaatggg   1320
cagaggtgag agagagagag agaaagagag agaatgaatg cagttgcatt gattcagtgc   1380
caaggtcact tccagaattc agagttgtga tgctctcttc tgacagccaa agatgaaaaa   1440
caaacagaaa aaaaaagta  aagagtctat ttatggctga catatttacg gctgacaaac   1500
tcctggaaga agctatgctg cttcccagcc tggcttcccc ggatgtttgg ctacctccac   1560
ccctccatct caaagaaata acatcatcca ttggggtaga aaggagagg  gtccgagggt   1620
ggtgggaggg atagaaatca catccgcccc aacttcccaa agagcagcat ccctccccg    1680
acccatagcc atgttttaaa gtcaccttcc gaagagaagt gaaaggttca aggacactgg   1740
ccttgcaggc ccgagggagc agccatcaca aactcacaga ccagcacatc ccttttgaga   1800
caccgccttc tgcccaccac tcacggacac atttctgcct agaaacagc  ttcttactgc   1860
tcttacatgt gatggcatat cttacactaa aagaatatta ttgggggaaa aactacaagt   1920
gctgtacata tgctgagaaa ctgcagagca taatagctgc cacccaaaaa tcttttttgaa  1980
aatcatttcc agacaacctc ttactttctg tgtagttttt aattgttaaa aaaaaaaagt   2040
tttaaacaga agcacatgac atatgaaagc ctgcaggact ggtcgttttt ttggcaattc   2100
ttccacgtgg gacttgtcca caagaatgaa agtagtggtt tttaaagagt taagttacat   2160
atttattttc tcacttaagt tatttatgca aaagtttttc ttgtagagaa tgacaatgtt   2220
aatattgctt tatgaattaa cagtctgttc ttccagagtc cagagacatt gttaataaag   2280
acaatgaatc atgaccgaaa g                                             2301
```

<210> SEQ ID NO 8
<211> LENGTH: 213
<212> TYPE: PRT
<213> ORGANISM: Homo sapien

<400> SEQUENCE: 8

```
Met Gln Leu Pro Leu Ala Leu Cys Leu Val Cys Leu Leu Val His Thr
 1               5                  10                  15

Ala Phe Arg Val Val Glu Gly Gln Gly Trp Gln Ala Phe Lys Asn Asp
                20                  25                  30

Ala Thr Glu Ile Ile Arg Glu Leu Gly Glu Tyr Pro Glu Pro Pro Pro
            35                  40                  45

Glu Leu Glu Asn Asn Lys Thr Met Asn Arg Ala Glu Asn Gly Gly Arg
        50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95
```

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
        130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
        180                 185                 190

Arg Lys Pro Arg Pro Arg Ala Arg Ser Ala Lys Ala Asn Gln Ala Glu
        195                 200                 205

Leu Glu Asn Ala Tyr
        210

<210> SEQ ID NO 9
<211> LENGTH: 642
<212> TYPE: DNA
<213> ORGANISM: Cercopithecus pygerythrus

<400> SEQUENCE: 9
atgcagctcc cactggccct gtgtcttgtc tgcctgctgg tacacgcagc cttccgtgta     60
gtggagggcc agggtggca ggccttcaag aatgatgcca cggaaatcat ccccgagctc    120
ggagagtacc ccgagcctcc accggagctg gagaacaaca agaccatgaa ccgggcggag    180
aatggagggc ggcctcccca ccaccccttt gagaccaaaa acgtgtccga gtacagctgc    240
cgagagctgc acttcacccg ctacgtgacc gatgggccgt gccgcagcgc caagccagtc    300
accgagttgg tgtgctccgg ccagtgcggc cggcacgcc tgctgcccaa cgccatcggc    360
cgcggcaagt ggtggcgccc gagtgggccc gacttccgct gcatccccga ccgctaccgc    420
gcgcagcgtg tgcagctgct gtgtcccggt ggtgccgcgc cgcgcgcgcg caaggtgcgc    480
ctggtggcct cgtgcaagtg caagcgcctc acccgcttcc acaaccagtc ggagctcaag    540
gacttcggtc ccgaggccgc tcggccgcag aagggccgga gccgcgcc ccgcgcccgg    600 ggggccaaag ccaatcaggc cgagctggag aacgcctact ag                       642

<210> SEQ ID NO 10
<211> LENGTH: 213
<212> TYPE: PRT
<213> ORGANISM: Cercopithecus pygerythrus

<400> SEQUENCE: 10

Met Gln Leu Pro Leu Ala Leu Cys Leu Val Cys Leu Leu Val His Ala
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser

|  |  |  |  | 85 |  |  |  | 90 |  |  |  | 95 |  |  |
|---|---|---|---|---|---|---|---|---|---|---|---|---|---|---|

Ala Lys Pro Val Thr Glu Leu Val Cys Ser Gly Gln Cys Gly Pro Ala
          100                105              110

Arg Leu Leu Pro Asn Ala Ile Gly Arg Gly Lys Trp Trp Arg Pro Ser
          115                120              125

Gly Pro Asp Phe Arg Cys Ile Pro Asp Arg Tyr Arg Ala Gln Arg Val
          130                135              140

Gln Leu Leu Cys Pro Gly Gly Ala Ala Pro Arg Ala Arg Lys Val Arg
145              150              155              160

Leu Val Ala Ser Cys Lys Cys Lys Arg Leu Thr Arg Phe His Asn Gln
          165                170              175

Ser Glu Leu Lys Asp Phe Gly Pro Glu Ala Ala Arg Pro Gln Lys Gly
          180                185              190

Arg Lys Pro Arg Pro Arg Ala Arg Gly Ala Lys Ala Asn Gln Ala Glu
          195                200              205

Leu Glu Asn Ala Tyr
    210

<210> SEQ ID NO 11
<211> LENGTH: 638
<212> TYPE: DNA
<213> ORGANISM: Mus musculus

<400> SEQUENCE: 11

```
atgcagccct cactagcccc gtgcctcatc tgcctacttg tgcacgctgc cttctgtgct      60
gtggagggcc aggggtggca agccttcagg aatgatgcca cagaggtcat cccagggctt     120
ggagagtacc ccgagcctcc tcctgagaac aaccagacca tgaaccgggc ggagaatgga     180
ggcagacctc cccaccatcc ctatgacgcc aaaggtgtgt ccgagtacag ctgccgcgag     240
ctgcactaca cccgcttcct gacagacggc ccatgccgca cgccaagcc ggtcaccgag      300
ttggtgtgct ccggccagtg cggccccgcg cggctgctgc ccaacgccat cgggcgcgtg     360
aagtggtggc gcccgaacgg accggatttc cgctgcatcc cggatcgcta ccgcgcgcag     420
cgggtgcagc tgctgtgccc cggggggcgc gcgccgcgct cgcgcaaggt gcgtctggtg     480
gcctcgtgca gtgcaagcg cctcacccgc ttccacaacc agtcggagct caaggacttc     540
gggccggaga ccgcgcggcc gcagaagggt cgcaagccgc ggcccggcgc ccggggagcc     600
aaagccaacc aggcggagct ggagaacgcc tactagag                            638
```

<210> SEQ ID NO 12
<211> LENGTH: 211
<212> TYPE: PRT
<213> ORGANISM: Mus musculus

<400> SEQUENCE: 12

Met Gln Pro Ser Leu Ala Pro Cys Leu Ile Cys Leu Leu Val His Ala
1             5                 10                15

Ala Phe Cys Ala Val Glu Gly Gln Gly Trp Gln Ala Phe Arg Asn Asp
          20                25              30

Ala Thr Glu Val Ile Pro Gly Leu Gly Glu Tyr Pro Glu Pro Pro Pro
          35                40              45

Glu Asn Asn Gln Thr Met Asn Arg Ala Glu Asn Gly Gly Arg Pro Pro
    50              55              60

His His Pro Tyr Asp Ala Lys Asp Val Ser Glu Tyr Ser Cys Arg Glu
65             70              75              80

Leu His Tyr Thr Arg Phe Leu Thr Asp Gly Pro Cys Arg Ser Ala Lys
                85                  90                  95
Pro Val Thr Glu Leu Val Cys Ser Gly Gln Cys Gly Pro Ala Arg Leu
            100                 105                 110
Leu Pro Asn Ala Ile Gly Arg Val Lys Trp Trp Arg Pro Asn Gly Pro
        115                 120                 125
Asp Phe Arg Cys Ile Pro Asp Arg Tyr Arg Ala Gln Arg Val Gln Leu
    130                 135                 140
Leu Cys Pro Gly Gly Ala Ala Pro Arg Ser Arg Lys Val Arg Leu Val
145                 150                 155                 160
Ala Ser Cys Lys Cys Lys Arg Leu Thr Arg Phe His Asn Gln Ser Glu
                165                 170                 175
Leu Lys Asp Phe Gly Pro Glu Thr Ala Arg Pro Gln Lys Gly Arg Lys
            180                 185                 190
Pro Arg Pro Gly Ala Arg Gly Ala Lys Ala Asn Gln Ala Glu Leu Glu
        195                 200                 205
Asn Ala Tyr
    210

<210> SEQ ID NO 13
<211> LENGTH: 674
<212> TYPE: DNA
<213> ORGANISM: Rattus norvegicus

<400> SEQUENCE: 13
gaggaccgag tgcccttcct ccttctggca ccatgcagct ctcactagcc ccttgccttg    60
cctgcctgct tgtacatgca gccttcgttg ctgtggagag ccaggggtgg caagccttca   120
agaatgatgc cacagaaatc atcccgggac tcagagagta cccagagcct cctcaggaac   180
tagagaacaa ccagaccatg aaccgggccg agaacggagg cagaccccc caccatcctt   240 atgacaccaa agacgtgtcc gagtacagct gccgcgagct gcactacacc cgcttcgtga   300
ccgacggccc gtgccgcagt gccaagccgg tcaccgagtt ggtgtgctcg ggccagtgcg   360
gccccgcgcg gctgctgccc aacgccatcg gccgcgtgaa gtggtggcgc ccgaacggac   420
ccgacttccg ctgcatcccg gatcgctacc gcgcgcagcg ggtgcagctg ctgtgccccg   480
gcggcgcggc gccgcgctcg cgcaaggtgc gtctggtggc ctcgtgcaag tgcaagcgcc   540
tcacccgctt ccacaaccag tcggagctca aggacttcgg acctgagacc gcgcggccgc   600
agaagggtcg caagccgcgg ccccgcgccc ggggagccaa agccaaccag gcggagctgg   660
agaacgccta ctag                                                    674

<210> SEQ ID NO 14
<211> LENGTH: 213
<212> TYPE: PRT
<213> ORGANISM: Rattus norvegicus

<400> SEQUENCE: 14

Met Gln Leu Ser Leu Ala Pro Cys Leu Ala Cys Leu Leu Val His Ala
1               5                   10                  15
Ala Phe Val Ala Val Glu Ser Gln Gly Trp Gln Ala Phe Lys Asn Asp
            20                  25                  30
Ala Thr Glu Ile Ile Pro Gly Leu Arg Glu Tyr Pro Glu Pro Pro Gln
        35                  40                  45
Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
65                  70                  75                  80

Arg Glu Leu His Tyr Thr Arg Phe Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Val Lys Trp Trp Arg Pro Asn
            115                 120                 125

Gly Pro Asp Phe Arg Cys Ile Pro Asp Arg Tyr Arg Ala Gln Arg Val
        130                 135                 140

Gln Leu Leu Cys Pro Gly Gly Ala Ala Pro Arg Ser Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Pro Glu Thr Ala Arg Pro Gln Lys Gly
            180                 185                 190

Arg Lys Pro Arg Pro Arg Ala Arg Gly Ala Lys Ala Asn Gln Ala Glu
        195                 200                 205

Leu Glu Asn Ala Tyr
        210

<210> SEQ ID NO 15
<211> LENGTH: 532
<212> TYPE: DNA
<213> ORGANISM: Bos torus

<400> SEQUENCE: 15
agaatgatgc cacagaaatc atccccgagc tgggcgagta ccccgagcct ctgccagagc      60
tgaacaacaa gaccatgaac cgggcggaga acggagggag acctccccac caccccttttg    120
agaccaaaga cgcctccgag tacagctgcc gggagctgca cttcacccgc tacgtgaccg    180
atgggccgtg ccgcagcgcc aagccggtca ccgagctggt gtgctcgggc cagtgcggcc    240
cggcgcgcct gctgcccaac gccatcggcc gggcaagtg gtggcgccca agcgggcccg    300
acttccgctg catccccgac cgctaccgcg cgcagcgggt gcagctgttg tgtcctggcg    360
gcgcggcgcc gcgcgcgcgc aaggtgcgcc tggtggcctc gtgcaagtgc aagcgcctca    420
ctcgcttcca caaccagtcc gagctcaagg acttcgggcc cgaggccgcg cggccgcaaa    480
cgggccggaa gctgcggccc cgcgcccggg gcaccaaagc cagccgggcc ga             532

<210> SEQ ID NO 16
<211> LENGTH: 176
<212> TYPE: PRT
<213> ORGANISM: Bos torus

<400> SEQUENCE: 16

Asn Asp Ala Thr Glu Ile Ile Pro Glu Leu Gly Glu Tyr Pro Glu Pro
1               5                   10                  15

Leu Pro Glu Leu Asn Asn Lys Thr Met Asn Arg Ala Glu Asn Gly Gly
            20                  25                  30

Arg Pro Pro His His Pro Phe Glu Thr Lys Asp Ala Ser Glu Tyr Ser
        35                  40                  45

Cys Arg Glu Leu His Phe Thr Arg Tyr Val Thr Asp Gly Pro Cys Arg
    50                  55                  60

Ser Ala Lys Pro Val Thr Glu Leu Val Cys Ser Gly Gln Cys Gly Pro
65                  70                  75                  80

```
Ala Arg Leu Leu Pro Asn Ala Ile Gly Arg Gly Lys Trp Trp Arg Pro
            85                  90                  95

Ser Gly Pro Asp Phe Arg Cys Ile Pro Asp Arg Tyr Arg Ala Gln Arg
            100                 105                 110

Val Gln Leu Leu Cys Pro Gly Gly Ala Ala Pro Arg Ala Arg Lys Val
            115                 120                 125

Arg Leu Val Ala Ser Cys Lys Cys Lys Arg Leu Thr Arg Phe His Asn
            130                 135                 140

Gln Ser Glu Leu Lys Asp Phe Gly Pro Glu Ala Ala Arg Pro Gln Thr
145                 150                 155                 160

Gly Arg Lys Leu Arg Pro Arg Ala Arg Gly Thr Lys Ala Ser Arg Ala
                165                 170                 175

<210> SEQ ID NO 17
<211> LENGTH: 35828
<212> TYPE: DNA
<213> ORGANISM: Mus musculus
<220> FEATURE:
<221> NAME/KEY: misc_feature
<222> LOCATION: (1)..(35828)
<223> OTHER INFORMATION: n = A,T,C or G

<400> SEQUENCE: 17
cgcgttttgg tgagcagcaa tattgcgctt cgatgagcct tggcgttgag attgatacct     60
ctgctgcaca aaaggcaatc gaccgagctg accagcgca ttcgtgacac cgtctccttc    120
gaacttattc gcaatggagt gtcattcatc aaggacngcc tgatcgcaaa tggtgctatc    180
cacgcagcgg caatcgaaaa ccctcagccg gtgaccaata tctacaacat cagccttggt    240
atcctgcgtg atgagccagc gcagaacaag gtaaccgtca gtgccgataa gttcaaagtt    300
aaacctggtg ttgataccaa cattgaaacg ttgatcgaaa acgcgctgaa aaacgctgct    360
gaatgtgcgg cgctggatgt cacaaagcaa atggcagcag acaagaaagc gatggatgaa    420
ctggcttcct atgtccgcac ggccatcatg atggaatgtt ccccggtgg tgttatctgg    480 cagcagtgcc gtcgatagta tgcaattgat aattattatc atttgcgggt cctttccggc    540
gatccgcctt gttacggggc ggcgacctcg cgggttttcg ctatttatga aaattttccg    600
gtttaaggcg tttccgttct tcttcgtcat aacttaatgt ttttatttaa aatacccttct   660 gaaaagaaag gaaacgacag gtgctgaaag cgagcttttt ggcctctgtc gtttcctttc    720 tctgttttg tccgtggaat gaacaatgga agtcaacaaa aagcagagct tatcgatgat     780
aagcggtcaa acatgagaat tcgcggccgc ataatacgac tcactatagg gatcgacgcc    840
tactccccgc gcatgaagcg gaggagctgg actccgcatg cccagagacg ccccccaacc    900
cccaaagtgc ctgacctcag cctctaccag ctctggcttg gcttgggcg gggtcaaggc     960 taccacgttc tcttaacagg tggctgggct gtctcttggc cgcgcgtcat gtgacagctg   1020
cctagttctg cagtgaggtc accgtggaat gtctgccttc gttgccatgg caacgggatg   1080
acgttacaat ctgggtgtgg agcttttcct gtccgtgtca ggaaatccaa atacccctaaa  1140 ataccctaga agaggaagta gctgagccaa ggctttcctg gcttctccag ataaagtttg   1200
acttagatgg aaaaaaacaa aatgataaag acccgagcca tctgaaaatt cctcctaatt   1260
gcaccactag gaaatgtgta tattattgag ctcgtatgtg ttcttatttt aaaaagaaaa   1320
ctttagtcat gttattaata agaatttctc agcagtggga gagaaccaat attaacacca    1380
agataaaagt tggcatgatc cacattgcag gaagatccac gttgggtttt catgaatgtg   1440
aagaccccat ttattaaagt cctaagctct gttttttgcac actaggaagc gatggccggg  1500
```

```
atggctgagg ggctgtaagg atctttcaat gtcttacatg tgtgtttcct gtcctgcacc    1560
taggacctgc tgcctagcct gcagcagagc cagaggggtt tcacatgatt agtctcagac    1620
acttgggggc aggttgcatg tactgcatcg cttatttcca tacggagcac ctactatgtg    1680
tcaaacacca tatggtgttc actcttcaga acggtggtgg tcatcatggt gcatttgctg    1740
acggttggat tggtggtaga gagctgagat atatggacgc actcttcagc attctgtcaa    1800
cgtggctgtg cattcttgct cctgagcaag tggctaaaca gactcacagg gtcagcctcc    1860
agctcagtcg ctgcatagtc ttagggaacc tctcccagtc ctccctacct caactatcca    1920
agaagccagg gggcttggcg gtctcaggag cctgcttgct gggggacagg ttgttgagtt    1980
ttatctgcag taggttgcct aggcatagtg tcaggactga tggctgcctt ggagaacaca    2040
tcctttgccc tctatgcaaa tctgaccttg acatggggc gctgctcagc tgggaggatc     2100
aactgcatac ctaaagccaa gcctaaagct tcttcgtcca cctgaaactc ctggaccaag    2160
gggcttccgg cacatcctct caggccagtg agggagtctg tgtgagctgc actttccaat    2220 ctcaggcgt gagaggcaga gggaggtggg ggcagagcct tgcagctctt tcctcccatc      2280
tggacagcgc tctggctcag cagcccatat gagcacaggc acatcccac cccaccccca      2340 cctttcctgt cctgcagaat ttaggctctg ttcacggggg ggggggggg ggggcagtcc      2400 tatcctctct taggtagaca ggactctgca ggagacactg ctttgtaaga tactgcagtt    2460
taaatttgga tgttgtgagg ggaaagcgaa gggcctcttt gaccattcag tcaaggtacc    2520
ttctaactcc catcgtattg gggggctact ctagtgctag acattgcaga gagcctcaga    2580
actgtagtta ccagtgtggt aggattgatc cttcagggag cctgacatgt gacagttcca    2640
ttcttcaccc agtcaccgaa catttattca gtacctaccc cgtaacaggc accgtagcag    2700
gtactgaggg acggaccact caaagaactg acagaccgaa gccttggaat ataaacacca    2760
aagcatcagg ctctgccaac agaacactct ttaacactca ggcccttaa cactcaggac    2820 ccccaccccc accccaagca gttggcactg ctatccacat tttacagaga ggaaaaacta    2880
ggcacaggac gatataagtg gcttgcttaa gcttgtctgc atggtaaatg gcagggctgg    2940
attgagaccc agacattcca actctagggt ctatttttct ttttctcgt tgttcgaatc     3000 tgggtcttac tgggtaaact caggctagcc tcacactcat atccttctcc catggcttac    3060
gagtgctagg attccaggtg tgtgctacca tgtctgactc cctgtagctt gtctatacca    3120
tcctcacaac ataggaattg tgatagcagc acacacaccg gaaggagctg gggaaatccc    3180
acagagggct ccgcaggatg acaggcgaat gcctacacag aaggtgggga agggaagcag    3240
agggaacagc atgggcgtgg gaccacaagt ctatttgggg aagctgccgg taaccgtata    3300
tggctggggt gaggggagag gtcatgagat gaggcaggaa gagccacagc aggcagcggg    3360
tacgggctcc ttattgccaa gaggctcgga tcttcctcct cttcctcctt ccggggctgc    3420
ctgttcattt tccaccactg cctcccatcc aggtctgtgg ctcaggacat cacccagctg    3480
cagaaactgg gcatcaccca cgtcctgaat gctgccgagg gcaggtcctt catgcacgtc    3540
aacaccagtg ctagcttcta cgaggattct ggcatcacct acttgggcat caaggccaat    3600
gatacgcagg agttcaacct cagtgcttac tttgaaaggg ccacagattt cattgaccag    3660
gcgctggccc ataaaaatgg taaggaacgt acattccggc acccatggag cgtaagccct    3720 ctggacctg cttcctccaa agaggccccc acttgaaaaa ggttccagaa agatcccaaa     3780
atatgccacc aactagggat taagtgtcct acatgtgagc cgatggggc cactgcatat     3840
```

```
agtctgtgcc atagacatga caatggataa taatatttca gacagagagc aggagttagg     3900
tagctgtgct cctttcccct taattgagtg tgcccatttt tttattcatg tatgtgtata     3960
catgtgtgtg cacacatgcc ataggttgat actgaacacc gtcttcaatc gttccccacc     4020
ccaccttatt ttttgaggca gggtctcttc cctgatcctg gggctcattg gtttatctag     4080
gctgctggcc agtgagctct ggagttctgc ttttctctac ctccctagcc ctgggactgc     4140
aggggcatgt gctgggccag gcttttatgt cgcgttgggg atctgaactt aggtccctag     4200
gcctgagcac cgtaaagact ctgccacatc cccagcctgt ttgagcaagt gaaccattcc     4260
ccagaattcc cccagtgggg cttcctaccc tttttattgg ctaggcattc atgagtggtc     4320
acctcgccag aggaatgagt ggccacgact ggctcagggt cagcagccta gagatactgg     4380
gttaagtctt cctgccgctc gctccctgca gccgcagaca gaaagtagga ctgaatgaga     4440
gctggctagt ggtcagacag gacagaaggc tgagagggtc acagggcaga tgtcagcaga     4500
gcagacaggt tctccctctg tgggggaggg gtggcccact gcaggtgtaa ttggccttct     4560
ttgtgctcca tagaggcttc ctgggtacac agcagcttcc ctgtcctggt gattcccaaa     4620
gagaactccc taccactgga cttacagaag ttctattgac tggtgtaacg gttcaacagc     4680
tttggctctt ggtggacggt gcatactgct gtatcagctc aagagctcat tcacgaatga     4740
acacacacac acacacacac acacacacac acaagctta attttgatat gccttaacta     4800
gctcagtgac tgggcatttc tgaacatccc tgaagttagc acacatttcc ctctggtgtt     4860
cctggcttaa caccttctaa atctatattt tatctttgct gccctgttac cttctgagaa     4920
gcccctaggg ccacttccct tcgcacctac attgctggat ggtttctctc ctgcagctct     4980
taaatctgat ccctctgcct ctgagccatg ggaacagccc aataactgag ttagacataa     5040
aaacgtctct agccaaaact tcagctaaat ttagacaata atcttactg gttgtggaat      5100
ccttaagatt cttcatgacc tccttcacat ggcacgagta tgaagcttta ttacaattgt     5160
ttattgatca aactaactca taaaaagcca gttgtctttc acctgctcaa ggaaggaaca     5220
aaattcatcc ttaactgatc tgtgcacctt gcacaatcca tacgaatatc ttaagagtac     5280
taagattttg gttgtgagag tcacatgtta cagaatgtac agctttgaca aggtgcatcc     5340
ttgggatgcc gaagtgacct gctgttccag cccccctacct tctgaggctg ttttggaagc    5400
aatgctctgg aagcaacttt aggaggtagg atgctggaac agcgggtcac ttcagcatcc     5460
cgatgacgaa tcccgtcaaa gctgtacatt ctgtaacaga ctgggaaagc tgcagacttt     5520
aaggccaggg ccctatggtc cctcttaatc cctgtcacac ccaacccgag cccttctcct     5580
ccagccgttc tgtgcttctc actctggata gatggagaac acggccttgc tagttaaagg     5640
agtgaggctt caccttctc acatggcagt ggttggtcat cctcattcag ggaactctgg      5700
ggcattctgc ctttacttcc tctttttgga ctacagggaa tatatgctga cttgttttga     5760
ccttgtgtat ggggagactg gatctttggt ctggaatgtt tcctgctagt ttttccccat     5820
cctttggcaa accctatcta tatcttacca ctaggcatag tggccctcgt tctggagcct     5880
gccttcaggc tggttctcgg ggaccatgtc cctggtttct ccccagcata tggtgttcac     5940
agtgttcact gcgggtggtt gctgaacaaa gcggggattg catcccagag ctccggtgcc     6000
ttgtgggtac actgctaaga taaaatggat actggcctct ctctgaccac ttgcagagct     6060
ctggtgcctt gtgggtacac tgctaagata aaatggatac tggcctctct ctatccactt     6120
gcaggactct agggaacagg aatccattac tgagaaaacc aggggctagg agcagggagg     6180
tagctgggca gctgaagtgc ttggcgacta accaatgaat accagagttt ggatctctag     6240
```

```
aatactctta aaatctgggt gggcagagtg gcctgcctgt aatcccagaa ctcgggaggc   6300
ggagacaggg aatcatcaga gcaaactggc taaccagaat agcaaaacac tgagctctgg   6360
gctctgtgag agatcctgcc ttaacatata agagagagaa taaaacattg aagaagacag   6420
tagatgccaa ttttaagccc ccacatgcac atggacaagt gtgcgtttga acacacatat   6480
gcactcatgt gaaccaggca tgcacactcg ggcttatcac acacataatt tgaaagagag   6540
agtgagagag gagagtgcac attagagttc acaggaaagt gtgagtgagc acccatgc    6600 acacagacat gtgtgccagg gagtaggaaa ggagcctggg tttgtgtata agagggagcc   6660
atcatgtgtt tctaaggagg gcgtgtgaag gaggcgttgt gtgggctggg actgagcat   6720 ggttgtaact gagcatgctc cctgtgggaa acaggagggg ggccaccctg cagagggtcc   6780
cactgtccag cgggatcagt aaaagcccct gctgagaact ttaggtaata gccagagaga   6840
gaaaggtagg aaagtggggg gactcccatc tctgatgtag gaggatctgg gcaagtagag   6900
gtgcgtttga ggtagaaaga ggggtgcaga ggagatgctc ttaattctgg gtcagcagtt   6960
tctttccaaa taatgcctgt gaggaggtgt aggtggtggc cattcactca ctcagcagag   7020
ggatgatgat gcccggtgga tgctggaaat ggccgagcat caaccctggc tctggaagaa   7080
ctccatcttt cagaaggaga gtggatctgt gtatggccag cggggtcaca ggtgcttggg   7140 gccctgggg gactcctagc actgggtgat gtttatcgag tgctcttgtg tgccaggcac   7200
tggcctgggg ctttgtttct gtctctgttt tgtttcgttt tttgagacag actcttgcta   7260
tgtatccgtg tcaatcttgg aatctcactg catagcccag gctgcggaga gaggggaggg   7320
caataggcct tgtaagcaag ccacacttca gagactagac tccaccctgc gaatgatgac   7380
aggtcagagc tgagttccgg aagattttt ttccagctgc caggtggagt gtggagtggc   7440
agctagcggc aagggtagag ggcgagctcc ctgtgcagga gaaatgcaag caagagatgg   7500
caagccagtg agttaagcat tctgtgtggg gagcaggtgg atgaagagag aggctgggct   7560
ttcgcctctg ggggggggt gaggggtggg gatgaggtga gaggagggca gctccctgca   7620
gtgtgatgag atttttcctg acagtgacct ttggcctctc cctcccccac ttcccttctt   7680
tcctttcttc ccaccattgc tttccttgtc cttgagaaat tctgagtttc cacttcactg   7740
gtgatgcaga cggaaacaga agccgtgtgt gtgtgtgtgt gtgtgtgtgt gtgtgtgtgt   7800
gtgtgtgtgt ttgtgtgtat gtgtgtgtgt gtgtttgtgt gtatgtgtgt cagtgggaat   7860
ggctcatagt ctgcaggaag gtgggcagga aggaataagc tgtaggctga ggcagtgtgg   7920
gatgcaggga gagaggagag gagggatacc agagaaggaa attaagggag ctacaagagg   7980
gcattgttgg ggtgtgtgtg tgtgtgtgtt gtttatattt gtattggaaa tacattcttt   8040 taaaaatac ttatccattt atttatttt atgtgcacgt gtgtgtgcct gcatgagttc   8100
atgtgtgcca cgtgtgtgcg ggaacccttg gaggccacaa gggggcatct gatcccctgg   8160
aactggagtt ggaggaggtt gtgagtcccc tgacatgttt gctgggaact gaaccccggt   8220
cctatgcaag agcaggaagt gcagttatct gctgagccat ctctccagtc ctgaaatcca   8280
ttctcttaaa atacacgtgg cagagacatg atgggattta cgtatggatt taatgtggcg   8340
gtcattaagt tccggcacag gcaagcacct gtaaagccat caccacaacc gcaacagtga   8400
atgtgaccat caccccatg ttcttcatgt cccctgtccc ctccatcctc cattctcaag   8460
cacctcttgc tctgcctctg tcgtggaga acagtgtgca tctgcacact cttatgtcag   8520
tgaagtcaca cagcctgcac cccttcctgg tctgagtatt tgggttctga ctctgctatc   8580
```

```
acacactact gtactgcatt ctctcgctct cttttttaa acatattttt atttgtttgt    8640
gtgtatgcac atgtgccaca tgtgtacaga tactatggag gccagaagag gccatggccg    8700
tccctggagc tggagttaca ggcagcgtgt gagctgcctg gtgtgggtgc tgggaaccaa    8760
acttgaatct aaagcaagca cttttaactg ctgaggcagc tctcagtacc cttcttcatt    8820
tctccgcctg ggttccattg tatggacaca tgtagctaga atatcttgct tatctaatta    8880
tgtacattgt tttgtgctaa gagagagtaa tgctctatag cctgagctgg cctcaacctt    8940
gccatcctcc tgcctcagcc tcctcctcct gagtgctagg atgacaggcg agtggtaact    9000
tacatggttt catgttttgt tcaagactga aggataacat tcatacagag aaggtctggg    9060
tcacaaagtg tgcagttcac tgaatggcac aacccgtgat caagaaacaa aactcagggg    9120
ctggagagat ggcactgact gctcttccag aggtccggag ttcaattccc agcaaccaca    9180
tggtggctca cagccatcta taacgagatc tgacgccctc ttctggtgtg tctgaagaca    9240
gctacagtgt actcacataa aataaataaa tcttaaaac acacacacac acacaattac    9300
caccccagaa agcccactcc atgttccctc ccacgtctct gcctacagta ctcccaggtt    9360
accactgttc aggcttctaa caacctggtt tacttgggcc tcttttctgc tctgtggagc    9420
cacacatttg tgtgcctcat acacgttctt tctagtaagt tgcatattac tctgcgtttt    9480
tacatgtatt tatttattgt agttgtgtgt gcgtgtgggc ccatgcatgg cacagtgtgt    9540
ggggatgtca gagtattgtg aacaggggac agttcttttc ttcaatcatg tgggttccag    9600
aggttgaact caggtcatca tgtgtggcag caaatgcctt tacccactga gacatctcca    9660
tattcttttt ttttcccctg aggtgggggc ttgttccata gcccaaactg gctttgcact    9720
tgcagttcaa agtgactccc tgtctccacc tcttagagta ttggaattac gatgtgtact    9780
accacacctg actggatcat taattctttg atggggcgg ggaagcgcac atgctgcagg    9840
tgaagggatg actggactgg acatgagcgt ggaagccaga gaacagcttc agtctaatgc    9900
tctcccaact gagctatttc ggtttgccag agaacaactt acagaaagtt ctcagtgcca    9960
tgtggattcg gggttggagt tcaactcatc agcttgacat tggctcctct acccactgag   10020
ccttctcact actctctacc tagatcatta attctttttt aaaaagactt attaggggc   10080 tggagagatg gctcagccgt taagagcacc gaatgccctt ccagaggtcc tgagttcaat   10140
tcccagcatg ccattgctgg gcagtagggg gcgcaggtgt tcaacgtgag tagctgttgc   10200
cagttttccg cggtggagaa cctcttgaca ccctgctgtc cctggtcatt ctgggtgggt   10260
gcatggtgat atgcttgttg tatggaagac tttgactgtt acagtgaagt tgggcttcca   10320
cagttaccac gtctcccctg tttcttgcag gccgggtgct tgtccattgc cgcgagggct   10380
acagccgctc cccaacgcta gttatcgcct acctcatgat gcggcagaag atggacgtca   10440
agtctgctct gagtactgtg aggcagaatc gtgagatcgg ccccaacgat ggcttcctgg   10500
cccaactctg ccagctcaat gacagactag ccaaggaggg caaggtgaaa ctctagggtg   10560
cccacagcct cttttgcaga ggtctgactg ggagggccct ggcagccatg tttaggaaac   10620
acagtatacc cactccctgc accaccagac acgtgcccac atctgtccca ctctggtcct   10680
cgggggccac tccacccctta gggagcacat gaagaagctc cctaagaagt tctgctcctt   10740
agccatcctt tcctgtaatt tatgtctctc cctgaggtga ggttcaggtt tatgtccctg   10800
tctgtggcat agatacatct cagtgaccca gggtgggagg gctatcaggg tgcatggccc   10860
gggacacggg cactcttcat gaccctccc ccacctgggt tcttcctgtg tggtccagaa   10920
ccacgagcct ggtaaaggaa ctatgcaaac acaggccctg acctccccat gtctgttcct   10980
```

```
ggtcctcaca gcccgacacg ccctgctgag gcagacgaat gacattaagt tctgaagcag    11040
agtggagata gattagtgac tagatttcca aaaagaagga aaaaaaaggc tgcattttaa    11100
aattatttcc ttagaattaa agatactaca taggggccct tgggtaagca aatccatttt    11160
tcccagaggc tatcttgatt ctttggaatg tttaaagtgt gccttgccag agagcttacg    11220
atctatatct gctgcttcag agccttccct gaggatggct ctgttccttt gcttgttaga    11280
agagcgatgc cttgggcagg gtttcccect tttcagaata cagggtgtaa agtccagcct    11340
attacaaaca aacaaacaaa caaacaaaca aaggacctcc atttggagaa ttgcaaggat    11400
tttatcctga attatagtgt tggtgagttc aagtcatcac gccaagtgct tgccatcctg    11460
gttgctattc taagaataat taggaggagg aacctagcca attgcagctc atgtccgtgg    11520
gtgtgtgcac gggtgcatat gttggaaggg gtgcctgtcc ccttggggac agaaggaaaa    11580
tgaaaggccc ctctgctcac cctggccatt tacgggaggc tctgctggtt ccacggtgtc    11640
tgtgcaggat cctgaaactg actcgctgga cagaaacgag acttggcggc accatgagaa    11700
tggagagaga gagagcaaag aaagaaacag cctttaaaag aactttctaa gggtggtttt    11760
tgaacctcgc tggaccttgt atgtgtgcac atttgccaga gattgaacat aatcctcttg    11820
ggacttcacg ttctcattat ttgtatgtct ccggggtcac gcagagccgt cagccaccac    11880
cccagcaccc ggcacatagg cgtctcataa aagcccattt tatgagaacc agagctgttt    11940
gagtaccccg tgtatagaga gagttgttgt cgtggggcac ccggatccca gcagcctggt    12000
tgcctgcctg taggatgtct tacaggagtt tgcagagaaa ccttccttgg agggaaagaa    12060
atatcaggga tttttgttga atatttcaaa ttcagcttta agtgtaagac tcagcagtgt    12120
tcatggttaa ggtaaggaac atgccttttc cagagctgct gcaagaggca ggagaagcag    12180
acctgtctta ggatgtcact cccagggtaa agacctctga tcacagcagg agcagagctg    12240
tgcagcctgg atggtcattg tcccctattc tgtgtgacca cagcaaccct ggtcacatag    12300
ggctggtcat cctttttttt tttttttttt ttttttttg cccagaatg aagtgaccat    12360 agccaagttg tgtacctcag tctttagttt ccaagcggct ctcttgctca atacaatgtg    12420
catttcaaaa taacactgta gagttgacag aactggttca tgtgttatga gagaggaaaa    12480
gagaggaaag aacaaaacaa aacaaaacac cacaaaccaa aaacatctgg gctagccagg    12540
catgattgca atgtctacag gcccagttca tgagaggcag agacaggaag accgccgaaa    12600
ggtcaaggat agcatggtct acgtatcgag actccagcca gggctacggt cccaagatcc    12660
taggttttgg attttgggct ttggttttg agacagggtt tctctgtgta gccctggctg    12720
tcctggaact cgctctgtag accaggctgg cctcaaactt agagatctgc ctgactctgc    12780
ctttgagggc tgggacgaat gccaccactg cccaactaag attccattaa aaaaaaaaaa    12840
agttcaagat aattaagagt tgccagctcg ttaaagctaa gtagaagcag tctcaggcct    12900
gctgcttgag gctgttcttg gcttggacct gaaatctgcc cccaacagtg tccaagtgca    12960
catgactttg agccatctcc agagaaggaa gtgaaaattg tggctcccca gtcgattggg    13020
acacagtctc tctttgtcta ggtaacacat ggtgacacat agcattgaac tctccactct    13080
gagggtgggt ttccctcccc ctgcctcttc tgggttggtc accccatagg acagccacag    13140
gacagtcact agcacctact ggaaacctct ttgtgggaac atgaagaaag agcctttggg    13200
agattcctgg ctttccatta gggctgaaag tacaacggtt cttggttggc tttgcctcgt    13260
gtttataaaa ctagctacta ttcttcaggt aaaataccga tgttgtggaa aagccaaccc    13320
```

```
cgtggctgcc cgtgagtagg gggtgggggtt gggaatcctg gatagtgttc tatccatgga   13380
aagtggtgga ataggaatta agggtgttcc cccccccccc aacctcttcc tcagacccag   13440
ccactttcta tgacttataa acatccaggt aaaaattaca aacataaaaa tggtttctct   13500
tctcaatctt ctaaagtctg cctgccttt ccaggggtag gtctgtttct ttgctgttct   13560
attgtcttga gagcacagac taacacttac caaatgaggg aactcttggc ccatactaag   13620
gctcttctgg gctccagcac tcttaagtta ttttaagaat tctcacttgg cctttagcac   13680
acccgccacc cccaagtggg tgtggataat gccatggcca gcaggggggca ctgttgaggc   13740 gggtgccttt ccaccttaag ttgcttatag tatttaagat gctaaatgtt ttaatcaaga   13800
gaagcactga tcttataata cgaggataag agattttctc acaggaaatt gtcttttca   13860 taattctttt acaggctttg tcctgatcgt agcatagaga gaatagctgg atatttaact   13920
tgtattccat tttcctctgc cagcgttagg ttaactccgt aaaaagtgat tcagtggacc   13980
gaagaggctc agagggcagg ggatggtggg gtgaggcaga gcactgtcac ctgccaggca   14040
tgggaggtcc tgccatccgg gaggaaaagg aaagtttagc ctctagtcta ccaccagtgt   14100
taacgcactc taaagttgta accaaaataa atgtcttaca ttacaaagac gtctgttttg   14160
tgtttccttt tgtgtgtttg ggctttttat gtgtgctttta taactgctgt ggtggtgctg   14220
ttgttagttt tgaggtagga tctcaggctg gccttgaact tctgatcgcc tgcccctgcc   14280 cctgccctg ccctgtccc tgcctccaag tgctaggact aaaagcacat gccaccacac   14340
cagtacagca ttttttctaac atttaaaaat aatcacctag ggctggaga gagggttcca   14400 gctaagagtg cacactgctc ttgggtagga cctgagttta gttcccagaa cctatactgg   14460
gtggctccag gtccagagga tccaggacct ctggcctcca tgggcatctg ctcttagcac   14520 atcccacat acagatacac acataaaaat aaaatgaagc cttaaaaac ctcctaaaac   14580 ctagcccttg gaggtacgac tctggaaagc tggcatactg tgtaagtcca tctcatggtg   14640
ttctggctaa cgtaagactt acagagacag aaaagaactc agggtgtgct gggggttggg   14700
atggaggaag agggatgagt agggggagca cggggaactt gggcagtgaa aattctttgc   14760
aggacactag aggaggataa ataccagtca ttgcacccac tactgacaa ctccaggaa   14820 ttatgctggg tgaaaagaga aggccccagg tattggctgc attggctgca tttgcgtaac   14880
atttttttaa attgaaaaga aaaagatgta aatcaaggtt agatgagtgg ttgctgtgag   14940
ctgagagctg gggtgagtga gacatgtgga caactccatc aaaaagcgac agaaagaacg   15000
ggctgtggtg acagctacct ctaatctcca cctccgggag gtgatcaagg ttagccctca   15060
gctagcctgt ggtgcatgag accctgtttc aaaaacttta ataaagaaat aatgaaaaaa   15120
gacatcaggg cagatccttg gggccaaagg cggacaggcg agtctcgtgg taaggtcgtg   15180
tagaagcgga tgcatgagca cgtgccgcag gcatcatgag agagccctag gtaagtaagg   15240
atggatgtga gtgtgtcggc gtcggcgcac tgcacgtcct ggctgtggtg ctggactggc   15300
atctttggtg agctgtggag gggaaatggg tagggagatc ataaaatccc tccgaattat   15360
ttcaagaact gtctattaca attatctcaa aatattaaaa aaaagaaga attaaaaaac   15420 aaaaaaccta tccaggtgtg gtggtgtgca cctatagcca cgggcacttg gaaagctgga   15480
gcaagaggat ggcgagtttg aaggtatctg ggctgtaca gcaagaccgt cgtcccaa   15540 ccaaaccaaa cagcaaaccc attatgtcac acaagagtgt ttatagtgag cggcctcgct   15600
gagagcatgg ggtggggtg gggtggggg acagaaatat ctaaactgca gtcaataggc   15660
atccactgag accctggggc ttgactgcag cttaaccttg ggaaatgata agggttttgt   15720
```

```
gttgagtaaa agcatcgatt actgacttaa cctcaaatga agaaaaagaa aaaaagaaaa    15780
caacaaaagc caaaccaagg ggctggtgag atggctcagt gggtaagagc acccgactgc    15840
tcttccgaag gtccagagtt caaatcccag caaccacatg gtggctcaca accatctgta    15900
acgagatatg atgccctctt ctggtgtgtc tgaagacagc tacagtgtac ttacatataa    15960
taaataaatc ttaaaaaaaa aaaaaaaaaa aaaagccaaa ccgagcaaac caggcccccca   16020 aacagaaggc aggcacgacg gcaggcacca cgagccatcc tgtgaaaagg cagggctacc    16080
catgggccga ggagggtcca gagagatagg ctggtaagct cagtttctct gtatacccctt   16140 tttcttgttg acactacttc aattacagat aaaataacaa ataaacaaaa tctagagcct    16200
ggccactctc tgctcgcttg attttttcctg ttacgtccag caggtggcgg aagtgttcca    16260
aggacagatc gcatcattaa ggtggccagc ataatctccc atcagcaggt ggtgctgtga    16320
gaaccattat ggtgctcaca gaatcccggg cccaggagct gccctctccc aagtctggag    16380
caataggaaa gctttctggc ccagacaggg ttaacagtcc acattccaga gcagggggaaa   16440 aggagactgg aggtcacaga caaaagggcc agcttctaac aacttcacag ctctggtagg    16500
agagatagat caccccccaac aatggccaca gctggttttg tctgccccga aggaaactga   16560
cttaggaagc aggtatcaga gtcccccttcc tgagggggact tctgtctgcc ttgtaaagct   16620
gtcagagcag ctgcattgat gtgtgggtga cagaagatga aaaggaggac ccaggcagat    16680
cgccacagat ggaccggcca cttacaagtc gaggcaggtg gcagagcctt gcagaagctc    16740
tgcaggtgga cgacactgat tcattaccca gttagcatac cacagcgggc taggcggacc    16800
acagcctcct tcccagtctt cctccagggc tggggagtcc tccaaccttc tgtctcagtg    16860
cagcttccgc cagcccctcc tccttttgca cctcaggtgt gaaccctccc tcctctcctt    16920
ctccctgtgg catggccctc ctgctactgc aggctgagca ttggatttct ttgtgcttag    16980
atagacctga gatggctttc tgatttatat atatatatcc atcccttgga tcttacatct    17040
aggacccaga gctgtttgtg ataccataag aggctgggga gatgatatgg taagagtgct    17100
tgctgtacaa gcatgaagac atgagttcga atccccagca accatgtgga aaaataacct    17160
tctaacctca gagttgaggg gaaaggcagg tggattctgg gggcttactg gccagctagc    17220
cagcctaacc taaatgtctc agtcagagat cctgtctcag ggaataactt gggagaatga    17280
ctgagaaaga cacctcctca ggtctcccat gcacccacac agacacacgg ggggggggta    17340
atgtaataag ctaagaaata atgagggaaa tgatttttttg ctaagaaatg aaattctgtg    17400
ttggccgcaa gaagcctggc cagggaagga actgcctttg gcacaccagc ctataagtca    17460
ccatgagttc cctggctaag aatcacatgt aatggagccc aggtccctct tgcctggtgg    17520
ttgcctctcc cactggtttt gaagagaaat tcaagagaga tctccttggt cagaattgta    17580
ggtgctgagc aatgtggagc tggggtcaat gggattcctt taaaggcatc cttcccaggg    17640
ctgggtcata cttcaatagt agggtgcttg cacagcaagc gtgagaccct aggttagagt    17700
ccccagaatc tgcccccaac cccccaaaaa ggcatcctttc tgcctctggg tgggtggggg    17760
gagcaaacac cttttaactaa gaccattagc tggcaggggt aacaaatgac cttggctaga    17820
ggaatttggt caagctggat tccgccttct gtagaagccc cacttgtttc ctttgttaag    17880
ctggcccaca gtttgttttg agaatgcctg aggggcccag ggagccagac aattaaaagc    17940
caagctcatt ttgatatctg aaaaccacag cctgactgcc ctgcccgtgg gaggtactgg    18000
gagagctggc tgtgtccctg cctcaccaac gccccccccc ccaacacaca ctcctcgggt    18060
```

```
cacctgggag gtgccagcag caatttggaa gtttactgag cttgagaagt cttgggaggg      18120
ctgacgctaa gcacacccct tctccacccc cccccacccc acccccgtga ggaggagggt      18180
gaggaaacat gggaccagcc ctgctccagc ccgtccttat tggctggcat gaggcagagg      18240
gggctttaaa aaggcaaccg tatctaggct ggacactgga gcctgtgcta ccgagtgccc      18300
tcctccacct ggcagcatgc agccctcact agccccgtgc ctcatctgcc tacttgtgca      18360
cgctgccttc tgtgctgtgg agggccaggg gtggcaagcc ttcaggaatg atgccacaga      18420
ggtcatccca gggcttggag agtaccccga gcctcctcct gagaacaacc agaccatgaa      18480
ccgggcggag aatggaggca gacctcccca ccatccctat gacgccaaag gtacgggatg      18540
aagaagcaca ttagtggggg gggggtcct gggaggtgac tggggtggtt ttagcatctt      18600
cttcagaggt ttgtgtgggt ggctagcctc tgctacatca gggcagggac acatttgcct      18660
ggaagaatac tagcacagca ttagaacctg gagggcagca ttgggggct ggtagagagc       18720 acccaaggca gggtggaggc tgaggtcagc cgaagctggc attaacacgg gcatgggctt      18780
gtatgatggt ccagagaatc tcctcctaag gatgaggaca caggtcagat ctagctgctg      18840
accagtgggg aagtgatatg gtgaggctgg atgccagatg ccatccatgg ctgtactata      18900
tcccacatga ccaccacatg aggtaaagaa ggccccagct tgaagatgga gaaaccgaga      18960
ggctcctgag ataaagtcac ctgggagtaa aagagctga gactgaaagc tggtttgatc       19020
cagatgcaag gcaaccctag attgggtttg ggtgggaacc tgaagccagg aggaatccct      19080
ttagttcccc cttgcccagg gtctgctcaa tgagcccaga gggttagcat taaaagaaca      19140
gggtttgtag gtggcatgtg acatgagggg cagctgagtg aaatgtcccc tgtatgagca      19200
caggtggcac cacttgccct gagcttgcac cctgacccca gctttgcctc attcctgagg      19260
acagcagaaa ctgtggaggc agagccagca cagagagatg cctggggtgg gggtgggggt      19320
atcacgcacg gaactagcag caatgaatgg ggtggggtgg cagctggagg gacactccag      19380
agaaatgacc ttgctggtca ccatttgtgt gggaggagag ctcattttcc agcttgccac      19440
cacatgctgt ccctcctgtc tcctagccag taagggatgt ggaggaaagg gccacccccaa     19500 aggagcatgc aatgcagtca cgttttttgca gaggaagtgc ttgacctaag ggcactattc      19560
ttggaaagcc ccaaaactag tccttccctg ggcaaacagg cctcccccac ataccacctc      19620 tgcagggtg agtaaattaa gccagccaca gaagggtggc aaggcctaca cctcccccct       19680
gttgtgcccc cccccccccc gtgaaggtgc atcctggcct ctgcccctct ggctttggta      19740
ctgggatttt ttttttcctt ttatgtcata ttgatcctga caccatggaa ctttttggagg     19800 tagacaggac ccacacatgg attagttaaa agcctcccat ccatctaagc tcatggtagg      19860
agatagagca tgtccaagag aggagggcag gcatcagacc tagaagatat ggctgggcat      19920
ccaacccaat ctccttcccc ggagaacaga ctctaagtca gatccagcca ccttgagta      19980 accagctcaa ggtacacaga acaagagagt ctggtataca gcaggtgcta aacaaatgct      20040
tgtggtagca aaagctatag gttttgggtc agaactccga cccaagtcgc gagtgaagag      20100
cgaaaggccc tctactcgcc accgccccgc ccccacctgg ggtcctataa cagatcactt      20160
tcacccttgc gggagccaga gagccctggc atcctaggta gccccccccg ccccccccc      20220 gcaagcagcc cagccctgcc tttggggcaa gttcttttct cagcctggac ctgtgataat      20280 gaggggggttg gacgcgccgc ctttggtcgc tttcaagtct aatgaattct tatccctacc    20340
acctgccctt ctacccgct cctccacagc agctgtcctg atttattacc ttcaattaac      20400
ctccactcct ttctccatct cctgggatac cgcccctgtc ccagtggctg gtaaaggagc     20460
```

```
ttaggaagga ccagagccag gtgtggctag aggctaccag gcagggctgg ggatgaggag    20520
ctaaactgga agagtgtttg gttagtaggc acaaagcctt gggtgggatc cctagtaccg    20580
gagaagtgga gatgggcgct gagaagttca agaccatcca tccttaacta cacagccagt    20640
ttgaggccag cctgggctac ataaaaaccc aatctcaaaa gctgccaatt ctgattctgt    20700
gccacgtagt gcccgatgta atagtggatg aagtcgttga atcctggggc aacctatttt    20760
acagatgtgg ggaaaagcaa ctttaagtac cctgcccaca gatcacaaag aaagtaagtg    20820
acagagctcc agtgtttcat ccctgggttc caaggacagg gagagagaag ccagggtggg    20880
atctcactgc tccccggtgc ctccttccta taatccatac agattcgaaa gcgcagggca    20940
ggtttggaaa aagagagaag ggtggaagga gcagaccagt ctggcctagg ctgcagcccc    21000
tcacgcatcc ctctctccgc agatgtgtcc gagtacagct gccgcgagct gcactacacc    21060
cgcttcctga cagacggccc atgccgcagc gccaagccgg tcaccgagtt ggtgtgctcc    21120
ggccagtgcg gccccgcgcg gctgctgccc aacgccatcg ggcgcgtgaa gtggtggcgc    21180
ccgaacggac cggatttccg ctgcatcccg gatcgctacc gcgcgcagcg ggtgcagctg    21240
ctgtgccccg ggggcgcggc gccgcgctcg cgcaaggtgc gtctggtggc ctcgtgcaag    21300
tgcaagcgcc tcacccgctt ccacaaccag tcggagctca aggacttcgg gccggagacc    21360
gcgcggccgc agaagggtcg caagccgcgg cccgcgcccc ggggagccaa agccaaccag    21420
gcggagctgg agaacgccta ctagagcgag cccgcgccta tgcagccccc gcgcgatccg    21480
attcgttttc agtgtaaagc ctgcagccca ggccaggggt gccaaacttt ccagaccgtg    21540
tggagttccc agcccagtag agaccgcagg tccttctgcc cgctgcgggg gatggggagg    21600
gggtggggtt cccgcgggcc aggagaggaa gcttgagtcc cagactctgc ctagccccgg    21660
gtgggatggg ggtctttcta cccctcgccgg acctatacag gacaaggcag tgtttccacc    21720
ttaaagggaa gggagtgtgg aacgaaagac ctgggactgg ttatggacgt acagtaagat    21780
ctactccttc cacccaaatg taaagcctgc gtgggctaga tagggtttct gaccctgacc    21840
tggccactga gtgtgatgtt gggctacgtg gttctctttt ggtacggtct tctttgtaaa    21900 ataggggaccg gaactctgct gagattccaa ggattggggt accccgtgta gactggtgag    21960
agagaggaga acaggggagg ggttagggga gagattgtgg tgggcaaccg cctagaagaa    22020
gctgtttgtt ggctcccagc ctcgccgcct cagaggtttg gcttccccca ctccttcctc    22080
tcaaatctgc cttcaaatcc atatctggga taggaaggc cagggtccga gagatggtgg    22140
aagggccaga aatcacactc ctggcccccc gaagagcagt gtcccgcccc caactgcctt    22200
gtcatattgt aaagggattt tctacacaac agtttaaggt cgttggagga aactgggctt    22260
gccagtcacc tcccatcctt gtcccttgcc aggacaccac ctcctgcctg ccacccacgg    22320
acacatttct gtctagaaac agagcgtcgt cgtgctgtcc tctgagacag catatcttac    22380
attaaaaaga ataatacggg ggggggggc ggagggcgca agtgttatac atatgctgag    22440
aagctgtcag gcgccacagc accacccaca atcttttttgt aaatcatttc cagacacctc    22500
ttactttctg tgtagatttt aattgttaaa aggggaggag agagagcgtt tgtaacagaa    22560
gcacatggag gggggggtag gggggttggg gctggtgagt ttgcgaact ttccatgtga    22620 gactcatcca caaagactga aagccgcgtt ttttttttta agagttcagt gacatattta    22680
ttttctcatt taagttattt atgccaacat ttttttcttg tagagaaagg cagtgttaat    22740
atcgctttgt gaagcacaag tgtgtgtggt ttttgttttt ttgttttttc cccgaccaga    22800
```

```
ggcattgtta ataaagacaa tgaatctcga gcaggaggct gtggtcttgt tttgtcaacc   22860
acacacaatg tctcgccact gtcatctcac tcccttccct tggtcacaag acccaaacct   22920
tgacaacacc tccgactgct ctctggtagc ccttgtggca atacgtgttt cctttgaaaa   22980
gtcacattca tcctttcctt tgcaaacctg gctctcattc cccagctggg tcatcgtcat   23040
accctcaccc cagcctccct ttagctgacc actctccaca ctgtcttcca aaagtgcacg   23100
tttcaccgag ccagttccct ggtccaggtc atcccattgc tcctccttgc tccagaccct   23160
tctcccacaa agatgttcat ctcccactcc atcaagcccc agtggccctg cggctatccc   23220
tgtctcttca gttagctgaa tctacttgct gacaccacat gaattcctcc cctgtctta   23280 aggttcatgg aactcttgcc tgcccctgaa ccttccagga ctgtcccagc gtctgatgtg   23340
tcctctctct tgtaaagccc caccccacta tttgattccc aattctagat cttcccttgt   23400
tcattccttc acgggatagt gtctcatctg gccaagtcct gcttgatatt gggataaatg   23460
caaagccaag tacaattgag gaccagttca tcattgggcc aagcttttc aaaatgtgaa   23520 ttttacacct atagaagtgt aaaagccttc caaagcagag gcaatgcctg gctcttcctt   23580
caacatcagg gctcctgctt tatgggtctg gtggggtagt acattcataa acccaacact   23640
aggggtgtga aagcaagatg attgggagtt cgaggccaat cttggctatg aggccctgtc   23700
tcaacctctc ctccctccct ccagggtttt gttttgtttt gttttttga tttgaaactg   23760 caacacttta aatccagtca agtgcatctt tgcgtgaggg aactctatc cctaatataa   23820 gcttccatct tgatttgtgt atgtgcacac tggggttga acctgggcct ttgtacctgc   23880
cgggcaagct ctctactgct ctaaacccag ccctcactgg cttctgtttt caactcccaa   23940
tgaattcccc taaatgaatt atcaatatca tgtctttgaa aaataccatt gagtgctgct   24000
ggtgtccctg tggttccaga ttccaggaag gacttttcag ggaatccagg catcctgaag   24060
aatgtcttag agcaggaggc catggagacc ttggccagcc ccacaaggca gtgtggtgca   24120
gagggtgagg atggaggcag gcttgcaatt gaagctgaga cagggtactc aggattaaaa   24180
agcttccccc aaaacaattc caagatcagt tcctggtact tgcacctgtt cagctatgca   24240
gagcccagtg ggcataggtg aagacaccgg ttgtactgtc atgtactaac tgtgcttcag   24300
agccggcaga gacaaataat gttatggtga ccccagggga cagtgattcc agaaggaaca   24360
cagaagagag tgctgctaga ggctgcctga aggagaaggg gtcccagact ctctaagcaa   24420
agactccact cacataaaga cacaggctga gcagagctgg ccgtggatgc agggagccca   24480
tccaccatcc tttagcatgc ccttgtattc ccatcacatg ccaggatga ggggcatcag   24540 agagtccaag tgatgcccaa acccaaacac acctaggact tgctttctgg gacagacaga   24600
tgcaggagag actaggttgg gctgtgatcc cattaccaca aagagggaaa aaacaaaaaa   24660
caaacaaaca aacaaaaaaa aacaaaacaa aacaaaaaaa aacccaaggt ccaaattgta   24720
ggtcaggtta gagtttattt atggaaagtt atattctacc tccatggggt ctacaaggct   24780
ggcgcccatc agaaagaaca aacaacaggc tgatctggga ggggtggtac tctatggcag   24840
ggagcacgtg tgcttggggt acagccgac acggggcttg tattaatcac agggcttgta   24900
ttaataggct gagagtcaag cagacagaga gacagaagga aacacacaca cacacacaca   24960
cacacacaca cacacacaca catgcacaca ccactcactt ctcactcgaa gagcccctac   25020
ttacattcta agaacaaacc attcctcctc ataaaggaga caaagttgca gaaacccaaa   25080
agagccacag ggtccccact ctctttgaaa tgacttggac ttgttgcagg gaagacagag   25140
gggtctgcag aggcttcctg ggtgacccag agccacagac actgaaatct ggtgctgaga   25200
```

```
cctgtataaa ccctcttcca caggttccct gaaaggagcc cacattcccc aaccctgtct   25260
cctgaccact gaggatgaga gcacttgggc cttccccatt cttggagtgc accctggttt   25320
ccccatctga gggcacatga ggtctccagt cttgggaaag ttccacaagt attgaaagtg   25380
ttcttgtttt gtttgtgatt taatttaggt gtatgagtgc ttttgcttga atatatgcct   25440
gtgtagcatt tacaagcctg gtgcctgagg agatcagaag atggcatcag ataccctgga   25500
actggacttg cagacagtta tgagccactg tgtgggtgct aggaacagaa cctggatcct   25560
ccggaagagc agacagccag cgctcttagc cactaagcca tcactgaggt tctttctgtg   25620
gctaaagaga caggagacaa aggagagttt cttttagtca ataggaccat gaatgttcct   25680
cgtaacgtga gactagggca gggtgatccc ccagtgacac cgatggccct gtgtagttat   25740
tagcagctct agtcttattc cttaataagt cccagtttgg ggcaggagat atgtattccc   25800
tgctttgaag tggctgaggt ccagttatct acttccaagt acttgtttct ctttctggag   25860
ttggggaagc tccctgcctg cctgtaaatg tgtccattct tcaaccttag acaagatcac   25920
tttccctgag cagtcaggcc agtccaaagc ccttcaattt agctttcata aggaacaccc   25980
cttttgttgg gtggaggtag cacttgcctt gaatcccagc attaagaagg cagagacagt   26040
cggatctctg tgagttcaca gccagcctgg tctacggagt gagttccaag acagccaggc   26100
ctacacagag aaaccctgtc tcgaaaaaaa caaaaacaaa agaaataaag aaaagaaaa   26160 caaaaacgaa caaacagaaa aacaagccag agtgtttgtc cccgtatttt attaatcata   26220
tttttgtccc tttgccattt tagactaaaa gactcgggaa agcaggtctc tctctgtttc   26280
tcatccggac acacccagaa ccagatgtat ggaagatggc taatgtgctg cagttgcaca   26340 tctgggctg ggtggattgg ttagatggca tgggctgggt gtggttacga tgactgcagg   26400
agcaaggagt atgtggtgca tagcaaacga ggaagtttgc acagaacaac actgtgtgta   26460
ctgatgtgca ggtatgggca catgcaagca gaagccaagg acagccttta gggtagtgtt   26520
tccacagacc cctccccct tttaacatgg gcatctctca ttggcctgga gcttgccaac   26580
tgggctgggc tggctagctt gtaggtccca gggatctgca tatctctgcc tcccctagtgc   26640 tgggattaca gtcatatatg agcacacctg gctttttat gtgggttctg ggctttgaac   26700
ccagatctga gtgcttgcaa ggcaatcggt tgaatgactg cttcatctcc ccagaccctg   26760
ggattctact ttctattaaa gtatttctat taaatcaatg agcccctgcc cctgcactca   26820
gcagttctta ggcctgctga gagtcaagtg gggagtgaga gcaagcctcg agaccccatc   26880
agcgaagcag aggacaaaga aatgaaaact tgggattcga ggctcgggat atggagatac   26940
agaaagggtc agggaaggaa atgaaccaga tgaatagagg caggaagggt agggccctgc   27000
atacatggaa cctggtgtac atgttatctg catggggttt gcattgcaat ggctcttcag   27060
caggttcacc acactgggaa acagaagcca aaaagaagag taggtggtgt tggagtcaga   27120
tactgtcagt catgcctgaa gaaatggaag caattaacga tgcgccgcaa ttaggatatt   27180
agctccctga agaaaggcaa gaagctgggc tgtgggcact gaagggagct ttgaatgatg   27240
tcacattctc tgtatgccta gcagggcagt attggagact gagacttgac ttgtgtgtcc   27300
atatgattcc tcctttcct acagtcatct gggctcctg agcttcgtcc ttgtccaaga   27360
acctggagct ggcagtgggc agctgcagtg atagatgtct gcaagaaaga tctgaaaaga   27420
gggaggaaga tgaaggaccc agaggaccac cgacctctgc tgcctgacaa agctgcagga   27480
ccagtctctc ctacagatgg gagacagagg cgagagatga atggtcaggg gaggagtcag   27540
```

```
agaaaggaga gggtgaggca gagaccaaag gagggaaaca cttgtgctct acagctactg   27600
actgagtacc agctgcgtgg cagacagcca atgccaaggc tcggctgatc atggcacctc   27660
gtgggactcc tagcccagtg ctggcagagg ggagtgctga atggtgcatg gtttggatat   27720
gatctgaatg tggtccagcc ctagtttcct tccagttgct gggataaagc accctgacca   27780
aagctacttt tttgtttgtt tgttttggtt tggttttgtt tggttttcg aggcagggtt    27840
tctctgtatc accctagctg tcctggaact cactctgtag accaggctgg cctcgaactc   27900
agaaatcccc ctgcctctgc ctcctaagtg ctggaattaa aggcctgcgc caccactgcc   27960
ggcccaaagc tactttaaga gagagagagg aatgtataag tattataatt ccaggttata   28020
gttcattgct gtagaattgg agtcttcata ttccaggtaa tctcccacag acatgccaca   28080
aaacaacctg ttctacgaaa tctctcatgg actcccttcc ccagtaattc taaactgtgt   28140
caaatctaca agaaatagtg acagtcacag tctctaacgt tttgggcatg agtctgaagt   28200
ctcattgcta agtactggga agatgaaaac tttacctagt gtcagcattt ggagcagagc   28260
ctttgggatt tgagatggtc ttttgcagag ctcctaatgg ctacatggag agaggggcc    28320
tgggagagac ccatacacct tttgctgcct tatgtcacct gacctgctcc ttgggaagct   28380
ctagcaagaa ggccttccct ggatcaccca ccaccttgca cctccagaac tcagagccaa   28440
attaaacttt cttgttactg tcgtcaaagc acagtcggtc tgggttgtat cactgtcaat   28500
gggaaacaga cttgcctgga tggataactt gtacattgca taatgtctag aaatgaaaag   28560
tcctatagag aaaaagaaaa ttagctggca cacagataga ggccctggag gaggctggct   28620
ttgtcctccc cgaggaggtg gcgagtaagg tgtaaatgtt catggatgta aatgggccca   28680
tatatgaggg tctggggtaa caagaaggcc tgtgaatata aagcactgaa ggtatgtcta   28740
gtctggagaa ggtcactaca gagagttctc caactcagtg cccatacaca cacacacaca   28800
cacacacaca cacacacaca cacacacaca ccacaaagaa aaaaaggaag aaaaatctga   28860
gagcaagtac agtacttaaa attgtgtgat tgtgtgtgtg actctgatgt cacatgctca   28920
tcttgcccta tgagttgaaa accaaatggc ccctgagagg cataacaacc acactgttgg   28980
ctgtgtgctc acgttttttct taaagcgtct gtctggtttg ctgctagcat caggcagact   29040
tgcagcagac tacatatgct cagccctgaa gtccttctag ggtgcatgtc tcttcagaat   29100
ttcagaaagt catctgtggc tccaggaccg cctgcactct ccctctgccg cgaggctgca   29160
gactctaggc tggggtggaa gcaacgctta cctctgggac aagtataaca tgttggcttt   29220
tctttccctc tgtggctcca acctggacat aaaatagatg caagctgtgt aataaatatt   29280
tcctcccgtc cacttagttc tcaacaataa ctactctgag agcacttatt aataggtggc   29340
ttagacataa gctttggctc attccccac tagctcttac ttctttaact ctttcaaacc    29400
attctgtgtc ttccacatgg ttagttacct ctccttccat cctggttcgc ttcttccttc   29460
gagtcgccct cagtgtctct aggtgatgct tgtaagatat tctttctaca aagctgagag   29520
tggtggcact ctgggagttc aaagccagcc tgatctacac agcaagctcc aggatatcca   29580
gggcaatgtt gggaaaacct ttctcaaaca aaaagagggg ttcagttgtc aggaggagac   29640
ccatgggtta agaagtctag acgagccatg gtgatgcata cctttcatcc aagcacttag   29700
gaggcaaaga aaggtgaaac tctttgactt tgaggccagc taggttacat agtgataccc   29760
tgcttagtgt gtgtgtgtgt gtgtgtgtgt gtgtgtgtgt gtgtgtaatt taaaagtcta   29820
aaaatgcatt cttttaaaaa tatgtataag tatttgcctg cacatatgta tgtatgtatg   29880
tataccatgt gtgtgtctgg tgctgaagga ctaggcatag actccctaga actagagtca   29940
```

```
tagacagttg tgacactccc caacccccca ccatgtgggt gcttgaagct aaactcctgt   30000
cctttgtaaa gcagcaggtg tctatgaacc ctgaaccatc tctccagtct ccagatgtgc   30060
attctcaaag aggagtcctt catatttccc taaactgaac atccttatca gtgagcatcc   30120
tcgagtcacc aaagctactg caaaccctct tagggaacat tcactattca cttctacttg   30180
gctcatgaaa cttaagtaca cacacacaaa cacacacaca cacacagagt catgcactca   30240
caaaagcatg catgtacacc attcttatta gactatgctt tgctaaaaga ctttcctaga   30300
tactttaaaa catcacttct gccttttggt gggcaggttc caagattggt actggcgtac   30360
tggaaactga acaaggtaga gatctagaaa tcacagcagg tcagaagggc cagcctgtac   30420
aagagagagt tccacacctt ccaggaacac tgagcagggg gctgggacct tgcctctcag   30480
cccaagaaac tagtgcgttt cctgtatgca tgcctctcag agattccata agatctgcct   30540
tctgccataa gatcctctgc atccagacaa gcctagggga agttgagagg ctgcctgagt   30600
ctctcccaca ggccccttct tgcctggcag tattttttta tctggaggag aggaatcagg   30660
gtgggaatga tcaaatacaa ttatcaagga aaagtaaaa aacatatata tatatatatt   30720
aactgatcta gggagctggc tcagcagtta agagttctgg ctgcccttgc ttcagatctt   30780
gctttgattc ccagcaccca catgatggct ttcaactgta tctctgcttc caggggatcc   30840
aacagcctct tctgacctcc atagacaaga cctagtcctc tgcaagagca ccaaatgctc   30900
ttatctgttg atccatctct ctagcctcat gccagatcat ttaaaactac tggacactgt   30960
cccatttac gaagatgtca ctgcccagtc atttgccatg agtggatatt tcgattcttt   31020
ctatgttctc acccttgcaa tttataagaa agatatctgc atttgtctcc tgagagaaca   31080
aagggtggag ggctactgag atggctctag gggtaaaggt gctgccaca aaatctgaca   31140
acttaagttt ggtcttggaa tccacatggt ggagagagag aagagattcc cgtaagttgt   31200
cctcaaactt cccacacatg tgctgtggct tatgtgtaac cccaataagt aaagatagtt   31260
ttaaacacta cataaggtag ggtttcttca tgaccccaag gaatgatgcc cctgatagag   31320
cttatgctga aaccccatct ccattgtgcc atctggaaag agacaattgc atcccggaaa   31380
cagaatcttc atgaatggat taatgagcta ttaagaaagt ggcttggtta ttgcacatgc   31440
tggcggcgta atgacctcca ccatgatgtt atccagcatg aaggtcctca ccagaagtca   31500
tacaaatctt cttaggcttc cagagtcgtg agcaaaaaaa gcacacctct aaataaatta   31560
actagcctca ggtagttaac caccgaaaat gaaccaaggc agttctaata caaaccact   31620
tcccttccct gttcaaacca cagtgcccta ttatctaaaa gataaacttc aagccaagct   31680
tttaggttgc cagtatttat gtaacaacaa ggcccgttga cacacatctg taactcctag   31740
tactgggcct caggggcaga gacaggtgga gccctggagt ttgaattcca ggttctgtga   31800
gaaactctgt ctgaaaagac aatatggtga gtgacccggg aggatatctg atattgactt   31860
ctggccaaca cacagccatc tctgcacatc tgtagttgca agccttttgc actaagtttg   31920
gccagagtca gagtttgcaa gtgtttgtgg actgaatgca cgtgttgctg gtgatctaca   31980
aagtcaccct ccttctcaag ctagcagcac tggcttcggc cagctgctca ttcaagcctc   32040
tttgcagagt catcacgggg atgggggagc agggcccctc cctagaacac caagcctgtg   32100
gttgtttatt caggacatta ttgagggcca agatgacaga taactctatc acttggccaa   32160
cagtcgggtg ttgcggtgtt aggttatttc tgtgtctgca gaaaacagtg caacctggac   32220
aaaagaaata aatgatatca tttttcattc aggcaactag attccgtggt acaaaaggct   32280
```

```
ccctggggaa cgaggccggg acagcgcggc tcctgagtcg ctatttccgt ctgtcaactt    32340
ctctaatctc ttgatttcct ccctctgtct gtttccttcc tcttgctggg gcccagtgga    32400
gtctgtgtac tcacagggag gagggtggca aagccctggt cctctacggg ctggggaag     32460
gggggaagct gtcggcccag tgacttttc ccctttctct ttttcttaga aaccagtctc     32520
aatttaagat aatgagtctc ctcattcacg tgtgctcact attcataggg acttatccac    32580
ccccgccctg tcaatctggc taagtaagac aagtcaaatt taaaagggaa cgttttcta    32640
aaaatgtggc tggaccgtgt gccggcacga aaccagggat ggcggtctaa gttacatgct    32700
ctctgccagc cccggtgcct tttccttcg gaaaggagac ccgaggtaa aacgaagttg      32760
ccaactttg atgatggtgt gcgccgggtg actctttaaa atgtcatcca tacctgggat    32820
agggaaggct cttcagggag tcatctagcc ctcccttcag gaaaagattc cacttccggt    32880
ttagttagct tccacctggt cccttatccg ctgtctctgc ccactagtcc tcatccatcc    32940
ggtttccgcc ctcatccacc ttgcccttt agttcctaga aagcagcacc gtagtcttgg     33000
caggtgggcc attggtcact ccgctaccac tgttaccatg gccaccaagg tgtcatttaa    33060
atatgagctc actgagtcct gcgggatggc ttggttggta atatgcttgc tgcaaaatcg    33120
tgagaactgg agttcaattc ccagcacatg gatgtatttc cagcacctgg aaggcaggga   33180
gcagagatct taaagctcct ggccagacag cccagcctaa ttagtaatca gtgagagacc    33240
ctgtctcaag aaacaagatg gaacatcaaa ggtcaacctc ttgtctccac acacacaaat   33300
acacacatgc acatacatcc acacacaggc aaacacatgc acacacctga acaccctcca   33360
caaatacata cataaaaaaa taaatacata cacacataca tacatacacc aacattccct    33420
ctccttagtc tcctggctac gctcttgtca ccccccacta aggcttcaact tcttctattt   33480
cttcatcttg actcctctgt acttttgcatg cctttttccag caaaggcttt tctttaaatc  33540
tccgtcattc ataaactccc tctaaatttc ttccccctgcc ctttttcttc tctctaggga  33600
gataaagaca cacactacaa agtcaccgtg ggaccagttt attcacccac ccaccctgc     33660
ttctgttcat ccggccagct aagtagtcca acctctctgg tgctgtaccc tggaccctgg   33720
cttcaccaca gctcctccat gctacccagc cctgcaaacc ttcagcctag cctctggttc    33780
tccaaccagc acaggcccag tctggcttct atgtcctaga aatctccttc attctctcca   33840
tttccctcct gaatctacca ccttctttct ccctctccct gacctctaat gtcttggtca    33900
aacgattaca aggaagccaa tgaaattagc agtttggggt acctcagagt cagcagggga    33960
gctgggatga attcacattt ccaggccttt gctttgctcc ccggattctg acaggcagtt    34020
ccgaagctga gtccaggaag ctgaatttaa aatcacactc cagctgggtt ctgaggcagc    34080
cctaccacat cagctggccc tgactgagct gtgtctgggt ggcagtggtg ctggtggtgc    34140
tggtggtgct ggtggtggtg gtggtggtgg tggtggtggt ggtggtggtg tgtgtgtgtg    34200
ttttctgctt ttacaaaact tttctaattc ttatacaaag acaaatctg cctcatatag     34260
gcagaaagat gacttatgcc tatataagat ataaagatga ctttatgcca cttattagca    34320
atagttactg tcaaaagtaa ttctatttat acacccttat acatggtatt gcttttgttg    34380
gagactctaa aatccagatt atgtatttaa aaaaaaattc cccagtcctt aaaaggtgaa    34440
gaatggaccc agatagaagg tcacggcaca agtatggagt cggagtgtgg agtcctgcca    34500
atggtctgga cagaagcatc cagagagggt ccaagacaaa tgcctcgcct cctaaggaac    34560
actggcagcc ctgatgaggt accagagatt gctaagtgga ggaatacagg atcagaccca    34620
tggagggggct taaagcgtga ctgtagcagc cctccgctga ggggctccag gtgggcgccc   34680
```

| | |
|---|---:|
| aaggtgctgc agtgggagcc acatgagagg tgatgtcttg gagtcacctc gggtaccatt | 34740 |
| gtttagggag gtggggattt gtggtgtgga gacaggcagc ctcaaggatg cttttcaaca | 34800 |
| atggttgatg agttggaact aaaacagggg ccatcacact ggctcccata gctctgggct | 34860 |
| tgccagcttc cacatctgcc ccccaccccc tgtctggcac cagctcaagc tctgtgattc | 34920 |
| tacacatcca aaagaggaag agtagcctac tgggcatgcc acctcttctg gaccatcagg | 34980 |
| tgagagtgtg gcaagcccta ggctcctgtc caggatgcag ggctgccaga taggatgctc | 35040 |
| agctatctcc tgagctggaa ctattttagg aataaggatt atgcccgccc ggggttggcc | 35100 |
| agcaccccag cagcctgtgc ttgcgtaaaa gcaagtgctg ttgatttatc taaaaacaga | 35160 |
| gccgtggacc cacccacagg acaagtatgt atgcatctgt ttcatgtatc tgaaaagcga | 35220 |
| cacaaccatt tttcacatca tggcatcttc ctaaccccca ttctttttg ttttgttttt | 35280 |
| ttgagacagg gtttctctgt gtagtcctgg ctgtcctgga actcactttg tagaccaggc | 35340 |
| tggcctcgaa ctcagaaatc ctgggattaa aggtgtgtgc caccacgccc ggccctaacc | 35400 |
| cccattctta atggtgatcc agtggttgaa atttcgggcc acacacatgt ccattaggga | 35460 |
| ttagctgctg tcttctgagc tacctggtac aatctttatc ccctggggcc tgggctcctg | 35520 |
| atccctgact cgggcccgat caagtccagt tcctgggccc gatcaagtcc agttcctggg | 35580 |
| cccgaacaag tccagtccct agctcgatta gctcatcctg gctccctggc ctgttcttac | 35640 |
| ttacactctt ccccttgctc tggacttgtt gctttcttta ctcaagttgt ctgccacagt | 35700 |
| ccctaagcca cctctgtaag acaactaaga taatacttcc ctcaagcacg gaaagtcctg | 35760 |
| agtcaccaca ccctctggag gtgtgtggac acatgttcat gcgtgtggtt gcgcttacgt | 35820 |
| acgtgtgc | 35828 |

<210> SEQ ID NO 18
<211> LENGTH: 9301
<212> TYPE: DNA
<213> ORGANISM: Homo sapien

<400> SEQUENCE: 18

| | |
|---|---:|
| tagaggagaa gtctttgggg agggtttgct ctgagcacac ccctttccct ccctccgggg | 60 |
| ctgagggaaa catgggacca gccctgcccc agcctgtcct cattggctgg catgaagcag | 120 |
| agagggctt taaaaaggcg accgtgtctc ggctggagac cagagcctgt gctactggaa | 180 |
| ggtggcgtgc cctcctctgg ctggtaccat gcagctccca ctggccctgt gtctcgtctg | 240 |
| cctgctggta cacacagcct tccgtgtagt ggagggccag gggtggcagg cgttcaagaa | 300 |
| tgatgccacg gaaatcatcc ccgagctcgg agagtacccc gagcctccac cggagctgga | 360 |
| gaacaacaag accatgaacc gggcggagaa cggagggcgg cctccccacc accccttga | 420 |
| gaccaaaggt atgggtgga ggagagaatt cttagtaaaa gatcctgggg aggttttaga | 480 |
| aacttctctt tgggaggctt ggaagactgg ggtagaccca gtgaagattg ctggcctctg | 540 |
| ccagcactgg tcgaggaaca gtcttgcctg gaggtggggg aagaatggct cgctggtgca | 600 |
| gccttcaaat tcaggtgcag aggcatgagg caacagacgc tggtgagagc ccagggcagg | 660 |
| gaggacgctg gggtggtgag ggtatggcat cagggcatca gaacaggctc aggggctcag | 720 |
| aaaagaaaag gtttcaaaga atctcctcct gggaatatag gagccacgtc cagctgctgg | 780 |
| taccactggg aagggaacaa ggtaaggag cctcccatcc acagaacagc acctgtgggg | 840 |
| caccggacac tctatgctgg tggtggctgt ccccaccaca cagacccaca tcatggaatc | 900 |

```
cccaggaggt gaaccccag ctcgaagggg aagaaacagg ttccaggcac tcagtaactt    960
ggtagtgaga agagctgagg tgtgaacctg gtttgatcca actgcaagat agccctggtg   1020
tgtgggggg tgtggggac agatctccac aaagcagtgg ggaggaaggc cagagaggca    1080
cccctgcagt gtgcattgcc catggcctgc ccagggagct ggcacttgaa ggaatgggag   1140
ttttcggcac agttttagcc cctgacatgg gtgcagctga gtccaggccc tggaggggag   1200
agcagcatcc tctgtgcagg agtagggaca tctgtcctca gcagccaccc cagtcccaac   1260
cttgcctcat tccaggggag ggagaaggaa gaggaaccct gggttcctgg tcaggcctgc   1320
acagagaagc ccaggtgaca gtgtgcatct ggctctataa ttggcaggaa tcctgaggcc   1380
atgggggcgt ctgaaatgac acttcagact aagagcttcc ctgtcctctg gccattatcc   1440
aggtggcaga gaagtccact gcccaggctc ctggacccca gccctcccg cctcacaacc   1500
tgttgggact atgggtgct aaaaagggca actgcatggg aggccagcca ggaccctccg   1560
tcttcaaaat ggaggacaag ggcgcctccc cccacagctc cccttctagg caaggtcagc   1620
tgggctccag cgactgcctg aagggctgta aggaacccaa acacaaaatg tccaccttgc   1680
tggactccca cgagaggcca cagccctga ggaagccaca tgctcaaaac aaagtcatga    1740
tctgcagagg aagtgcctgg cctaggggcg ctattctcga aaagccgcaa aatgccccct   1800
tccctgggca aatgccccc tgaccacaca cacattccag ccctgcagag gtgaggatgc    1860
aaaccagccc acagaccaga aagcagcccc agacgatggc agtggccaca tctcccctgc   1920
tgtgcttgct cttcagagtg ggggtgggg gtggccttct ctgtccctc tctggtttgg    1980
tcttaagact attttttcatt ctttcttgtc acattggaac tatccccatg aaacctttgg  2040
gggtggactg gtactcacac gacgaccagc tatttaaaaa gctcccaccc atctaagtcc   2100
accataggag acatggtcaa ggtgtgtgca ggggatcagg ccaggcctcg gagcccaatc   2160
tctgcctgcc cagggagtat caccatgagg cgcccattca gataacacag aacaagaaat   2220
gtgcccagca gagagccagg tcaatgtttg tggcagctga acctgtaggt tttgggtcag   2280
agctcagggc ccctatggta ggaaagtaac gacagtaaaa agcagccctc agctccatcc   2340
cccagcccag cctcccatgg atgctcgaac gcagagcctc cactcttgcc ggagccaaaa   2400
ggtgctggga ccccagggaa gtggagtccg gagatgcagc ccagcctttt gggcaagttc   2460
ttttctctgg ctgggcctca gtattctcat tgataatgag ggggttggac acactgcctt   2520
tgattccttt caagtctaat gaattcctgt cctgatcacc tcccctttcag tccctcgcct   2580
ccacagcagc tgccctgatt tattaccttc aattaacctc tactcctttc tccatcccct   2640
gtccacccct cccaagtggc tggaaaagga atttgggaga agccagagcc aggcagaagg   2700
tgtgctgagt acttaccctg cccaggccag ggaccctgcg gcacaagtgt ggcttaaatc   2760
ataagaagac cccagaagag aaatgataat aataatacat aacagccgac gctttcagct   2820
atatgtgcca aatggtattt tctgcattgc gtgtgtaatg gattaactcg caatgcttgg   2880
ggcggcccat tttgcagaca ggaagaagag agaggttaag gaacttgccc aagatgacac   2940
ctgcagtgag cgatggagcc ctggtgtttg aaccccagca gtcatttggc tccgagggga   3000
cagggtgcgc aggagagctt tccaccagct ctagagcatc tgggaccttc ctgcaataga   3060
tgttcagggg caaaagcctc tggagacagg cttggcaaaa gcagggctgg ggtggagaga   3120
gacgggccgg tccagggcag gggtggccag gcggcggcc accctcacgc gcgcctctct   3180
ccacagacgt gtccgagtac agctgccgcg agctgcactt cacccgctac gtgaccgatg   3240
ggccgtgccg cagcgccaag ccggtcaccg agctggtgtg ctccggccag tgcggcccgg   3300
```

```
cgcgcctgct gcccaacgcc atcggccgcg gcaagtggtg gcgacctagt gggcccgact    3360
tccgctgcat ccccgaccgc taccgcgcgc agcgcgtgca gctgctgtgt cccggtggtg    3420
aggcgccgcg cgcgcgcaag gtgcgcctgg tggcctcgtg caagtgcaag cgcctcaccc    3480
gcttccacaa ccagtcggag ctcaaggact tcgggaccga ggccgctcgg ccgcagaagg    3540
gccggaagcc gcggccccgc gcccggagcg ccaaagccaa ccaggccgag ctggagaacg    3600
cctactagag cccgcccgcg cccctcccca ccggcgggcg cccggccct gaacccgcgc    3660 cccacatttc tgtcctctgc gcgtggtttg attgtttata tttcattgta aatgcctgca    3720
acccagggca gggggctgag accttccagg ccctgaggaa tcccgggcgc cggcaaggcc    3780
cccctcagcc cgccagctga ggggtcccac ggggcagggg agggaattga gagtcacaga    3840
cactgagcca cgcagccccg cctctggggc cgcctacctt tgctggtccc acttcagagg    3900
aggcagaaat ggaagcattt tcaccgccct ggggttttaa gggagcggtg tgggagtggg    3960
aaagtccagg gactggttaa gaaagttgga taagattccc ccttgcacct cgctgcccat    4020
cagaaagcct gaggcgtgcc cagagcacaa gactgggggc aactgtagat gtggtttcta    4080
gtcctggctc tgccactaac ttgctgtgta accttgaact acacaattct ccttcgggac    4140
ctcaatttcc actttgtaaa atgagggtgg aggtgggaat aggatctcga ggagactatt    4200
ggcatatgat tccaaggact ccagtgcctt ttgaatgggc agaggtgaga gagagagaga    4260
gaaagagaga gaatgaatgc agttgcattg attcagtgcc aaggtcactt ccagaattca    4320
gagttgtgat gctctcttct gacagccaaa gatgaaaaac aaacagaaaa aaaaaagtaa    4380
agagtctatt tatggctgac atatttacgg ctgacaaact cctggaagaa gctatgctgc    4440
ttcccagcct ggcttccccg gatgtttggc tacctccacc cctccatctc aaagaaataa    4500
catcatccat tggggtagaa aaggagaggg tccgagggtg gtgggaggga tagaaatcac    4560
atccgcccca acttcccaaa gagcagcatc cctcccccga cccatagcca tgttttaaag    4620
tcaccttccg aagagaagtg aaaggttcaa ggacactggc cttgcaggcc cgagggagca    4680
gccatcacaa actcacagac cagcacatcc cttttgagac accgccttct gcccaccact    4740
cacggacaca tttctgccta gaaaacagct tcttactgct cttacatgtg atggcatatc    4800
ttacactaaa agaatattat tgggggaaaa actacaagtg ctgtacatat gctgagaaac    4860
tgcagagcat aatagctgcc acccaaaaat cttttgaaa atcatttcca gacaacctct    4920
tactttctgt gtagttttta attgttaaaa aaaaaaagtt ttaaacagaa gcacatgaca    4980
tatgaaagcc tgcaggactg gtcgtttttt tggcaattct tccacgtggg acttgtccac    5040
aagaatgaaa gtagtggttt ttaaagagtt aagttacata tttatttct cacttaagtt    5100 atttatgcaa aagttttct tgtagagaat gacaatgtta atattgcttt atgaattaac    5160
agtctgttct tccagagtcc agagacattg ttaataaaga caatgaatca tgaccgaaag    5220
gatgtggtct cattttgtca accacacatg acgtcatttc tgtcaaagtt gacacccttc    5280
tcttggtcac tagagctcca accttggaca cacctttgac tgctctctgg tggcccttgt    5340
ggcaattatg tcttcctttg aaaagtcatg tttatcccttt cctttccaaa cccagaccgc    5400
atttcttcac ccagggcatg gtaataacct cagccttgta tccttttagc agcctcccct    5460
ccatgctggc ttccaaaatg ctgttctcat tgtatcactc cctgctcaa aagccttcca    5520 tagctccccc ttgcccagga tcaagtgcag tttccctatc tgacatggga ggccttctct    5580
gcttgactcc cacctcccac tccaccaagc ttcctactga ctccaaatgg tcatgcagat    5640
```

```
ccctgcttcc ttagtttgcc atccacactt agcaccccca ataactaatc ctctttcttt    5700
aggattcaca ttacttgtca tctcttcccc taaccttcca gagatgttcc aatctcccat    5760
gatccctctc tcctctgagg ttccagcccc ttttgtctac accactactt tggttcctaa    5820
ttctgttttc catttgacag tcattcatgg aggaccagcc tggccaagtc ctgcttagta    5880
ctggcataga caacacaaag ccaagtacaa ttcaggacca gctcacagga aacttcatct    5940
tcttcgaagt gtggatttga tgcctcctgg gtagaaatgt aggatcttca aaagtgggcc    6000
agcctcctgc acttctctca aagtctcgcc tccccaaggt gtcttaatag tgctggatgc    6060
tagctgagtt agcatcttca gatgaagagt aaccctaaag ttactcttca gttgccctaa    6120
ggtgggatgg tcaactggaa agctttaaat taagtccagc ctaccttggg ggaacccacc    6180
cccacaaaga aagctgaggt ccctcctgat gacttgtcag tttaactacc aataacccac    6240
ttgaattaat catcatcatc aagtctttga taggtgtgag tgggtatcag tggccggtcc    6300
cttcctgggc tccagccccc cgaggaggcc tcagtgagcc cctgcagaaa atccatgcat    6360
catgagtgtc tcagggccca gaatatgaga gcaggtagga aacagagaca tcttccatcc    6420
ctgagaggca gtgcggtcca gtgggtgggg acacgggctc tgggtcaggt ttgtgttgtt    6480
tgtttgtttg ttttgagaca gagtctcgct ctattgccca ggctggagtg cagtgtcaca    6540
atctcggctt actgcaactt ctgccttccc ggattcaagt gattctcctg cctcagcctc    6600
cagagtagct gggattacag gtgcgtgcca ccacgcctgg ctaattttg tattttgat    6660
agagacgggg tttcaccatg ttggccaggc tagtctcgaa ctcttgacct caagtgatct    6720
gcctgcctcg gcctcccaaa gtgctgggat tacaggcgtg agccaccaca cccagcccca    6780
ggttggtgtt tgaatctgag gagactgaag caccaagggg ttaaatgttt tgcccacagc    6840
catacttggg ctcagttcct tgccctaccc ctcacttgag ctgcttagaa cctggtgggc    6900
acatgggcaa taaccaggtc acactgtttt gtaccaagtg ttatgggaat ccaagatagg    6960
agtaatttgc tctgtggagg ggatgaggga tagtggttag ggaaagcttc acaaagtggg    7020
tgttgcttag agattttcca ggtggagaag ggggcttcta gcagaaggc atagcccaag    7080
caaagactgc aagtgcatgg ctgctcatgg gtagaagaga atccaccatt cctcaacatg    7140
taccgagtcc ttgccatgtg caaggcaaca tgggggtacc aggaattcca agcaatgtcc    7200
aaacctaggg tctgctttct gggacctgaa gatacaggat ggatcagccc aggctgcaat    7260
cccattacca cgaggggaa aaaaacctga aggctaaatt gtaggtcggg ttagaggtta    7320
tttatggaaa gttatattct acctacatgg ggtctataag cctggcgcca atcagaaaag    7380
gaacaaacaa cagacctagc tgggaggggc agcattttgt tgtaggggc ggggcacatg    7440
ttctgggggt acagccagac tcaggcttg tattaatagt ctgagagtaa gacagacaga    7500
gggatagaag gaaataggtc cctttctctc tctctctctc tctctctctc actctctctc    7560
tctctcacac acacacacag acacacacac acgctctgta ggggtctact tatgctccaa    7620
gtacaaatca ggccacattt acacaaggag gtaaaggaaa agaacgttgg aggagccaca    7680
ggaccccaaa attccctgtt ttccttgaat caggcaggac ttacgcagct gggagggtgg    7740
agagcctgca gaagccacct gcgagtaagc caagttcaga gtcacagaca ccaaaagctg    7800
gtgccatgtc ccacacccgc ccacctccca cctgctcctt gacacagccc tgtgctccac    7860
aacccggctc ccagatcatt gattatagct ctggggcctg caccgtcctt cctgccacat    7920
ccccacccca ttcttggaac ctgccctctg tcttctccct tgtccaaggg caggcaaggg    7980
ctcagctatt gggcagcttt gaccaacagc tgaggctcct tttgtggctg gagatgcagg    8040
```

-continued

```
aggcagggga atattcctct tagtcaatgc gaccatgtgc ctggttttgcc cagggtggtc    8100 tcgtttacac ctgtaggcca agcgtaatta ttaacagctc ccacttctac tctaaaaaat    8160
gacccaatct gggcagtaaa ttatatggtg cccatgctat taagagctgc aacttgctgg    8220
gcgtggtggc tcacacctgt aatcccagta ctttgggacg tcaaggcggg tggatcacct    8280
gaggtcacga gttagagact ggcctggcca gcatggcaaa accccatctt tactaaaaat    8340
acaaaaatta gcaaggcatg gtggcatgca cctgtaatcc caggtactcg ggaggctgag    8400
acaggagaat ggcttgaacc caggaggcag aggttgcagt gagccaagat tgtgccactg    8460
ccctccagcc ctggcaacag agcaagactt catctcaaaa gaaaaggat actgtcaatc     8520 actgcaggaa gaacccaggt aatgaatgag gagaagagag gggctgagtc accatagtgg    8580
cagcaccgac tcctgcagga aaggcgagac actgggtcat gggtactgaa gggtgccctg    8640
aatgacgttc tgctttagag accgaacctg agccctgaaa gtgcatgcct gttcatgggt    8700
gagagactaa attcatcatt ccttggcagg tactgaatcc tttcttacgg ctgccctcca    8760
atgcccaatt tccctacaat tgtctggggt gcctaagctt ctgccaccaa agagggccag    8820
agctggcagc gagcagctgc aggtaggaga gataggtacc cataagggag gtgggaaaga    8880
gagatggaag gagaggggtg cagagcacac acctcccctg cctgacaact tcctgagggc    8940
tggtcatgcc agcagattta aggcggaggc agggagatg gggcgggaga ggaagtgaaa     9000
aaggagaggg tggggatgga gaggaagaga gggtgatcat tcattcattc cattgctact    9060
gactggatgc cagctgtgag ccaggcacca ccctagctct gggcatgtgg ttgtaatctt    9120
ggagcctcat ggagctcaca gggagtgctg gcaaggagat ggataatgga cggataacaa    9180
ataaacattt agtacaatgt ccgggaatgg aaagttctcg aaagaaaaat aaagctggtg    9240
agcatataga cagccctgaa ggcggccagg ccaggcattt ctgaggaggt ggcatttgag    9300
c                                                                    9301
```

<210> SEQ ID NO 19
<211> LENGTH: 21
<212> TYPE: DNA
<213> ORGANISM: Artificial Sequence
<220> FEATURE:
<223> OTHER INFORMATION: Primer for PCR

<400> SEQUENCE: 19
ccggagctgg agaacaacaa g                                              21

<210> SEQ ID NO 20
<211> LENGTH: 19
<212> TYPE: DNA
<213> ORGANISM: Artificial Sequence
<220> FEATURE:
<223> OTHER INFORMATION: PRimer for PCR

<400> SEQUENCE: 20
gcactggccg gagcacacc                                                 19

<210> SEQ ID NO 21
<211> LENGTH: 23
<212> TYPE: DNA
<213> ORGANISM: Artificial Sequence
<220> FEATURE:
<223> OTHER INFORMATION: Primer for PCR

<400> SEQUENCE: 21
aggccaaccg cgagaagatg acc                                        23

<210> SEQ ID NO 22
<211> LENGTH: 21
<212> TYPE: DNA
<213> ORGANISM: Artificial Sequence
<220> FEATURE:
<223> OTHER INFORMATION: Primer for PCR

<400> SEQUENCE: 22
gaagtccagg gcgacgtagc a                                          21

<210> SEQ ID NO 23
<211> LENGTH: 25
<212> TYPE: DNA
<213> ORGANISM: Artificial Sequence
<220> FEATURE:
<223> OTHER INFORMATION: Primer for PCR

<400> SEQUENCE: 23
aagcttggta ccatgcagct cccac                                      25

<210> SEQ ID NO 24
<211> LENGTH: 50
<212> TYPE: DNA
<213> ORGANISM: Artificial Sequence
<220> FEATURE:
<223> OTHER INFORMATION: Primer for PCR

<400> SEQUENCE: 24
aagcttctac ttgtcatcgt cgtccttgta gtcgtaggcg ttctccagct            50

<210> SEQ ID NO 25
<211> LENGTH: 19
<212> TYPE: DNA
<213> ORGANISM: Artificial Sequence
<220> FEATURE:
<223> OTHER INFORMATION: Primer for PCR

<400> SEQUENCE: 25
gcactggccg gagcacacc                                             19

<210> SEQ ID NO 26
<211> LENGTH: 39
<212> TYPE: DNA
<213> ORGANISM: Artificial Sequence
<220> FEATURE:
<223> OTHER INFORMATION: Primer for PCR

<400> SEQUENCE: 26
gtcgtcggat ccatggggtg gcaggcgttc aagaatgat                       39

<210> SEQ ID NO 27
<211> LENGTH: 57
<212> TYPE: DNA
<213> ORGANISM: Artificial Sequence
<220> FEATURE:
<223> OTHER INFORMATION: Primer for PCR

<400> SEQUENCE: 27
gtcgtcaagc ttctacttgt catcgtcctt gtagtcgtag gcgttctcca gctcggc   57

<210> SEQ ID NO 28
<211> LENGTH: 29
<212> TYPE: DNA
<213> ORGANISM: Artificial Sequence

```
<220> FEATURE:
<223> OTHER INFORMATION: Primer for PCR

<400> SEQUENCE: 28
gacttggatc ccaggggtgg caggcgttc                                29

<210> SEQ ID NO 29
<211> LENGTH: 29
<212> TYPE: DNA
<213> ORGANISM: Artificial Sequence
<220> FEATURE:
<223> OTHER INFORMATION: Primer for PCR

<400> SEQUENCE: 29
agcataagct tctagtaggc gttctccag                                29

<210> SEQ ID NO 30
<211> LENGTH: 29
<212> TYPE: DNA
<213> ORGANISM: Artificial Sequence
<220> FEATURE:
<223> OTHER INFORMATION: Primer for PCR

<400> SEQUENCE: 30
gacttggatc cgaagggaaa aagaaaggg                                29

<210> SEQ ID NO 31
<211> LENGTH: 29
<212> TYPE: DNA
<213> ORGANISM: Artificial Sequence
<220> FEATURE:
<223> OTHER INFORMATION: Primer for PCR

<400> SEQUENCE: 31
agcataagct tttaatccaa atcgatgga                                29

<210> SEQ ID NO 32
<211> LENGTH: 33
<212> TYPE: DNA
<213> ORGANISM: Artificial Sequence
<220> FEATURE:
<223> OTHER INFORMATION: Primer for PCR

<400> SEQUENCE: 32
actacgagct cggccccacc acccatcaac aag                           33

<210> SEQ ID NO 33
<211> LENGTH: 34
<212> TYPE: DNA
<213> ORGANISM: Artificial Sequence
<220> FEATURE:
<223> OTHER INFORMATION: Primer for PCR

<400> SEQUENCE: 33
acttagaagc tttcagtcct cagccccctc ttcc                          34

<210> SEQ ID NO 34
<211> LENGTH: 66
<212> TYPE: DNA
<213> ORGANISM: Artificial Sequence
<220> FEATURE:
<223> OTHER INFORMATION: Primer for PCR

<400> SEQUENCE: 34
aatctggatc cataacttcg tatagcatac attatacgaa gttatctgca ggattcgagg    60
```

```
gcccct                                                          66

<210> SEQ ID NO 35
<211> LENGTH: 82
<212> TYPE: DNA
<213> ORGANISM: Artificial Sequence
<220> FEATURE:
<223> OTHER INFORMATION: Primer for PCR

<400> SEQUENCE: 35
aatctgaatt ccaccggtgt taattaaata acttcgtata atgtatgcta tacgaagtta    60
tagatctaga gtcagcttct ga                                             82

<210> SEQ ID NO 36
<211> LENGTH: 62
<212> TYPE: DNA
<213> ORGANISM: Artificial Sequence
<220> FEATURE:
<223> OTHER INFORMATION: Primer for PCR

<400> SEQUENCE: 36
atttaggtga cactatagaa ctcgagcagc tgaagcttaa ccacatggtg gctcacaacc    60
at                                                                   62

<210> SEQ ID NO 37
<211> LENGTH: 54
<212> TYPE: DNA
<213> ORGANISM: Artificial Sequence
<220> FEATURE:
<223> OTHER INFORMATION: Primer for PCR

<400> SEQUENCE: 37
aacgacggcc agtgaatccg taatcatggt catgctgcca ggtggaggag ggca          54

<210> SEQ ID NO 38
<211> LENGTH: 31
<212> TYPE: DNA
<213> ORGANISM: Artificial Sequence
<220> FEATURE:
<223> OTHER INFORMATION: Primer for PCR

<400> SEQUENCE: 38
attaccaccg gtgacacccg cttcctgaca g                                   31

<210> SEQ ID NO 39
<211> LENGTH: 61
<212> TYPE: DNA
<213> ORGANISM: Artificial Sequence
<220> FEATURE:
<223> OTHER INFORMATION: Primer for PCR

<400> SEQUENCE: 39
attacttaat taaacatggc gcgccatatg gccggcccct aattgcggcg catcgttaat    60
t                                                                    61

<210> SEQ ID NO 40
<211> LENGTH: 34
<212> TYPE: DNA
<213> ORGANISM: Artificial Sequence
<220> FEATURE:
<223> OTHER INFORMATION: Primer for PCR

<400> SEQUENCE: 40
attacggccg gccgcaaagg aattcaagat ctga                                34
```

<210> SEQ ID NO 41
<211> LENGTH: 34
<212> TYPE: DNA
<213> ORGANISM: Artificial Sequence
<220> FEATURE:
<223> OTHER INFORMATION: Primer for PCR

<400> SEQUENCE: 41
attacggcgc gccccctcaca ggccgcaccc agct         34

<210> SEQ ID NO 42
<211> LENGTH: 184
<212> TYPE: PRT
<213> ORGANISM: Homo sapiens

<400> SEQUENCE: 42

```
Met Ser Arg Thr Ala Tyr Thr Val Gly Ala Leu Leu Leu Leu Leu Gly
 1               5                  10                  15

Thr Leu Leu Pro Ala Ala Glu Gly Lys Lys Gly Ser Gln Gly Ala
            20                  25                  30

Ile Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
 50                  55                  60

Gly Thr Ala Met Pro Gly Glu Glu Val Leu Glu Ser Ser Gln Glu Ala
 65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180
```

<210> SEQ ID NO 43
<211> LENGTH: 267
<212> TYPE: PRT
<213> ORGANISM: Homo sapiens

<400> SEQUENCE: 43

```
Met His Leu Leu Leu Phe Gln Leu Leu Val Leu Leu Pro Leu Gly Lys
 1               5                  10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
 65                  70                  75                  80
```

```
Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
    210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
                260                 265

<210> SEQ ID NO 44
<211> LENGTH: 180
<212> TYPE: PRT
<213> ORGANISM: Homo sapiens

<400> SEQUENCE: 44

Met Leu Arg Val Leu Val Gly Ala Val Leu Pro Ala Met Leu Leu Ala
  1               5                  10                  15

Ala Pro Pro Pro Ile Asn Lys Leu Ala Leu Phe Pro Asp Lys Ser Ala
                20                  25                  30

Trp Cys Glu Ala Lys Asn Ile Thr Gln Ile Val Gly His Ser Gly Cys
            35                  40                  45

Glu Ala Lys Ser Ile Gln Asn Arg Ala Cys Leu Gly Gln Cys Phe Ser
    50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Gly His Glu Glu Val Pro Arg Val Asp Lys Leu Val Glu
            100                 105                 110

Lys Ile Leu His Cys Ser Cys Gln Ala Cys Gly Lys Glu Pro Ser His
        115                 120                 125

Glu Gly Leu Ser Val Tyr Val Gln Gly Glu Asp Gly Pro Gly Ser Gln
    130                 135                 140

Pro Gly Thr His Pro His Pro His Pro His Pro Gly Gly Gln
145                 150                 155                 160

Thr Pro Glu Pro Glu Asp Pro Pro Gly Ala Pro His Thr Glu Glu Glu
                165                 170                 175

Gly Ala Glu Asp
```

<210> SEQ ID NO 45
<211> LENGTH: 642
<212> TYPE: DNA
<213> ORGANISM: Homo sapiens
<220> FEATURE:
<221> NAME/KEY: CDS
<222> LOCATION: (1)..(639)

<400> SEQUENCE: 45

| | | | | | | | | | | | | | | | | |
|---|---|---|---|---|---|---|---|---|---|---|---|---|---|---|---|---|
| atg | cag | ctc | cca | ctg | gcc | ctg | tgt | ctc | gtc | tgc | ctg | ctg | gta | cac | aca | 48 |
| Met | Gln | Leu | Pro | Leu | Ala | Leu | Cys | Leu | Val | Cys | Leu | Leu | Val | His | Thr | |
| 1 | | | | 5 | | | | | 10 | | | | | 15 | | |
| gcc | ttc | cgt | gta | gtg | gag | ggc | cag | ggg | tgg | cag | gcg | ttc | aag | aat | gat | 96 |
| Ala | Phe | Arg | Val | Val | Glu | Gly | Gln | Gly | Trp | Gln | Ala | Phe | Lys | Asn | Asp | |
| | | | 20 | | | | | 25 | | | | | 30 | | | |
| gcc | acg | gaa | atc | atc | ccc | gag | ctc | gga | gag | tac | ccc | gag | cct | cca | ccg | 144 |
| Ala | Thr | Glu | Ile | Ile | Pro | Glu | Leu | Gly | Glu | Tyr | Pro | Glu | Pro | Pro | Pro | |
| | 35 | | | | | 40 | | | | | 45 | | | | | |
| gag | ctg | gag | aac | aac | aag | acc | atg | aac | cgg | gcg | gag | aac | gga | ggg | cgg | 192 |
| Glu | Leu | Glu | Asn | Asn | Lys | Thr | Met | Asn | Arg | Ala | Glu | Asn | Gly | Gly | Arg | |
| | 50 | | | | | 55 | | | | | 60 | | | | | |
| cct | ccc | cac | cac | ccc | ttt | gag | acc | aaa | gac | gtg | tcc | gag | tac | agc | tgc | 240 |
| Pro | Pro | His | His | Pro | Phe | Glu | Thr | Lys | Asp | Val | Ser | Glu | Tyr | Ser | Cys | |
| 65 | | | | | 70 | | | | | 75 | | | | | 80 | |
| cgc | gag | ctg | cac | ttc | acc | cgc | tac | gtg | acc | gat | ggg | ccg | tgc | cgc | agc | 288 |
| Arg | Glu | Leu | His | Phe | Thr | Arg | Tyr | Val | Thr | Asp | Gly | Pro | Cys | Arg | Ser | |
| | | | | 85 | | | | | 90 | | | | | 95 | | |
| gcc | aag | ccg | gtc | acc | gag | ctg | gtg | tgc | tcc | ggc | cag | tgc | ggc | ccg | gcg | 336 |
| Ala | Lys | Pro | Val | Thr | Glu | Leu | Val | Cys | Ser | Gly | Gln | Cys | Gly | Pro | Ala | |
| | | | 100 | | | | | 105 | | | | | 110 | | | |
| cgc | ctg | ctg | ccc | aac | gcc | atc | ggc | cgc | ggc | aag | tgg | tgg | cga | cct | agt | 384 |
| Arg | Leu | Leu | Pro | Asn | Ala | Ile | Gly | Arg | Gly | Lys | Trp | Trp | Arg | Pro | Ser | |
| | | 115 | | | | | 120 | | | | | 125 | | | | |
| ggg | ccc | gac | ttc | cgc | tgc | atc | ccc | gac | cgc | tac | cgc | gcg | cag | cgc | gtg | 432 |
| Gly | Pro | Asp | Phe | Arg | Cys | Ile | Pro | Asp | Arg | Tyr | Arg | Ala | Gln | Arg | Val | |
| | 130 | | | | | 135 | | | | | 140 | | | | | |
| cag | ctg | ctg | tgt | ccc | ggt | ggt | gag | gcg | ccg | cgc | gcg | cgc | aag | gtg | cgc | 480 |
| Gln | Leu | Leu | Cys | Pro | Gly | Gly | Glu | Ala | Pro | Arg | Ala | Arg | Lys | Val | Arg | |
| 145 | | | | | 150 | | | | | 155 | | | | | 160 | |
| ctg | gtg | gcc | tcg | tgc | aag | tgc | aag | cgc | ctc | acc | cgc | ttc | cac | aac | cag | 528 |
| Leu | Val | Ala | Ser | Cys | Lys | Cys | Lys | Arg | Leu | Thr | Arg | Phe | His | Asn | Gln | |
| | | | | 165 | | | | | 170 | | | | | 175 | | |
| tcg | gag | ctc | aag | gac | ttc | ggg | acc | gag | gcc | gct | cgg | ccg | cag | aag | ggc | 576 |
| Ser | Glu | Leu | Lys | Asp | Phe | Gly | Thr | Glu | Ala | Ala | Arg | Pro | Gln | Lys | Gly | |
| | | | 180 | | | | | 185 | | | | | 190 | | | |
| cgg | aag | ccg | cgg | ccc | cgc | gcc | cgg | agc | gcc | aaa | gcc | aac | cag | gcc | gag | 624 |
| Arg | Lys | Pro | Arg | Pro | Arg | Ala | Arg | Ser | Ala | Lys | Ala | Asn | Gln | Ala | Glu | |
| | | 195 | | | | | 200 | | | | | 205 | | | | |
| ctg | gag | aac | gcc | tac | tag | | | | | | | | | | | 642 |
| Leu | Glu | Asn | Ala | Tyr | | | | | | | | | | | | |
| | 210 | | | | | | | | | | | | | | | |

<210> SEQ ID NO 46
<211> LENGTH: 190
<212> TYPE: PRT
<213> ORGANISM: Homo sapiens

<400> SEQUENCE: 46

Gln Gly Trp Gln Ala Phe Lys Asn Asp Ala Thr Glu Ile Ile Pro Glu
1               5                   10                  15

```
Leu Gly Glu Tyr Pro Glu Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser Cys Arg Glu Leu His Phe Thr Arg
    50                  55                  60

Tyr Val Thr Asp Gly Pro Cys Arg Ser Ala Lys Pro Val Thr Glu Leu
65                  70                  75                  80

Val Cys Ser Gly Gln Cys Gly Pro Ala Arg Leu Leu Pro Asn Ala Ile
                85                  90                  95

Gly Arg Gly Lys Trp Trp Arg Pro Ser Gly Pro Asp Phe Arg Cys Ile
            100                 105                 110

Pro Asp Arg Tyr Arg Ala Gln Arg Val Gln Leu Leu Cys Pro Gly Gly
        115                 120                 125

Glu Ala Pro Arg Ala Arg Lys Val Arg Leu Val Ala Ser Cys Lys Cys
    130                 135                 140

Lys Arg Leu Thr Arg Phe His Asn Gln Ser Glu Leu Lys Asp Phe Gly
145                 150                 155                 160

Thr Glu Ala Ala Arg Pro Gln Lys Gly Arg Lys Pro Arg Pro Arg Ala
                165                 170                 175

Arg Ser Ala Lys Ala Asn Gln Ala Glu Leu Glu Asn Ala Tyr
            180                 185                 190

<210> SEQ ID NO 47
<211> LENGTH: 20
<212> TYPE: PRT
<213> ORGANISM: Homo sapiens

<400> SEQUENCE: 47

Gln Gly Trp Gln Ala Phe Lys Asn Asp Ala Thr Glu Ile Ile Pro Glu
1               5                   10                  15

Leu Gly Glu Tyr
            20

<210> SEQ ID NO 48
<211> LENGTH: 20
<212> TYPE: PRT
<213> ORGANISM: Homo sapiens

<400> SEQUENCE: 48

Thr Glu Ile Ile Pro Glu Leu Gly Glu Tyr Pro Glu Pro Pro Pro Glu
1               5                   10                  15

Leu Glu Asn Asn
            20

<210> SEQ ID NO 49
<211> LENGTH: 20
<212> TYPE: PRT
<213> ORGANISM: Homo sapiens

<400> SEQUENCE: 49

Pro Glu Pro Pro Pro Glu Leu Glu Asn Asn Lys Thr Met Asn Arg Ala
1               5                   10                  15

Glu Asn Gly Gly
            20

<210> SEQ ID NO 50
<211> LENGTH: 20
```

```
<212> TYPE: PRT
<213> ORGANISM: Homo sapiens

<400> SEQUENCE: 50

Lys Thr Met Asn Arg Ala Glu Asn Gly Gly Arg Pro Pro His His Pro
1               5                   10                  15

Phe Glu Thr Lys
            20

<210> SEQ ID NO 51
<211> LENGTH: 16
<212> TYPE: PRT
<213> ORGANISM: Homo sapiens

<400> SEQUENCE: 51

Arg Pro Pro His His Pro Phe Glu Thr Lys Asp Val Ser Glu Tyr Ser
1               5                   10                  15

<210> SEQ ID NO 52
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 52

Gln Gly Trp Gln Ala Phe Lys Asn Asp Ala Thr Glu Ile Ile Pro Glu
1               5                   10                  15

Leu Gly Glu Tyr Cys
            20

<210> SEQ ID NO 53
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 53

Thr Glu Ile Ile Pro Glu Leu Gly Glu Tyr Pro Glu Pro Pro Pro Glu
1               5                   10                  15

Leu Glu Asn Asn Cys
            20

<210> SEQ ID NO 54
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 54

Pro Glu Pro Pro Pro Glu Leu Glu Asn Asn Lys Thr Met Asn Arg Ala
1               5                   10                  15

Glu Asn Gly Gly Cys
            20

<210> SEQ ID NO 55
<211> LENGTH: 21
<212> TYPE: PRT
<213> ORGANISM: Artificial Sequence
<220> FEATURE:
```

```
<223> OTHER INFORMATION: Human SOST peptide fragment with additional
      cysteine added

<400> SEQUENCE: 55

Lys Thr Met Asn Arg Ala Glu Asn Gly Gly Arg Pro Pro His His Pro
 1               5                  10                  15

Phe Glu Thr Lys Cys
            20

<210> SEQ ID NO 56
<211> LENGTH: 17
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 56

Arg Pro Pro His His Pro Phe Glu Thr Lys Asp Val Ser Glu Tyr Ser
 1               5                  10                  15

Cys

<210> SEQ ID NO 57
<211> LENGTH: 24
<212> TYPE: PRT
<213> ORGANISM: Rattus norvegicus

<400> SEQUENCE: 57

Gln Gly Trp Gln Ala Phe Lys Asn Asp Ala Thr Glu Ile Ile Pro Gly
 1               5                  10                  15

Leu Arg Glu Tyr Pro Glu Pro Pro
            20

<210> SEQ ID NO 58
<211> LENGTH: 20
<212> TYPE: PRT
<213> ORGANISM: Rattus morvegicus

<400> SEQUENCE: 58

Pro Glu Pro Pro Gln Glu Leu Glu Asn Asn Gln Thr Met Asn Arg Ala
 1               5                  10                  15

Glu Asn Gly Gly
            20

<210> SEQ ID NO 59
<211> LENGTH: 20
<212> TYPE: PRT
<213> ORGANISM: Rattus norvegicus

<400> SEQUENCE: 59

Glu Asn Gly Gly Arg Pro Pro His His Pro Tyr Asp Thr Lys Asp Val
 1               5                  10                  15

Ser Glu Tyr Ser
            20

<210> SEQ ID NO 60
<211> LENGTH: 20
<212> TYPE: PRT
<213> ORGANISM: Rattus norvegicus

<400> SEQUENCE: 60

Thr Glu Ile Ile Pro Gly Leu Arg Glu Tyr Pro Glu Pro Pro Gln Glu
 1               5                  10                  15
```

-continued

Leu Glu Asn Asn
         20

<210> SEQ ID NO 61
<211> LENGTH: 25
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 61

Gln Gly Trp Gln Ala Phe Lys Asn Asp Ala Thr Glu Ile Ile Pro Gly
1               5                   10                  15

Leu Arg Glu Tyr Pro Glu Pro Pro Cys
            20                  25

<210> SEQ ID NO 62
<211> LENGTH: 21
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 62

Pro Glu Pro Pro Gln Glu Leu Glu Asn Asn Gln Thr Met Asn Arg Ala
1               5                   10                  15

Glu Asn Gly Gly Cys
            20

<210> SEQ ID NO 63
<211> LENGTH: 21
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 63

Glu Asn Gly Gly Arg Pro Pro His His Pro Tyr Asp Thr Lys Asp Val
1               5                   10                  15

Ser Glu Tyr Ser Cys
            20

<210> SEQ ID NO 64
<211> LENGTH: 21
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 64

Thr Glu Ile Ile Pro Gly Leu Arg Glu Tyr Pro Glu Pro Pro Gln Glu
1               5                   10                  15

Leu Glu Asn Asn Cys
            20

<210> SEQ ID NO 65
<211> LENGTH: 190
<212> TYPE: PRT
<213> ORGANISM: Rattus norvegicus

<400> SEQUENCE: 65

```
Gln Gly Trp Gln Ala Phe Lys Asn Asp Ala Thr Glu Ile Ile Pro Gly
 1               5                  10                  15

Leu Arg Glu Tyr Pro Glu Pro Pro Gln Glu Leu Glu Asn Asn Gln Thr
            20                  25                  30

Met Asn Arg Ala Glu Asn Gly Gly Arg Pro Pro His His Pro Tyr Asp
         35                  40                  45

Thr Lys Asp Val Ser Glu Tyr Ser Cys Arg Glu Leu His Tyr Thr Arg
     50                  55                  60

Phe Val Thr Asp Gly Pro Cys Arg Ser Ala Lys Pro Val Thr Glu Leu
 65                  70                  75                  80

Val Cys Ser Gly Gln Cys Gly Pro Ala Arg Leu Leu Pro Asn Ala Ile
                85                  90                  95

Gly Arg Val Lys Trp Trp Arg Pro Asn Gly Pro Asp Phe Arg Cys Ile
            100                 105                 110

Pro Asp Arg Tyr Arg Ala Gln Arg Val Gln Leu Leu Cys Pro Gly Gly
         115                 120                 125

Ala Ala Pro Arg Ser Arg Lys Val Arg Leu Val Ala Ser Cys Lys Cys
     130                 135                 140

Lys Arg Leu Thr Arg Phe His Asn Gln Ser Glu Leu Lys Asp Phe Gly
145                 150                 155                 160

Pro Glu Thr Ala Arg Pro Gln Lys Gly Arg Lys Pro Arg Pro Arg Ala
                165                 170                 175

Arg Gly Ala Lys Ala Asn Gln Ala Glu Leu Glu Asn Ala Tyr
            180                 185                 190

<210> SEQ ID NO 66
<211> LENGTH: 20
<212> TYPE: PRT
<213> ORGANISM: Homo sapiens

<400> SEQUENCE: 66

Ile Pro Asp Arg Tyr Arg Ala Gln Arg Val Gln Leu Leu Cys Pro Gly
 1               5                  10                  15

Gly Glu Ala Pro
            20

<210> SEQ ID NO 67
<211> LENGTH: 20
<212> TYPE: PRT
<213> ORGANISM: Homo sapiens

<400> SEQUENCE: 67

Gln Leu Leu Cys Pro Gly Gly Glu Ala Pro Arg Ala Arg Lys Val Arg
 1               5                  10                  15

Leu Val Ala Ser
            20

<210> SEQ ID NO 68
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 68

Ile Pro Asp Arg Tyr Arg Ala Gln Arg Val Gln Leu Leu Cys Pro Gly
 1               5                  10                  15
```

```
Gly Glu Ala Pro Cys
            20

<210> SEQ ID NO 69
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 69

Gln Leu Leu Cys Pro Gly Gly Glu Ala Pro Arg Ala Arg Lys Val Arg
1               5                   10                  15

Leu Val Ala Ser Cys
            20

<210> SEQ ID NO 70
<211> LENGTH: 17
<212> TYPE: PRT
<213> ORGANISM: Rattus Norvegicus

<400> SEQUENCE: 70

Ile Pro Asp Arg Tyr Arg Ala Gln Arg Val Gln Leu Leu Cys Pro Gly
1               5                   10                  15

Gly

<210> SEQ ID NO 71
<211> LENGTH: 16
<212> TYPE: PRT
<213> ORGANISM: Rattus norvegicus

<400> SEQUENCE: 71

Pro Gly Gly Ala Ala Pro Arg Ser Arg Lys Val Arg Leu Val Ala Ser
1               5                   10                  15

<210> SEQ ID NO 72
<211> LENGTH: 18
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 72

Ile Pro Asp Arg Tyr Arg Ala Gln Arg Val Gln Leu Leu Ser Pro Gly
1               5                   10                  15

Gly Cys

<210> SEQ ID NO 73
<211> LENGTH: 17
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 73

Pro Gly Gly Ala Ala Pro Arg Ser Arg Lys Val Arg Leu Val Ala Ser
1               5                   10                  15

Cys

<210> SEQ ID NO 74
<211> LENGTH: 20
```

```
<212> TYPE: PRT
<213> ORGANISM: Homo sapiens

<400> SEQUENCE: 74

Cys Gly Pro Ala Arg Leu Leu Pro Asn Ala Ile Gly Arg Gly Lys Trp
1               5                   10                  15

Trp Arg Pro Ser
            20

<210> SEQ ID NO 75
<211> LENGTH: 16
<212> TYPE: PRT
<213> ORGANISM: Homo sapiens

<400> SEQUENCE: 75

Ile Gly Arg Gly Lys Trp Trp Arg Pro Ser Gly Pro Asp Phe Arg Cys
1               5                   10                  15

<210> SEQ ID NO 76
<211> LENGTH: 18
<212> TYPE: PRT
<213> ORGANISM: Rattus norvegicus

<400> SEQUENCE: 76

Pro Asn Ala Ile Gly Arg Val Lys Trp Trp Arg Pro Asn Gly Pro Asp
1               5                   10                  15

Phe Arg

<210> SEQ ID NO 77
<211> LENGTH: 19
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 77

Pro Asn Ala Ile Gly Arg Val Lys Trp Trp Arg Pro Asn Gly Pro Asp
1               5                   10                  15

Phe Arg Cys

<210> SEQ ID NO 78
<211> LENGTH: 20
<212> TYPE: PRT
<213> ORGANISM: Homo sapiens

<400> SEQUENCE: 78

Lys Arg Leu Thr Arg Phe His Asn Gln Ser Glu Leu Lys Asp Phe Gly
1               5                   10                  15

Thr Glu Ala Ala
            20

<210> SEQ ID NO 79
<211> LENGTH: 20
<212> TYPE: PRT
<213> ORGANISM: Homo sapiens

<400> SEQUENCE: 79

Glu Leu Lys Asp Phe Gly Thr Glu Ala Ala Arg Pro Gln Lys Gly Arg
1               5                   10                  15

Lys Pro Arg Pro
            20
```

```
<210> SEQ ID NO 80
<211> LENGTH: 20
<212> TYPE: PRT
<213> ORGANISM: Homo sapiens

<400> SEQUENCE: 80

Arg Pro Gln Lys Gly Arg Lys Pro Arg Pro Arg Ala Arg Ser Ala Lys
 1               5                  10                  15

Ala Asn Gln Ala
            20

<210> SEQ ID NO 81
<211> LENGTH: 16
<212> TYPE: PRT
<213> ORGANISM: Homo sapiens

<400> SEQUENCE: 81

Arg Ala Arg Ser Ala Lys Ala Asn Gln Ala Glu Leu Glu Asn Ala Tyr
 1               5                  10                  15

<210> SEQ ID NO 82
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 82

Lys Arg Leu Thr Arg Phe His Asn Gln Ser Glu Leu Lys Asp Phe Gly
 1               5                  10                  15

Thr Glu Ala Ala Cys
            20

<210> SEQ ID NO 83
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 83

Glu Leu Lys Asp Phe Gly Thr Glu Ala Ala Arg Pro Gln Lys Gly Arg
 1               5                  10                  15

Lys Pro Arg Pro Cys
            20

<210> SEQ ID NO 84
<211> LENGTH: 21
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 84

Arg Pro Gln Lys Gly Arg Lys Pro Arg Pro Arg Ala Arg Ser Ala Lys
 1               5                  10                  15

Ala Asn Gln Ala Cys
            20

<210> SEQ ID NO 85
<211> LENGTH: 17
```

```
<212> TYPE: PRT
<213> ORGANISM: Artificial Sequence
<220> FEATURE:
<223> OTHER INFORMATION: Human SOST peptide fragment with additional
      cysteine added

<400> SEQUENCE: 85

Arg Ala Arg Ser Ala Lys Ala Asn Gln Ala Glu Leu Glu Asn Ala Tyr
  1               5                  10                  15

Cys

<210> SEQ ID NO 86
<211> LENGTH: 23
<212> TYPE: PRT
<213> ORGANISM: Rattus norvegicus

<400> SEQUENCE: 86

Lys Arg Leu Thr Arg Phe His Asn Gln Ser Glu Leu Lys Asp Phe Gly
  1               5                  10                  15

Pro Glu Thr Ala Arg Pro Gln
             20

<210> SEQ ID NO 87
<211> LENGTH: 23
<212> TYPE: PRT
<213> ORGANISM: Rattus norvegicus

<400> SEQUENCE: 87

Lys Gly Arg Lys Pro Arg Pro Arg Ala Arg Gly Ala Lys Ala Asn Gln
  1               5                  10                  15

Ala Glu Leu Glu Asn Ala Tyr
             20

<210> SEQ ID NO 88
<211> LENGTH: 24
<212> TYPE: PRT
<213> ORGANISM: Rattus norvegicus

<400> SEQUENCE: 88

Ser Glu Leu Lys Asp Phe Gly Pro Glu Thr Ala Arg Pro Gln Lys Gly
  1               5                  10                  15

Arg Lys Pro Arg Pro Arg Ala Arg
             20

<210> SEQ ID NO 89
<211> LENGTH: 24
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 89

Lys Arg Leu Thr Arg Phe His Asn Gln Ser Glu Leu Lys Asp Phe Gly
  1               5                  10                  15

Pro Glu Thr Ala Arg Pro Gln Cys
             20

<210> SEQ ID NO 90
<211> LENGTH: 24
<212> TYPE: PRT
<213> ORGANISM: Artificial Sequence
<220> FEATURE:
<223> OTHER INFORMATION: Rat SOST peptide fragment with additional
```

```
                             cysteine added

<400> SEQUENCE: 90

Lys Gly Arg Lys Pro Arg Pro Arg Ala Arg Gly Ala Lys Ala Asn Gln
 1               5                  10                  15

Ala Glu Leu Glu Asn Ala Tyr Cys
            20

<210> SEQ ID NO 91
<211> LENGTH: 25
<212> TYPE: PRT
<213> ORGANISM: Artificial Sequence
<220> FEATURE:
<223> OTHER INFORMATION: Rat SOST peptide fragment with additional
      cysteine added

<400> SEQUENCE: 91

Ser Glu Leu Lys Asp Phe Gly Pro Glu Thr Ala Arg Pro Gln Lys Gly
 1               5                  10                  15

Arg Lys Pro Arg Pro Arg Ala Arg Cys
            20                  25

<210> SEQ ID NO 92
<211> LENGTH: 56
<212> TYPE: PRT
<213> ORGANISM: Homo sapiens

<400> SEQUENCE: 92

Gln Gly Trp Gln Ala Phe Lys Asn Asp Ala Thr Glu Ile Ile Pro Glu
 1               5                  10                  15

Leu Gly Glu Tyr Pro Glu Pro Pro Glu Leu Glu Asn Asn Lys Thr
            20                  25                  30

Met Asn Arg Ala Glu Asn Gly Gly Arg Pro Pro His His Pro Phe Glu
        35                  40                  45

Thr Lys Asp Val Ser Glu Tyr Ser
    50                  55

<210> SEQ ID NO 93
<211> LENGTH: 56
<212> TYPE: PRT
<213> ORGANISM: Rattus norvegicus

<400> SEQUENCE: 93

Gln Gly Trp Gln Ala Phe Lys Asn Asp Ala Thr Glu Ile Ile Pro Gly
 1               5                  10                  15

Leu Arg Glu Tyr Pro Glu Pro Pro Gln Glu Leu Glu Asn Asn Gln Thr
            20                  25                  30

Met Asn Arg Ala Glu Asn Gly Gly Arg Pro Pro His His Pro Tyr Asp
        35                  40                  45

Thr Lys Asp Val Ser Glu Tyr Ser
    50                  55

<210> SEQ ID NO 94
<211> LENGTH: 32
<212> TYPE: PRT
<213> ORGANISM: Homo sapiens

<400> SEQUENCE: 94

Cys Ile Pro Asp Arg Tyr Arg Ala Gln Arg Val Gln Leu Leu Cys Pro
 1               5                  10                  15

Gly Gly Glu Ala Pro Arg Ala Arg Lys Val Arg Leu Val Ala Ser Cys
```

```
                    20                  25                  30

<210> SEQ ID NO 95
<211> LENGTH: 32
<212> TYPE: PRT
<213> ORGANISM: Rattus norvegicus

<400> SEQUENCE: 95

Cys Ile Pro Asp Arg Tyr Arg Ala Gln Arg Val Gln Leu Leu Cys Pro
 1               5                  10                  15

Gly Gly Ala Ala Pro Arg Ser Arg Lys Val Arg Leu Val Ala Ser Cys
            20                  25                  30

<210> SEQ ID NO 96
<211> LENGTH: 44
<212> TYPE: PRT
<213> ORGANISM: Homo sapiens

<400> SEQUENCE: 96

Leu Thr Arg Phe His Asn Gln Ser Glu Leu Lys Asp Phe Gly Thr Glu
 1               5                  10                  15

Ala Ala Arg Pro Gln Lys Gly Arg Lys Pro Arg Pro Ala Arg Ser
            20                  25                  30

Ala Lys Ala Asn Gln Ala Glu Leu Glu Asn Ala Tyr
        35                  40

<210> SEQ ID NO 97
<211> LENGTH: 44
<212> TYPE: PRT
<213> ORGANISM: Rattus norvegicus

<400> SEQUENCE: 97

Leu Thr Arg Phe His Asn Gln Ser Glu Leu Lys Asp Phe Gly Pro Glu
 1               5                  10                  15

Thr Ala Arg Pro Gln Lys Gly Arg Lys Pro Arg Pro Ala Arg Gly
            20                  25                  30

Ala Lys Ala Asn Gln Ala Glu Leu Glu Asn Ala Tyr
        35                  40

<210> SEQ ID NO 98
<211> LENGTH: 26
<212> TYPE: PRT
<213> ORGANISM: Homo sapiens

<400> SEQUENCE: 98

Cys Gly Pro Ala Arg Leu Leu Pro Asn Ala Ile Gly Arg Gly Lys Trp
 1               5                  10                  15

Trp Arg Pro Ser Gly Pro Asp Phe Arg Cys
            20                  25

<210> SEQ ID NO 99
<211> LENGTH: 26
<212> TYPE: PRT
<213> ORGANISM: Rattus norvegicus

<400> SEQUENCE: 99

Cys Gly Pro Ala Arg Leu Leu Pro Asn Ala Ile Gly Arg Val Lys Trp
 1               5                  10                  15

Trp Arg Pro Asn Gly Pro Asp Phe Arg Cys
            20                  25
```

-continued

<210> SEQ ID NO 100
<211> LENGTH: 570
<212> TYPE: DNA
<213> ORGANISM: Homo sapiens

<400> SEQUENCE: 100

```
cagggggtggc aggcgttcaa gaatgatgcc acggaaatca tccccgagct cggagagtac      60
cccgagcctc caccggagct ggagaacaac aagaccatga accgggcgga aacggaggg      120
cggcctcccc accacccctt tgagaccaaa gacgtgtccg agtacagctg ccgcgagctg      180
cacttcaccc gctacgtgac cgatgggccg tgccgcagcg ccaagccggt caccgagctg      240
gtgtgctccg gccagtgcgg cccggcgcgc ctgctgccca cgccatcgg ccgcggcaag       300
tggtggcgac ctagtgggcc cgacttccgc tgcatccccg accgctaccg cgcgcagcgc      360
gtgcagctgc tgtgtcccgg tggtgaggcg ccgcgcgcgc gcaaggtgcg cctggtggcc      420
tcgtgcaagt gcaagcgcct cacccgcttc acaaccagt cggagctcaa ggacttcggg       480
accgaggccg ctcggccgca aagggccgg aagccgcggc cccgcgcccg gagcgccaaa       540
gccaaccagg ccgagctgga aacgcctac                                        570
```

<210> SEQ ID NO 101
<211> LENGTH: 570
<212> TYPE: DNA
<213> ORGANISM: Rattus norvegicus

<400> SEQUENCE: 101

```
caggggtggc aagccttcaa gaatgatgcc acagaaatca tcccgggact cagagagtac       60
ccagagcctc ctcaggaact agagaacaac cagaccatga accgggccga aacggaggc      120
agaccccccc accatcctta tgacaccaaa gacgtgtccg agtacagctg ccgcgagctg      180
cactacaccc gcttcgtgac cgacggcccg tgccgcagtg ccaagccggt caccgagttg      240
gtgtgctcgg gccagtgcgg cccgcgcgcg ctgctgccca cgccatcgg gcgcgtgaag       300
tggtggcgcc cgaacggacc cgacttccgc tgcatcccgg atcgctaccg cgcgcagcgg      360
gtgcagctgc tgtgccccgg cggcgcggcg ccgcgctcgc gcaaggtgcg tctggtggcc      420
tcgtgcaagt gcaagcgcct cacccgcttc acaaccagt cggagctcaa ggacttcgga       480
cctgagaccg cgcggccgca aagggtcgc aagccgcggc cccgcgcccg gggagccaaa       540
gccaaccagg cggagctgga aacgcctac                                        570
```

<210> SEQ ID NO 102
<211> LENGTH: 532
<212> TYPE: PRT
<213> ORGANISM: Homo sapiens

<400> SEQUENCE: 102

```
Met Thr Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
```

-continued

```
                 85                  90                  95
Ala Ser Gly Cys Met Lys Tyr Glu Gly Ser Asp Phe Gln Cys Lys Asp
            100                 105                 110
Ser Pro Lys Ala Gln Leu Arg Arg Thr Ile Glu Cys Arg Thr Asn
        115                 120                 125
Leu Cys Asn Gln Tyr Leu Gln Pro Thr Leu Pro Val Val Ile Gly
    130                 135                 140
Pro Phe Phe Asp Gly Ser Ile Arg Trp Leu Val Leu Leu Ile Ser Met
145                 150                 155                 160
Ala Val Cys Ile Ile Ala Met Ile Ile Phe Ser Ser Cys Phe Cys Tyr
                165                 170                 175
Lys His Tyr Cys Lys Ser Ile Ser Ser Arg Arg Tyr Asn Arg Asp
            180                 185                 190
Leu Glu Gln Asp Glu Ala Phe Ile Pro Val Gly Glu Ser Leu Lys Asp
        195                 200                 205
Leu Ile Asp Gln Ser Gln Ser Ser Gly Ser Gly Ser Gly Leu Pro Leu
    210                 215                 220
Leu Val Gln Arg Thr Ile Ala Lys Gln Ile Gln Met Val Arg Gln Val
225                 230                 235                 240
Gly Lys Gly Arg Tyr Gly Glu Val Trp Met Gly Lys Trp Arg Gly Glu
                245                 250                 255
Lys Val Ala Val Lys Val Phe Phe Thr Thr Glu Glu Ala Ser Trp Phe
            260                 265                 270
Arg Glu Thr Glu Ile Tyr Gln Thr Val Leu Met Arg His Glu Asn Ile
        275                 280                 285
Leu Gly Phe Ile Ala Ala Asp Ile Lys Gly Thr Gly Ser Trp Thr Gln
    290                 295                 300
Leu Tyr Leu Ile Thr Asp Tyr His Glu Asn Gly Ser Leu Tyr Asp Phe
305                 310                 315                 320
Leu Lys Cys Ala Thr Leu Asp Thr Arg Ala Leu Leu Lys Leu Ala Tyr
                325                 330                 335
Ser Ala Ala Cys Gly Leu Cys His Leu His Thr Glu Ile Tyr Gly Thr
            340                 345                 350
Gln Gly Lys Pro Ala Ile Ala His Arg Asp Leu Lys Ser Lys Asn Ile
        355                 360                 365
Leu Ile Lys Lys Asn Gly Ser Cys Cys Ile Ala Asp Leu Gly Leu Ala
    370                 375                 380
Val Lys Phe Asn Ser Asp Thr Asn Glu Val Asp Val Pro Leu Asn Thr
385                 390                 395                 400
Arg Val Gly Thr Lys Arg Tyr Met Ala Pro Glu Val Leu Asp Glu Ser
                405                 410                 415
Leu Asn Lys Asn His Phe Gln Pro Tyr Ile Met Ala Asp Ile Tyr Ser
            420                 425                 430
Phe Gly Leu Ile Ile Trp Glu Met Ala Arg Arg Cys Ile Thr Gly Gly
        435                 440                 445
Ile Val Glu Glu Tyr Gln Leu Pro Tyr Tyr Asn Met Val Pro Ser Asp
    450                 455                 460
Pro Ser Tyr Glu Asp Met Arg Glu Val Val Cys Val Lys Arg Leu Arg
465                 470                 475                 480
Pro Ile Val Ser Asn Arg Trp Asn Ser Asp Glu Cys Leu Arg Ala Val
                485                 490                 495
Leu Lys Leu Met Ser Glu Cys Trp Ala His Asn Pro Ala Ser Arg Leu
            500                 505                 510
```

```
Thr Ala Leu Arg Ile Lys Lys Thr Leu Ala Lys Met Val Glu Ser Gln
        515                 520                 525

Asp Val Lys Ile
    530

<210> SEQ ID NO 103
<211> LENGTH: 502
<212> TYPE: PRT
<213> ORGANISM: Homo sapiens

<400> SEQUENCE: 103

Met Leu Leu Arg Ser Ala Gly Lys Leu Asn Val Gly Thr Lys Lys Glu
 1               5                  10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Ser Gly Leu
 50                  55                  60

Pro Val Val Thr Ser Gly Cys Leu Gly Leu Gly Ser Asp Phe Gln
 65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
```

```
                    340                 345                 350
Leu Ala Val Lys Phe Ile Ser Asp Thr Asn Glu Val Asp Ile Pro Pro
                355                 360                 365

Asn Thr Arg Val Gly Thr Lys Arg Tyr Met Pro Pro Glu Val Leu Asp
            370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
        450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 104
<211> LENGTH: 502
<212> TYPE: PRT
<213> ORGANISM: Homo sapiens

<400> SEQUENCE: 104

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205
```

```
Gln Ile Gly Lys Gly Arg Tyr Gly Glu Val Trp Met Gly Lys Trp Arg
    210                 215                 220

Gly Glu Lys Val Ala Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 105
<211> LENGTH: 532
<212> TYPE: PRT
<213> ORGANISM: Rattus sp.

<400> SEQUENCE: 105

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65              70                  75                  80
```

-continued

```
His Cys Phe Ala Ile Ile Glu Glu Asp Asp Gln Gly Glu Thr Thr Leu
                 85                  90                  95
Thr Ser Gly Cys Met Lys Tyr Glu Gly Ser Asp Phe Gln Cys Lys Asp
            100                 105                 110
Ser Pro Lys Ala Gln Leu Arg Arg Thr Ile Glu Cys Cys Arg Thr Asn
        115                 120                 125
Leu Cys Asn Gln Tyr Leu Gln Pro Thr Leu Pro Pro Val Val Ile Gly
    130                 135                 140
Pro Phe Phe Asp Gly Ser Val Arg Trp Leu Ala Val Leu Ile Ser Met
145                 150                 155                 160
Ala Val Cys Ile Val Ala Met Ile Val Phe Ser Ser Cys Phe Cys Tyr
                165                 170                 175
Lys His Tyr Cys Lys Ser Ile Ser Ser Arg Gly Arg Tyr Asn Arg Asp
            180                 185                 190
Leu Glu Gln Asp Glu Ala Phe Ile Pro Val Gly Glu Ser Leu Lys Asp
        195                 200                 205
Leu Ile Asp Gln Ser Gln Ser Ser Gly Ser Gly Ser Gly Leu Pro Leu
    210                 215                 220
Leu Val Gln Arg Thr Ile Ala Lys Gln Ile Gln Met Val Arg Gln Val
225                 230                 235                 240
Gly Lys Gly Arg Tyr Gly Glu Val Trp Met Gly Lys Trp Arg Gly Glu
                245                 250                 255
Lys Val Ala Val Lys Val Phe Phe Thr Thr Glu Glu Ala Ser Trp Phe
            260                 265                 270
Arg Glu Thr Glu Ile Tyr Gln Thr Val Leu Met Arg His Glu Asn Ile
        275                 280                 285
Leu Gly Phe Ile Ala Ala Asp Ile Lys Gly Thr Gly Ser Trp Thr Gln
    290                 295                 300
Leu Tyr Leu Ile Thr Asp Tyr His Glu Asn Gly Ser Leu Tyr Asp Phe
305                 310                 315                 320
Leu Lys Cys Ala Thr Leu Asp Thr Arg Ala Leu Leu Lys Leu Ala Tyr
                325                 330                 335
Ser Ala Ala Cys Gly Leu Cys His Leu His Thr Glu Ile Tyr Gly Thr
            340                 345                 350
Gln Gly Lys Pro Ala Ile Ala His Arg Asp Leu Lys Ser Lys Asn Ile
        355                 360                 365
Leu Ile Lys Lys Asn Gly Ser Cys Cys Ile Ala Asp Leu Gly Leu Ala
    370                 375                 380
Val Lys Phe Asn Ser Asp Thr Asn Glu Val Asp Ile Pro Leu Asn Thr
385                 390                 395                 400
Arg Val Gly Thr Arg Arg Tyr Met Ala Pro Glu Val Leu Asp Glu Ser
                405                 410                 415
Leu Ser Lys Asn His Phe Gln Pro Tyr Ile Met Ala Asp Ile Tyr Ser
            420                 425                 430
Phe Gly Leu Ile Ile Trp Glu Met Ala Arg Arg Cys Ile Thr Gly Gly
        435                 440                 445
Ile Val Glu Glu Tyr Gln Leu Pro Tyr Tyr Asn Met Val Pro Ser Asp
    450                 455                 460
Pro Ser Tyr Glu Asp Met Arg Glu Val Val Cys Val Lys Arg Leu Arg
465                 470                 475                 480
Pro Ile Val Ser Asn Arg Trp Asn Ser Asp Glu Cys Leu Arg Ala Val
                485                 490                 495
```

```
Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530

<210> SEQ ID NO 106
<211> LENGTH: 532
<212> TYPE: PRT
<213> ORGANISM: Rattus norvegicus

<400> SEQUENCE: 106

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
                20                  25                  30

Thr Gly Met Lys Ser Asp Val Asp Gln Lys Lys Pro Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
                165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335
```

```
Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
            450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
        530

<210> SEQ ID NO 107
<211> LENGTH: 532
<212> TYPE: PRT
<213> ORGANISM: Rattus norvegicus

<400> SEQUENCE: 107

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
            20                  25                  30

Thr Gly Met Lys Ser Asp Val Asp Gln Lys Lys Pro Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
            115                 120                 125

Leu Cys Asn Gln Tyr Leu Gln Pro Thr Leu Pro Pro Val Val Ile Gly
        130                 135                 140

Pro Phe Phe Asp Gly Ser Val Arg Trp Leu Ala Val Leu Ile Ser Met
145                 150                 155                 160

Ala Val Cys Ile Val Ala Met Ile Val Phe Ser Ser Cys Phe Cys Tyr
```

```
                165                 170                 175
Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
    210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
        355                 360                 365

Leu Ile Lys Lys Asn Gly Ser Cys Cys Ile Ala Asp Leu Gly Leu Ala
    370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
                405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
        435                 440                 445

Ile Val Glu Glu Tyr Gln Leu Pro Tyr Tyr Asn Met Val Pro Ser Asp
    450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
        515                 520                 525

Asp Val Lys Ile
    530

<210> SEQ ID NO 108
<211> LENGTH: 502
<212> TYPE: PRT
<213> ORGANISM: Homo sapiens

<400> SEQUENCE: 108
```

-continued

```
Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
                35                  40                  45

Thr Asp Gly Tyr Cys Phe Thr Met Ile Glu Glu Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
                100                 105                 110

Leu Lys Asn Arg Asp Phe Val Asp Gly Pro Ile His His Arg Ala Leu
            115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
```

```
                420                 425                 430
Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 109
<211> LENGTH: 502
<212> TYPE: PRT
<213> ORGANISM: Homo sapiens

<400> SEQUENCE: 109

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285
```

```
Asp Tyr Leu Lys Ser Thr Thr Leu Asp Ala Lys Ser Met Leu Lys Leu
        290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
                340                 345                 350

Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 110
<211> LENGTH: 532
<212> TYPE: PRT
<213> ORGANISM: Rattus sp.

<400> SEQUENCE: 110

Met Thr Gln Leu Tyr Thr Tyr Ile Arg Leu Leu Gly Ala Cys Leu Phe
1               5                   10                  15

Ile Ile Ser His Val Gln Gly Gln Asn Leu Asp Ser Met Leu His Gly
                20                  25                  30

Thr Gly Met Lys Ser Asp Val Asp Gln Lys Lys Pro Glu Asn Gly Val
            35                  40                  45

Thr Leu Ala Pro Glu Asp Thr Leu Pro Phe Leu Lys Cys Tyr Cys Ser
        50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Thr Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
130                 135                 140

Pro Phe Phe Asp Gly Ser Val Arg Trp Leu Ala Val Leu Ile Ser Met
145                 150                 155                 160
```

Ala Val Cys Ile Val Ala Met Ile Val Phe Ser Ser Cys Phe Cys Tyr
            165                 170                 175

Lys His Tyr Cys Lys Ser Ile Ser Ser Arg Gly Arg Tyr Asn Arg Asp
            180                 185                 190

Leu Glu Gln Asp Glu Ala Phe Ile Pro Val Gly Glu Ser Leu Lys Asp
            195                 200                 205

Leu Ile Asp Gln Ser Gln Ser Ser Gly Ser Gly Ser Gly Leu Pro Leu
            210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
            245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
            275                 280                 285

Leu Gly Phe Ile Ala Ala Asp Ile Lys Gly Thr Gly Ser Trp Thr Gln
            290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
            325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Ile Pro Leu Asn Thr
385                 390                 395                 400

Arg Val Gly Thr Arg Arg Tyr Met Ala Pro Glu Val Leu Asp Glu Ser
            405                 410                 415

Leu Ser Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
            450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
            485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
        530

<210> SEQ ID NO 111
<211> LENGTH: 530
<212> TYPE: PRT
<213> ORGANISM: Homo sapiens

<400> SEQUENCE: 111

```
Met Thr Ser Ser Leu Gln Arg Pro Trp Arg Val Pro Trp Leu Pro Trp
  1               5                  10                  15

Thr Ile Leu Leu Val Ser Thr Ala Ala Ala Ser Gln Asn Gln Glu Arg
             20                  25                  30

Leu Cys Ala Phe Lys Asp Pro Tyr Gln Gln Asp Leu Gly Ile Gly Glu
             35                  40                  45

Ser Arg Ile Ser His Glu Asn Gly Thr Ile Leu Cys Ser Lys Gly Ser
     50                  55                  60

Thr Cys Tyr Gly Leu Trp Glu Lys Ser Lys Gly Asp Ile Asn Leu Val
 65                  70                  75                  80

Lys Gln Gly Cys Trp Ser His Ile Gly Asp Pro Gln Glu Cys His Tyr
                 85                  90                  95

Glu Glu Cys Val Val Thr Thr Pro Pro Ser Ile Gln Asn Gly Thr
            100                 105                 110

Tyr Arg Phe Cys Cys Cys Ser Thr Asp Leu Cys Asn Val Asn Phe Thr
            115                 120                 125

Glu Asn Phe Pro Pro Pro Asp Thr Thr Pro Leu Ser Pro Pro His Ser
130                 135                 140

Phe Asn Arg Asp Glu Thr Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
                180                 185                 190

Ala Ser Glu Pro Ser Leu Asp Leu Asp Asn Leu Lys Leu Leu Glu Leu
            195                 200                 205

Ile Gly Arg Gly Arg Tyr Gly Ala Val Tyr Lys Gly Ser Leu Asp Glu
210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415
```

```
Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
            435                 440                 445

Met Gln Val Leu Val Ser Arg Glu Lys Gln Arg Pro Lys Phe Pro Glu
            450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
            485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
            515                 520                 525

Arg Arg
    530

<210> SEQ ID NO 112
<211> LENGTH: 530
<212> TYPE: PRT
<213> ORGANISM: Homo sapiens

<400> SEQUENCE: 112

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
            35                  40                  45

Ser Arg Ile Ser His Glu Asn Gly Thr Ile Leu Cys Ser Lys Gly Ser
        50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
            85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
            115                 120                 125

Glu Asn Phe Pro Pro Pro Asp Thr Thr Pro Leu Ser Pro Pro His Ser
            130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
            165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
            195                 200                 205

Ile Gly Arg Gly Arg Tyr Gly Ala Val Tyr Lys Gly Ser Leu Asp Glu
            210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
```

-continued

```
                245                 250                 255
Ile Ala Arg Phe Ile Val Gly Asp Glu Arg Val Thr Ala Asp Gly Arg
                260                 265                 270

Met Glu Tyr Leu Leu Val Met Glu Tyr Tyr Pro Asn Gly Ser Leu Cys
                275                 280                 285

Lys Tyr Leu Ser Leu His Thr Ser Asp Trp Val Ser Ser Cys Arg Leu
                290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
                340                 345                 350

Gly Leu Ser Met Arg Leu Thr Gly Asn Arg Leu Val Arg Pro Gly Glu
                355                 360                 365

Glu Asp Asn Ala Ala Ile Ser Glu Val Gly Thr Ile Arg Tyr Met Ala
                370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
                420                 425                 430

Gln Met Ala Phe Gln Thr Glu Val Gly Asn His Pro Thr Phe Glu Asp
                435                 440                 445

Met Gln Val Leu Val Ser Arg Glu Lys Gln Arg Pro Lys Phe Pro Glu
                450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Glu Arg Asn Lys
                500                 505                 510

Ser Val Ser Pro Thr Val Asn Pro Met Ser Thr Ala Met Gln Asn Glu
                515                 520                 525

Arg Arg
    530

<210> SEQ ID NO 113
<211> LENGTH: 1038
<212> TYPE: PRT
<213> ORGANISM: Homo sapiens

<400> SEQUENCE: 113

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
                20                  25                  30

Leu Cys Ala Phe Lys Asp Pro Tyr Gln Gln Asp Leu Gly Ile Gly Glu
                35                  40                  45

Ser Arg Ile Ser His Glu Asn Gly Thr Ile Leu Cys Ser Lys Gly Ser
            50                  55                  60

Thr Cys Tyr Gly Leu Trp Glu Lys Ser Lys Gly Asp Ile Asn Leu Val
65              70                  75                  80
```

-continued

```
Lys Gln Gly Cys Trp Ser His Ile Gly Asp Pro Gln Glu Cys His Tyr
                85                  90                  95
Glu Glu Cys Val Val Thr Thr Thr Pro Pro Ser Ile Gln Asn Gly Thr
            100                 105                 110
Tyr Arg Phe Cys Cys Cys Ser Thr Asp Leu Cys Asn Val Asn Phe Thr
        115                 120                 125
Glu Asn Phe Pro Pro Pro Asp Thr Thr Pro Leu Ser Pro Pro His Ser
    130                 135                 140
Phe Asn Arg Asp Glu Thr Ile Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
Gly Asp Arg Lys Gln Gly Leu His Ser Met Asn Met Met Glu Ala Ala
            180                 185                 190
Ala Ser Glu Pro Ser Leu Asp Leu Asp Asn Leu Lys Leu Leu Glu Leu
        195                 200                 205
Ile Gly Arg Gly Arg Tyr Gly Ala Val Tyr Lys Gly Ser Leu Asp Glu
    210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
            260                 265                 270
Met Glu Tyr Leu Leu Val Met Glu Tyr Tyr Pro Asn Gly Ser Leu Cys
        275                 280                 285
Lys Tyr Leu Ser Leu His Thr Ser Asp Trp Val Ser Ser Cys Arg Leu
    290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
        355                 360                 365
Glu Asp Asn Ala Ala Ile Ser Glu Val Gly Thr Ile Arg Tyr Met Ala
    370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
            420                 425                 430
Gln Met Ala Phe Gln Thr Glu Val Gly Asn His Pro Thr Phe Glu Asp
        435                 440                 445
Met Gln Val Leu Val Ser Arg Glu Lys Gln Arg Pro Lys Phe Pro Glu
    450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
```

-continued

```
                500                 505                 510
Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
        530                 535                 540

Asp Tyr Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
                580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
        610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
                660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
        690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
                740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
        770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
                820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
        850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
        900                 905                 910

Gln Asp Val Leu Ala Gln Gly Val Pro Ser Thr Ala Ala Asp Pro Gly
        915                 920                 925
```

```
Pro Ser Lys Pro Arg Arg Ala Gln Arg Pro Asn Ser Leu Asp Leu Ser
    930             935             940

Ala Thr Asn Val Leu Asp Gly Ser Ser Ile Gln Ile Gly Glu Ser Thr
945             950             955             960

Gln Asp Gly Lys Ser Gly Ser Gly Glu Lys Ile Lys Lys Arg Val Lys
                965             970             975

Thr Pro Tyr Ser Leu Lys Arg Trp Arg Pro Ser Thr Trp Val Ile Ser
            980             985             990

Thr Glu Ser Leu Asp Cys Glu Val Asn Asn Asn Gly Ser Asn Arg Ala
        995             1000            1005

Val His Ser Lys Ser Ser Thr Ala Val Tyr Leu Ala Glu Gly Gly Thr
    1010            1015            1020

Ala Thr Thr Met Val Ser Lys Asp Ile Gly Met Asn Cys Leu
1025            1030            1035
```

<210> SEQ ID NO 114
<211> LENGTH: 1038
<212> TYPE: PRT
<213> ORGANISM: Homo sapiens

<400> SEQUENCE: 114

```
Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
```

-continued

```
                260                 265                 270
Met Glu Tyr Leu Leu Val Met Glu Tyr Tyr Pro Asn Gly Ser Leu Cys
            275                 280                 285
Lys Tyr Leu Ser Leu His Thr Ser Asp Trp Val Ser Ser Cys Arg Leu
        290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
        355                 360                 365
Glu Asp Asn Ala Ala Ile Ser Glu Val Gly Thr Ile Arg Tyr Met Ala
        370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
            405                 410                 415
Phe Met Arg Cys Thr Asp Leu Phe Pro Gly Glu Ser Val Pro Glu Tyr
        420                 425                 430
Gln Met Ala Phe Gln Thr Glu Val Gly Asn His Pro Thr Phe Glu Asp
        435                 440                 445
Met Gln Val Leu Val Ser Arg Glu Lys Gln Arg Pro Lys Phe Pro Glu
    450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
            500                 505                 510
Ser Val Ser Pro Thr Val Asn Pro Met Ser Thr Ala Met Gln Asn Glu
        515                 520                 525
Arg Asn Leu Ser His Asn Arg Arg Val Pro Lys Ile Gly Pro Tyr Pro
    530                 535                 540
Asp Tyr Ser Ser Ser Ser Tyr Ile Glu Asp Ser Ile His His Thr Asp
545                 550                 555                 560
Ser Ile Val Lys Asn Ile Ser Ser Glu His Ser Met Ser Ser Thr Pro
                565                 570                 575
Leu Thr Ile Gly Glu Lys Asn Arg Asn Ser Ile Asn Tyr Glu Arg Gln
            580                 585                 590
Gln Ala Gln Ala Arg Ile Pro Ser Pro Glu Thr Ser Val Thr Ser Leu
        595                 600                 605
Ser Thr Asn Thr Thr Thr Thr Asn Thr Thr Gly Leu Thr Pro Ser Thr
    610                 615                 620
Gly Met Thr Thr Ile Ser Glu Met Pro Tyr Pro Asp Glu Thr Asn Leu
625                 630                 635                 640
His Thr Thr Asn Val Ala Gln Ser Ile Gly Pro Thr Pro Val Cys Leu
                645                 650                 655
Gln Leu Thr Glu Glu Asp Leu Glu Thr Asn Lys Leu Asp Pro Lys Glu
            660                 665                 670
Val Asp Lys Asn Leu Lys Glu Ser Ser Asp Glu Asn Leu Met Glu His
        675                 680                 685
```

Ser Leu Lys Gln Phe Ser Gly Pro Asp Pro Leu Ser Ser Thr Ser Ser
    690             695                 700

Ser Leu Leu Tyr Pro Leu Ile Lys Leu Ala Val Glu Ala Thr Gly Gln
705             710                 715                 720

Gln Asp Phe Thr Gln Thr Ala Asn Gly Gln Ala Cys Leu Ile Pro Asp
            725                 730                 735

Val Leu Pro Thr Gln Ile Tyr Pro Leu Pro Lys Gln Gln Asn Leu Pro
        740                 745                 750

Lys Arg Pro Thr Ser Leu Pro Leu Asn Thr Lys Asn Ser Thr Lys Glu
            755                 760                 765

Pro Arg Leu Lys Phe Gly Ser Lys His Lys Ser Asn Leu Lys Gln Val
    770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Arg Thr Val Leu Ser
            820                 825                 830

Gly Gln Thr Thr Asn Ile Val Thr His Arg Ala Gln Glu Met Leu Gln
        835                 840                 845

Asn Gln Phe Ile Gly Glu Asp Thr Arg Leu Asn Ile Asn Ser Ser Pro
    850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
        915                 920                 925

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly Thr
    1010                1015                1020

Ala Thr Thr Met Val Ser Lys Asp Ile Gly Met Asn Cys Leu
1025                1030                1035

<210> SEQ ID NO 115
<211> LENGTH: 1038
<212> TYPE: PRT
<213> ORGANISM: Homo sapiens

<400> SEQUENCE: 115

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg

-continued

```
                20                  25                  30
Leu Cys Ala Phe Lys Asp Pro Tyr Gln Gln Asp Leu Gly Ile Gly Glu
         35                  40                  45
Ser Arg Ile Ser His Glu Asn Gly Thr Ile Leu Cys Ser Lys Gly Ser
 50                  55                  60
Thr Cys Tyr Gly Leu Trp Glu Lys Ser Lys Gly Asp Ile Asn Leu Val
 65                  70                  75                  80
Lys Gln Gly Cys Trp Ser His Ile Gly Asp Pro Gln Glu Cys His Tyr
                 85                  90                  95
Glu Glu Cys Val Val Thr Thr Pro Pro Ser Ile Gln Asn Gly Thr
                100                 105                 110
Tyr Arg Phe Cys Cys Cys Ser Thr Asp Leu Cys Asn Val Asn Phe Thr
            115                 120                 125
Glu Asn Phe Pro Pro Pro Asp Thr Thr Pro Leu Ser Pro Pro His Ser
            130                 135                 140
Phe Asn Arg Asp Glu Thr Ile Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
Gly Asp Arg Lys Gln Gly Leu His Ser Met Asn Met Met Glu Ala Ala
            180                 185                 190
Ala Ser Glu Pro Ser Leu Asp Leu Asp Asn Leu Lys Leu Leu Glu Leu
            195                 200                 205
Ile Gly Arg Gly Arg Tyr Gly Ala Val Tyr Lys Gly Ser Leu Asp Glu
    210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
            260                 265                 270
Met Glu Tyr Leu Leu Val Met Glu Tyr Tyr Pro Asn Gly Ser Leu Cys
            275                 280                 285
Lys Tyr Leu Ser Leu His Thr Ser Asp Trp Val Ser Ser Cys Arg Leu
    290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
            355                 360                 365
Glu Asp Asn Ala Ala Ile Ser Glu Val Gly Thr Ile Arg Tyr Met Ala
    370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
            420                 425                 430
Gln Met Ala Phe Gln Thr Glu Val Gly Asn His Pro Thr Phe Glu Asp
            435                 440                 445
```

```
Met Gln Val Leu Val Ser Arg Glu Lys Gln Arg Pro Lys Phe Pro Glu
    450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Gly Arg Asn Lys
            500                 505                 510
Ser Val Ser Pro Thr Val Asn Pro Met Ser Thr Ala Met Gln Asn Glu
        515                 520                 525
Arg Asn Leu Ser His Asn Arg Arg Val Pro Lys Ile Gly Pro Tyr Pro
    530                 535                 540
Asp Tyr Ser Ser Ser Ser Tyr Ile Glu Asp Ser Ile His His Thr Asp
545                 550                 555                 560
Ser Ile Val Lys Asn Ile Ser Ser Glu His Ser Met Ser Ser Thr Pro
                565                 570                 575
Leu Thr Ile Gly Glu Lys Asn Arg Asn Ser Ile Asn Tyr Glu Arg Gln
            580                 585                 590
Gln Ala Gln Ala Arg Ile Pro Ser Pro Glu Thr Ser Val Thr Ser Leu
        595                 600                 605
Ser Thr Asn Thr Thr Thr Thr Asn Thr Thr Gly Leu Thr Pro Ser Thr
    610                 615                 620
Gly Met Thr Thr Ile Ser Glu Met Pro Tyr Pro Asp Glu Thr Asn Leu
625                 630                 635                 640
His Thr Thr Asn Val Ala Gln Ser Ile Gly Pro Thr Pro Val Cys Leu
                645                 650                 655
Gln Leu Thr Glu Glu Asp Leu Glu Thr Asn Lys Leu Asp Pro Lys Glu
            660                 665                 670
Val Asp Lys Asn Leu Lys Glu Ser Ser Asp Glu Asn Leu Met Glu His
        675                 680                 685
Ser Leu Lys Gln Phe Ser Gly Pro Asp Pro Leu Ser Ser Thr Ser Ser
    690                 695                 700
Ser Leu Leu Tyr Pro Leu Ile Lys Leu Ala Val Glu Ala Thr Gly Gln
705                 710                 715                 720
Gln Asp Phe Thr Gln Thr Ala Asn Gly Gln Ala Cys Leu Ile Pro Asp
                725                 730                 735
Val Leu Pro Thr Gln Ile Tyr Pro Leu Pro Lys Gln Gln Asn Leu Pro
            740                 745                 750
Lys Arg Pro Thr Ser Leu Pro Leu Asn Thr Lys Asn Ser Thr Lys Glu
        755                 760                 765
Pro Arg Leu Lys Phe Gly Ser Lys His Lys Ser Asn Leu Lys Gln Val
    770                 775                 780
Glu Thr Gly Val Ala Lys Met Asn Thr Ile Asn Ala Ala Glu Pro His
785                 790                 795                 800
Val Val Thr Val Thr Met Asn Gly Val Ala Gly Arg Asn His Ser Val
                805                 810                 815
Asn Ser His Ala Ala Thr Thr Gln Tyr Ala Asn Arg Thr Val Leu Ser
            820                 825                 830
Gly Gln Thr Thr Asn Ile Val Thr His Arg Ala Gln Glu Met Leu Gln
        835                 840                 845
Asn Gln Phe Ile Gly Glu Asp Thr Arg Leu Asn Ile Asn Ser Ser Pro
    850                 855                 860
```

-continued

Asp Glu His Glu Pro Leu Leu Arg Arg Glu Gln Ala Gly His Asp
865                 870                 875                 880

Glu Gly Val Leu Asp Arg Leu Val Asp Arg Glu Arg Pro Leu Glu
            885                 890                 895

Gly Gly Arg Thr Asn Ser Asn Asn Asn Asn Ser Asn Pro Cys Ser Glu
                900                 905                 910

Gln Asp Val Leu Ala Gln Gly Val Pro Ser Thr Ala Ala Asp Pro Gly
            915                 920                 925

Pro Ser Lys Pro Arg Arg Ala Gln Arg Pro Asn Ser Leu Asp Leu Ser
        930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly Thr
    1010                1015                1020

Ala Thr Thr Met Val Ser Lys Asp Ile Gly Met Asn Cys Leu
1025                1030                1035

<210> SEQ ID NO 116
<211> LENGTH: 2932
<212> TYPE: DNA
<213> ORGANISM: Homo sapiens

<400> SEQUENCE: 116
gctccgcgcc gagggctgga ggatgcgttc cctggggtcc ggacttatga aaatatgcat      60
cagtttaata ctgtcttgga attcatgaga tggaagcata ggtcaaagct gtttggagaa     120
aatcagaagt acagttttat ctagccacat cttggaggag tcgtaagaaa gcagtgggag     180
ttgaagtcat tgtcaagtgc ttgcgatctt ttacaagaaa atctcactga atgatagtca     240
tttaaattgg tgaagtagca agaccaatta ttaaaggtga cagtacacag gaaacattac     300
aattgaacaa tgactcagct atacatttac atcagattat tgggagccta tttgttcatc     360
atttctcgtg ttcaaggaca gaatctggat agtatgcttc atggcactgg gatgaaatca     420
gactccgacc agaaaaagtc agaaaatgga gtaaccttag caccagagga taccttgcct     480
tttttaaagt gctattgctc agggcactgt ccagatgatg ctattaataa cacatgcata     540
actaatggac attgctttgc catcatagaa gaagatgacc aggagaaaac cacattagct     600
tcagggtgta tgaaatatga aggatctgat tttcagtgca agattctcc aaaagcccag     660 ctacgccgga caatagaatg ttgtcggacc aatttatgta accagtattt gcaacccaca     720 ctgcccctg ttgtcatagg tccgtttttt gatggcagca ttcgatggct ggttttgctc     780
atttctatgg ctgtctgcat aattgctatg atcatcttct ccagctgctt ttgttacaaa     840
cattattgca agagcatctc aagcagacgt cgttacaatc gtgatttgga acaggatgaa     900
gcatttattc cagttggaga atcactaaaa gaccttattg accagtcaca agttctggt      960 agtgggtctg gactaccttt attggttcag cgaactattg ccaaacagat tcagatggtc    1020
cggcaagttg gtaaaggccg atatggagaa gtatggatgg gcaaatggcg tggcgaaaaa    1080
gtggcggtga agtattcttt taccactgaa gaagccagct ggtttcgaga aacagaaatc    1140

```
taccaaactg tgctaatgcg ccatgaaaac atacttggtt tcatagcggc agacattaaa      1200
ggtacaggtt cctggactca gctctatttg attactgatt accatgaaaa tggatctctc      1260
tatgacttcc tgaaatgtgc tacactggac accagagccc tgcttaaatt ggcttattca      1320
gctgcctgtg gtctgtgcca cctgcacaca gaaatttatg gcacccaagg aaagcccgca      1380
attgctcatc gagacctaaa gagcaaaaac atcctcatca agaaaaatgg gagttgctgc      1440
attgctgacc tgggccttgc tgttaaattc aacagtgaca caaatgaagt tgatgtgccc      1500
ttgaatacca gggtgggcac caaacgctac atggctcccg aagtgctgga cgaaagcctg      1560
aacaaaaacc acttccagcc ctacatcatg gctgacatct acagcttcgg cctaatcatt      1620
tgggagatgg ctcgtcgttg tatcacagga gggatcgtgg aagaatacca attgccatat      1680
tacaacatgt accgagtgga tccgtcatac gaagatatgc gtgaggttgt gtgtgtcaaa      1740
cgtttgcggc caattgtgtc taatcggtgg aacagtgatg aatgtctacg agcagttttg      1800
aagctaatgt cagaatgctg ggcccacaat ccagcctcca gactcacagc attgagaatt      1860
aagaagacgc ttgccaagat ggttgaatcc aagatgtaa aaatctgatg gttaaaccat      1920
cggaggagaa actctagact gcaagaactg ttttacccca tggcatgggt ggaattagag      1980
tggaataagg atgttaactt ggttctcaga ctctttcttc actacgtgtt cacaggctgc      2040
taatattaaa cctttcagta ctcttattag gatacaagct gggaacttct aaacacttca      2100
ttctttatat atggacagct ttattttaaa tgtggttttt gatgcctttt tttaagtggg      2160
tttttatgaa ctgcatcaag acttcaatcc tgattagtgt ctccagtcaa gctctgggta      2220
ctgaattgcc tgttcataaa acggtgcttt ctgtgaaagc cttaagaaga taaatgagcg      2280
cagcagagat ggagaaatag actttgcctt ttacctgaga cattcagttc gtttgtattc      2340
tacctttgta aaacagccta tagatgatga tgtgtttggg atactgctta ttttatgata      2400
gtttgtcctg tgtccttagt gatgtgtgtg tgtctccatg cacatgcacg ccgggattcc      2460
tctgctgcca tttgaattag aagaaaataa tttatatgca tgcacaggaa gatattggtg      2520
gccggtggtt ttgtgcttta aaatgcaat atctgaccaa gattcgccaa tctcatacaa      2580
gccatttact ttgcaagtga gatagcttcc ccaccagctt tatttttaa catgaaagct      2640 gatgccaagg ccaaaagaag tttaaagcat ctgtaaattt ggactgtttt ccttcaacca      2700
ccattttttt tgtggttatt attttgtca cggaaagcat cctctccaaa gttggagctt      2760
ctattgccat gaaccatgct tacaaagaaa gcacttctta ttgaagtgaa ttcctgcatt      2820
tgatagcaat gtaagtgcct ataaccatgt tctatattct ttattctcag taactttaa       2880 aagggaagtt atttatattt tgtgtataat gtgctttatt tgcaaatcac cc              2932
```

<210> SEQ ID NO 117
<211> LENGTH: 1575
<212> TYPE: DNA
<213> ORGANISM: Homo sapiens
<400> SEQUENCE: 117

```
gcaaacttcc ttgataacat gcttttgcga agtgcaggaa aattaaatgt gggcaccaag        60
aaagaggatg gtgagagtac agcccccacc ccccgtccaa aggtcttgcg ttgtaaatgc       120
caccaccatt gtccagaaga ctcagtcaac aatatttgca gcacagacgg atattgtttc       180
acgatgatag aagaggatga ctctgggttg cctgtggtca cttctggttg cctaggacta       240
gaaggctcag attttcagtg tcgggacact cccattcctc atcaaagaag atcaattgaa       300
tgctgcacag aaaggaacga atgtaataaa gacctacacc ctacactgcc tccattgaaa       360
```

| | |
|---|---|
| aacagagatt tgttgatgg acctatacac cacagggctt tacttatatc tgtgactgtc | 420 |
| tgtagtttgc tcttggtcct tatcatatta ttttgttact tccggtataa aagacaagaa | 480 |
| accagacctc gatacagcat tgggttagaa caggatgaaa cttacattcc tcctggagaa | 540 |
| tccctgagag acttaattga gcagtctcag agctcaggaa gtggatcagg cctccctctg | 600 |
| ctggtccaaa ggactatagc taagcagatt cagatggtga aacagattgg aaaaggtcgc | 660 |
| tatggggaag tttggatggg aaagtggcgt ggcgaaaagg tagctgtgaa agtgttcttc | 720 |
| accacagagg aagccagctg gttcagagag acagaaatat atcagacagt gttgatgagg | 780 |
| catgaaaaca ttttgggttt cattgctgca gatatcaaag gacagggtc ctggacccag | 840 |
| ttgtacctaa tcacagacta tcatgaaaat ggttcccttt atgattatct gaagtccacc | 900 |
| accctagacg ctaaatcaat gctgaagtta gcctactctt ctgtcagtgg cttatgtcat | 960 |
| ttacacacag aaatctttag tactcaaggc aaaccagcaa ttgcccatcg agatctgaaa | 1020 |
| agtaaaaaca ttctggtgaa gaaaaatgga acttgctgta ttgctgacct gggcctggct | 1080 |
| gttaaattta ttagtgatac aaatgaagtt gacataccac ctaacactcg agttggcacc | 1140 |
| aaacgctata tgcctccaga agtgttggac gagagcttga acagaaatca cttccagtct | 1200 |
| tacatcatgg ctgacatgta tagttttggc ctcatccttt gggaggttgc taggagatgt | 1260 |
| gtatcaggag gtatagtgga agaataccag cttccttatc atgacctagt gcccagtgac | 1320 |
| ccctcttatg aggacatgag ggagattgtt tgcatcaaga agttacgccc ctcattccca | 1380 |
| aaccggtgga gcagtgatga gtgtctaagg cagatgggaa aactcatgac agaatgctgg | 1440 |
| gctcacaatc ctgcatcaag gctgacagcc ctgcgggtta agaaaacact tgccaaaatg | 1500 |
| tcagagtccc aggacattaa actctgatag gagaggaaaa gtaagcatct ctgcagaaag | 1560 |
| ccaacaggta ccctt | 1575 |

<210> SEQ ID NO 118
<211> LENGTH: 2032
<212> TYPE: DNA
<213> ORGANISM: Homo sapiens

<400> SEQUENCE: 118

| | |
|---|---|
| cgcggggcgc ggagtcggcg gggcctcgcg ggacgcgggc agtgcggaga ccgcggcgct | 60 |
| gaggacgcgg gagccgggag cgcacgcgcg gggtggagtt cagcctactc tttcttagat | 120 |
| gtgaaaggaa aggaagatca tttcatgcct tgttgataaa ggttcagact tctgctgatt | 180 |
| cataaccatt tggctctgag ctatgacaag agaggaaaca aaagttaaa cttacaagcc | 240 |
| tgccataagt gagaagcaaa cttccttgat aacatgcttt tgcgaagtgc aggaaaatta | 300 |
| aatgtgggca ccaagaaaga ggatggtgag agtacagccc ccacccccg tccaaaggtc | 360 |
| ttgcgttgta aatgccacca ccattgtcca gaagactcag tcaacaatat ttgcagcaca | 420 |
| gacggatatt gtttcacgat gatagaagag gatgactctg ggttgcctgt ggtcacttct | 480 |
| ggttgcctag gactagaagg ctcagatttt cagtgtcggg acactcccat tcctcatcaa | 540 |
| agaagatcaa ttgaatgctg cacagaaagg aacgaatgta ataaagacct acaccctaca | 600 |
| ctgcctccat tgaaaacag agattttgtt gatggaccta tacaccacag gctttacttt | 660 |
| atatctgtga ctgtctgtag tttgctcttg gtccttatca tattattttg ttacttccgg | 720 |
| tataaaagac aagaaccag acctcgatac agcattgggt tagaacagga tgaaacttac | 780 |
| attcctcctg gagaatccct gagagactta attgagcagt ctcagagctc aggaagtgga | 840 |

```
tcaggcctcc ctctgctggt ccaaaggact atagctaagc agattcagat ggtgaaacag      900
attggaaaag gtcgctatgg ggaagtttgg atgggaaagt ggcgtggcga aaaggtagct      960
gtgaaagtgt tcttcaccac agaggaagcc agctggttca gagagacaga aatatatcag     1020
acagtgttga tgaggcatga aaacattttg ggtttcattg ctgcagatat caaagggaca     1080
gggtcctgga cccagttgta cctaatcaca gactatcatg aaaatggttc cctttatgat     1140
tatctgaagt ccaccaccct agacgctaaa tcaatgctga gttagccta ctcttctgtc      1200
agtggcttat gtcatttaca cacagaaatc tttagtactc aaggcaaacc agcaattgcc     1260
catcgagatc tgaaaagtaa aaacattctg gtgaagaaaa atggaacttg ctgtattgct     1320
gacctgggcc tggctgttaa atttattagt gatacaaatg aagttgacat accacctaac     1380
actcgagttg gcaccaaacg ctatatgcct ccagaagtgt tggacgagag cttgaacaga     1440
aatcacttcc agtcttacat catggctgac atgtatagtt ttggcctcat cctttgggag     1500
gttgctagga gatgtgtatc aggaggtata gtggaagaat accagcttcc ttatcatgac     1560
ctagtgccca gtgacccctc ttatgaggac atgagggaga ttgtgtgcat caagaagtta     1620
cgcccctcat tcccaaaccg gtggagcagt gatgagtgtc taaggcagat gggaaaactc     1680
atgacagaat gctgggctca caatcctgca tcaaggctga cagccctgcg ggttaagaaa     1740
acacttgcca aaatgtcaga gtcccaggac attaaactct gataggagag gaaagtaag     1800
catctctgca gaaagccaac aggtactctt ctgtttgtgg gcagagcaaa agacatcaaa     1860
taagcatcca cagtacaagc cttgaacatc gtcctgcttc ccagtgggtt cagacctcac     1920
cttttcaggga gcgacctggg caaagacaga gaagctccca aaggagaga ttgatccgtg     1980
tctgtttgta ggcggagaaa ccgttgggta acttgttcaa gatatgatgc at             2032

<210> SEQ ID NO 119
<211> LENGTH: 3167
<212> TYPE: DNA
<213> ORGANISM: Rattus sp.

<400> SEQUENCE: 119
gaattcatga gatggaaaca taggtcaaag ctgtttggag aaattggaac tacagtttta       60
tctagccaca tctctgagaa gtctgaagaa agcagcaggt gaaagtcatt gtcaagtgat      120
tttgttcttc tgtaaggaaa cctcgttcag taaggccgtt tacttcagtg aaacagcagg      180
accagtaatc aaggtggccc ggacaggaca cgtgcgaatt ggacaatgac tcagctatac      240
acttacatca gattactggg agcctgtctg ttcatcattt ctcatgttca agggcagaat      300
ctagatagta tgctccatgg tactggtatg aaatcagacg tggaccagaa gaagccggaa      360
aatggagtga cgttagcacc agaggacacc ttaccttct taaaatgcta ttgctcagga      420
cactgcccag atgacgctat taataacaca tgcataacta atggccattg ctttgccatt      480
atagaagaag atgatcaggg agaaaccacg ttaacttctg ggtgtatgaa gtatgaaggc      540
tctgattttc aatgcaagga ttcaccaaaa gcccagctac gcaggacaat agaatgttgt      600
cggaccaatt tgtgcaacca atatttgcag cctacactgc ccctgtcgt tataggccca      660
ttctttgatg gcagcgtccg atggctggct gtgctcatct ctatggctgt ctgtattgtc      720
gccatgatcc tcttctccag ctgcttctgt tacaaacatt actgtaagag tatctcaagc      780
agaggtcgtt acaaccgtga cttggaacag gatgaagcat ttattccagt aggagaatca      840
ctgaaagacc tgattgacca gtcacaaagc tctggtagtg gatctggatt acctttattg      900
gttcagcgaa ctattgccaa acagattcag atggttcggc aggttggtaa aggccggtat      960
```

```
ggagaagtat ggatgggtaa atggcgtggt gaaaaagtgg ctgtcaaagt atttttacc    1020 actgaagaag ctagctggtt tagagaaaca gaaatctacc agacggtgtt aatgcgtcat   1080
gaaaatatac ttggttttat agctgcagac attaaaggca ccggttcctg gactcagctg   1140
tatttgatta ctgattacca tgagaatggg tctctctatg acttcctgaa atgtgccacc   1200
ctggacacca gagccctact caagttagct tattctgctg cctgtggtct gtgccacctc   1260
cacacagaaa tttatggcac gcaaggcaag cctgcaattg ctcatcgaga cctgaagagc   1320
aaaaacatcc ttattaagaa aaatggtagt tgctgtattg ctgacctggg cctagctgtt   1380
aaattcaaca gtgacacaaa tgaagttgac atacccttga acaccagggt gggcaccagg   1440
cggtacatgg ctccagaagt gctggacgag agcctgagta aaaaccattt ccagccctac   1500
atcatggctg acatctacag ctttggtttg atcatttggg agatggcccg tcgctgtatt   1560
acaggaggaa tcgtgcagga atatcaatta ccatattaca catggtgcc tagtgaccca    1620 tcttatgaag acatgcgtga ggtcgtgtgt gtgaaacgct tgcggccaat cgtctctaac   1680
cgctggaaca gtgatgaatg tcttcgagcc gttttgaagc tgatgtcaga atgctgggcc   1740
cataatccag catccagact cacagctttg agaatcaaga agacgctcgc aaagatggtt   1800
gaatcccagg atgtaaagat tgacaaaaca gttttgagaa agaatttaga ctgcaagaaa   1860
ttcacccgag aagggtgga gttagcatgg actaggatgt cggcttggtt tccagactct    1920
ctcctctaca tcttcacagg ctgctaacag taaactttca ggactctgca gaatgcaggg   1980
ttggagcttc agacatagga cttcagacat gctgttcttt gcgtatggac agctttgttt   2040
taaatgtggg cttttgatgc ctttttggtt tttatgaatt gcatcaagac tccaatcctg   2100
ataagaagtc tctggtcaaa ctctggttac tcactatcct gtccataaag tggtgctttc   2160
tgtgaaagcc ttaaggaaat tagtgagctc agcagagatg gagaaaggca tatttgccct   2220
ctacagagaa aatatctgtc tgtgttctgt ctctgtaaac agcctggact atgatctctt   2280
tgggatgctg cctggttgat gatggtgcat catgcctctg atatgcatac cagacttcct   2340
ctgctgccat gggcttacaa gacaagaatg tgaaggttgc acaggacggt atttgtggcc   2400
agtggtttaa atatgcaata tctaatcgac attcgccaat ctcataaaag ccatctacct   2460
tgtaactgaa gtaacttctc taccaacttt attttagca taatagttgt aaaggccaaa    2520
ctatgtataa agtgtccata gactcgaact gttttcctcc agtcaccatt tgttttcct    2580 tttggtaatt attttgtta tataattcct cctatccaga attggcgctc actgtcttga    2640
accatacttt gaaagaaatg cctcttcctg gagtctgcct tactgcatct gatcaccatg   2700
tgcatacctc tgatcaaatt ctggagtctt tgttctcggt acctcttaaa aagggaaatt   2760
gtgtatcatg tgtagtgtgc tttatttc aaaatcttca tagcctttat tctagccatt     2820
tttacctaca tactcattct gtacaaaaca gctcactcgg tctcacggct gatcctcagt   2880
ggaaatgatt taaagtagag ctgtgtacga atttcagaat tcatgtattt aaaaacttca   2940
cactaacact ttactaagat attgtctcat atcttttatg aggatgtcag ctgattttca   3000
atgactataa atgtatctta gctatctaaa tcttttgaaa tttggtttta aatttctgg    3060 tccctaactt gtgaagacaa agaggcagaa gtacccagtc taccacattt acactgtaca   3120
ttattaaata aaaaaatgta tatttaaaa aaaaaaaaa aaaaaa                    3167

<210> SEQ ID NO 120
<211> LENGTH: 3167
<212> TYPE: DNA
```

<213> ORGANISM: Rattus norvegicus

<400> SEQUENCE: 120

| | | | | | |
|---|---|---|---|---|---|
| gaattcatga | gatggaaaca | taggtcaaag | ctgtttggag | aaattggaac | tacagtttta | 60 |
| tctagccaca | tctctgagaa | gtctgaagaa | agcagcaggt | gaaagtcatt | gtcaagtgat | 120 |
| tttgttcttc | tgtaaggaaa | cctcgttcag | taaggccgtt | tacttcagtg | aaacagcagg | 180 |
| accagtaatc | aaggtggccc | ggacaggaca | cgtgcgaatt | ggacaatgac | tcagctatac | 240 |
| acttacatca | gattactggg | agcctgtctg | ttcatcattt | ctcatgttca | agggcagaat | 300 |
| ctagatagta | tgctccatgg | tactggtatg | aaatcagacg | tggaccagaa | gaagccggaa | 360 |
| aatggagtga | cgttagcacc | agaggacacc | ttacctttct | aaaatgcta | ttgctcagga | 420 |
| cactgcccag | atgacgctat | aataacaca | tgcataacta | atggccattg | ctttgccatt | 480 |
| atagaagaag | atgatcaggg | agaaaccacg | ttaacttctg | ggtgtatgaa | gtatgaaggc | 540 |
| tctgattttc | aatgcaagga | ttcaccaaaa | gcccagctac | gcaggacaat | agaatgttgt | 600 |
| cggaccaatt | tgtgcaacca | atatttgcag | cctacactgc | ccctgtcgt | tataggccca | 660 |
| ttctttgatg | gcagcgtccg | atggctggct | gtgctcatct | ctatggctgt | ctgtattgtc | 720 |
| gccatgatcg | tcttctccag | ctgcttctgt | tacaaacatt | actgtaagag | tatctcaagc | 780 |
| agaggtcgtt | acaaccgtga | cttggaacag | gatgaagcat | ttattccagt | aggagaatca | 840 |
| ctgaaagacc | tgattgacca | gtcacaaagc | tctggtagtg | gatctggatt | acctttattg | 900 |
| gttcagcgaa | ctattgccaa | acagattcag | atggttcggc | aggttggtaa | aggccggtat | 960 |
| ggagaagtat | ggatgggtaa | atggcgtggt | gaaaaagtgg | ctgtcaaagt | atttttacc | 1020 |
| actgaagaag | ctagctggtt | tagagaaaca | gaaatctacc | agacggtgtt | aatgcgtcat | 1080 |
| gaaaatatac | ttggttttat | agctgcagac | attaaaggca | ccggttcctg | gactcagctg | 1140 |
| tatttgatta | ctgattacca | tgagaatggg | tctctctatg | acttcctgaa | atgtgccacc | 1200 |
| ctggacacca | gagccctact | caagttagct | tattctgctg | cctgtggtct | gtgccacctc | 1260 |
| cacacagaaa | tttatggcac | gcaaggcaag | cctgcaattg | ctcatcgaga | cctgaagagc | 1320 |
| aaaaacatcc | ttattaagaa | aaatggtagt | tgctgtattg | ctgacctggg | cctagctgtt | 1380 |
| aaattcaaca | gtgacacaaa | tgaagttgac | ataccttga | acaccagggt | gggcaccagg | 1440 |
| cggtacatgg | ctccagaagt | gctggacgag | agcctgagta | aaaaccattt | ccagccctac | 1500 |
| atcatggctg | acatctacag | ctttggtttg | atcatttggg | agatggcccg | tcgctgtatt | 1560 |
| acaggaggaa | tcgtggagga | atatcaatta | ccatattaca | acatggtgcc | tagtgaccca | 1620 |
| tcttatgaag | acatgcgtga | ggtcgtgtgt | gtgaaacgct | tgcggccaat | cgtctctaac | 1680 |
| cgctggaaca | gtgatgaatg | tcttcgagcc | gttttgaagc | tgatgtcaga | atgctgggcc | 1740 |
| cataatccag | catccagact | cacagctttg | agaatcaaga | agacgctcgc | aaagatggtt | 1800 |
| gaatcccagg | atgtaaagat | tgacaaaca | gttttgaaga | agaatttaga | ctgcaagaaa | 1860 |
| ttcacccgag | gaagggtgga | gttagcatgg | actaggatgt | cggcttggtt | tccagactct | 1920 |
| ctcctctaca | tcttcacagg | ctgctaacag | taaactttca | ggactctgca | gaatgcaggg | 1980 |
| ttggagcttc | agacatagga | cttcagacat | gctgttcttt | gcgtatggac | agctttgttt | 2040 |
| taaatgtggg | cttttgatgc | cttttggtt | tttatgaatt | gcatcaagac | tccaatcctg | 2100 |
| ataagaagtc | tctggtcaaa | ctctggttac | tcactatcct | gtccataaag | tggtgctttc | 2160 |
| tgtgaaagcc | ttaaggaaat | tagtgagctc | agcagagatg | gagaaaggca | tatttgccct | 2220 |
| ctacagagaa | aatatctgtc | tgtgttctgt | ctctgtaaac | agcctggact | atgatctctt | 2280 |

-continued

| | |
|---|---|
| tgggatgctg cctggttgat gatggtgcat catgcctctg atatgcatac cagacttcct | 2340 |
| ctgctgccat gggcttacaa gacaagaatg tgaaggttgc acaggacggt atttgtggcc | 2400 |
| agtggtttaa atatgcaata tctaatcgac attcgccaat ctcataaaag ccatctacct | 2460 |
| tgtaactgaa gtaacttctc taccaacttt attttagca taatagttgt aaaggccaaa | 2520 |
| ctatgtataa agtgtccata gactcgaact gttttcctcc agtcaccatt ttgttttcct | 2580 |
| tttggtaatt attttgtta tataattcct cctatccaga attggcgctc actgtcttga | 2640 |
| accatacttt gaaagaaatg cctcttcctg gagtctgcct tactgcatct gatcaccatg | 2700 |
| tgcataccctc tgatcaaatt ctggagtctt tgttctcggt acctcttaaa aagggaaatt | 2760 |
| gtgtatcatg tgtagtgtgc ttttattttc aaaatcttca tagcctttat tctagccatt | 2820 |
| tttacctaca tactcattct gtacaaaaca gctcactcgg tctcacggct gatcctcagt | 2880 |
| ggaaatgatt taaagtagag ctgtgtacga atttcagaat tcatgtattt aaaaacttca | 2940 |
| cactaacact ttactaagat attgtctcat atcttttatg aggatgtcag ctgattttca | 3000 |
| atgactataa atgtatctta gctatctaaa tcttttgaaa tttggtttta taatttctgg | 3060 |
| tccctaactt gtgaagacaa agaggcagaa gtacccagtc taccacattt acactgtaca | 3120 |
| ttattaaata aaaaaatgta tattttaaaa aaaaaaaaa aaaaaaa | 3167 |

<210> SEQ ID NO 121
<211> LENGTH: 3003
<212> TYPE: DNA
<213> ORGANISM: Rattus norvegicus

<400> SEQUENCE: 121

| | |
|---|---|
| cgttcagtaa ggccgtttac ttcagtgaaa cagcaggacc agtaatcaag gtggcccgga | 60 |
| caggacacgt gcgaattgga caatgactca gctatacact tacatcagat tactgggagc | 120 |
| ctgtctgttc atcatttctc atgttcaagg gcagaatcta gatagtatgc tccatggtac | 180 |
| tggtatgaaa tcagacgtgg accagaagaa gccggaaaat ggagtgacgt tagcaccaga | 240 |
| ggacacctta cctttcttaa aatgctattg ctcaggacac tgcccagatg acgctattaa | 300 |
| taacacatgc ataactaatg gccattgctt tgccattata aagaagatg atcagggaga | 360 |
| aaccacgtta acttctgggt gtatgaagta tgaaggctct gattttcaat gcaaggattc | 420 |
| accaaaagcc cagctacgca ggacaataga atgttgtcgg accaatttgt gcaaccaata | 480 |
| tttgcagcct acactgcccc ctgtcgttat aggcccattc tttgatggca gcgtccgatg | 540 |
| gctggctgtg ctcatctcta tggctgtctg tattgtcgcc atgatcgtct tctccagctg | 600 |
| cttctgttac aaacattact gtaagagtat ctcaagcaga ggtcgttaca accgtgactt | 660 |
| ggaacaggat gaagcattta ttccagtagg agaatcactg aaagacctga ttgaccagtc | 720 |
| acaaagctct ggtagtggat ctggattacc tttattggtt cagcgaacta ttgccaaaca | 780 |
| gattcagatg gttcggcagg ttggtaaagg ccggtatgga gaagtatgga tgggtaaatg | 840 |
| gcgtggtgaa aaagtggctg tcaaagtatt ttttaccact gaagaagcta gctggtttag | 900 |
| agaaacagaa atctaccaga cggtgttaat gcgtcatgaa aatatacttg gttttatagc | 960 |
| tgcagacatt aaaggcaccg gttcctggac tcagctgtat ttgattactg attaccatga | 1020 |
| gaatgggtct ctctatgact tcctgaaatg tgccaccctg gacaccagag ccctactcaa | 1080 |
| gttagctta ttctgctgcct gtggtctgtg ccacctccac acagaaattt atggcacgca | 1140 |
| aggcaagcct gcaattgctc atcgagacct gaagagcaaa aacatcctta ttaagaaaaa | 1200 |

-continued

```
tggtagttgc tgtattgctg acctgggcct agctgttaaa ttcaacagtg acacaaatga      1260
agttgacata cccttgaaca ccagggtggg caccaggcgg tacatggctc cagaagtgct      1320
ggacgagagc ctgagtaaaa accatttcca gccctacatc atggctgaca tctacagctt      1380
tggtttgatc atttgggaga tggcccgtcg ctgtattaca ggaggaatcg tggaggaata      1440
tcaattacca tattacaaca tggtgcctag tgacccatct tatgaagaca tgcgtgaggt      1500
cgtgtgtgtg aaacgcttgc ggccaatcgt ctctaaccgc tggaacagtg atgaatgtct      1560
tcgagccgtt ttgaagctga tgtcagaatg ctgggcccat aatccagcat ccagactcac      1620
agctttgaga atcaagaaga cgctcgcaaa gatggttgaa tcccaggatg taaagatttg      1680
acaaacagtt ttgagaaaga atttagactg caagaaattc acccgaggaa gggtggagtt      1740
agcatggact aggatgtcgg cttggtttcc agactctctc ctctacatct tcacaggctg      1800
ctaacagtaa actttcagga ctctgcagaa tgcagggttg gagcttcaga cataggactt      1860
cagacatgct gttctttgcg tatggacagc tttgttttaa atgtgggctt ttgatgcctt      1920
tttggttttt atgaattgca tcaagactcc aatcctgata agaagtctct ggtcaaactc      1980
tggttactca ctatcctgtc cataaagtgg tgctttctgt gaaagcctta aggaaattag      2040
tgagctcagc agagatggag aaaggcatat ttgccctcta cagagaaaat atctgtctgt      2100
gttctgtctc tgtaaacagc ctggactatg atctctttgg gatgctgcct ggttgatgat      2160
ggtgcatcat gcctctgata tgcataccag acttcctctg ctgccatggg cttacaagac      2220
aagaatgtga aggttgcaca ggacggtatt tgtggccagt ggtttaaata tgcaatatct      2280
aatcgacatt cgccaatctc ataaaagcca tctaccttgt aactgaagta acttctctac      2340
caactttatt tttagcataa tagttgtaaa ggccaaacta tgtataaagt gtccatagac      2400
tcgaactgtt ttcctccagt caccattttg ttttcctttt ggtaattatt tttgttatat      2460
aattcctcct atccagaatt ggcgctcact gtcttgaacc atactttgaa agaaatgcct      2520
cttcctggag tctgccttac tgcatctgat caccatgtgc atacctctga tcaaattctg      2580
gagtctttgt tctcggtacc tcttaaaaag ggaaattgtg tatcatgtgt agtgtgcttt      2640
tattttcaaa atcttcatag cctttattct agccattttt acctacatac tcattctgta      2700
caaaacagct cactcggtct cacggctgat cctcagtgga aatgatttaa agtagagctg      2760
tgtacgaatt tcagaattca tgtatttaaa aacttcacac taacacttta ctaagatatt      2820
gtctcatatc ttttatgagg atgtcagctg attttcaatg actataaatg tatcttagct      2880
atctaaatct tttgaaattt ggttttataa tttctggtcc ctaacttgtg aagacaaaga      2940
ggcagaagta cccagtctac cacatttaca ctgtacatta ttaaataaaa aatgtatat       3000 ttt                                                                    3003
```

<210> SEQ ID NO 122
<211> LENGTH: 2063
<212> TYPE: DNA
<213> ORGANISM: Homo sapiens

<400> SEQUENCE: 122

```
gaattccggt gatgatgatg gtgatggtga tgatggtgat gaggatgatg gtgatgatga       60
tgatggtgtt ggtgatggtt tttgcatctt ccattcatga actaagtact cttattagtg      120
aatttctttt ctttgccctc ctgattcttg gctggcccag ggatgacttc ctcgctgcag      180
cggccctggc gggtgccctg gctaccatgg accatcctgc tggtcagcac tgcggctgct      240
tcgcagaatc aagaacggct atgtgcgttt aaagatccgt atcagcaaga ccttgggata      300
```

```
ggtgagagta gaatctctca tgaaaatggg acaatattat gctcgaaagg tagcacctgc     360
tatggccttt gggagaaatc aaaaggggac ataaatcttg taaaacaagg atgttggtct     420
cacattggag atccccaaga gtgtcactat gaagaatgtg tagtaactac cactcctccc     480
tcaattcaga atggaacata ccgtttctgc tgttgtagca cagatttatg taatgtcaac     540
tttactgaga attttccacc tcctgacaca acaccactca gtccacctca ttcatttaac     600
cgagatgaga caataatcat tgctttggca tcagtctctg tattagctgt tttgatagtt     660
gccttatgct ttggatacag aatgttgaca ggagaccgta acaaggtct tcacagtatg      720 aacatgatgg aggcagcagc atccgaaccc tctcttgatc tagataatct gaaactgttg     780
gagctgattg gccgaggtcg atatggagca gtatataaag gctccttgga tgagcgtcca     840
gttgctgtaa aagtgttttc cttttgcaaac cgtcagaatt ttatcaacga aaagaacatt    900
tacagagtgc ctttgatgga acatgacaac attgcccgct ttatagttgg agatgagaga    960
gtcactgcag atggacgcat ggaatatttg cttgtgatgg agtactatcc caatggatct    1020
ttatgcaagt atttaagtct ccacacaagt gactgggtaa gctcttgccg tcttgctcat    1080
tctgttacta gaggactggc ttatcttcac acagaattac cacgaggaga tcattataaa    1140
cctgcaattt cccatcgaga tttaaacagc agaaatgtcc tagtgaaaaa tgatggaacc    1200
tgtgttatta gtgactttgg actgtccatg aggctgactg gaaatagact ggtgcgccca    1260
ggggaggaag ataatgcagc cataagcgag gttggcacta tcagatatat ggcaccagaa    1320
gtgctagaag gagctgtgaa cttgagggac tgtgaatcag cttttgaaaca gtagacatg    1380 tatgctcttg gactaatcta ttgggagata tttatgagat gtacagacct cttcccaggg    1440
gaatccgtac cagagtacca gatggctttt cagacagagt ttggaaacca tcccactttt    1500
gaggatatgc aggttctcgt gtctagggaa aaacagagac ccaagttccc agaagcctgg    1560
aaagaaaata gcctggcagt gaggtcactc aaggagacaa tcgaagactg ttgggaccag    1620
gatgcagagg ctcggcttac tgcacagtgt gctgaggaaa ggatggctga acttatgatg    1680
atttgggaaa gaaacaaatc tgtgagccca acagtcaatc caatgtctac tgctatgcag    1740
aatgaacgta ggtgagtcaa cacaagatgg caaatcagga tcaggtgaaa agatcaagaa    1800
acgtgtgaaa actccctatt ctcttaagcg gtggcgcccc tccacctggg tcatctccac    1860
tgaatcgctg gactgtgaag tcaacaataa tggcagtaac agggcagttc attccaaatc    1920
cagcactgct gtttaccttg cagaaggagg cactgctaca accatggtgt ctaaagatat    1980
aggaatgaac tgtctgtgaa atgttttcaa gcctatggag tgaaattatt ttttgcatca    2040
tttaaacatg cagaagatgt tta                                            2063

<210> SEQ ID NO 123
<211> LENGTH: 1964
<212> TYPE: DNA
<213> ORGANISM: Homo sapiens

<400> SEQUENCE: 123
atttcttttc tttgccctcc tgattcttgg ctggcccagg gatgacttcc tcgctgcagc      60
ggccctggcg ggtgccctgg ctaccatgga ccatcctgct ggtcagcact gcggctgctt     120
cgcagaatca agaacggcta tgtgcgttta aagatccgta tcagcaagac cttgggatag     180
gtgagagtag aatctctcat gaaaatggga caatattatg ctcgaaaggt agcacctgct     240
atggcctttg ggagaaatca aaaggggaca taaatcttgt aaaacaagga tgttggtctc     300
```

```
acattggaga tccccaagag tgtcactatg aagaatgtgt agtaactacc actcctccct    360
caattcagaa tggaacatac cgtttctgct gttgtagcac agatttatgt aatgtcaact    420
ttactgagaa ttttccacct cctgacacaa caccactcag tccacctcat tcatttaacc    480
gagatgagac aataatcatt gctttggcat cagtctctgt attagctgtt ttgatagttg    540
ccttatgctt tggatacaga atgttgacag gagaccgtaa acaaggtctt cacagtatga    600
acatgatgga ggcagcagca tccgaaccct ctcttgatct agataatctg aaactgttgg    660
agctgattgg ccgaggtcga tatggagcag tatataaagg ctccttggat gagcgtccag    720
ttgctgtaaa agtgttttcc tttgcaaacc gtcagaattt tatcaacgaa agaacatttt    780
acagagtgcc tttgatggaa catgacaaca ttgcccgctt tatagttgga gatgagagag    840
tcactgcaga tggacgcatg gaatatttgc ttgtgatgga gtactatccc aatggatctt    900
tatgcaagta tttaagtctc cacacaagtg actgggtaag ctcttgccgt cttgctcatt    960
ctgttactag aggactggct tatcttcaca cagaattacc acgaggagat cattataaac   1020
ctgcaatttc ccatcgagat ttaaacagca gaaatgtcct agtgaaaaat gatggaacct   1080
gtgttattag tgactttgga ctgtccatga ggctgactgg aaatagactg gtgcgcccag   1140
gggaggaaga taatgcagcc ataagcgagg ttggcactat cagatatatg gcaccagaag   1200
tgctagaagg agctgtgaac ttgagggact gtgaatcagc tttgaaacaa gtagacatgt   1260
atgctcttgg actaatctat tgggagatat ttatgagatg tacagacctc ttcccagggg   1320
aatccgtacc agagtaccag atggcttttc agacagaggt tggaaaccat cccacttttg   1380
aggatatgca ggttctcgtg tctagggaaa acagagacc caagttccca gaagcctgga   1440
aagaaaatag cctggcagtg aggtcactca aggagacaat cgaagactgt tgggaccagg   1500
atgcagaggc tcggcttact gcacagtgtg ctgaggaaag gatggctgaa cttatgatga   1560
tttgggaaag aaacaaatct gtgagcccaa cagtcaatcc aatgtctact gctatgcaga   1620
atgaacgtag gtgagtcaac acaagatggc aaatcaggat caggtgaaaa gatcaagaaa   1680
cgtgtgaaaa ctccctattc tcttaagcgg tggcgcccct ccacctgggt catctccact   1740
gaatcgctgg actgtgaagt caacaataat ggcagtaaca gggcagttca ttccaaatcc   1800
agcactgctg tttaccttgc agaaggaggc actgctacaa ccatggtgtc taaagatata   1860
ggaatgaact gtctgtgaaa tgttttcaag cctatggagt gaaattattt tttgcatcat   1920
ttaaacatgc agaagatgtt taaaataaa aaaaaactg cttt                      1964
```

<210> SEQ ID NO 124
<211> LENGTH: 3611
<212> TYPE: DNA
<213> ORGANISM: Homo sapiens

<400> SEQUENCE: 124

```
cgcccccga ccccggatcg aatccccgcc ctccgcaccc tggatatgtt ttctcccaga     60
cctggatatt tttttgatat cgtgaaacta cgagggaaat aatttggggg atttcttctt    120
ggctccctgc tttccccaca gacatgcctt ccgtttggag ggccgcggca ccccgtccga    180
ggcgaaggaa cccccccagc cgcgagggag agaaatgaag ggaatttctg cagcggcatg    240
aaagctctgc agctaggtcc tctcatcagc catttgtcct ttcaaactgt attgtgatac    300
gggcaggatc agtccacggg agagaagacg agcctcccgg ctgtttctcc gccggtctac    360
ttcccatatt tcttttcttt gccctcctga ttccttggctg gcccagggat gacttcctcg    420
ctgcagcggc cctggcgggt gccctggcta ccatggacca tcctgctggt cagcactgcg    480
```

-continued

```
gctgcttcgc agaatcaaga acggctatgt gcgtttaaag atccgtatca gcaagacctt    540
gggataggtg agagtagaat ctctcatgaa aatgggacaa tattatgctc gaaaggtagc    600
acctgctatg gcctttggga gaaatcaaaa ggggacataa atcttgtaaa caaggatgt     660 tggtctcaca ttggagatcc ccaagagtgt cactatgaag aatgtgtagt aactaccact    720
cctccctcaa ttcagaatgg aacataccgt ttctgctgtt gtagcacaga tttatgtaat    780
gtcaacttta ctgagaattt ccacctcct gacacaacac cactcagtcc acctcattca     840
tttaaccgag atgagacaat aatcattgct ttggcatcag tctctgtatt agctgttttg    900
atagttgcct tatgctttgg atacagaatg ttgacaggag accgtaaaca aggtcttcac    960
agtatgaaca tgatggaggc agcagcatcc gaaccctctc ttgatctaga taatctgaaa   1020
ctgttggagc tgattggccg aggtcgatat ggagcagtat ataaaggctc cttggatgag   1080
cgtccagttg ctgtaaaagt gttttccttt gcaaaccgtc agaattttat caacgaaaag   1140
aacatttaca gagtgccttt gatggaacat gacaacattg cccgctttat agttggagat   1200
gagagagtca ctgcagatgg acgcatggaa tatttgcttg tgatggagta ctatcccaat   1260
ggatctttat gcaagtattt aagtctccac acaagtgact gggtaagctc ttgccgtctt   1320
gctcattctg ttactagagg actggcttat cttcacacag aattaccacg aggagatcat   1380
tataaacctg caatttccca tcgagattta acagcagaa atgtcctagt gaaaaatgat    1440
ggaacctgtg ttattagtga ctttggactg tccatgaggc tgactggaaa tagactggtg   1500
cgcccagggg aggaagataa tgcagccata agcgaggttg gcactatcag atatatggca   1560
ccagaagtgc tagaaggagc tgtgaacttg agggactgtg aatcagcttt gaaacaagta   1620
gacatgtatg ctcttggact aatctattgg gagatattta tgagatgtac agacctcttc   1680
ccaggggaat ccgtaccaga gtaccagatg gcttttcaga cagaggttgg aaaccatccc   1740
acttttgagg atatgcaggt tctcgtgtct agggaaaaac agagacccaa gttcccagaa   1800
gcctggaaag aaaatagcct ggcagtgagg tcactcaagg agacaatcga agactgttgg   1860
gaccaggatg cagaggctcg gcttactgca cagtgtgctg aggaaggat ggctgaactt     1920 atgatgattt gggaagaaa caaatctgtg agcccaacag tcaatccaat gtctactgct    1980
atgcagaatg aacgcaacct gtcacataat aggcgtgtgc caaaaattgg tccttatcca   2040
gattattctt cctcctcata cattgaagac tctatccatc atactgacag catcgtgaag   2100
aatatttcct ctgagcattc tatgtccagc acacctttga ctataggga aaaaaaccga    2160 aattcaatta actatgaacg acagcaagca caagctcgaa tccccagccc tgaaacaagt   2220
gtcaccagcc tctccaccaa cacaacaacc acaaacacca caggactcac gccaagtact   2280
ggcatgacta ctatatctga gatgccatac ccagatgaaa caaatctgca taccacaaat   2340
gttgcacagt caattgggcc aacccctgtc tgcttacagc tgacagaaga agacttggaa   2400
accaacaagc tagacccaaa agaagttgat aagaacctca ggaaaagctc tgatgagaat   2460
ctcatggagc actctcttaa acagttcagt ggcccagacc cactgagcag tactagttct   2520
agcttgcttt acccactcat aaaaacttgca gtagaagcaa ctggacagca ggacttcaca   2580
cagactgcaa atggccaagc atgtttgatt cctgatgttc tgcctactca gatctatcct   2640
ctccccaagc agcagaacct tcccaagaga cctactagtt tgccttttgaa caccaaaaat   2700 tcaacaaaag agccccggct aaaatttggc agcaagcaca aatcaaactt gaaacaagtc   2760
gaaactggag ttgccaagat gaatacaatc aatgcagcag aacctcatgt ggtgacagtc   2820
```

```
accatgaatg gtgtggcagg tagaaaccac agtgttaact cccatgctgc cacaacccaa    2880
tatgccaatg ggacagtact atctggccaa acaaccaaca tagtgacaca tagggcccaa    2940
gaaatgttgc agaatcagtt tattggtgag acacccggc tgaatattaa ttccagtcct     3000
gatgagcatg agcctttact gagacgagag caacaagctg gccatgatga aggtgttctg    3060
gatcgtcttg tggacaggag ggaacggcca ctagaaggtg gccgaactaa ttccaataac    3120
aacaacagca atccatgttc agaacaagat gttcttgcac agggtgttcc aagcacagca    3180
gcagatcctg ggccatcaaa gcccagaaga gcacagaggc ctaattctct ggatctttca    3240
gccacaaatg tcctggatgg cagcagtata cagataggga gtcaacaca agatggcaaa     3300 tcaggatcag gtgaaaagat caagaaacgt gtgaaaactc cctattctct aagcggtgg     3360 cgcccctcca cctgggtcat ctccactgaa tcgctggact gtgaagtcaa caataatggc    3420
agtaacaggg cagttcattc caaatccagc actgctgttt accttgcaga aggaggcact    3480
gctacaacca tggtgtctaa agatatagga atgaactgtc tgtgaaatgt tttcaagcct    3540
atggagtgaa attatttttt gcatcattta acatgcaga agatgtttaa aaataaaaaa     3600
aaaactgctt t                                                         3611

<210> SEQ ID NO 125
<211> LENGTH: 3871
<212> TYPE: DNA
<213> ORGANISM: Homo sapiens

<400> SEQUENCE: 125
ggcctccgca ccctggatat gttttctccc agacctggat attttttga tatcgtgaaa      60 ctacgaggga ataatttggg gggatttctt cttggctccc tgctttcccc acagacatac    120
cttccgtttg gagggccgcg gcaccccgtc cgaggcgaag gaaccccccc atccgcgagg    180
gagagaaatg aagggaattt ctgcagcggc atgaaagctc tgcagctagg tcctctcatc    240
agccatttgt cctttcaaac tgtattgtga tacgggcagg atcagtccac gggagagaag    300
acgagcctcc cggctgtttc tccgccggtc tacttcccat atttcttttc tttgccctcc    360
tgattcttgg ctggcccagg gatgacttcc tcgctgcagc ggccctggcg ggtgccctgg    420
ctaccatgga ccatcctgct ggtcagcact gcggctgctt cgcagaatca agaacggcta    480
tgtgcgttta aagatccgta tcagcaagac cttgggatag gtgagagtag aatctctcat    540
gaaaatggga caatattatg ctcgaaaggt agcacctgct atggcctttg ggagaaatca    600 aaagggaca taaatcttgt aaaacaagga tgttggtctc acattggaga tccccaagag    660
tgtcactatg aagaatgtgt agtaactacc actcctccct caattcagaa tggaacatac    720
cgtttctgct gttgtagcac agatttatgt aatgtcaact ttactgagaa ttttccacct    780
cctgacacaa caccactcag tccacctcat tcatttaacc gagatgagac aataatcatt    840
gctttggcat cagtctctgt attagctgtt ttgatagttc ccttatgctt tggatacaga    900
atgttgacag gagaccgtaa acaaggtctt cacagtatga acatgatgga ggcagcagca   960
tccgaacccr ctcttgatct agataatctg aaactgttgg agctgattgg ccgaggtcga   1020
tatggagcag tatataaagg ctccttggat gagcgtccag ttgctgtaaa agtgttttcc   1080
tttgcaaacc gtcagaattt tatcaacgaa agaacatttt acagagtgcc tttgatggaa   1140
catgacaaca ttgcccgctt tatagttgga gatgagagag tcactgcaga tggacgcatg   1200
gaatatttgc ttgtgatgga gtactatccc aatggatctt tatgcaagta tttaagtctc   1260
cacacaagtg actgggtaag ctcttgccgt cttgctcatt ctgttactag aggactggct   1320
```

-continued

```
tatcttcaca cagaattacc acgaggagat cattataaac ctgcaatttc ccatcgagat    1380
ttaaacagca gaaatgtcct agtgaaaaat gatggaacct gtgttattag tgactttgga    1440
ctgtccatga ggctgactgg aaatagactg gtgcgcccag gggaggaaga taatgcagcc    1500
ataagcgagg ttggcactat cagatatatg gcaccagaag tgctagaagg agctgtgaac    1560
ttgagggact gtgaatcagc tttgaaacaa gtagacatgt atgctcttgg actaatctat    1620
tgggagatat ttatgagatg tacagacctc ttcccagggg aatccgtacc agagtaccag    1680
atggcttttc agacagaggt tggaaaccat cccacttttg aggatatgca ggttctcgtg    1740
tctagggaaa aacagagacc caagttccca gaagcctgga agaaaaatag cctggcagtg    1800
aggtcactca aggagacaat cgaagactgt tgggaccagg atgcagaggc tcggcttact    1860
gcacagtgtg ctgaggaaag gatggctgaa cttatgatga tttgggaaag aaacaaatct    1920
gtgagcccaa cagtcaatcc aatgtctact gctatgcaga atgaacgcaa cctgtcacat    1980
aataggcgtg tgccaaaaat tggtccttat ccagattatt cttcctcctc atacattgaa    2040
gactctatcc atcatactga cagcatcgtg aagaatattt cctctgagca ttctatgtcc    2100
agcacacctt tgactatagg ggaaaaaaac cgaaattcaa ttaactatga acgacagcaa    2160
gcacaagctc gaatcccccag ccctgaaaca agtgtcacca gcctctccac caacacaaca    2220
accacaaaca ccacaggact cacgccaagt actggcatga ctactatatc tgagatgcca    2280
tacccagatg aaacaaatct gcataccaca aatgttgcac agtcaattgg gccaaccccct   2340
gtctgcttac agctgacaga agaagacttg gaaaccaaca gctagaccc aaaagaagtt    2400
gataagaacc tcaaggaaag ctctgatgag aatctcatgg agcactctct taaacagttc    2460
agtggcccag acccactgag cagtactagt tctagcttgc tttacccact cataaaactt    2520
gcagtagaag caactggaca gcaggacttc acacagactg caaatggcca agcatgtttg    2580
attcctgatg ttctgcctac tcagatctat cctctcccca gcagcagaa ccttcccaag    2640
agacctacta gtttgccttt gaacaccaaa aattcaacaa agagccccg gctaaaattt    2700
ggcagcaagc acaaatcaaa cttgaaacaa gtcgaaactg gagttgccaa gatgaataca    2760
atcaatgcag cagaacctca tgtggtgaca gtcaccatga atggtgtggc aggtagaaac    2820
cacagtgtta actcccatgc tgccacaacc caatatgcca ataggacagt actatctggc    2880
caaacaacca acatagtgac acatagggcc caagaaatgt tgcagaatca gtttattggt    2940
gaggacaccc ggctgaatat taattccagt cctgatgagc atgagccttt actgagacga    3000
gagcaacaag ctggccatga tgaaggtgtt ctggatcgtc ttgtggacag gagggaacgg    3060
ccactagaag gtgccgaac taattccaat aacaacaaca gcaatccatg ttcagaacaa    3120
gatgttcttg cacagggtgt tccaagcaca gcagcagatc ctgggccatc aaagcccaga    3180
agagcacaga ggcctaattc tctggatctt tcagccacaa atgtcctgga tggcagcagt    3240
atacagatag gtgagtcaac acaagatggc aaatcaggat caggtgaaaa gatcaagaaa    3300
cgtgtgaaaa ctccctattc tcttaagcgg tggcgcccct ccacctgggt catctccact    3360
gaatcgctgg actgtgaagt caacaataat ggcagtaaca gggcagttca ttccaaatcc    3420
agcactgctg tttaccttgc agaaggaggc actgctacaa ccatggtgtc taaagatata    3480
ggaatgaact gtctgtgaaa tgttttcaag cctatggagt gaaattattt tttgcatcat    3540
ttaaacatgc agaagatgtt taccgggcgg ggtgacagga gagagcgtca gcggcaagct    3600
gtggaggatg gggctcagaa tgcagacctg ggctggccgc atggcctctc cctgagccct    3660
```

```
gatttgtggt agggaagcag tatgggtgca gtcccctcct aggcctccct ctggggtccc      3720
ccgatcctat cccacctctt cagggtgagc cagcctcacc tcttcctagt cctgagggtg      3780
agggcaggct gaggcaacga gtgggaggtt caaacaagag tgggctggag ccaagggaaa      3840
atagagatga tgtaatttct ttccggaatt c                                    3871
```

```
<210> SEQ ID NO 126
<211> LENGTH: 88
<212> TYPE: PRT
<213> ORGANISM: Homo sapiens

<400> SEQUENCE: 126

Cys Arg Glu Leu His Phe Thr Arg Tyr Val Thr Asp Gly Pro Cys Arg
  1               5                  10                  15

Ser Ala Lys Pro Val Thr Glu Leu Val Cys Ser Gly Gln Cys Gly Pro
             20                  25                  30

Ala Arg Leu Leu Pro Asn Ala Ile Gly Arg Gly Lys Trp Trp Arg Pro
         35                  40                  45

Ser Gly Pro Asp Phe Arg Cys Ile Pro Asp Arg Tyr Arg Ala Gln Arg
     50                  55                  60

Val Gln Leu Leu Cys Pro Gly Gly Glu Ala Pro Arg Ala Arg Lys Val
 65                  70                  75                  80

Arg Leu Val Ala Ser Cys Lys Cys
                 85

<210> SEQ ID NO 127
<211> LENGTH: 82
<212> TYPE: PRT
<213> ORGANISM: Homo sapiens

<400> SEQUENCE: 127

Cys Arg Pro Ile Asn Ala Thr Leu Ala Val Glu Lys Glu Gly Cys Pro
  1               5                  10                  15

Val Cys Ile Thr Val Asn Thr Thr Ile Cys Ala Gly Tyr Cys Pro Thr
             20                  25                  30

Met Thr Arg Val Leu Gln Gly Val Leu Pro Ala Leu Pro Gln Val Val
         35                  40                  45

Cys Asn Tyr Arg Asp Val Arg Phe Glu Ser Ile Arg Leu Pro Gly Cys
     50                  55                  60

Pro Arg Gly Val Asn Pro Val Val Ser Tyr Ala Val Ala Leu Ser Cys
 65                  70                  75                  80

Gln Cys

<210> SEQ ID NO 128
<211> LENGTH: 82
<212> TYPE: PRT
<213> ORGANISM: Homo sapiens

<400> SEQUENCE: 128

Cys Glu Leu Thr Asn Ile Thr Ile Ala Ile Glu Lys Glu Glu Cys Arg
  1               5                  10                  15

Phe Cys Ile Ser Ile Asn Thr Thr Trp Cys Ala Gly Tyr Cys Tyr Thr
             20                  25                  30

Arg Asp Leu Val Tyr Lys Asp Pro Ala Arg Pro Lys Ile Gln Lys Thr
         35                  40                  45

Cys Thr Phe Lys Glu Leu Val Tyr Glu Thr Val Arg Val Pro Gly Cys
     50                  55                  60
```

Ala His His Ala Asp Ser Leu Tyr Thr Tyr Pro Val Ala Thr Gln Cys
65                  70                  75                  80

His Cys

<210> SEQ ID NO 129
<211> LENGTH: 84
<212> TYPE: PRT
<213> ORGANISM: Homo sapiens

<400> SEQUENCE: 129

Cys Ile Pro Thr Glu Tyr Thr Met His Ile Glu Arg Arg Glu Cys Ala
1               5                   10                  15

Tyr Cys Leu Thr Ile Asn Thr Thr Ile Cys Ala Gly Tyr Cys Met Thr
                20                  25                  30

Arg Asp Ile Asn Gly Lys Leu Phe Leu Pro Lys Tyr Ala Leu Ser Gln
            35                  40                  45

Asp Val Cys Thr Tyr Arg Asp Phe Ile Tyr Arg Thr Val Glu Ile Pro
        50                  55                  60

Gly Cys Pro Leu His Val Ala Pro Tyr Phe Ser Tyr Pro Val Ala Leu
65                  70                  75                  80

Ser Cys Lys Cys

<210> SEQ ID NO 130
<211> LENGTH: 83
<212> TYPE: PRT
<213> ORGANISM: Homo sapiens

<400> SEQUENCE: 130

Cys Asn Asp Ile Thr Ala Arg Leu Gln Tyr Val Lys Val Gly Ser Cys
1               5                   10                  15

Lys Ser Glu Val Glu Val Asp Ile His Tyr Cys Gln Gly Lys Cys Ala
                20                  25                  30

Ser Lys Ala Met Tyr Ser Ile Asp Ile Asn Asp Val Gln Asp Gln Cys
            35                  40                  45

Ser Cys Cys Ser Pro Thr Arg Thr Glu Pro Met Gln Val Ala Leu His
        50                  55                  60

Cys Thr Asn Gly Ser Val Val Tyr His Glu Val Leu Asn Ala Met Glu
65                  70                  75                  80

Cys Lys Cys

<210> SEQ ID NO 131
<211> LENGTH: 80
<212> TYPE: PRT
<213> ORGANISM: Homo sapiens

<400> SEQUENCE: 131

Cys Ser Thr Val Pro Val Thr Thr Glu Val Ser Tyr Ala Gly Cys Thr
1               5                   10                  15

Lys Thr Val Leu Met Asn His Cys Ser Gly Ser Cys Gly Thr Phe Val
                20                  25                  30

Met Tyr Ser Ala Lys Ala Gln Ala Leu Asp His Ser Cys Ser Cys Cys
            35                  40                  45

Lys Glu Glu Lys Thr Ser Gln Arg Glu Val Val Leu Ser Cys Pro Asn
        50                  55                  60

Gly Gly Ser Leu Thr His Thr Tyr Thr His Ile Glu Ser Cys Gln Cys
65                  70                  75                  80

```
<210> SEQ ID NO 132
<211> LENGTH: 80
<212> TYPE: PRT
<213> ORGANISM: Homo sapiens

<400> SEQUENCE: 132

Cys Arg Thr Val Pro Phe Ser Gln Thr Ile Thr His Glu Gly Cys Glu
 1               5                  10                  15

Lys Val Val Gln Asn Asn Leu Cys Phe Gly Lys Cys Gly Ser Val
                20                  25                  30

His Phe Pro Gly Ala Ala Gln His Ser His Thr Ser Cys Ser His Cys
                35                  40                  45

Leu Pro Ala Lys Phe Thr Thr Met His Leu Pro Leu Asn Cys Thr Glu
        50                  55                  60

Leu Ser Ser Val Ile Lys Val Val Met Leu Val Glu Glu Cys Gln Cys
65                  70                  75                  80

<210> SEQ ID NO 133
<211> LENGTH: 85
<212> TYPE: PRT
<213> ORGANISM: Homo sapiens

<400> SEQUENCE: 133

Cys Lys Thr Gln Pro Leu Lys Gln Thr Ile His Glu Glu Gly Cys Asn
 1               5                  10                  15

Ser Arg Thr Ile Ile Asn Arg Phe Cys Tyr Gly Gln Cys Asn Ser Phe
                20                  25                  30

Tyr Ile Pro Arg His Ile Arg Lys Glu Glu Gly Ser Phe Gln Ser Cys
                35                  40                  45

Ser Phe Cys Lys Pro Lys Lys Phe Thr Thr Met Met Val Thr Leu Asn
        50                  55                  60

Cys Pro Glu Leu Gln Pro Pro Thr Lys Lys Arg Val Thr Arg Val
65                  70                  75                  80

Lys Gln Cys Arg Cys
                85

<210> SEQ ID NO 134
<211> LENGTH: 86
<212> TYPE: PRT
<213> ORGANISM: Homo sapiens

<400> SEQUENCE: 134

Cys Glu Ala Lys Asn Ile Thr Gln Ile Val Gly His Ser Gly Cys Glu
 1               5                  10                  15

Ala Lys Ser Ile Gln Asn Arg Ala Cys Leu Gly Gln Cys Phe Ser Tyr
                20                  25                  30

Ser Val Pro Asn Thr Phe Pro Gln Ser Thr Glu Ser Leu Val His Cys
                35                  40                  45

Asp Ser Cys Met Pro Ala Gln Ser Met Trp Glu Ile Val Thr Leu Glu
        50                  55                  60

Cys Pro Gly His Glu Glu Val Pro Arg Val Asp Lys Leu Val Glu Lys
65                  70                  75                  80

Ile Leu His Cys Ser Cys
                85

<210> SEQ ID NO 135
<211> LENGTH: 70
<212> TYPE: PRT
<213> ORGANISM: Homo sapies
```

<400> SEQUENCE: 135

Cys Ile Arg Thr Pro Lys Ile Ser Lys Pro Ile Lys Phe Glu Leu Ser
1               5                   10                  15

Gly Cys Thr Ser Met Lys Thr Tyr Arg Ala Lys Phe Cys Gly Val Cys
            20                  25                  30

Thr Asp Gly Arg Cys Cys Thr Pro His Arg Thr Thr Thr Leu Pro Val
        35                  40                  45

Glu Phe Lys Cys Pro Asp Gly Glu Val Met Lys Lys Asn Met Met Phe
    50                  55                  60

Ile Lys Thr Cys Ala Cys
65                  70

<210> SEQ ID NO 136
<211> LENGTH: 70
<212> TYPE: PRT
<213> ORGANISM: Homo sapiens

<400> SEQUENCE: 136

Cys Leu Arg Thr Lys Lys Ser Leu Lys Ala Ile His Leu Gln Phe Lys
1               5                   10                  15

Asn Cys Thr Ser Leu His Thr Tyr Lys Pro Arg Phe Cys Gly Val Cys
            20                  25                  30

Ser Asp Gly Arg Cys Cys Thr Pro His Asn Thr Lys Thr Ile Gln Ala
        35                  40                  45

Glu Phe Gln Cys Ser Pro Gly Gln Ile Val Lys Lys Pro Val Met Val
    50                  55                  60

Ile Gly Thr Cys Thr Cys
65                  70

<210> SEQ ID NO 137
<211> LENGTH: 70
<212> TYPE: PRT
<213> ORGANISM: Homo sapiens

<400> SEQUENCE: 137

Cys Ser Lys Thr Lys Lys Ser Pro Glu Pro Val Arg Phe Thr Tyr Ala
1               5                   10                  15

Gly Cys Leu Ser Val Lys Lys Tyr Arg Pro Lys Tyr Cys Gly Ser Cys
            20                  25                  30

Val Asp Gly Arg Cys Cys Thr Pro Gln Leu Thr Arg Thr Val Lys Met
        35                  40                  45

Arg Phe Arg Cys Glu Asp Gly Glu Thr Phe Ser Lys Asn Val Met Met
    50                  55                  60

Ile Gln Ser Cys Lys Cys
65                  70

<210> SEQ ID NO 138
<211> LENGTH: 205
<212> TYPE: PRT
<213> ORGANISM: Homo sapiens

<400> SEQUENCE: 138

Gln His Tyr Leu His Ile Arg Pro Ala Pro Ser Asp Asn Leu Pro Leu
1               5                   10                  15

Val Asp Leu Ile Glu His Pro Asp Pro Ile Phe Asp Pro Lys Glu Lys
            20                  25                  30

Asp Leu Asn Glu Thr Leu Leu Arg Ser Leu Leu Gly Gly His Tyr Asp

-continued

```
                35                  40                  45
Pro Gly Phe Met Ala Thr Ser Pro Pro Glu Asp Arg Pro Gly Gly Gly
 50                  55                  60

Gly Gly Ala Ala Gly Ala Glu Asp Leu Ala Glu Leu Asp Gln Leu
 65                  70                  75                  80

Leu Arg Gln Arg Pro Ser Gly Ala Met Pro Ser Glu Ile Lys Gly Leu
                 85                  90                  95

Glu Phe Ser Glu Gly Leu Ala Gln Gly Lys Lys Gln Arg Leu Ser Lys
                100                 105                 110

Lys Leu Arg Arg Lys Leu Gln Met Trp Leu Trp Ser Gln Thr Phe Cys
                115                 120                 125

Pro Val Leu Tyr Ala Trp Asn Asp Leu Gly Ser Arg Phe Trp Pro Arg
130                 135                 140

Tyr Val Lys Val Gly Ser Cys Phe Ser Lys Arg Ser Cys Ser Val Pro
145                 150                 155                 160

Glu Gly Met Val Cys Lys Pro Ser Lys Ser Val His Leu Thr Val Leu
                165                 170                 175

Arg Trp Arg Cys Gln Arg Arg Gly Gly Gln Arg Cys Gly Trp Ile Pro
                180                 185                 190

Ile Gln Tyr Pro Ile Ile Ser Glu Cys Lys Cys Ser Cys
                195                 200                 205

<210> SEQ ID NO 139
<211> LENGTH: 197
<212> TYPE: PRT
<213> ORGANISM: Gallus gallus

<400> SEQUENCE: 139

Gln His Tyr Leu His Ile Arg Pro Ala Pro Ser Asp Asn Leu Pro Leu
 1               5                  10                  15

Val Asp Leu Ile Glu His Pro Asp Pro Ile Phe Asp Pro Lys Glu Lys
                 20                  25                  30

Asp Leu Asn Glu Thr Leu Leu Arg Ser Leu Met Gly Gly His Phe Asp
             35                  40                  45

Pro Asn Phe Met Ala Met Ser Leu Pro Glu Asp Arg Leu Gly Val Asp
 50                  55                  60

Asp Leu Ala Glu Leu Asp Leu Leu Arg Gln Arg Pro Ser Gly Ala
 65                  70                  75                  80

Met Pro Gly Glu Ile Lys Gly Leu Glu Phe Tyr Asp Gly Leu Gln Pro
                 85                  90                  95

Gly Lys Lys His Arg Leu Ser Lys Lys Leu Arg Arg Lys Leu Gln Met
                100                 105                 110

Trp Leu Trp Ser Gln Thr Phe Cys Pro Val Leu Tyr Thr Trp Asn Asp
             115                 120                 125

Leu Gly Ser Arg Phe Trp Pro Arg Tyr Val Lys Val Gly Ser Cys Tyr
             130                 135                 140

Ser Lys Arg Ser Cys Ser Val Pro Glu Gly Met Val Cys Lys Pro Ala
145                 150                 155                 160

Lys Ser Val His Leu Thr Ile Leu Arg Trp Arg Cys Gln Arg Arg Gly
                165                 170                 175

Gly Gln Arg Cys Thr Trp Ile Pro Ile Gln Tyr Pro Ile Ile Ala Glu
                180                 185                 190

Cys Lys Cys Ser Cys
            195
```

```
<210> SEQ ID NO 140
<211> LENGTH: 196
<212> TYPE: PRT
<213> ORGANISM: Xenopus laevis

<400> SEQUENCE: 140

Gln His Tyr Leu His Ile Arg Pro Ala Pro Ser Glu Asn Leu Pro Leu
1               5                   10                  15

Val Asp Leu Ile Glu His Pro Asp Pro Ile Tyr Asp Pro Lys Glu Lys
            20                  25                  30

Asp Leu Asn Glu Thr Leu Leu Arg Thr Leu Met Val Gly His Phe Asp
        35                  40                  45

Pro Asn Phe Met Ala Thr Ile Leu Pro Glu Glu Arg Leu Gly Val Glu
    50                  55                  60

Asp Leu Gly Glu Leu Asp Leu Leu Arg Gln Lys Pro Ser Gly Ala
65                  70                  75                  80

Met Pro Ala Glu Ile Lys Gly Leu Glu Phe Tyr Glu Gly Leu Gln Ser
                85                  90                  95

Lys Lys His Arg Leu Ser Lys Lys Leu Arg Arg Lys Leu Gln Met Trp
            100                 105                 110

Leu Trp Ser Gln Thr Phe Cys Pro Val Leu Tyr Thr Trp Asn Asp Leu
        115                 120                 125

Gly Thr Arg Phe Trp Pro Arg Tyr Val Lys Val Gly Ser Cys Tyr Ser
    130                 135                 140

Lys Arg Ser Cys Ser Val Pro Glu Gly Met Val Cys Lys Ala Ala Lys
145                 150                 155                 160

Ser Met His Leu Thr Ile Leu Arg Trp Arg Cys Gln Arg Arg Val Gln
                165                 170                 175

Gln Lys Cys Ala Trp Ile Thr Ile Gln Tyr Pro Val Ile Ser Glu Cys
            180                 185                 190

Lys Cys Ser Cys
        195

<210> SEQ ID NO 141
<211> LENGTH: 195
<212> TYPE: PRT
<213> ORGANISM: Takifugu rubripes

<400> SEQUENCE: 141

Gln Pro Tyr Tyr Leu Leu Arg Pro Ile Pro Ser Asp Ser Leu Pro Ile
1               5                   10                  15

Val Glu Leu Lys Glu Asp Pro Gly Pro Val Phe Asp Pro Lys Glu Arg
            20                  25                  30

Asp Leu Asn Glu Thr Glu Leu Lys Ser Val Leu Gly Asp Phe Asp Ser
        35                  40                  45

Arg Phe Leu Ser Val Leu Pro Ala Glu Asp Gly His Ala Gly Asn
    50                  55                  60

Asp Glu Leu Asp Asp Phe Asp Ala Gln Arg Trp Gly Ala Leu Pro
65                  70                  75                  80

Lys Glu Ile Arg Ala Val Asp Phe Asp Ala Pro Gln Leu Gly Lys Lys
                85                  90                  95

His Lys Pro Ser Lys Lys Leu Lys Arg Arg Leu Gln Gln Trp Leu Trp
            100                 105                 110

Ala Tyr Ser Phe Cys Pro Leu Ala His Ala Trp Thr Asp Leu Gly Ser
        115                 120                 125
```

```
Arg Phe Trp Pro Arg Phe Val Arg Ala Gly Ser Cys Leu Ser Lys Arg
    130                 135                 140

Ser Cys Ser Val Pro Glu Gly Met Thr Cys Lys Pro Ala Thr Ser Thr
145                 150                 155                 160

His Leu Thr Ile Leu Arg Trp Arg Cys Val Gln Arg Lys Val Gly Leu
                165                 170                 175

Lys Cys Ala Trp Ile Pro Met Gln Tyr Pro Val Ile Thr Asp Cys Lys
                180                 185                 190

Cys Ser Cys
        195

<210> SEQ ID NO 142
<211> LENGTH: 196
<212> TYPE: PRT
<213> ORGANISM: Danio rerio

<400> SEQUENCE: 142

Gln His Tyr Tyr Leu Leu Arg Pro Ile Pro Ser Asp Ser Leu Pro Ile
1               5                   10                  15

Val Glu Leu Lys Glu Asp Pro Asp Pro Val Leu Asp Pro Lys Glu Arg
                20                  25                  30

Asp Leu Asn Glu Thr Glu Leu Arg Ala Ile Leu Gly Ser His Phe Glu
            35                  40                  45

Gln Asn Phe Met Ser Ile Asn Pro Pro Glu Asp Lys His Ala Gly Gln
        50                  55                  60

Asp Glu Leu Asn Glu Ser Glu Leu Met Lys Gln Arg Pro Asn Gly Ile
65                  70                  75                  80

Met Pro Lys Glu Ile Lys Ala Met Glu Phe Asp Ile Gln His Gly Lys
                85                  90                  95

Lys His Lys Pro Ser Lys Lys Leu Arg Arg Arg Leu Gln Leu Trp Leu
                100                 105                 110

Trp Ser Tyr Thr Phe Cys Pro Val His Thr Trp Gln Asp Leu Gly
                115                 120                 125

Asn Arg Phe Trp Pro Arg Tyr Leu Lys Val Gly Ser Cys Tyr Asn Lys
    130                 135                 140

Arg Ser Cys Ser Val Pro Glu Gly Met Val Cys Lys Pro Pro Lys Ser
145                 150                 155                 160

Ser His Leu Thr Val Leu Arg Trp Arg Cys Val Gln Arg Lys Gly Gly
                165                 170                 175

Leu Lys Cys Ala Trp Ile Pro Val Gln Tyr Pro Val Ile Ser Glu Cys
                180                 185                 190

Lys Cys Ser Cys
        195

<210> SEQ ID NO 143
<211> LENGTH: 188
<212> TYPE: PRT
<213> ORGANISM: Mus musculus

<400> SEQUENCE: 143

Gln Gly Trp Gln Ala Phe Arg Asn Asp Ala Thr Glu Val Ile Pro Gly
1               5                   10                  15

Leu Gly Glu Tyr Pro Glu Pro Pro Glu Asn Asn Gln Thr Met Asn
                20                  25                  30

Arg Ala Glu Asn Gly Gly Arg Pro Pro His His Pro Tyr Asp Ala Lys
            35                  40                  45
```

-continued

```
Gly Val Ser Glu Tyr Ser Cys Arg Glu Leu His Tyr Thr Arg Phe Leu
    50              55                  60
Thr Asp Gly Pro Cys Arg Ser Ala Lys Pro Val Thr Glu Leu Val Cys
65              70                  75                  80
Ser Gly Gln Cys Gly Pro Ala Arg Leu Leu Pro Asn Ala Ile Gly Arg
            85                  90                  95
Val Lys Trp Trp Arg Pro Asn Gly Pro Asp Phe Arg Cys Ile Pro Asp
            100                 105                 110
Arg Tyr Arg Ala Gln Arg Val Gln Leu Leu Cys Pro Gly Gly Ala Ala
        115             120                 125
Pro Arg Ser Arg Lys Val Arg Leu Val Ala Ser Cys Lys Cys Lys Arg
    130             135                 140
Leu Thr Arg Phe His Asn Gln Ser Glu Leu Lys Asp Phe Gly Pro Glu
145             150                 155                 160
Thr Ala Arg Pro Gln Lys Gly Arg Lys Pro Arg Pro Gly Ala Arg Gly
            165                 170                 175
Ala Lys Ala Asn Gln Ala Glu Leu Glu Asn Ala Tyr
            180                 185
```

ANTIBODIES SPECIFIC FOR SCLEROSTIN

CROSS-REFERENCE TO RELATED APPLICATIONS

This application is a continuation of U.S. application Ser. No. 10/463,190, filed (filed Jun. 16, 2003). The contents of the application is incorporated herein by reference in its entirety.

TECHNICAL FIELD

The present invention relates generally to pharmaceutical products and methods and, more specifically, to methods and compositions suitable for increasing the mineral content of bone. Such compositions and methods may be utilized to treat a wide variety of conditions, including for example, osteopenia, osteoporosis, fractures and other disorders in which low bone mineral density are a hallmark of the disease.

BACKGROUND OF THE INVENTION

Two or three distinct phases of changes to bone mass occur over the life of an individual (see Riggs, *West J. Med.* 154: 63-77, 1991). The first phase occurs in both men and women, and proceeds to attainment of a peak bone mass. This first phase is achieved through linear growth of the endochondral growth plates, and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss, and occurs in both men and women. In women, a third phase of bone loss also occurs, most likely due to postmenopausal estrogen deficiencies. During this phase alone, women may lose an additional 10% of bone mass from the cortical bone and 25% from the trabecular compartment (see Riggs, supra).

Loss of bone mineral content can be caused by a wide variety of conditions, and may result in significant medical problems. For example, osteoporosis is a debilitating disease in humans characterized by marked decreases in skeletal bone mass and mineral density, structural deterioration of bone including degradation of bone microarchitecture and corresponding increases in bone fragility and susceptibility to fracture in afflicted individuals. Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing tens of billions of dollars annually in the United States. In addition to health care-related costs, long-term residential care and lost working days add to the financial and social costs of this disease. Worldwide approximately 75 million people are at risk for osteoporosis.

The frequency of osteoporosis in the human population increases with age, and among Caucasians is predominant in women (who comprise 80% of the osteoporosis patient pool in the United States). The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Although osteoporosis has been defined as an increase in the risk of fracture due to decreased bone mass, none of the presently available treatments for skeletal disorders can substantially increase the bone density of adults. There is a strong perception among all physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity (particularly in weight-bearing activities) with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer.

High doses of dietary calcium, with or without vitamin D has also been suggested for postmenopausal women. However, high doses of calcium can often have unpleasant gastrointestinal side effects, and serum and urinary calcium levels must be continuously monitored (see Khosla and Rigss, *Mayo Clin. Proc.* 70:978-982, 1995).

Other therapeutics which have been suggested include calcitonin, bisphosphonates, anabolic steroids and sodium fluoride. Such therapeutics however, have undesirable side effects (e.g., calcitonin and steroids may cause nausea and provoke an immune reaction, bisphosphonates and sodium fluoride may inhibit repair of fractures, even though bone density increases modestly) that may prevent their usage (see Khosla and Rigss, supra).

No currently practiced therapeutic strategy involves a drug that stimulates or enhances the growth of new bone mass. The present invention provides compositions and methods which can be utilized to increase bone mineralization, and thus may be utilized to treat a wide variety of conditions where it is desired to increase bone mass. Further, the present invention provides other, related advantages.

SUMMARY OF THE INVENTION

As noted above, the present invention provides a novel class or family of TGF-beta binding-proteins, as well as assays for selecting compounds which increase bone mineral content and bone mineral density, compounds which increase bone mineral content and bone mineral density and methods for utilizing such compounds in the treatment or prevention of a wide variety of conditions.

Within one aspect of the present invention, isolated nucleic acid molecules are provided, wherein said nucleic acid molecules are selected from the group consisting of: (a) an isolated nucleic acid molecule comprising sequence ID Nos. 1, 5, 7, 9, 11, 13, or, 15, or complementary sequence thereof; (b) an isolated nucleic acid molecule that specifically hybridizes to the nucleic acid molecule of (a) under conditions of high stringency; and (c) an isolated nucleic acid that encodes a TGF-beta binding-protein according to (a) or (b). Within related aspects of the present invention, isolated nucleic acid molecules are provided based upon hybridization to only a portion of one of the above-identified sequences (e.g., for (a) hybridization may be to a probe of at least 20, 25, 50, or 100 nucleotides selected from nucleotides 156 to 539 or 555 to 687 of Sequence ID No. 1). As should be readily evident, the necessary stringency to be utilized for hybridization may vary based upon the size of the probe. For example, for a 25-mer probe high stringency conditions could include: 60 mM Tris pH 8.0, 2 mM EDTA, 5× Denhardt's, 6×SSC, 0.1% (w/v) N-laurylsarcosine, 0.5% (w/v) NP-40 (nonidet P-40) overnight at 45 degrees C., followed by two washes with 0.2× SSC/0.1% SDS at 45-50 degrees. For a 100-mer probe under low stringency conditions, suitable conditions might include the following: 5×SSPE, 5× Denhardt's, and 0.5% SDS overnight at 42-50 degrees, followed by two washes with 2×SSPE (or 2×SSC)/0.1% SDS at 42-50 degrees.

Within related aspects of the present invention, isolated nucleic acid molecules are provided which have homology to Sequence ID Nos. 1, 5, 7, 9, 11, 13, or 15, at a 50%, 60%, 75%, 80%, 90%, 95%, or 98% level of homology utilizing a Wilbur-Lipman algorithm. Representative examples of such isolated molecules include, for example, nucleic acid molecules which encode a protein comprising Sequence ID NOs. 2, 6, 10, 12, 14, or 16, or have homology to these sequences at a level of 50%, 60%, 75%, 80%, 90%, 95%, or 98% level of homology utilizing a Lipman-Pearson algorithm.

Isolated nucleic acid molecules are typically less than 100 kb in size, and, within certain embodiments, less than 50 kb, 25 kb, 10 kb, or even 5 kb in size. Further, isolated nucleic acid molecules, within other embodiments, do not exist in a "library" of other unrelated nucleic acid molecules (e.g., a subclone BAC such as described in GenBank Accession No. AC003098 and EMB No. AQ171546). However, isolated nucleic acid molecules can be found in libraries of related molecules (e.g., for shuffling, such as is described in U.S. Pat. Nos. 5,837,458; 5,830,721; and 5,811,238). Finally, isolated nucleic acid molecules as described herein do not include nucleic acid molecules which encode Dan, Cerberus, Gremlin, or SCGF (U.S. Pat. No. 5,780,263).

Also provided by the present invention are cloning vectors which contain the above-noted nucleic acid molecules, and expression vectors which comprise a promoter (e.g., a regulatory sequence) operably linked to one of the above-noted nucleic acid molecules. Representative examples of suitable promoters include tissue-specific promoters, and viral-based promoters (e.g., CMV-based promoters such as CMV I-E, SV40 early promoter, and MuLV LTR). Expression vectors may also be based upon, or derived from viruses (e.g., a "viral vector"). Representative examples of viral vectors include herpes simplex viral vectors, adenoviral vectors, adenovirus-associated viral vectors and retroviral vectors. Also provided are host cells containing or comprising any of above-noted vectors (including for example, host cells of human, monkey, dog, rat, or mouse origin).

Within other aspects of the present invention, methods of producing TGF-beta binding-proteins are provided, comprising the step of culturing the aforementioned host cell containing vector under conditions and for a time sufficient to produce the TGF-beta binding protein. Within further embodiments, the protein produced by this method may be further purified (e.g., by column chromatography, affinity purification, and the like). Hence, isolated proteins which are encoded by the above-noted nucleic acid molecules (e.g., Sequence ID NOs. 2, 4, 6, 8, 10, 12, 14, or 16) may be readily produced given the disclosure of the subject application.

It should also be noted that the aforementioned proteins, or fragments thereof, may be produced as fusion proteins. For example, within one aspect fusion proteins are provided comprising a first polypeptide segment comprising a TGF-beta binding-protein encoded by a nucleic acid molecule as described above, or a portion thereof of at least 10, 20, 30, 50, or 100 amino acids in length, and a second polypeptide segment comprising a non-TGF-beta binding-protein. Within certain embodiments, the second polypeptide may be a tag suitable for purification or recognition (e.g., a polypeptide comprising multiple anionic amino acid residues—see U.S. Pat. No. 4,851,341), a marker (e.g., green fluorescent protein, or alkaline phosphatase), or a toxic molecule (e.g., ricin).

Within another aspect of the present invention, antibodies are provided which are capable of specifically binding the above-described class of TGF-beta binding proteins (e.g., human BEER). Within various embodiments, the antibody may be a polyclonal antibody, or a monoclonal antibody (e.g., of human or murine origin). Within further embodiments, the antibody is a fragment of an antibody which retains the binding characteristics of a whole antibody (e.g., an F(ab')$_2$, F(ab)$_2$, Fab', Fab, or Fv fragment, or even a CDR). Also provided are hybridomas and other cells which are capable of producing or expressing the aforementioned antibodies.

Within related aspects of the invention, methods are provided detecting a TGF-beta binding protein, comprising the steps of incubating an antibody as described above under conditions and for a time sufficient to permit said antibody to bind to a TGF-beta binding protein, and detecting the binding. Within various embodiments the antibody may be bound to a solid support to facilitate washing or separation, and/or labeled. (e.g., with a marker selected from the group consisting of enzymes, fluorescent proteins, and radioisotopes).

Within other aspects of the present invention, isolated oligonucleotides are provided which hybridize to a nucleic acid molecule according to Sequence ID NOs. 1, 3, 5, 7, 9, 11, 13, 15, 17, or 18 or the complement thereto, under conditions of high stringency. Within further embodiments, the oligonucleotide may be found in the sequence which encodes Sequence ID Nos. 2, 4, 6, 8, 10, 12, 14, or 16. Within certain embodiments, the oligonucleotide is at least 15, 20, 30, 50, or 100 nucleotides in length. Within further embodiments, the oligonucleotide is labeled with another molecule (e.g., an enzyme, fluorescent molecule, or radioisotope). Also provided are primers which are capable of specifically amplifying all or a portion of the above-mentioned nucleic acid molecules which encode TGF-beta binding-proteins. As utilized herein, the term "specifically amplifying" should be understood to refer to primers which amplify the aforementioned TGF-beta binding-proteins, and not other TGF-beta binding proteins such as Dan, Cerberus, Gremlin, or SCGF (U.S. Pat. No. 5,780,263).

Within related aspects of the present invention, methods are provided for detecting a nucleic acid molecule which encodes a TGF-beta binding protein, comprising the steps of incubating an oligonucleotide as described above under conditions of high stringency, and detecting hybridization of said oligonucleotide. Within certain embodiments, the oligonucleotide may be labeled and/or bound to a solid support.

Within other aspects of the present invention, ribozymes are provided which are capable of cleaving RNA which encodes one of the above-mentioned TGF-beta binding-proteins (e.g., Sequence ID NOs. 2, 6, 8, 10, 12, 14, or 16). Such ribozymes may be composed of DNA, RNA (including 2'-O-methyl ribonucleic acids), nucleic acid analogs (e.g., nucleic acids having phosphorothioate linkages) or mixtures thereof. Also provided are nucleic acid molecules (e.g., DNA or cDNA) which encode these ribozymes, and vectors which are capable of expressing or producing the ribozymes. Representative examples of vectors include plasmids, retrotransposons, cosmids, and viral-based vectors (e.g., viral vectors generated at least in part from a retrovirus, adenovirus, or, adeno-associated virus). Also provided are host cells (e.g., human, dog, rat, or mouse cells) which contain these vectors. In certain embodiments, the host cell may be stably transformed with the vector.

Within further aspects of the invention, methods are provided for producing ribozymes either synthetically, or by in vitro or in vivo transcription. Within further embodiments, the ribozymes so produced may be further purified and/or formulated into pharmaceutical compositions (e.g., the ribozyme or nucleic acid molecule encoding the ribozyme along with a pharmaceutically acceptable carrier or diluent). Similarly, the antisense oligonucleotides and antibodies or other selected molecules described herein may be formulated into pharmaceutical compositions.

Within other aspects of the present invention, antisense oligonucleotides are provided comprising a nucleic acid molecule which hybridizes to a nucleic acid molecule according to Sequence ID NOs. 1, 3, 5, 7, 9, 11, 13, or 15, or the complement thereto, and wherein said oligonucleotide inhibits the expression of TGF-beta binding protein as described herein (e.g., human BEER). Within various embodiments, the oligonucleotide is 15, 20, 25, 30, 35, 40, or 50 nucleotides in length. Preferably, the oligonucleotide is less than 100, 75, or 60 nucleotides in length. As should be readily evident, the oligonucleotide may be comprised of one or more nucleic acid analogs, ribonucleic acids, or deoxyribonucleic acids. Further, the oligonucleotide may be modified by one or more linkages, including for example, covalent linkage such as a phosphorothioate linkage, a phosphotriester linkage, a methyl phosphonate linkage, a methylene(methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage. One representative example of a chimeric oligonucleotide is provied in U.S. Pat. No. 5,989,912.

Within yet another aspect of the present invention, methods are provided for increasing bone mineralization, comprising introducing into a warm-blooded animal an effective amount of the ribozyme as described above. Within related aspects, such methods comprise the step of introducing into a patient an effective amount of the nucleic acid molecule or vector as described herein which is capable of producing the desired ribozyme, under conditions favoring transcription of the nucleic acid molecule to produce the ribozyme.

Within other aspects of the invention transgenic, non-human animals are provided. Within one embodiment a transgenic animal is provided whose germ cells and somatic cells contain a nucleic acid molecule encoding a TGF-beta binding-protein as described above which is operably linked to a promoter effective for the expression of the gene, the gene being introduced into the animal, or an ancestor of the animal, at an embryonic stage, with the proviso that said animal is not a human. Within other embodiments, transgenic knockout animals are provided, comprising an animal whose germ cells and somatic cells comprise a disruption of at least one allele of an endogenous nucleic acid molecule which hybridizes to a nucleic acid molecule which encodes a TGF-binding protein as described herein, wherein the disruption prevents transcription of messenger RNA from said allele as compared to an animal without the disruption, with the proviso that the animal is not a human. Within various embodiments, the disruption is a nucleic acid deletion, substitution, or, insertion. Within other embodiments the transgenic animal is a mouse, rat, sheep, pig, or dog.

Within further aspects of the invention, kits are provided for the detection of TGF-beta binding-protein gene expression, comprising a container that comprises a nucleic acid molecule, wherein the nucleic acid molecule is selected from the group consisting of (a) a nucleic acid molecule comprising the nucleotide sequence of SEQ ID NOs: 1, 3, 5, 7, 9, 11, 13, 15, 100, or 101; (b) a nucleic acid molecule comprising the complement of the nucleotide sequence of (a); (c) a nucleic acid molecule that is a fragment of (a) or (b) of at least 15, 20, 30, 50, 75, or, 100 nucleotides in length. Also provided are kits for the detection of a TGF-beta binding-protein which comprise a container that comprise one of the TGF-beta binding protein antibodies described herein.

For example, within one aspect of the present invention methods are provided for determining whether a selected molecule is capable of increasing bone mineral content, comprising the steps of (a) mixing one or more candidate molecules with TGF-beta-binding-protein encoded by the nucleic acid molecule according to claim 1 and a selected member of the TGF-beta family of proteins (e.g., BMP 5 or 6), (b) determining whether the candidate molecule alters the signaling of the TGF-beta family member, or alters the binding of the TGF-beta binding-protein to the TGF-beta family member. Within certain embodiments, the molecule alters the ability of TGF-beta to function as a positive regulator of mesenchymal cell differentiation. Within this aspect of the present invention, the candidate molecule(s) may alter signaling or binding by, for example, either decreasing (e.g., inhibiting), or increasing (e.g. enhancing) signaling or binding.

Within yet another aspect, methods are provided for determining whether a selected molecule is capable of increasing bone mineral content, comprising the step of determining whether a selected molecule inhibits the binding of TGF-beta binding-protein to bone, or an analogue thereof. Representative examples of bone or analogues thereof include hydroxyapatite and primary human bone samples obtained via biopsy.

Within certain embodiments of the above-recited methods, the selected molecule is contained within a mixture of molecules and the methods may further comprise the step of isolating one or more molecules which are functional within the assay. Within yet other embodiments, TGF-beta family of proteins is bound to a solid support and the binding of TGF-beta binding-protein is measured or TGF-beta binding-protein are bound to a solid support and the binding of TGF-beta proteins are measured.

Utilizing methods such as those described above, a wide variety of molecules may be assayed for their ability to increase bone mineral content by inhibiting the binding of the TGF-beta binding-protein to the TGF-beta family of proteins. Representative examples of such molecules include proteins or peptides, organic molecules, and nucleic acid molecules.

Within other related aspects of the invention, methods are provided for increasing bone mineral content in a warm-blooded animal, comprising the step of administering to a warm-blooded animal a therapeutically effective amount of a molecule identified from the assays recited herein. Within another aspect, methods are provided for increasing bone mineral content in a warm-blooded animal, comprising the step of administering to a warm-blooded animal a therapeutically effective amount of a molecule which inhibits the binding of the TGF-beta binding-protein to the TGF-beta super-family of proteins, including bone morphogenic proteins (BMPs). Representative examples of suitable molecules include antisense molecules, ribozymes, ribozyme genes, and antibodies (e.g., a humanized antibody) which specifically recognize and alter the activity of the TGF-beta binding-protein.

Within another aspect of the present invention, methods are provided for increasing bone mineral content in a warm-blooded animal, comprising the steps of (a) introducing into cells which home to the bone a vector which directs the expression of a molecule which inhibits the binding of the TGF-beta binding-protein to the TGF-beta family of proteins and bone morphogenic proteins (BMPs), and (b) administering the vector-containing cells to a warm-blooded animal. As utilized herein, it should be understood that cells "home to bone" if they localize within the bone matrix after peripheral administration. Within one embodiment, such methods further comprise, prior to the step of introducing, isolating cells from the marrow of bone which home to the bone. Within a further embodiment, the cells which home to bone are selected from the group consisting of CD34+ cells and osteoblasts.

Within other aspects of the present invention, molecules are provided (preferably isolated) which inhibit the binding of the TGF-beta binding-protein to the TGF-beta super-family of proteins.

Within further embodiments, the molecules may be provided as a composition, and can further comprise an inhibitor of bone resorption. Representative examples of such inhibitors include calcitonin, estrogen, a bisphosphonate, a growth factor having anti-resorptive activity and tamoxifen.

Representative examples of molecules which may be utilized in the aforementioned therapeutic contexts include, e.g., ribozymes, ribozyme genes, antisense molecules, and/or antibodies (e.g., humanized antibodies). Such molecules may depending upon their selection, used to alter, antagonize, or agonize the signalling or binding of a TGF-beta binding-protein family member as described herein Within various embodiments of the invention, the above-described molecules and methods of treatment or prevention may be utilized on conditions such as osteoporosis, osteomalasia, periodontal disease, scurvy, Cushing's Disease, bone fracture and conditions due to limb immobilization and steroid usage.

The present invention also provides antibodies that specifically bind to a TGF-beta binding protein, sclerostin (SOST), and provides immunogens comprising sclerostin peptides derived from regions of sclerostin that interact with a member of the TGF-beta superfamily such as a bone morphogenic protein. In one embodiment, the invention provides an antibody, or an antigen-binding fragment thereof, that binds specifically to a sclerostin polypeptide, said sclerostin polypeptide comprising an amino acid sequence set forth in SEQ ID NO:2, 6, 8, 14, 46, or 65, wherein the antibody competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide comprising an amino acid sequence set forth in GenBank Acc. Nos. NM_004329 (SEQ ID NO:102); D89675 (SEQ ID NO:103); NM_001203 (SEQ ID NO:104); S75359 (SEQ ID NO:105); NM_030849 (SEQ ID NO:106); D38082 (SEQ ID NO:107); NP_001194 (SEQ ID NO:108); BAA19765 (SEQ ID NO:109); or AAB33865 (SEQ ID NO:110) and wherein the BMP Type II Receptor binding site is capable of binding to a BMP Type II Receptor polypeptide comprising the amino acid sequence set forth in GenBank Acc. NOs. U25110 (SEQ ID NO:111); NM_033346 (SEQ ID NO:112); Z48923 (SEQ ID NO:114); CAA88759 (SEQ ID NO:115); or NM_001204 (SEQ ID NO:113). In another embodiment, the invention provides an antibody, or an antigen-binding fragment thereof, that binds specifically to a sclerostin polypeptide and that impairs formation of a sclerostin homodimer, wherein the sclerostin polypeptide comprises an amino acid sequence set forth in SEQ ID NOs: 2, 6, 8, 14, 46, or 65.

In certain particular embodiments of the invention, the antibody is a polygonal antibody. In other embodiments, the antibody is a monoclonal antibody, which is a mouse, human, rat, or hamster monoclonal antibody. The invention also provides a hybridoma cell or a host cell that is capable of producing the monoclonal antibody. In other embodiments of the invention, the antibody is a humanized antibody or a chimeric antibody. The invention further provides a host cell that produces the humanized or chimeric antibody. In certain embodiments the antigen-binding fragment of the antibody is a F(ab')$_2$, Fab', Fab, Fd, or Fv fragment. The invention also provides an antibody that is a single chain antibody and provides a host cell that is capable of expressing the single chain antibody. In another embodiment, the invention provides a composition comprising such antibodies and a physiologically acceptable carrier.

In another embodiment, the invention provides an immunogen comprising a peptide comprising at least 21 consecutive amino acids and no more than 50 consecutive amino acids of a SOST polypeptide, said SOST polypeptide comprising an amino acid sequence set forth in SEQ ID NOs: 2, 6, 8, 14, 46, or 65, wherein the peptide is capable of eliciting in a non-human animal an antibody that binds specifically to the SOST polypeptide and that competitively inhibits binding of the SOST polypeptide to at least one of (i) a bone morphogenic protein (BMP) Type I Receptor binding site and (ii) a BMP Type II Receptor binding site, wherein the BMP Type I Receptor binding site is capable of binding to a BMP Type I Receptor polypeptide comprising an amino acid sequence set forth in GenBank Acc. Nos. NM_004329 (SEQ ID NO:102); D89675 (SEQ ID NO:103); NM_001203 (SEQ ID NO:104); S75359 (SEQ ID NO:105); NM_030849 (SEQ ID NO:106); D38082 (SEQ ID NO:107); NP_001194 (SEQ ID NO:108); BAA19765 (SEQ ID NO:109); or AAB33865 (SEQ ID NO:110) and wherein the BMP Type II Receptor binding site is capable of binding to a BMP Type II Receptor polypeptide comprising the amino acid sequence set forth in GenBank Acc. NOs. U25110 (SEQ ID NO:111); NM_033346 (SEQ ID NO:112); Z48923 (SEQ ID NO:114); CAA88759 (SEQ ID NO:115); or NM_001204 (SEQ ID NO:113). The invention also provides an immunogen comprising a peptide that comprises at least 21 consecutive amino acids and no more than 50 consecutive amino acids of a SOST polypeptide, said SOST polypeptide comprising an amino acid sequence set forth in SEQ ID NO: 2, 6, 8, 14, 46, or 65, wherein the peptide is capable of eliciting in a non-human animal an antibody that binds specifically to the SOST polypeptide and that impairs formation of a SOST homodimer.

In certain particular embodiments, the subject invention immunogens are associated with a carrier molecule. In certain embodiments, the carrier molecule is a carrier polypeptide, and in particular embodiments, the carrier polypeptide is keyhole limpet hemocyanin.

The invention also provides a method for producing an antibody that specifically binds to a SOST polypeptide, comprising immunizing a non-human animal with an immunogen comprising a peptide comprising at least 21 consecutive amino acids and no more than 50 consecutive amino acids of a SOST polypeptide, wherein (a) the SOST polypeptide comprises an amino acid sequence set forth in SEQ ID NO: 2, 6, 8, 14, 46, or 65; (b) the antibody competitively inhibits binding of the SOST polypeptide to at least one of (i) a bone morphogenic protein (BMP) Type I Receptor binding site and (ii) a BMP Type II Receptor binding site; (c) the BMP Type I Receptor binding site is capable of binding to a BMP Type I Receptor polypeptide comprising the amino acid sequence set forth in GenBank Acc. Nos. NM_004329 (SEQ ID NO:102); D89675 (SEQ ID NO:103); NM_001203 (SEQ ID NO:104); S75359 (SEQ ID NO:105); NM_030849 (SEQ ID NO:106); D38082 (SEQ ID NO:107); NP_001194 (SEQ ID NO:108); BAA19765 (SEQ ID NO:109); or AAB33865 (SEQ ID NO:110); and (d) the BMP Type II Receptor binding site is capable of binding to a BMP Type II Receptor polypeptide comprising the amino acid sequence set forth in GenBank Acc. NOs. U25110 (SEQ ID NO:111); NM_033346 (SEQ ID NO:112); Z48923 (SEQ ID NO:114); CAA88759 (SEQ ID NO:115); or NM_001204 (SEQ ID NO:113).

In another embodiment, the invention provides a method for producing an antibody that specifically binds to a SOST polypeptide, said SOST polypeptide comprising an amino acid sequence set forth in SEQ ID NO: 2, 6, 8, 14, 46, or 65; comprising immunizing a non-human animal with an immunogen comprising a peptide that comprises at least 21 consecutive amino acids and no more than 50 consecutive amino acids of a SOST polypeptide, said SOST polypeptide comprising an amino acid sequence set forth in SEQ ID NO: 2, 6, 8, 14, 46, or 65, wherein the antibody impairs formation of a SOST homodimer.

These and other aspects of the present invention will become evident upon reference to the following detailed description and attached drawings. In addition, documents including various references set forth herein that describe in more detail certain procedures or compositions (e.g., plasmids, etc.), are incorporated by reference in their entirety.

BRIEF DESCRIPTION OF THE DRAWINGS

FIG. 1 is a schematic illustration comparing the amino acid sequence of Human Dan; Human Gremlin; Human Cerberus and Human Beer. Arrows indicate the Cysteine backbone.

FIG. 4A shows specific reactivity of an anti-H. Beer antibody for H. Beer antigen, but not H. Dan or H. Gremlin. FIG. 4B shows reactivity of an anti-H. Gremlin antibody for H. Gremlin antigen, but not H. Beer or H. Dan. FIG. 4C shows reactivity of an anti-H. Dan antibody for H. Dan, but not H. Beer or H. Gremlin.

FIG. 6 demonstrates that the ionic interaction between the TGF-beta binding-protein, Beer, and BMP-5 has a dissociation constant in the 15-30 nM range.

FIGS. 10A and 10B provide an amino acid sequence alignment of Noggin from five different animals: human (NOGG_HUMAN (SEQ ID NO:138); chicken (NOGG_CHICK, SEQ ID NO:139); African clawed frog (NOGG_XENLA, SEQ ID NO:140); NOGG_FUGRU, SEQ ID NO:141); and zebrafish (NOGG_ZEBRA, SEQ ID NO:142); and SOST from human (SOST_HUMAN, SEQ ID NO:46), rat (SOST_RAT, SEQ ID NO:65), and mouse (SOST_Mouse, SEQ ID NO:143).

DETAILED DESCRIPTION OF THE INVENTION

Definitions

Figure 2:
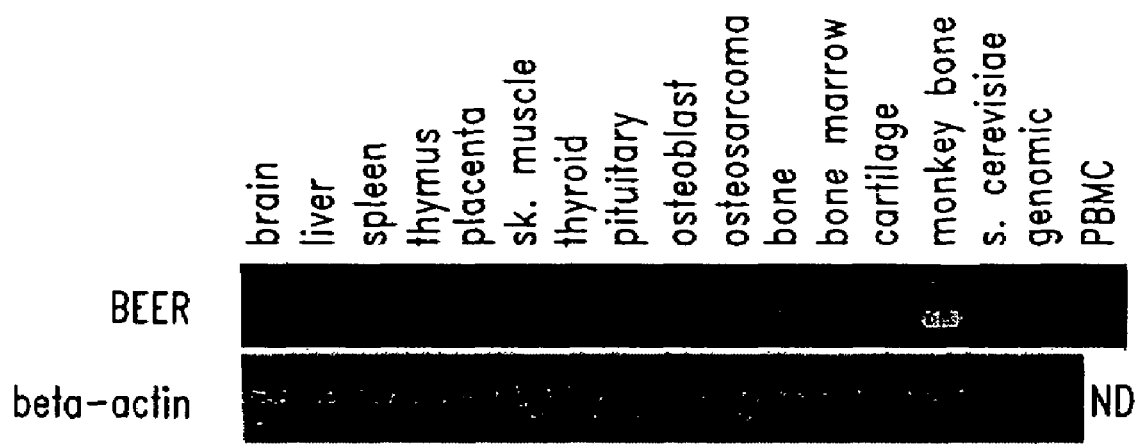
FIG. 2 summarizes the results obtained from surveying a variety of human tissues for the expression of a TGF-beta binding-protein gene, specifically, the Human Beer gene. A semi-quantitative Reverse Transcription-Polymerase Chain Reaction (RT-PCR) procedure was used to amplify a portion of the gene from first-strand cDNA synthesized from total RNA (described in more detail in EXAMPLE 2A).
Figure 3B:
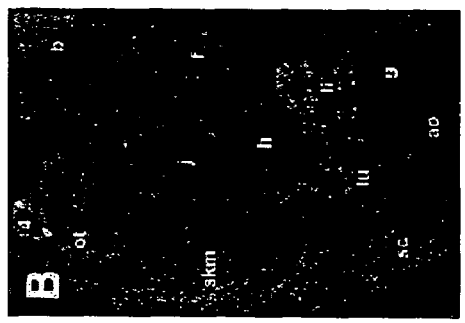
FIGS. 3A-3D summarize the results obtained from RNA in situ hybridization of mouse embryo sections, using a cRNA probe that is complementary to the mouse Beer transcript (described in more detail in EXAMPLE 2B). Panel 3A is a transverse section of 10.5 dpc embryo. Panel 3B is a sagittal section of 12.5 dpc embryo and panels 3C and 3D are sagittal sections of 15.5 dpc embryos.
Figure 3A:
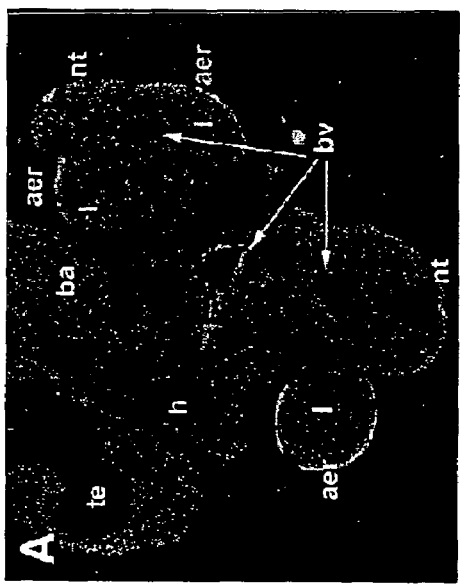
Figure 3D:
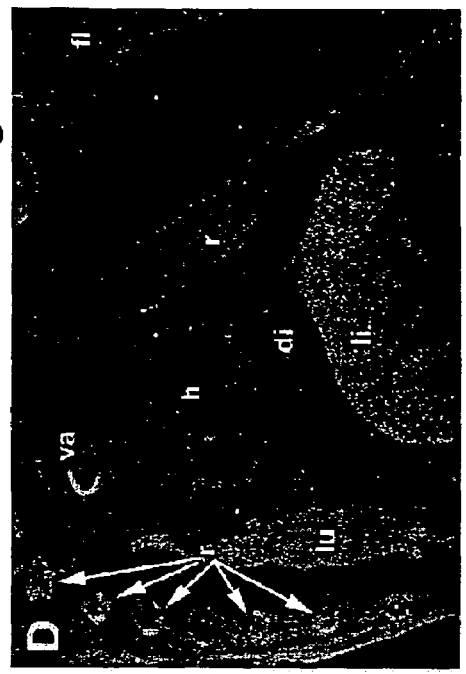
Figure 3C:
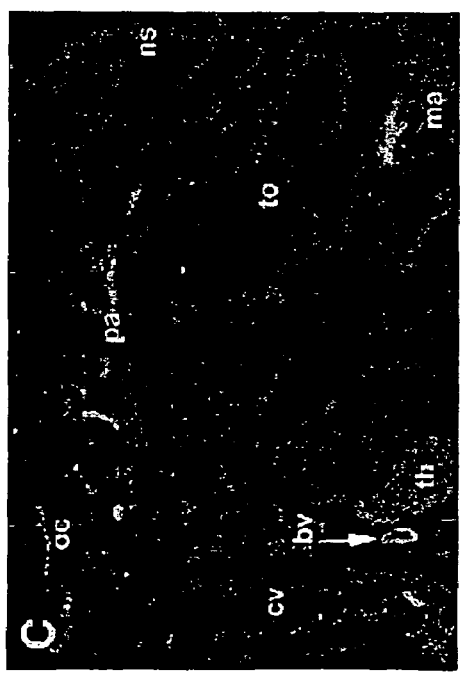
Figure 4A:
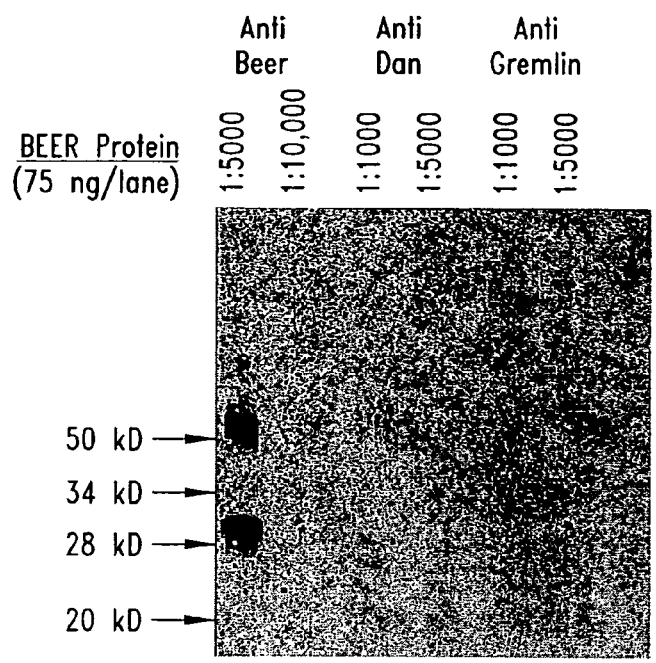
FIGS. 4A-4C illustrate, by western blot analysis, the specificity of three different polyclonal antibodies for their respective antigens (described in more detail in EXAMPLE 4).
Figure 4B:
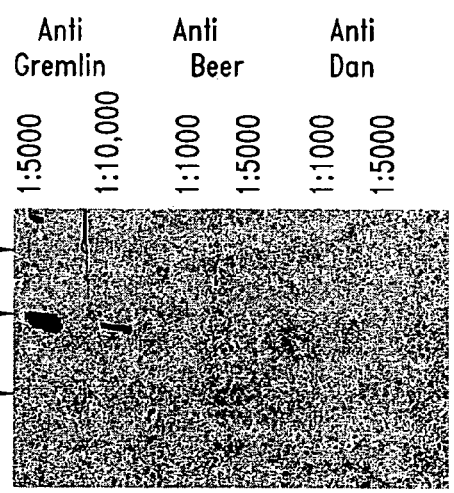
Figure 4C:
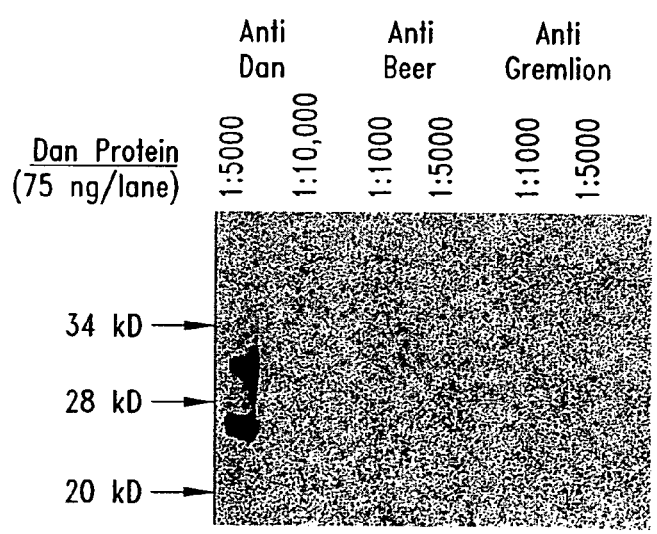

Prior to setting forth the invention in detail, it may be helpful to an understanding thereof to set forth definitions of certain terms and to list and to define the abbreviations that will be used hereinafter.

"Molecule" should be understood to include proteins or peptides (e.g., antibodies, recombinant binding partners, peptides with a desired binding affinity), nucleic acids (e.g., DNA, RNA, chimeric nucleic acid molecules, and nucleic acid analogues such as PNA); and organic or inorganic compounds.

"TGF-beta" should be understood to include any known or novel member of the TGF-beta super-family, which also includes bone morphogenic proteins (BMPs).

"TGF-beta receptor" should be understood to refer to the receptor specific for a particular member of the TGF-beta super-family (including bone morphogenic proteins (BMPs)).

"TGF-beta binding-protein" should be understood to refer to a protein with specific binding affinity for a particular member or subset of members of the TGF-beta super-family (including bone morphogenic proteins (BMPs)). Specific examples of TGF-beta binding-proteins include proteins encoded by Sequence ID Nos. 1, 5, 7, 9, 11, 13, 15, 100, and 101.

Inhibiting the "binding of the TGF-beta binding-protein to the TGF-beta family of proteins and bone morphogenic proteins (BMPs)" should be understood to refer to molecules which allow the activation of TGF-beta or bone morphogenic proteins (BMPs), or allow the binding of TGF-beta family members including bone morphogenic proteins (BMPs) to their respective receptors, by removing or preventing TGF-beta from binding to TGF-binding-protein. Such inhibition may be accomplished, for example, by molecules which inhibit the binding of the TGF-beta binding-protein to specific members of the TGF-beta super-family.

"Vector" refers to an assembly that is capable of directing the expression of desired protein. The vector must include transcriptional promoter elements that are operably linked to the gene(s) of interest. The vector may be composed of deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

An "isolated nucleic acid molecule" is a nucleic acid molecule that is not integrated in the genomic DNA of an organism. For example, a DNA molecule that encodes a TGF-binding protein that has been separated from the genomic DNA of a eukaryotic cell is an isolated DNA molecule. Another example of an isolated nucleic acid molecule is a chemically-synthesized nucleic acid molecule that is not integrated in the genome of an organism. The isolated nucleic acid molecule may be genomic DNA, cDNA, RNA, or composed at least in part of nucleic acid analogs.

An "isolated polypeptide" is a polypeptide that is essentially free from contaminating cellular components, such as carbohydrate, lipid, or other proteinaceous impurities associated with the polypeptide in nature. Preferably, such isolated polypeptides are at least about 90% pure, more preferably at least about 95% pure, and most preferably at least about 99% pure. Within certain embodiments, a particular protein preparation contains an isolated polypeptide if it appears nominally as a single band on SDS-PAGE gel with Coomassie Blue staining. The term "isolated" when referring to organic molecules (e.g., organic small molecules) means that the compounds are greater than 90% pure utilizing methods which are well known in the art (e.g., NMR, melting point).

"Sclerosteosis" is a term that was applied by Hansen (1967) (Hansen, H. G., Sklerosteose. in: Opitz, H.; Schmid, F., *Handbuch der Kinderheilkunde*. Berlin: Springer (pub.) 6 1967. Pp. 351-355) to a disorder similar to van Buchem hyperostosis corticalis generalisata but possibly differing in radiologic appearance of the bone changes and in the presence of asymmetric cutaneous syndactyly of the index and middle fingers in many cases. The jaw has an unusually square appearance in this condition.

"Humanized antibodies" are recombinant proteins in which murine or other non-human animal complementary determining regions of monoclonal antibodies have been transferred from heavy and light variable chains of the murine or other non-human animal immunoglobulin into a human variable domain.

As used herein, an "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-TGF-beta binding-protein monoclonal antibody fragment binds to an epitope of TGF-beta binding-protein.

The term antibody fragment or antigen-binding fragment also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

A "detectable label" is a molecule or atom that can be conjugated to a polypeptide moiety such as an antibody moiety or a nucleic acid moiety to produce a molecule useful for diagnosis. Examples of detectable labels include chelators, photoactive agents, radioisotopes, fluorescent agents, paramagnetic ions, enzymes, and other marker moieties.

As used herein, an "immunoconjugate" is a molecule comprising an anti-TGF-beta binding-protein antibody, or an antibody fragment, and a detectable label or an effector molecule. Preferably, an immunoconjugate has roughly the same, or only slightly reduced, ability to bind TGF-beta binding-protein after conjugation as before conjugation.

Abbreviations: TGF-beta—"Transforming Growth Factor-beta"; TGF-bBP—"Transforming Growth Factor-beta binding-protein" (one representative TGF-bBP is designated "H. Beer"); BMP—"bone morphogenic protein"; PCR—"polymerase chain reaction"; RT-PCR—PCR process in which RNA is first transcribed into DNA using reverse transcriptase (RT); cDNA—any DNA made by copying an RNA sequence into DNA form.

As noted above, the present invention provides a novel class of TGF-beta binding-proteins, as well as methods and compositions for increasing bone mineral content in warm-blooded animals. Briefly, the present inventions are based upon the unexpected discovery that a mutation in the gene which encodes a novel member of the TGF-beta binding-protein family results in a rare condition (sclerosteosis) characterized by bone mineral contents which are one- to four-fold higher than in normal individuals. Thus, as discussed in more detail below this discovery has led to the development of assays which may be utilized to select molecules which inhibit the binding of the TGF-beta binding-protein to the TGF-beta family of proteins and bone morphogenic proteins (BMPs), and methods of utilizing such molecules for increasing the bone mineral content of warm-blooded animals (including for example, humans).

Discussion of the Disease Known as Sclerosteosis

Sclerosteosis is a disease related to abnormal bone mineral density in humans. Sclerosteosis is a term that was applied by Hansen (1967) (Hansen, H. G., Sklerosteose. In: Opitz, H.; Schmid, F., Handbuch der Kinderheilkunde. Berlin: Springer (pub.) 6 1967. Pp. 351-355) to a disorder similar to van Buchem hyperostosis corticalis generalisata but possibly differing in radiologic appearance of the bone changes and differing in the presence of asymmetric cutaneous syndactyly of the index and middle fingers in many cases.

Sclerosteosis is now known to be an autosomal semi-dominant disorder that is characterized by widely disseminated sclerotic lesions of the bone in the adult. The condition is progressive. Sclerosteosis also has a developmental aspect that is associated with syndactyly (two or more fingers are fused together). The Sclerosteosis Syndrome is associated with large stature and many affected individuals attain a height of six feet or more. The bone mineral content of homozygotes can be 1 to 6 fold greater than observed in normal individuals, and bone mineral density can be 1 to 4 fold above normal values (e.g., from unaffected siblings).

The Sclerosteosis Syndrome occurs primarily in Afrikaaners of Dutch descent in South Africa. Approximately 1/140 individuals in the Afrikaaner population are carriers of the mutated gene (heterozygotes). The mutation shows 100% penetrance. There are anecdotal reports of increased of bone mineral density in heterozygotes with no associated pathologies (syndactyly or skull overgrowth).

No abnormality of the pituitary-hypothalamus axis has been observed in patients with sclerosteosis. In particular, there appears to be no over-production of growth hormone and cortisone. In addition, sex hormone levels are normal in affected individuals. However, bone turnover markers (osteoblast specific alkaline phosphatase, osteocalcin, type 1 procollagen C' propeptide (PICP), and total alkaline phosphatase; (see Comier, C., Curr. Opin. in Rheu. 7:243, 1995) indicate that there is hyperosteoblastic activity associated with the disease but that there is normal to slightly decreased osteoclast activity as measured by markers of bone resorption (pyridinoline, deoxypryridinoline, N-telopeptide, urinary hydroxyproline, plasma tartrate-resistant acid phosphatases and galactosyl hydroxylysine (see Comier, supra)).

Sclerosteosis is characterized by the continual deposition of bone throughout the skeleton during the lifetime of the affected individuals. In homozygotes the continual deposition of bone mineral leads to an overgrowth of bone in areas of the skeleton where there is an absence of mechanoreceptors (skull, jaw, cranium). In homozygotes with Sclerosteosis, the overgrowth of the bones of the skull leads to cranial compression and eventually to death due to excessive hydrostatic pressure on the brain stem. In all other parts of the skeleton there is a generalized and diffuse sclerosis. Cortical areas of the long bones are greatly thickened resulting in a substantial increase in bone strength. Trabecular connections are increased in thickness which in turn increases the strength of the trabecular bone. Sclerotic bones appear unusually opaque to x-rays.

As described in more detail in Example 1, the rare genetic mutation that is responsible for the Sclerosteosis syndrome has been localized to the region of human chromosome 17 that encodes a novel member of the TGF-beta binding-protein family (one representative example of which is designated "H. Beer"). As described in more detail below, based upon this discovery, the mechanism of bone mineralization is more fully understood, allowing the development of assays for molecules that increase bone mineralization, and use of such molecules to increase bone mineral content, and in the treatment or prevention of a wide number of diseases.

TGF-beta Super-family

The Transforming Growth Factor-beta (TGF-beta) superfamily contains a variety of growth factors that share common sequence elements and structural motifs (at both the secondary and tertiary levels). This protein family is known to exert a wide spectrum of biological responses that affect a large variety of cell types. Many of the TGF-beta family members have important functions during the embryonal development in pattern formation and tissue specification; in adults the family members are involved, e.g., in wound healing and bone repair and bone remodeling, and in the modulation of the immune system. In addition to the TGF-beta's, the superfamily includes the Bone Morphogenic Proteins (BMPs), Activins, Inhibins, Growth and Differentiation Factors (GDFs), and Glial-Derived Neurotrophic Factors (GDNFs). Primary classification is established through general sequence features that bin a specific protein into a general sub-family. Additional stratification within the sub-family is possible due to stricter sequence conservation between members of the smaller group. In certain instances, such as with BMP-5, BMP-6 and BMP-7, the amino acid identity can be as high as 75% among members of the smaller group. This level of identity enables a single representative sequence to illustrate the key biochemical elements of the sub-group that separates it from other members of the larger family.

The crystal structure of TGF-beta2 has been determined. The general fold of the TGF-beta2 monomer contains a stable, compact, cysteine knotlike structure formed by three disulphide bridges. Dimerization, stabilized by one disulfide bridge, is antiparallel.

TGF-beta signals by inducing the formation of hetero-oligomeric complexes of type I and type II receptors. Transduction of TGF-beta signals involves these two distinct type I and type II subfamilies of transmembrane serine/threonine kinase receptors. At least seven type I receptors and five type II receptors have been identified (see Kawabata et al., Cytokine Growth Factor Rev. 9:49-61 (1998); Miyazono et al., Adv. Immunol. 75:115-57 (2000). TGF-beta family members initiate their cellular action by binding to receptors with intrinsic serine/threonine kinase activity. Each member of the TGF-beta family binds to a characteristic combination of type I and type II receptors, both of which are needed for signaling. In the current model for TGF-beta receptor activation, a TGF-beta ligand first binds to the type II receptor (TbR-II), which occurs in the cell membrane in an oligomeric form with activated kinase. Thereafter, the type I receptor (TbR-I), which cannot bind ligand in the absence of TbR-II, is recruited into the complex to form a ligand/type II/type I ternary complex. TbR-II then phosphorylates TbR-I predominantly in a domain rich in glycine and serine residues (GS domain) in the juxtamembrane region, and thereby activates TbR-I. The activated type I receptor kinase then phosphorylates particular members of the Smad family of proteins that translocate to the nucleus where they modulate transcription of specific genes.

Bone Morphogenic Proteins (BMPs) are Key Regulatory Proteins in Determining Bone Mineral Density in Humans A major advance in the understanding of bone formation was the identification of the bone morphogenic proteins (BMPs), also known as osteogenic proteins (OPs), which regulate cartilage and bone differentiation in vivo. BMPs/OPs induce endochondral bone differentiation through a cascade of events that include formation of cartilage, hypertrophy and calcification of the cartilage, vascular invasion, differentiation of osteoblasts, and formation of bone. As described above, the BMPs/OPs (BMP 2-14, and osteogenic protein 1 and -2, OP-1 and OP-2) see, e.g., GenBank P12643 (BMP-2); GenBank P12645 (BMP3); GenBank P55107 (BMP-3b, Growth/differentiation factor 10) (GDF-10)); GenBank P12644 (BMP4); GenBank P22003 (BMP5); GenBank P22004 (BMP6); GenBank P18075 (BMP7); GenBank P34820 (BMP8); GenBank Q9UK05 (BMP9); GenBank 095393 (BM10); GenBank 095390 (BMP11, Growth/differentiation factor 11 precursor (GDF-11)); GenBank 095972 (BM15)) are members of the TGF-beta super-family. The striking evolutionary conservation between members the BMP/OP sub-family suggests that they are critical in the normal development and function of animals. Moreover, the presence of multiple forms of BMPs/OPs raises an important question about the biological relevance of this apparent redundancy. In addition to postfetal chondrogenesis and osteogenesis, the BMPs/OPs play multiple roles in skeletogenesis (including the development of craniofacial and dental tissues) and in embryonic development and organogenesis of parenchymatous organs, including the kidney. It is now understood that nature relies on common (and few) molecular mechanisms tailored to provide the emergence of specialized tissues and organs. The BMP/OP super-family is an elegant example of nature parsimony in programming multiple specialized functions deploying molecular isoforms with minor variation in amino acid motifs within highly conserved carboxy-terminal regions.

BMPs are synthesized as large precursor proteins. Upon dimerization, the BMPs are proteolyically cleaved within the cell to yield carboxy-terminal mature proteins that are then secreted from the cell. BMPs, like other TGF-beta family members, initiate signal transduction by binding cooperatively to both type I and type II serine/threonine kinase receptors. Type I receptors for which BMPs may act as ligands include BMPR-IA (also known as ALK-3), BMPR-IB (also known as ALK-6), ALK-1, and ALK-2 (also known as ActR-I). Of the type II receptors, BMPs bind to BMP type II receptor (BMPR-II), Activin type II (ActR-II), and Activin type IIB (ActR-IIB). (See Balemans et al., supra, and references cited therein). Polynucleotide sequences and the encoded amino acid sequence of BMP type I receptor polypeptides are provided in the GenBank database, for example, GenBank NM_004329 (SEQ ID NO:102 encoded by SEQ ID NO:116); D89675 (SEQ ID NO:103 encoded by SEQ ID NO:117); NM_001203 (SEQ ID NO:104 encoded by SEQ ID NO:118); S75359 (SEQ ID NO:105 encoded by SEQ ID NO:119); NM_030849 (SEQ ID NO:106 encoded by SEQ ID NO:120); and D38082 (SEQ ID NO:107 encoded by SEQ ID NO:121). Other polypeptide sequences of type I receptors are provided in the GenBank database, for example, NP_001194 (SEQ ID NO:108); BAA19765 (SEQ ID NO:109); and AAB33865 (SEQ ID NO:110). Polynucleotide sequences and the encoded amino acid sequence of BMP type II receptor polypeptides are provided in the GenBank database and include, for example, U25110 (SEQ ID NO:111 encoded by SEQ ID NO:122); NM_033346 (SEQ ID NO:112 encoded by SEQ ID NO:123); NM_001204 (SEQ ID NO:113 encoded by SEQ ID NO:124); and Z48923 (SEQ ID NO:114 encoded by SEQ ID NO:125). Additional polypeptide sequences of type II receptors are also provided in the GenBank database, for example, CAA88759 (SEQ ID NO:115).

BMPs, similar to other cystine-knot proteins, form a homodimer structure (Scheufler et al., *J. Mol. Biol.* 287:103-15 (1999)). According to evolutionary trace analysis performed on the BMP/TGF-β family, the BMP type I receptor binding site and type II receptor binding site were mapped to the surface of the BMP structure (Innis et al., *Protein Eng.* 13:839-47 (2000)). The location of the type I receptor binding site on BMP was later confirmed by the x-ray structure of BMP-2/BMP Receptor IA complex (Nickel et al., *J Joint Surg. Am.* 83A (Suppl 1(Pt 1)):S7-S14 (2001)). The predicted type II receptor binding site is in good agreement with the x-ray structure of TGF-β3/TGF-β Type II receptor complex (Hart et al., *Nat. Struct. Biol.* 9:203-208 (2002)), which is highly similar to the BMP/BMP Receptor IIA system.

BMP Antagonism

The BMP and Activin sub-families are subject to significant post-translational regulation, such as by TGF-beta binding proteins. An intricate extracellular control system exists, whereby a high affinity antagonist is synthesized and exported, and subsequently complexes selectively with BMPs or activins to disrupt their biological activity (W. C. Smith (1999) TIG 15(1) 3-6). A number of these natural antagonists have been identified, and on the basis of sequence divergence, the antagonists appear to have evolved independently due to the lack of primary sequence conservation. Earlier studies of these antagonists highlighted a distinct preference for interacting and neutralizing BMP-2 and BMP-4. In vertebrates, antagonists include noggin, chordin, chordin-like, follistatin, FSRP, the DAN/Cerberus protein family, and sclerostin (SOST) (see Balemans et al., supra, and references cited therein). The mechanism of antagonism or inhibition seems to differ for the different antagonists (Iemura et al. (1998) *Proc. Natl. Acad. Sci. USA* 95 9337-9342).

The type I and type II receptor binding sites on the BMP antagonist noggin have also been mapped. Noggin binds to BMPs with high affinity (Zimmerman et al, 1996). A study of the noggin/BMP-7 complex structure revealed the binding interactions between the two proteins (Groppe et al., *Nature* 420:636-42 (2002)). Superposition of the noggin-BMP-7 structure onto a model of the BMP signaling complex showed that noggin binding effectively masks both pairs of binding epitopes (i.e., BMP Type I and Type II receptor binding sites) on BMP-7. The cysteine-rich scaffold sequence of noggin is preceded by an N-terminal segment of about 20 amino acid residues that are referred to as the "clip" (residues 28-48). The type I receptor-binding site is occluded by the N-terminal portion of the clip domain of Noggin, and the type II receptor binding site is occluded by the carboxy terminal portion of the clip domain. Two β-strands in the core region near the C-terminus of noggin also contact BMP-7 at the type II receptor binding site. This binding mode enables a noggin dimer to efficiently block all the receptor binding sites (two type I and two type II receptor binding sites) on a BMP dimer.

Novel TGF-beta Binding-proteins

As noted above, the present invention provides a novel class of TGF-beta binding-proteins that possess a nearly identical cysteine (disulfide) scaffold when compared to Human DAN, Human Gremlin, and Human Cerberus, and SCGF (U.S. Pat. No. 5,780,263) but almost no homology at the nucleotide level (for background information, see generally Hsu, D. R., Economides, A. N., Wang, X., Eimon, P. M., Harland, R. M., "The *Xenopus* Dorsalizing Factor Gremlin Identifies a Novel Family of Secreted Proteins that Antagonize BMP Activities," *Molecular Cell* 1:673-683, 1998).

Representative example of the novel class of nucleic acid molecules encoding TGF-beta binding-proteins are disclosed in SEQ ID NOs: 1, 5, 7, 9, 11, 13, 15, 100, and 101. The polynucleotides disclosed herein encode a polypeptide called Beer, which is also referred to herein as sclerostin or SOST. Representative members of this class of binding proteins should also be understood to include variants of the TGF-beta binding-protein (e.g., SEQ ID NOs: 5 and 7). As utilized herein, a "TGF-beta binding-protein variant gene" (e.g., an isolated nucleic acid molecule that encodes a TGF-beta binding protein variant) refers to nucleic acid molecules that encode a polypeptide having an amino acid sequence that is a modification of SEQ ID Nos: 2, 10, 12, 14, 16, 46, or 65. Such variants include naturally-occurring polymorphisms or allelic variants of TGF-beta binding-protein genes, as well as synthetic genes that contain conservative amino acid substitutions of these amino acid sequences. A variety of criteria known to those skilled in the art indicate whether amino acids at a particular position in a peptide or polypeptide are similar. For example, a similar amino acid or a conservative amino acid substitution is one in which an amino acid residue is replaced with an amino acid residue having a similar side chain, which include amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively.

Additional variant forms of a TGF-beta binding-protein gene are nucleic acid molecules that contain insertions or deletions of the nucleotide sequences described herein. TGF-beta binding-protein variant genes can be identified by determining whether the genes hybridize with a nucleic acid molecule having the nucleotide sequence of SEQ ID Nos: 1, 5, 7, 9, 11, 13, 15, 100, or 101 under stringent conditions. In addition, TGF-beta binding-protein variant genes should encode a protein having a cysteine backbone.

As an alternative, TGF-beta binding-protein variant genes can be identified by sequence comparison. As used herein, two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in Methods in Gene Biotechnology, pages 123-151 (CRC Press, Inc. 1997), and Bishop (ed.), Guide to Human Genome Computing, 2nd Edition (Academic Press, Inc. 1998)).

A variant TGF-beta binding-protein should have at least a 50% amino acid sequence identity to SEQ ID NOs: 2, 6, 10, 12, 14, 16, 46, or 65 and preferably, greater than 60%, 65%, 70%, 75%, 80%, 85%, 90%, or 95% identity. Alternatively, TGF-beta binding-protein variants can be identified by having at least a 70% nucleotide sequence identity to SEQ ID NOs: 1, 5, 9, 11, 13, 15, 100, or 101. Moreover, the present invention contemplates TGF-beta binding-protein gene variants having greater than 75%, 80%, 85%, 90%, or 95% identity to SEQ ID NO:1 or SEQ ID NO:100. Regardless of the particular method used to identify a TGF-beta binding-protein variant gene or variant TGF-beta binding-protein, a variant TGF-beta binding-protein or a polypeptide encoded by a variant TGF-beta binding-protein gene can be functionally characterized by, for example, its ability to bind to and/or inhibit the signaling of a selected member of the TGF-beta family of proteins, or by its ability to bind specifically to an anti-TGF-beta binding-protein antibody.

The present invention includes functional fragments of TGF-beta binding-protein genes. Within the context of this invention, a "functional fragment" of a TGF-beta binding-protein gene refers to a nucleic acid molecule that encodes a portion of a TGF-beta binding-protein polypeptide which either (1) possesses the above-noted function activity, or (2) specifically binds with an anti-TGF-beta binding-protein antibody. For example, a functional fragment of a TGF-beta binding-protein gene described herein comprises a portion of the nucleotide sequence of SEQ ID Nos: 1, 5, 9, 11, 13, 15, 100, or 101.

2. Isolation of the TGF-beta Binding-protein Gene

DNA molecules encoding a TGF-beta binding-protein can be obtained by screening a human cDNA or genomic library using polynucleotide probes based upon, for example, SEQ ID NO:1. For example, the first step in the preparation of a cDNA library is to isolate RNA using methods well-known to those of skill in the art. In general, RNA isolation techniques provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology*, 3rd Edition, pages 4-1 to 4-6 (John Wiley & Sons 1995) ["Ausubel (1995)"]; Wu et al., *Methods in Gene Biotechnology*, pages 33-41 (CRC Press, Inc. 1997) ["Wu (1997)"]). Alternatively, total RNA can be isolated by extracting ground tissue with guanidinium isothiocyanate, extracting with organic solvents, and separating RNA from contaminants using differential centrifugation (see, for example, Ausubel (1995) at pages 4-1 to 4-6; Wu (1997) at pages 33-41).

In order to construct a cDNA library, poly(A)$^+$ RNA is preferably isolated from a total RNA preparation. Poly(A)$^+$ RNA can be isolated from total RNA by using the standard technique of oligo(dT)-cellulose chromatography (see, for example, Ausubel (1995) at pages 4-11 to 4-12). Double-stranded cDNA molecules may be synthesized from poly(A)$^+$ RNA using techniques well-known to those in the art. (see, for example, Wu (1997) at pages 41-46). Moreover, commercially available kits can be used to synthesize double-stranded cDNA molecules (for example, Life Technologies, Inc. (Gaithersburg, Md.); CLONTECH Laboratories, Inc. (Palo Alto, Calif.); Promega Corporation (Madison, Wis.); and Stratagene Cloning Systems (La Jolla, Calif.)).

The basic approach for obtaining TGF-beta binding-protein cDNA clones can be modified by constructing a subtracted cDNA library that is enriched in TGF-binding-protein-specific cDNA molecules. Techniques for constructing subtracted libraries are well-known to those of skill in the art (see, for example, Sargent, "Isolation of Differentially Expressed Genes," in *Meth. Enzymol.* 152:423, 1987; and Wu et al. (eds.), "Construction and Screening of Subtracted and Complete Expression cDNA Libraries," in *Methods in Gene Biotechnology*, pages 29-65 (CRC Press, Inc. 1997)).

Various cloning vectors are appropriate for the construction of a cDNA library. For example, a cDNA library can be prepared in a vector derived from bacteriophage, such as a λgt10 vector (see, for example, Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47-52). Alternatively, double-stranded cDNA molecules can be inserted into a plasmid vector, such as a pBluescript vector (Stratagene Cloning Systems; La Jolla, Calif.), a LambdaGEM4 (Promega Corp.; Madison, Wis.) or other commercially available vectors. Suitable cloning vectors also can be obtained from the American Type Culture Collection (Rockville, Md.).

In order to amplify the cloned cDNA molecules, the cDNA library is inserted into a prokaryotic host, using standard techniques. For example, a cDNA library can be introduced into competent *E. coli* DH5 cells, which can be obtained from Life Technologies, Inc. (Gaithersburg, Md.).

A human genomic DNA library can be prepared by means well-known in the art (see, for example, Ausubel (1995) at pages 5-1 to 5-6; Wu (1997) at pages 307-327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307-327).

Nucleic acid molecules that encode a TGF-beta binding-protein can also be obtained using the polymerase chain reaction (PCR) with oligonucleotide primers having nucleotide sequences that are based upon the nucleotide sequences of the human TGF-beta binding-protein gene, as described herein. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), pages 211-215 (Humana Press, Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), pages 317-337 (Humana Press, Inc. 1993).

Alternatively, human genomic libraries can be obtained from commercial sources such as Research Genetics (Huntsville, Ala.) and the American Type Culture Collection (Rockville, Md.). A library containing cDNA or genomic clones can be screened with one or more polynucleotide probes based upon SEQ ID NO:1, using standard methods as described herein and known in the art (see, for example, Ausubel (1995) at pages 6-1 to 6-11).

Anti-TGF-beta binding-protein antibodies, produced as described herein, can also be used to isolate DNA sequences that encode a TGF-beta binding-protein from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning 2: Expression Systems, 2nd Edition*, Glover et al. (eds.), pages 1-14 (Oxford University Press 1995)).

The sequence of a TGF-beta binding-protein cDNA or TGF-beta binding-protein genomic fragment can be determined using standard methods. Moreover, the identification of genomic fragments containing a TGF-beta binding-protein promoter or regulatory element can be achieved using well-established techniques, such as deletion analysis (see generally Ausubel (1995), supra).

As an alternative, a TGF-beta binding-protein gene can be obtained by synthesizing DNA molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993); Holowachuk et al., *PCR Methods Appl.* 4:299, 1995).

3. Production of TGF-beta Binding-protein Genes

Nucleic acid molecules encoding variant TGF-beta binding-protein genes can be obtained by screening various cDNA or genomic libraries with polynucleotide probes having nucleotide sequences based upon SEQ ID NO:1, 5, 9, 11, 13, 15, 100, or 101 using procedures described herein. TGF-beta binding-protein gene variants can also be constructed synthetically. For example, a nucleic acid molecule can be devised that encodes a polypeptide having a conservative amino acid change, compared with the amino acid sequence of SEQ ID NOs: 2, 6, 8, 10, 12, 14, 16, 46, or 65. That is, variants can be obtained that contain one or more amino acid substitutions of SEQ ID NOs: 2, 6, 8, 10, 12, 14, 16, 46, or 65, in which an alkyl amino acid is substituted for an alkyl amino acid in a TGF-beta binding-protein amino acid sequence, an aromatic amino acid is substituted for an aromatic amino acid in a TGF-beta binding-protein amino acid sequence, a sulfur-containing amino acid is substituted for a sulfur-containing amino acid in a TGF-beta binding-protein amino acid sequence, a hydroxy-containing amino acid is substituted for a hydroxy-containing amino acid in a TGF-beta binding-protein amino acid sequence, an acidic amino acid is substituted for an acidic amino acid in a TGF-beta binding-protein amino acid sequence, a basic amino acid is substituted for a basic amino acid in a TGF-beta binding-protein amino acid sequence, or a dibasic monocarboxylic amino acid is substituted for a dibasic monocarboxylic amino acid in a TGF-beta binding-protein amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. In making such substitutions, it is important, when possible, to maintain the cysteine backbone outlined in FIG. 1.

Conservative amino acid changes in a TGF-beta binding-protein gene can be introduced by substituting nucleotides for the nucleotides recited in SEQ ID NO:1, 5, 9, 11, 13, 15, 100, or 101. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; McPherson (ed.), *Directed Mutagenesis: A Practical Approach* (IRL Press 1991)). The functional ability of such variants can be determined using a standard method, such as the assay described herein. Alternatively, a variant TGF-beta binding-protein polypeptide can be identified by the ability to specifically bind anti-TGF-beta binding-protein antibodies.

Routine deletion analyses of nucleic acid molecules can be performed to obtain "functional fragments" of a nucleic acid molecule that encodes a TGF-beta binding-protein polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for activity, or for the ability to bind anti-TGF-beta binding-protein antibodies. One alternative to exonuclease digestion is to use oligonucleotide-directed mutagenesis to introduce deletions or stop codons to specify production of a desired fragment. Alternatively, particular fragments of a TGF-beta binding-protein gene can be synthesized using the polymerase chain reaction.

Standard techniques for functional analysis of proteins are described by, for example, Treuter et al., *Molec. Gen. Genet.* 240:113, 1993; Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation, Vol. 1*, Boynton et al., (eds.) pages 169-199 (Academic Press 1985); Coumailleau et al., *J. Biol. Chem.* 270:29270, 1995; Fukunaga et al., *J. Biol. Chem.* 270:25291, 1995; Yamaguchi et al., *Biochem. Pharmacol.* 50:1295, 1995; Meisel et al., *Plant Molec. Biol.* 30:1, 1996.

The present invention also contemplates functional fragments of a TGF-beta binding-protein gene that have conservative amino acid changes.

A TGF-beta binding-protein variant gene can be identified on the basis of structure by determining the level of identity with nucleotide and amino acid sequences of SEQ ID NOs: 1, 5, 9, 11, 13, 15, 100, or 101 and 2, 6, 10, 12, 14, 16, 46, or 65 as discussed above. An alternative approach to identifying a variant gene on the basis of structure is to determine whether a nucleic acid molecule encoding a potential variant TGF-beta binding-protein gene can hybridize under stringent conditions to a nucleic acid molecule having the nucleotide sequence of SEQ ID Nos: 1, 5, 9, 11, 13, 15, 100, or 101, or a portion thereof of at least 15 or 20 nucleotides in length. As an illustration of stringent hybridization conditions, a nucleic acid molecule having a variant TGF-beta binding-protein sequence can bind with a fragment of a nucleic acid molecule having a sequence from SEQ ID NO:1 in a buffer containing, for example, 5×SSPE (1×SSPE=180 mM sodium chloride, 10 mM sodium phosphate, 1 mM EDTA (pH 7.7), 5× Denhardt's solution (100× Denhardt's=2% (w/v) bovine serum albumin, 2% (w/v) Ficoll, 2% (w/v) polyvinylpyrrolidone) and 0.5% SDS incubated overnight at 55-60° C. Post-hybridization washes at high stringency are typically performed in 0.5×SSC (1×SSC=150 mM sodium chloride, 15 mM trisodium citrate) or in 0.5×SSPE at 55-60° C.

Regardless of the particular nucleotide sequence of a variant TGF-beta binding-protein gene, the gene encodes a polypeptide that can be characterized by its functional activity, or by the ability to bind specifically to an anti-TGF-beta binding-protein antibody. More specifically, variant TGF-beta binding-protein genes encode polypeptides which exhibit at least 50%, and preferably, greater than 60, 70, 80 or 90%, of the activity of polypeptides encoded by the human TGF-beta binding-protein gene described herein.

4. Production of TGF-Beta Binding-Protein in Cultured Cells

To express a TGF-beta binding-protein gene, a nucleic acid molecule encoding the polypeptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene that is suitable for selection of cells that carry the expression vector. Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

TGF-beta binding-proteins of the present invention are preferably expressed in mammalian cells. Examples of mammalian host cells include African green monkey kidney cells (Vero; ATCC CRL 1587), human embryonic kidney cells (293-HEK; ATCC CRL 1573), baby hamster kidney cells (BHK-21; ATCC CRL 8544), canine kidney cells (MDCK; ATCC CCL 34), Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene [Hamer et al., *J Molec. Appl. Genet* 1:273, 1982], the TK promoter of Herpes virus [McKnight, *Cell* 31:355, 1982], the SV40 early promoter [Benoist et al., *Nature* 290:304, 1981], the Rous sarcoma virus promoter [Gorman et al., *Proc. Nat'l Acad. Sci. USA* 79:6777, 1982], the cytomegalovirus promoter [Foecking et al., *Gene* 45:101, 1980], and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control TGF-beta binding-protein gene expression in mammalian cells if the prokaryotic promoter is regulated by a eukaryotic promoter (Zhou et al., *Mol. Cell. Biol.* 10:4529, 1990; Kaufman et al., *Nucleic Acids Res.* 19:4485, 1991).

TGF-beta binding-protein genes may also be expressed in bacterial, yeast, insect, or plant cells. Suitable promoters that can be used to express TGF-beta binding-protein polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277, 1987, Watson et al., *Molecular Biology of the Gene, 4th Ed.* (Benjamin Cummins 1987), and by Ausubel et al. (1995).

Preferred prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (Ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (Ed.) (IRL Press 1985)).

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995); Ward et al., "Genetic Manipulation and Expression of Antibodies," in *Monoclonal Antibodies: Principles and Applications*, page 137 (Wiley-Liss, Inc. 1995); and Georgiou, "Expression of Proteins in Bacteria," in *Protein Engineering: Principles and Practice*, Cleland et al. (eds.), page 101 (John Wiley & Sons, Inc. 1996)).

The baculovirus system provides an efficient means to introduce cloned TGF-beta binding-protein genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila* metallothionein promoter. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells. Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. One skilled in the art will appreciate that there are a wide variety of suitable vectors for expression in yeast cells.

Expression vectors can also be introduced into plant protoplasts, intact plant tissues, or isolated plant cells. General methods of culturing plant tissues are provided, for example, by Miki et al., "Procedures for Introducing Foreign DNA into Plants," in *Methods in Plant Molecular Biology and Biotechnology*, Glick et al. (eds.), pages 67-88 (CRC Press, 1993).

An expression vector can be introduced into host cells using a variety of standard techniques including calcium phosphate transfection, liposome-mediated transfection, microprojectile-mediated delivery, electroporation, and the like. Preferably, the transfected cells are selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991). Methods for introducing expression vectors into bacterial, yeast, insect, and plant cells are also provided by Ausubel (1995).

General methods for expressing and recovering foreign protein produced by a mammalian cell system is provided by, for example, Etcheverry, "Expression of Engineered Proteins in Mammalian Cell Culture," *in Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc., 1995).

More generally, TGF-beta binding-protein can be isolated by standard techniques, such as affinity chromatography, size exclusion chromatography, ion exchange chromatography, HPLC and the like. Additional variations in TGF-beta binding-protein isolation and purification can be devised by those of skill in the art. For example, anti-TGF-beta binding-protein antibodies, obtained as described below, can be used to isolate large quantities of protein by immunoaffinity purification.

5. Production of Antibodies to TGF-beta Binding-proteins

The present invention provides antibodies that specifically bind to sclerostin as described herein in detail. Antibodies to TGF-beta binding-protein can be obtained, for example, using the product of an expression vector as an antigen. Antibodies that specifically bind to sclerostin may also be prepared by using peptides derived from any one of the sclerostin polypeptide sequences provided herein (SEQ ID NOs: 2, 6, 8, 10, 12, 14, 16, 46, and 65). Particularly useful anti-TGF-beta binding-protein antibodies "bind specifically" with TGF-beta binding-protein of Sequence ID Nos. 2, 6, 8, 10, 12, 14, 16, 46, or 65 but not to other TGF-beta binding-proteins such as Dan, Cerberus, SCGF, or Gremlin. Antibodies of the present invention (including fragments and derivatives thereof) may be a polyclonal or, especially a monoclonal antibody. The antibody may belong to any immunoglobulin class, and may be for example an IgG, (including isotypes of IgG, which for human antibodies are known in the art as $IgG_1$, $IgG_2$, $IgG_3$, IgG$_4$); IgE; IgM; or IgA antibody. An antibody may be obtained from fowl or mammals, preferably, for example, from a murine, rat, human or other primate antibody. When desired the antibody may be an internalising antibody.

Polyclonal antibodies to recombinant TGF-beta binding-protein can be prepared using methods well-known to those of skill in the art (see, for example, Green et al., "Production of Polyclonal Antisera," in *Immunochemical Protocols* (Manson, ed.), pages 1-5 (Humana Press 1992); Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995)). Although polyclonal antibodies are typically raised in animals such as rats, mice, rabbits, goats, or sheep, an anti-TGF-beta binding-protein antibody of the present invention may also be derived from a subhuman primate antibody. General techniques for raising diagnostically and therapeutically useful antibodies in baboons may be found, for example, in Goldenberg et al., international patent publication No. WO 91/11465 (1991), and in Losman et al., *Int. J. Cancer* 46:310, 1990.

The antibody should comprise at least a variable region domain. The variable region domain may be of any size or amino acid composition and will generally comprise at least one hypervariable amino acid sequence responsible for antigen binding embedded in a framework sequence. In general terms the variable (V) region domain may be any suitable arrangement of immunoglobulin heavy (V$_H$) and/or light (V$_L$) chain variable domains. Thus for example the V region domain may be monomeric and be a V$_H$ or V$_L$ domain where these are capable of independently binding antigen with acceptable affinity. Alternatively the V region domain may be dimeric and contain V$_H$-V$_H$, V$_H$-V$_L$, or V$_L$-V$_L$, dimers in which the V$_H$ and V$_L$ chains are non-covalently associated (abbreviated hereinafter as F$_v$). Where desired, however, the chains may be covalently coupled either directly, for example via a disulphide bond between the two variable domains, or through a linker, for example a peptide linker, to form a single chain domain (abbreviated hereinafter as scF$_v$).

The variable region domain may be any naturally occuring variable domain or an engineered version thereof. By engineered version is meant a variable region domain that has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The variable region domain may be covalently attached at a C-terminal amino acid to at least one other antibody domain or a fragment thereof. Thus, for example where a V$_H$ domain is present in the variable region domain this may be linked to an immunoglobulin C$_H$1 domain or a fragment thereof. Similarly a V$_L$ domain may be linked to a C$_K$ domain or a fragment thereof. In this way for example the antibody may be a Fab fragment wherein the antigen binding domain contains associated V$_H$ and V$_L$ domains covalently linked at their C-termini to a CH1 and C$_K$ domain respectively. The CH1 domain may be extended with further amino acids, for example to provide a hinge region domain as found in a Fab' fragment, or to provide further domains, such as antibody CH2 and CH3 domains.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Antibodies for use in the invention may in general be monoclonal (prepared by conventional immunisation and cell fusion procedures) or in the case of fragments, derived therefrom using any suitable standard chemical such as reduction or enzymatic cleavage and/or digestion techniques, for example by treatment with pepsin. More specifically, monoclonal anti-TGF-beta binding-protein antibodies can be generated utilizing a variety of techniques. Rodent monoclonal antibodies to specific antigens may be obtained by methods known to those skilled in the art (see, for example, Kohler et al., *Nature* 256:495, 1975; and Coligan et al. (eds.), *Current Protocols in Immunology*, 1:2.5.1-2.6.7 (John Wiley & Sons 1991) ["Coligan"]; Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a TGF-beta binding-protein gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-TGF-beta binding-protein antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol 10, pages 79-104 (The Humana Press, Inc. 1992)).

For particular uses, it may be desirable to prepare fragments of anti-TGF-beta binding-protein antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology* 1:422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Alternatively, the antibody may be a recombinant or engineered antibody obtained by the use of recombinant DNA techniques involving the manipulation and re-expression of DNA encoding antibody variable and/or constant regions. Such DNA is known and/or is readily available from DNA libraries including for example phage-antibody libraries (see Chiswell, D J and McCafferty, J. Tibtech. 10 80-84 (1992)) or where desired can be synthesised. Standard molecular biology and/or chemistry procedures may be used to sequence and manipulate the DNA, for example, to introduce codons to create cysteine residues, to modify, add or delete other amino acids or domains as desired.

One or more replicable expression vectors containing the DNA encoding a variable and/or constant region may be prepared and used to transform an appropriate cell line, e.g. a non-producing myeloma cell line, such as a mouse NSO line or a bacterial, such as *E. coli*, in which production of the antibody will occur. In order to obtain efficient transcription and translation, the DNA sequence in each vector should include appropriate regulatory sequences, particularly a promoter and leader sequence operably linked to a variable domain sequence. Particular methods for producing antibodies in this way are generally well known and routinely used. For example, basic molecular biology procedures are described by Maniatis et al (Molecular Cloning, Cold Spring Harbor Laboratory, New York, 1989); DNA sequencing can be performed as described in Sanger et al (*Proc. Natl. Acad. Sci. USA* 74: 5463, (1977)) and the Amersham International plc sequencing handbook; site directed mutagenesis can be carried out according to the method of Kramer et al. (*Nucleic Acids Res.* 12, 9441, (1984)); the Anglian Biotechnology Ltd handbook; Kunkel *Proc. Natl. Acad. Sci. USA* 82:488-92 (1985); Kunkel et al., *Methods in Enzymol.* 154:367-82 (1987). Additionally, numerous publications detail techniques suitable for the preparation of antibodies by manipulation of DNA, creation of expression vectors, and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in International Patent Specification No. WO 91/09967.

In certain embodiments, the antibody according to the invention may have one or more effector or reporter molecules attached to it and the invention extends to such modified proteins. A reporter molecule may be a detectable moiety or label such as an enzyme, cytotoxic agent or other reporter molecule, including a dye, radionuclide, luminescent group, fluorescent group, or biotin, or the like. The TGF-beta binding protein-specific immunoglobulin or fragment thereof may be radiolabeled for diagnostic or therapeutic applications. Techniques for radiolabeling of antibodies are known in the art. See, e.g., Adams 1998 In Vivo 12:11-21; Hiltunen 1993 *Acta Oncol.* 32:831-9. Therapeutic applications are described in greater detail below and may include use of the TGF-beta binding protein specific antibody (or fragment thereof) in conjunction with other therapeutic agents. The effector or reporter molecules may be attached to the antibody through any available amino acid side-chain, terminal amino acid or, where present carbohydrate functional group located in the antibody, provided that the attachment or the attachment process does not adversely affect the binding properties and the usefulness of the molecule. Particular functional groups include, for example any free amino, imino, thiol, hydroxyl, carboxyl or aldehyde group. Attachment of the antibody and the effector and/or reporter molecule(s) may be achieved via such groups and an appropriate functional group in the effector or reporter molecules. The linkage may be direct or indirect through spacing or bridging groups.

Effector molecules include, for example, antineoplastic agents, toxins (such as enzymatically active toxins of bacterial (such as *P. aeruginosa* exotoxin A) or plant origin and fragments thereof (e.g. ricin and fragments thereof; plant gelonin, bryodin from *Bryonia dioica*, or the like. See, e.g., Thrush et al., 1996 *Annu. Rev. Immunol.* 14:49-71; Frankel et al., 1996 *Cancer Res.* 56:926-32); biologically active proteins, for example enzymes; nucleic acids and fragments thereof such as. DNA, RNA and fragments thereof; naturally occurring and synthetic polymers (e.g., polysaccharides and polyalkylene polymers such as poly(ethylene glycol) and derivatives thereof); radionuclides, particularly radioiodide; and chelated metals. Suitable reporter groups include chelated metals, fluorescent compounds, or compounds that may be detected by NMR or ESR spectroscopy. Particularly useful effector groups are calichaemicin and derivatives thereof (see, for example, South African Patent Specifications Nos. 85/8794, 88/8127 and 90/2839).

Numerous other toxins, including chemotherapeutic agents, anti-mitotic agents, antibiotics, inducers of apoptosis (or "apoptogens", see, e.g., Green and Reed, 1998, *Science* 281:1309-1312), or the like, are known to those familiar with the art, and the examples provided herein are intended to be illustrative without limiting the scope and spirit of the invention. Particular antineoplastic agents include cytotoxic and cytostatic agents, for example alkylating agents, such as nitrogen mustards (e.g., chlorambucil, melphalan, mechlorethamine, cyclophosphamide, or uracil mustard) and derivatives thereof, triethylenephosphoramide, triethylenethiophosphor-amide, busulphan, or cisplatin; antimetabolites, such as methotrexate, fluorouracil, floxuridine, cytarabine, mercaptopurine, thioguanine, fluoroacetic acid or fluorocitric acid, antibiotics, such as bleomycins (e.g., bleomycin sulphate), doxorubicin, daunorubicin, mitomycins (e.g., mitomycin C), actinomycins (e.g., dactinomycin) plicamycin, calichaemicin and derivatives thereof, or esperamicin and derivatives thereof, mitotic inhibitors, such as etoposide, vincristine or vinblastine and derivatives thereof, alkaloids, such as ellipticine; polyols such as taxicin-I or taxicin-II; hormones, such as androgens (e.g., dromostanolone or testolactone), progestins (e.g., megestrol acetate or medroxyprogesterone acetate), estrogens (e.g., dimethylstilbestrol diphosphate, polyestradiol phosphate or estramustine phosphate) or antiestrogens (e.g., tamoxifen); anthraquinones, such as mitoxantrone, ureas, such as hydroxyurea; hydrazines, such as procarbazine; or imidazoles, such as dacarbazine.

Chelated metals include chelates of di-or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Tb), gadolinium (Gd), and scandium (Sc). In general the metal is preferably a radionuclide. Particular radionuclides include $^{99m}$Tc, $^{186}$Re, $^{188}$Re, $^{58}$Co, $^{60}$Co, $^{67}$Cu, $^{195}$Au, $^{199}$Au, $^{110}$Ag, $^{203}$Pb, $^{206}$Bi, $^{207}$Bi, $^{111}$In, $^{67}$Ga, $^{68}$Ga, $^{88}$Y, $^{90}$Y, $^{160}$Tb, $^{153}$Gd, and $^{47}$Sc.

The chelated metal may be for example one of the above types of metal chelated with any suitable polydentate chelating agent, for example acyclic or cyclic polyamines, polyethers, (e.g., crown ethers and derivatives thereof); polyamides; porphyrins; and carbocyclic derivatives. In general, the type of chelating agent will depend on the metal in use. One particularly useful group of chelating agents in conjugates according to the invention, however, comprises acyclic and cyclic polyamines, especially polyaminocarboxylic acids, for example diethylenetriaminepentaacetic acid and derivatives thereof, and macrocyclic amines, such as cyclic tri-aza and tetra-aza derivatives (for example, as described in International Patent Specification No. WO 92/22583), and polyamides, especially desferrioxamine and derivatives thereof.

When a thiol group in the antibody is used as the point of attachment this may be achieved through reaction with a thiol reactive group present in the effector or reporter molecule. Examples of such groups include an á-halocarboxylic acid or ester, such as iodoacetamide, an imide, such as maleimide, a vinyl sulphone, or a disulphide. These and other suitable linking procedures are generally and more particularly described in International Patent Specifications Nos. WO 93/06231, WO 92/22583, WO 90/091195, and WO 89/01476.

Assays for Selecting Molecules that Increase Bone Density

As discussed above, the present invention provides methods for selecting and/or isolating compounds that are capable of increasing bone density. For example, within one aspect of the present invention methods are provided for determining whether a selected molecule (e.g., a candidate agent) is capable of increasing bone mineral content, comprising the steps of (a) mixing (or contacting) a selected molecule with TGF-beta binding protein and a selected member of the TGF-beta family of proteins, (b) determining whether the selected molecule stimulates signaling by the TGF-beta family of proteins, or inhibits the binding of the TGF-beta binding protein to at least one member of the TGF-beta family of proteins. Within certain embodiments, the molecule enhances the ability of TGF-beta to function as a positive regulator of mesenchymal cell differentiation.

Within other aspects of the invention, methods are provided for determining whether a selected molecule (candidate agent) is capable of increasing bone mineral content, comprising the steps of (a) exposing (contacting, mixing, combining) a selected molecule to cells which express TGF-beta binding-protein and (b) determining whether the expression (or activity) of TGF-beta binding-protein in the exposed cells decreases, or whether an activity of the TGF-beta binding protein decreases, and therefrom determining whether the compound is capable of increasing bone mineral content. Within one embodiment, the cells are selected from the group consisting of the spontaneously transformed or untransformed normal human bone from bone biopsies and rat parietal bone osteoblasts. Methods for detecting the level of expression of a TGF-beta binding protein may be accomplished in a wide variety of assay formats known in the art and described herein. Immunoassays may be used for detecting and quantifying the expression of a TGF-beta binding protein and include, for example, Countercurrent Immuno-Electrophoresis (CIEP), radioimmunoassays, radioimmunoprecipitations, Enzyme-Linked Immuno-Sorbent Assays (ELISA), immunoblot assays such as dot blot assays and Western blots, inhibition or competition assays, and sandwich assays (see U.S. Pat. Nos. 4,376,110 and 4,486,530; see also *Antibodies: A Laboratory Manual*, supra). Such immunoassays may use an antibody that is specific for a TGF-beta binding protein such as the anti-sclerostin antibodies described herein, or may use an antibody that is specific for a reporter molecule that is attached to the TGF-beta binding protein. The level of polypeptide expression may also be determined by quantifying the amount of TGF-beta binding protein that binds to a TGF-beta binding protein ligand. By way of example, binding of sclerostin in a sample to a BMP may be detected by surface plasmon resonance (SPR). Alternatively, the level of expression of mRNA encoding the specific TGF-beta binding protein may be quantified.

Representative embodiments of such assays are provided below in Examples 5 and 6. Briefly, a family member of the TGF-beta super-family or a TGF-beta binding protein is first bound to a solid phase, followed by addition of a candidate molecule. A labeled family member of the TGF-beta super-family or a TGF-beta binding protein is then added to the assay (i.e., the labeled polypeptide is the ligand for whichever polypeptide was bound to the solid phase), the solid phase washed, and the quantity of bound or labeled TGF-beta super-family member or TGF-beta binding protein on the solid support determined. Molecules which are suitable for use in increasing bone mineral content as described herein are those molecules which decrease the binding of TGF-beta binding protein to a member or members of the TGF-beta super-family in a statistically significant manner. Obviously, assays suitable for use within the present invention should not be limited to the embodiments described within Examples 2 and 3. In particular, numerous parameters may be altered, such as by binding TGF-beta to a solid phase, or by elimination of a solid phase entirely.

Within other aspects of the invention, methods are provided for determining whether a selected molecule is capable of increasing bone mineral content, comprising the steps of (a) exposing (contacting, mixing, combining) a selected molecule (candidate agent) to cells which express TGF-beta and (b) determining whether the activity of TGF-beta from said exposed cells is altered, and therefrom determining whether the compound is capable of increasing bone mineral content. Similar to the methods described herein, a wide variety of methods may be utilized to assess the changes of TGF-beta binding-protein expression due to a selected test compound. In one embodiment of the invention, the candidate agent is an antibody that binds to the TGF-beta binding protein sclerostin disclosed herein.

In a preferred embodiment of the invention, a method is provided for identifying an antibody that modulates a TGF-beta signaling pathway comprising contacting an antibody that specifically binds to a SOST polypeptide with a SOST peptide, including but not limited to the peptides disclosed herein, under conditions and for a time sufficient to permit formation of an antibody plus (+) SOST (antibody/SOST) complex and then detecting the level (e.g., quantifying the amount) of the SOST/antibody complex to determine the presence of an antibody that modulates a TGF-beta signaling pathway. The method may be performed using SPR or any number of different immunoassays known in the art and disclosed herein, including an ELISA, immunoblot, or the like. A TGF-beta signaling pathway includes a signaling pathway by which a BMP binds to a type I and a type II receptor on a cell to stimulate or induce the pathway that modulates bone mineral content. In certain preferred embodiments of the invention, an antibody that specifically binds to SOST stimulates or enhances the pathway for increasing bone mineral content. Such an antibody may be identified using the methods disclosed herein to detect binding of an antibody to SOST specific peptides.

The subject invention methods may also be used for identifying antibodies that impair, inhibit (including competitively inhibit), or prevent binding of a BMP to a SOST polypeptide by detecting whether an antibody binds to SOST peptides that are located in regions or portions of regions on SOST to which a BMP binds, such as peptides at the amino terminal end of SOST and peptides that include amino terminal amino acid residues and a portion of the core region (docking core) of SOST (e.g., SEQ ID NOs:47-64, 66-73, and 92-95). The methods of the present invention may also be used to identify an antibody that impairs, prevents, or inhibits, formation of SOST homodimers. Such an antibody that binds specifically to SOST may be identified by detecting binding of the antibody to peptides that are derived from the core or the carboxy terminal region of SOST (e.g., SEQ ID NOs: 74-91 and 96-99).

Within another embodiment of the present invention, methods are provided for determining whether a selected molecule is capable of increasing bone mineral content, comprising the steps of (a) mixing or contacting a selected molecule (candidate agent) with a TGF-beta-binding-protein and a selected member of the TGF-beta family of proteins, (b) determining whether the selected molecule up-regulates the signaling of the TGF-beta family of proteins, or inhibits the binding of the TGF-beta binding-protein to the TGF-beta family of proteins. Within certain embodiments, the molecule enhances the ability of TGF-beta to function as a positive regulator of mesenchymal cell differentiation.

Similar to the above described methods, a wide variety of methods may be utilized to assess stimulation of TGF-beta due to a selected test compound. One such representative method is provided below in Example 6 (see also Durham et al., *Endo*. 136:1374-1380.

Within yet other aspects of the present invention, methods are provided for determining whether a selected molecule (candidate agent) is capable of increasing bone mineral content, comprising the step of determining whether a selected molecule inhibits the binding of TGF-beta binding-protein to bone, or an analogue thereof. As utilized herein, it should be understood that bone or analogues thereof refers to hydroxyapatite, or a surface composed of a powdered form of bone, crushed bone or intact bone. Similar to the above described methods, a wide variety of methods may be utilized to assess the inhibition of TGF-beta binding-protein localization to bone matrix. One such representative method is provided below in Example 7 (see also Nicolas et al., *Calcif. Tissue Int*. 47:206-12 (1995)).

In one embodiment of the invention, an antibody or antigen-binding fragment thereof that specifically binds to a sclerostin polypeptide is capable of competitively inhibiting binding of a TGF-beta family member to the sclerostin polypeptide. The capability of the antibody or antibody fragment to impair or blocking binding of a TGF-beta family member, such as a BMP, to sclerostin may be determined according to any of the methods described herein. The antibody or fragment thereof that specifically binds to sclerostin may impair, block, or prevent binding of a TGF-beta family member to sclerostin by impairing sclerostin homodimer formation. An antibody that specifically binds to sclerostin may also be used to identify an activity of scierostin by inhibiting or impairing scierostin from binding to a BMP. Alternatively, the antibody or fragment thereof may be incorporated in a cell-based assay or in an animal model in which sclerostin has a defined activity to determine whether the antibody alters (increases or decreases in a statistically significant manner) that activity. An antibody or fragment thereof that specifically binds to sclerostin may be used to examine the effect of such an antibody in a signal transduction pathway and thereby modulate (stimulate or inhibit) the signaling pathway. Preferably, binding of an antibody to SOST results in a stimulation or induction of a signaling pathway.

While the methods recited herein may refer to the analysis of an individual test molecule, that the present invention should not be so limited. In particular, the selected molecule may be contained within a mixture of compounds. Hence, the recited methods may further comprise the step of isolating a molecule that inhibits the binding of TGF-beta binding-protein to a TGF-beta family member.

Candidate Molecules

A wide variety of molecules may be assayed for their ability to inhibit the binding of TGF-beta binding-protein to a TGF-beta family member. Representative examples discussed in more detail below include organic molecules (e.g., organic small molecules), proteins or peptides, and nucleic acid molecules. Although it should be evident from the discussion below that the candidate molecules described herein may be utilized in the assays described herein, it should also be readily apparent that such molecules can also be utilized in a variety of diagnostic and therapeutic settins.

1. Organic Molecules

Numerous organic small molecules may be assayed for their ability to inhibit the binding of TGF-beta binding-protein to a TGF-beta family member. For example, within one embodiment of the invention suitable organic molecules may be selected from either a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," *Tet. Letters* 37:4887-90, 1996; Ruhland, B. et al., "Solid-supported Combinatorial Synthesis of Structurally Diverse β-Lactams," *J. Amer. Chem. Soc.* 111:253-4, 1996; Look, G. C. et al., "The Indentification of Cyclooxygenase-1 Inhibitors from 4-Thiazolidinone Combinatorial Libraries," *Bioorg and Med. Chem. Letters* 6:707-12, 1996.

2. Proteins and Peptides

A wide range of proteins and peptides may likewise be utilized as candidate molecules for inhibitors of the binding of TGF-beta binding-protein to a TGF-beta family member.

a. Combinatorial Peptide Libraries

Peptide molecules which are putative inhibitors of the binding of TGF-beta binding-protein to a TGF-beta family member may be obtained through the screening of combinatorial peptide libraries. Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

b. Antibodies

The present invention provides antibodies that specifically bind to a sclerostin polypeptide methods for using such antibodies. The present invention also provides sclerostin polypeptide immunogens that may be used for generation and analysis of these antibodies. The antibodies may be useful to block or impair binding of a sclerostin polypeptide, which is a TGF-beta binding protein, to a ligand, particularly a bone morphogenic protein, and may also block or impair binding of the sclerostin polypeptide to one or more other ligands.

A molecule such as an antibody that inhibits the binding of the TGF-beta binding protein to one or more members of the TGF-beta family of proteins, including one or more bone morphogenic proteins (BMPs), should be understood to refer to, for example, a molecule that allows the activation of a TGF-beta family member or BMP, or allows binding of TGF-beta family members including one or more BMPs to their respective receptors by removing or preventing the TGF-beta member from binding to the TGF-binding-protein.

The present invention also provides peptide and polypeptide immunogens that may be used to generate and/or identify antibodies or fragments thereof that are capable of inhibiting, preventing, or impairing binding of the TGF-beta binding protein sclerostin to one or more BMPs. The present invention also provides peptide and polypeptide immunogens that may be used to generate and/or identify antibodies or fragments thereof that are capable of inhibiting, preventing, or impairing (e.g., decreasing in a statistically significant manner) the formation of sclerostin homodimers. The antibodies of the present invention are useful for increasing the mineral content and mineral density of bone, thereby ameliorating numerous conditions that result in the loss of bone mineral content, including for example, disease, genetic predisposition, accidents that result in the lack of use of bone (e.g., due to fracture), therapeutics that effect bone resorption or that kill bone forming cells, and normal aging.

Polypeptides or peptides useful for immunization and/or analysis of sclerostin-specific antibodies may also be selected by analyzing the primary, secondary, and tertiary structure of a TGF-beta binding protein according to methods known to those skilled in the art and described herein, in order to determine amino acid sequences more likely to generate an antigenic response in a host animal. See, e.g., Novotny, *Mol. Immunol.* 28:201-207 (1991); Berzofsky, *Science* 229:932-40 (1985)). Modeling and x-ray crystallography data may also be used to predict and/or identify which portions or regions of a TGF-beta binding protein interact with which portions of a TGF-beta binding protein ligand, such as a BMP. TGF-beta binding protein peptide immunogens may be designed and prepared that include amino acid sequences within or surrounding the portions or regions of interaction. These antibodies may be useful to block or impair binding of the TGF-beta binding protein to the same ligand and may also block or impair binding of the TGF-beta binding protein to one or more other ligands.

Antibodies or antigen binding fragments thereof contemplated by the present invention include antibodies that are capable of specifically binding to sclerostin and competitively inhibiting binding of a TGF-beta polypeptide, such as a BMP, to sclerostin. For example, the antibodies contemplated by the present invention competitively inhibit binding of the sclerostin polypeptide to the BMP Type I receptor site on a BMP, or to the BMP Type II receptor binding site, or may competitively inhibit binding of sclerostin to both the Type I and Type II receptor binding sites on a BMP. Without wishing to be bound by theory, when an anti-sclerostin antibody competitively inhibits binding of the Type I and/or Type II binding sites of the BMP polypeptide to sclerostin, thus blocking the antagonistic activity of sclerostin, the receptor binding sites on BMP are available to bind to the Type I and Type II receptors, thereby increasing bone mineralization. The binding interaction between a TGF-beta binding protein such as sclerostin and a TGF-beta polypeptide such as a BMP generally occurs when each of the ligand pairs forms a homodimer. Therefore instead of or in addition to using an antibody specific for sclerostin to block, impair, or prevent binding of sclerostin to a BMP by competitively inhibiting binding of sclerostin to BMP, a sclerostin specific antibody may be used to block or impair sclerostin homodimer formation.

By way of example, one dimer of human Noggin, which is a BMP antagonist that has the ability to bind a BMP with high affinity (Zimmerman et al., supra), was isolated in complex with one dimer of human BMP-7 and analyzed by multiwavelength anomalous diffraction (MAD) (Groppe et al., *Nature* 420:636-42 (2002)). As discussed herein, this study revealed that Noggin dimer may efficiently block all the receptor binding sites (two type I and two type II receptor binding sites) on a BMP dimer. The location of the amino acids of Noggin that contact BMP-7 may be useful in modeling the interaction between other TGF-beta binding proteins, such as sclerostin (SOST), and BMPs, and thus aiding the design of peptides that may be used as immunogens to generate antibodies that block or impair such an interaction.

In one embodiment of the present invention, an antibody, or an antigen-binding fragment thereof, that binds specifically to a SOST polypeptide competitively inhibits binding of the SOST polypeptide to at least one or both of a bone morphogenic protein (BMP) Type I Receptor binding site and a BMP Type II Receptor binding site that are located on a BMP. The epitopes on SOST to which these antibodies bind may include or be included within contiguous amino acid sequences that are located at the N-terminus of the SOST polypeptide (amino acids at about positions 1-56 of SEQ ID NO:46). The polypeptides may also include a short linker peptide sequence that connects the N-terminal region to the core region, for example, polypeptides as provided in SEQ ID NO:92 (human) and SEQ ID NO:93 (rat). Shorter representative N-terminus peptide sequences of human SOST (e.g., SEQ ID NO:46) include SEQ ID NOS:47-51, and representative rat SOST (e.g., SEQ ID NO:65) peptide sequences include SEQ ID NOS:57-60.

Antibodies that specifically bind to a SOST polypeptide and block or competitively inhibit binding of the SOST polypeptide to a BMP, for example, by blocking or inhibiting binding to amino acids of a BMP corresponding to one or more of the Type I and Type II receptor binding sites may also specifically bind to peptides that comprise an amino acid sequence corresponding to the core region of SOST (amino acids at about positions 57-146 of SEQ ID NO:46). Polypeptides that include the core region may also include additional amino acids extending at either or both the N-terminus and C-terminus, for example, to include cysteine residues that may be useful for conjugating the polypeptide to a carrier molecule. Representative core polypeptides of human and rat SOST, for example, comprise the amino acid sequences set forth in SEQ ID NO:94 and SEQ ID NO:95, respectively. Such antibodies may also bind shorter polypeptide sequences. Representative human SOST core peptide sequences are provided in SEQ ID NOs:66-69 and representative rat SOST core sequences are provided in SEQ ID NOs: 70-73.

In another embodiment, antibodies that specifically bind to a SOST polypeptide impair (inhibit, prevent, or block, e.g., decrease in a statistically significant manner) formation of a SOST homodimer. Because the interaction between SOST and a BMP may involve a homodimer of SOST and a homodimer of the BMP, an antibody that prevents or impairs homodimer formation of SOST may thereby alter bone mineral density, preferably increasing bone mineral density. In one embodiment, antibodies that bind to the core region of SOST prevent homodimer formation. Such antibodies may also bind to peptides that comprise contiguous amino acid sequences corresponding the core region, for example, SEQ ID NOs: 74, 75, and 98 (human SOST) and SEQ ID NOs:76 and 99 (rat SOST). Antibodies that bind to an epitope located on the C-terminal region of a SOST polypeptide (at about amino acid positions 147-190 of either SEQ ID NO:46 or 65) may also impair homodimer formation. Representative C-terminal polypeptides of human and rat SOST, for example, comprise the amino acid sequences set forth in SEQ ID NO:96 and SEQ ID NO:97, respectively. Such antibodies may also bind shorter polypeptide sequences. Representative human SOST C-terminal peptide sequences are provided in SEQ ID NOs:78-81 and representative rat SOST C-terminal sequences are provided in SEQ ID NOs:86-88.

The SOST polypeptides and peptides disclosed herein to which antibodies may specifically bind are useful as immunogens. These immunogens of the present invention may be used for immunizing an animal to generate a humoral immune response that results in production of antibodies that specifically bind to a Type I or Type II receptor binding site or both located on a BMP include peptides derived from the N-terminal region of SOST or that may prevent SOST homodimer formation.

Such SOST polypeptides and peptides that are useful as immunogens may also be used in methods for screening samples containing antibodies, for example, samples of purified antibodies, antisera, or cell culture supernatants or any other biological sample that may contain one or more antibodies specific for SOST. These peptides may also be used in methods for identifying and selecting from a biological sample one or more B cells that are producing an antibody that specifically binds to SOST (e.g., plaque forming assays and the like). The B cells may then be used as source of a SOST specific antibody-encoding polynucleotide that can be cloned and/or modified by recombinant molecular biology techniques known in the art and described herein.

A "biological sample" as used herein refers in certain embodiments to a sample containing at least one antibody specific for a SOST polypeptide, and a biological sample may be provided by obtaining a blood sample, biopsy specimen, tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., B cells immunized in vitro), or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

SOST peptide immunogens may also be prepared by synthesizing a series of peptides that, in total, represent the entire polypeptide sequence of a SOST polypeptide and that each have a portion of the SOST amino acid sequence in common with another peptide in the series. This overlapping portion would preferably be at least four amino acids, and more preferably 5, 6, 7, 8, 9, or 10 amino acids. Each peptide may be used to immunize an animal, the sera collected from the animal, and tested in an assay to identify which animal is producing antibodies that impair or block binding of SOST to a TGF-beta protein. Antibodies are then prepared from such identified immunized animals according to methods known in the art and described herein.

Antibodies which inhibit the binding of TGF-beta binding-protein to a TGF-beta family member may readily be prepared given the disclosure provided herein. Particularly useful are anti-TGF-beta binding-protein antibodies that "specifically bind" TGF-beta binding-protein of SEQ ID NOs: 2, 6, 8, 10, 12, 14, 16, 46, or 65, but not to other TGF-beta binding-proteins such as Dan, Cerberus, SCGF, or Gremlin. Within the context of the present invention, antibodies are understood to include monoclonal antibodies, polyclonal antibodies, single chain, chimeric, CDR-grafted immunoglobulings, anti-idiotypic antibodies, and antibody fragments thereof (e.g., Fab, Fd, Fab', and F(ab')$_2$, Fv variable regions, or complementarity determining regions). As discussed above, antibodies are understood to be specific against TGF-beta binding-protein, or against a specific TGF-beta family member, if they bind with a $K_a$ of greater than or equal to $10^7$ $M^{-1}$, preferably greater than or equal to $10^8$ $M^{-1}$, and do not bind to other TGF-beta binding-proteins, or bind with a $K_a$ of less than or equal to $10^6$ $M^{-1}$. Affinity of an antibody for its cognate antigen is also commonly expressed as a dissociation constant $K_D$, and an anti-SOST antibody specifically binds to a TGF-beta family member if it binds with a $K_D$ of less than or equal to about $10^{-5}$ M, more preferably less than or equal to about $10^{-6}$ M, still more preferably less than or equal to $10^{-7}$ M, and still more preferably less than or equal to $10^{-8}$ M. Furthermore, antibodies of the present invention preferably block, impair, or inhibit (e.g., decrease with statistical significance) the binding of TGF-beta binding-protein to a TGF-beta family member. The affinity of a monoclonal antibody or binding partner, as well as inhibition of binding can be readily determined by one of ordinary skill in the art (see Scatchard, *Ann. N.Y. Acad. Sci.* 51:660-672, 1949).

Affinity may also be determined by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., Cancer Res. 53:2560-65 (1993)).

An antibody according to the present invention may belong to any immunoglobulin class, for example IgG, IgE, IgM, IgD, or IgA, and may be any one of the different isotypes that may comprise a class (such as IgG1, IgG2, IgG3, and IgG4 of the human IgG class). It may be obtained from or derived from an animal, for example, fowl (e.g., chicken) and mammals, which includes but is not limited to a mouse, rat, hamster, rabbit, or other rodent, a cow, horse, sheep, goat, camel, human, or other primate. The antibody may be an internalising antibody.

Methods well known in the art may be used to generate antibodies, polyclonal antisera, or monoclonal antibodies that are specific for a TGF-beta binding protein such as SOST. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species. Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions. Fragments of these molecules may be generated by proteolytic digestion, or optionally, by proteolytic digestion followed by mild reduction of disulfide bonds and alkylation. Alternatively, such fragments may also be generated by recombinant genetic engineering techniques.

Certain preferred antibodies are those antibodies that inhibit or block a TGF-beta binding protein activity within an in vitro assay, as described herein. Binding properties of an antibody to a TGF-beta binding protein may generally be assessed using immunodetection methods including, for example, an enzyme-linked immunosorbent assay (ELISA), immunoprecipitation, immunoblotting, countercurrent immunoelectrophoresis, radioimmunoassays, dot blot assays, inhibition or competition assays, and the like, which may be readily performed by those having ordinary skill in the art (see, e.g., U.S. Pat. Nos. 4,376,110 and 4,486,530; Harlow et al., *Antibodies: A Laboratory Manual*, Cold Spring Harbor Laboratory (1988)).

An immunogen may be comprised of cells expressing a TGF-beta binding protein, purified or partially purified TGF-beta binding polypeptides, or variants or fragments (i.e., peptides) thereof, or peptides derived from a TG F-beta binding protein. Such peptides may be generated by proteolytic cleavage of a larger polypeptide, by recombinant molecular methodologies, or may be chemically synthesized. For instance, nucleic acid sequences encoding TGF-beta binding proteins are provided herein, such that those skilled in the art may routinely prepare TGF-beta binding proteins for use as immunogens. Peptides may be chemically synthesized by methods as described herein and known in the art. Alternatively, peptides may be generated by proteolytic cleavage of a TGF-beta binding protein, and individual peptides isolated by methods known in the art such as polyacrylamide gel electrophoresis or any number of liquid chromatography or other separation methods. Peptides useful as immunogens typically may have an amino acid sequence of at least 4 or 5 consecutive amino acids from a TGF-beta binding protein amino acid sequence such as those described herein, and preferably have at least 6, 7, 8, 9, 10, 11, 12, 14, 15, 16, 18, 19 or 20 consecutive amino acids of a TGF-beta binding protein. Certain other preferred peptide immunogens comprise at least 6 but no more than 12 or more consecutive amino acids of a TGF-beta binding protein sequence, and other preferred peptide immunogens comprise at least 21 but no more than 50 consecutive amino acids of a SOST polypeptide. Other preferred peptide immunogens comprise 21-25, 26-30, 31-35, 36-40, 41-50, or any whole integer number of amino acids between and including 21 and 100 consecutive amino acids, and between 100 and 190 consecutive amino acids of a TGF-beta binding protein sequence.

As disclosed herein, polyclonal antibodies may be readily generated by one of ordinary skill in the art from a variety of warm-blooded animals such as horses, cows, various fowl, rabbits, mice, sheep, goats, baboons, or rats. Typically, the TGF-beta binding-protein or unique peptide thereof of 13-20 amino acids or as described herein (preferably conjugated to keyhole limpet hemocyanin by cross-linking with glutaraldehyde) is used to immunize the animal through intraperitoneal, intramuscular, intraocular, intradermal, or subcutaneous injections, along with an adjuvant such as Freund's complete or incomplete adjuvant, or the Ribi Adjuvant System (Corixa Corporation, Seattle, Wash.). See also, e.g., Harlow et al., supra. In general, after the first injection, animals receive one or more booster immunizations according to a preferred schedule that may vary according to, inter alia, the antigen, the adjuvant (if any), and/or the particular animal species. The immune response may be monitored by periodically bleeding the animal and preparing and analyzing sera in an immunoassay, such as an ELISA or Ouchterlony diffusion assay, or the like, to determine the specific antibody titer. Particularly preferred polyclonal antisera will give a detectable signal on one of these assays, such as an ELISA, that is preferably at least three times greater than background. Once the titer of the animal has reached a plateau in terms of its reactivity to the protein, larger quantities of antisera may be readily obtained either by weekly bleedings, or by exsanguinating the animal.

Polyclonal antibodies that bind specifically to the TGF-beta binding protein or peptide may then be purified from such antisera, for example, by affinity chromatography using protein A. Alternatively, affinity chromatography may be performed wherein the TGF-beta binding protein or peptide or an antibody specific for an Ig constant region of the particular immunized animal species is immobilized on a suitable solid support.

Antibodies for use in the invention include monoclonal antibodies that are prepared by conventional immunization and cell fusion procedures as described herein an known in the art. Monoclonal antibodies may be readily generated using conventional techniques (see, e.g., Kohler et al., *Nature* 256:495, 1975; Coligan et al. (eds.), *Current Protocols in Immunology*, 1:2.5.1-2.6.7 (John Wiley & Sons 1991) ["Coligan"]; U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference; Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques.

Briefly, within one embodiment a subject animal such as a rat or mouse or hamster is immunized with TGF-beta binding-protein or a portion of a region thereof, including peptides within a region, as described herein. The protein may be admixed with an adjuvant such as Freund's complete or incomplete adjuvant or Ribi adjuvant in order to increase the resultant immune response. Between one and three weeks after the initial immunization the animal may be reimmunized with another booster immunization, and tested for reactivity to the protein using assays described herein. Once the animal has reached a plateau in its reactivity to the injected protein, it is sacrificed, and organs which contain large numbers of B cells such as the spleen and lymph nodes are harvested. The harvested spleen and/or lymph node cell suspensions are fused with a suitable myeloma cell that is drug-sensitized in order to create a "hybridoma" which secretes monoclonal antibody. Suitable myeloma lines include, for example, NS-0, SP20, NS-1 (ATCC No. TIB 18), and P3X63-Ag 8.653 (ATCC No. CRL 1580).

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. Following the fusion, the cells may be placed into culture plates containing a suitable medium, such as RPMI 1640, or DMEM (Dulbecco's Modified Eagles Medium) (JRH Biosciences, Lenexa, Kans.), as well as additional ingredients, such as fetal bovine serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive with TGF-beta binding-protein (depending on the antigen used), and which block, impair, or inhibit the binding of TGF-beta binding-protein to a TGF-beta family member. Hybridomas that produce monoclonal antibodies that specifically bind to sclerostin or a variant thereof are preferred.

A wide variety of assays may be utilized to determine the presence of antibodies which are reactive against the proteins of the present invention, including for example countercurrent immuno-electrophoresis, radioimmunoassays, radioimmunoprecipitations, enzyme-linked immuno-sorbent assays (ELISA), dot blot assays, western blots, immunoprecipitation, inhibition or competition assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). The hybridomas are cloned, for example, by limited dilution cloning or by soft agar plaque isolation, and reassayed. Thus, a hybridoma producing antibodies reactive against the desired protein may be isolated.

The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, and a TGF-beta binding protein, or fragment or variant thereof.

In addition, an anti-TGF-beta binding-protein antibody of the present invention may be a human monoclonal antibody. Human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, human monoclonal antibodies may be obtained from transgenic mice that have been engineered to produce specific human antibodies in response to antigenic challenge. Methods for obtaining human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N.Y. Acad. Sci.* 764: 525-35. In this technique, elements of the human heavy and light chain locus are introduced into strains of mice derived from embryonic stem cell lines that contain targeted disruptions of the endogenous heavy chain and light chain loci. (See also Bruggemann et al., *Curr. Opin. Biotechnol.* 8:455-58 (1997)). For example, human immunoglobulin transgenes may be mini-gene constructs, or transloci on yeast artificial chromosomes, which undergo B cell-specific DNA rearrangement and hypermutation in the mouse lymphoid tissue. Human monoclonal antibodies may be obtained by immunizing the transgenic mice, which may then produce human antibodies specific for the antigen. Lymphoid cells of the immunized transgenic mice can be used to produce human antibody-secreting hybridomas according to the methods described herein. Polyclonal sera containing human antibodies may also be obtained from the blood of the immunized animals.

Another method for generating human TGF-beta binding protein specific monoclonal antibodies includes immortalizing human peripheral blood cells by EBV transformation.

See, e.g., U.S. Pat. No. 4,464,456. Such an immortalized B cell line (or lymphoblastoid cell line) producing a monoclonal antibody that specifically binds to a TGF-beta binding protein (or a variant or fragment thereof) can be identified by immunodetection methods as provided herein, for example, an ELISA, and then isolated by standard cloning techniques. The stability of the lymphoblastoid cell line producing an anti-TGF-beta binding protein antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B cells with antigen, followed by fusion of primed B cells with a heterohybrid fusion partner. See, e.g., Boerner et al., 1991 *J. Immunol.* 147:86-95.

In certain embodiments, a B cell that is producing an anti-SOST antibody is selected and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. Preferably B cells from an immunized animal are isolated from the spleen, lymph node, or peripheral blood sample by selecting a cell that is producing an antibody that specifically binds to SOST. B cells may also be isolated from humans, for example, from a peripheral blood sample. Methods for detecting single B cells that are producing an antibody with the desired specificity are well known in the art, for example, by plaque formation, fluorescence-activated cell sorting, in vitro stimulation followed by detection of specific antibody, and the like. Methods for selection of specific antibody producing B cells include, for example, preparing a single cell suspension of B cells in soft agar that contains SOST or a peptide fragment thereof. Binding of the specific antibody produced by the B cell to the antigen results in the formation of a complex, which may be visible as an immunoprecipitate. After the B cells producing the specific antibody are selected, the specific antibody genes may be cloned by isolating and amplifying DNA or mRNA according to methods known in the art and described herein.

For particular uses, fragments of anti-TGF-beta binding protein antibodies may be desired. Antibody fragments, F(ab')$_2$, Fab, Fab', Fv, Fc, Fd, retain the antigen binding site of the whole antibody and therefore bind to the same epitope. These antigen-binding fragments derived from an antibody can be obtained, for example, by proteolytic hydrolysis of the antibody, for example, pepsin or papain digestion of whole antibodies according to conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Coligan at pages 2.8.1-2.8.10 and 2.10.-2.10.4. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein that acts like an antibody in that it binds to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins), and minimal recognition units consisting of the amino acid residues that mimic the hypervariable region. The antibody of the present invention preferably comprises at least one variable region domain. The variable region domain may be of any size or amino acid composition and will generally comprise at least one hypervariable amino acid sequence responsible for antigen binding and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding antigen with acceptable affinity. Alternatively, the V region domain may be dimeric and contain $V_H$-$V_H$, $V_H$-$V_L$, or $V_L$-$V_L$, dimers. Preferably, the V region dimer comprises at least one $V_H$ and at least one $V_L$ chain that are non-covalently associated (hereinafter referred to as $F_v$). If desired, the chains may be covalently coupled either directly, for example via a disulphide bond between the two variable domains, or through a linker, for example a peptide linker, to form a single chain Fv (sc$F_v$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a $V_H$ domain that is present in the variable region domain may be linked to an immunoglobulin $C_H1$ domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Another form of an antibody fragment is a peptide comprising for a single complementarity-determining region (CDR). CDR peptides ("minimal recognition units") can be obtained by constructing polynucleotides that encode the CDR of an antibody of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, the antibody may be a recombinant or engineered antibody obtained by the use of recombinant DNA techniques involving the manipulation and re-expression of DNA encoding antibody variable and/or constant regions. Such DNA is known and/or is readily available from DNA libraries including for example phage-antibody libraries (see Chiswell and McCafferty, *Tibtech.* 10:80-84 (1992)) or if desired can be synthesized. Standard molecular biology and/or chemistry procedures may be used to sequence and manipulate the DNA, for example, to introduce codons to create cysteine residues, or to modify, add or delete other amino acids or domains as desired.

Chimeric antibodies, specific for a TGF-beta binding protein, and which include humanized antibodies, may also be generated according to the present invention. A chimeric antibody has at least one constant region domain derived from a first mammalian species and at least one variable region domain derived from a second, distinct mammalian species (see, e.g., Morrison et al., *Proc. Natl. Acad. Sci. USA*, 81:6851-55 (1984)). In preferred embodiments, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleotide sequence that encodes at least one human constant region (see, e.g., Shin et al., *Methods Enzymol.* 178:459-76 (1989); Walls et al., *Nucleic Acids Res.* 21:2921-29 (1993)). By way of example, the polynucleotide sequence encoding the light chain variable region of a murine monoclonal antibody may be inserted into a vector containing a nucleotide sequence encoding the human kappa light chain constant region sequence. In a separate vector, the polynucleotide sequence encoding the heavy chain variable region of the monoclonal antibody may be cloned in frame with sequences encoding a human IgG constant region, for example, the human IgG1 constant region. The particular human constant region selected may depend upon the effector functions desired for the particular antibody (e.g., complement fixing, binding to a particular Fc receptor, etc.). Preferably, the constructed vectors will be transfected into eukaryotic cells for stable expression of the chimeric antibody. Another method known in the art for generating chimeric antibodies is homologous recombination (e.g., U.S. Pat. No. 5,482,856).

A non-human/human chimeric antibody may be further genetically engineered to create a "humanized" antibody. Such a humanized antibody may comprise a plurality of CDRs derived from an immunoglobulin of a non-human mammalian species, at least one human variable framework region, and at least one human immunoglobulin constant region. Useful strategies for designing humanized antibodies may include, for example by way of illustration and not limitation, identification of human variable framework regions that are most homologous to the non-human framework regions of the chimeric antibody. Without wishing to be bound by theory, such a strategy may increase the likelihood that the humanized antibody will retain specific binding affinity for a TGF-beta binding protein, which in some preferred embodiments may be substantially the same affinity for a TGF-beta binding protein or variant or fragment thereof, and in certain other preferred embodiments may be a greater affinity for TGF-beta binding protein. See, e.g., Jones et al., 1986 *Nature* 321:522-25; Riechmann et al., 1988 *Nature* 332:323-27. Designing such a humanized antibody may therefore include determining CDR loop conformations and structural determinants of the non-human variable regions, for example, by computer modeling, and then comparing the CDR loops and determinants to known human CDR loop structures and determinants. See, e.g., Padlan et al., 1995 *FASEB* 9:133-39; Chothia et al., 1989 *Nature,* 342:377-383. Computer modeling may also be used to compare human structural templates selected by sequence homology with the non-human variable regions. See, e.g., Bajorath et al., 1995 *Ther. Immunol.* 2:95-103; EP-0578515-A3. If humanization of the non-human CDRs results in a decrease in binding affinity, computer modeling may aid in identifying specific amino acid residues that could be changed by site-directed or other mutagenesis techniques to partially, completely or supra-optimally (i.e., increase to a level greater than that of the non-humanized antibody) restore affinity. Those having ordinary skill in the art are familiar with these techniques, and will readily appreciate numerous variations and modifications to such design strategies.

One such method for preparing a humanized antibody is called veneering. As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site that retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al., *Ann. Rev. Biochem.* 59:439-73, 1990. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues that are readily encountered by the immune system are selectively replaced with human residues to provide a hybrid molecule that comprises either a weakly immunogenic, or substantially nonimmunogenic veneered surface.

The process of veneering makes use of the available sequence data for human antibody variable domains compiled by Kabat et al., in *Sequences of Proteins of Immunological Interest*, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR that differ from the human counterpart are replaced by the residues present in the human moiety using recombinant techniques well known in the art. Residue switching is only carried out with moieties which are at least partially exposed (solvent accessible), and care is exercised in the replacement of amino acid residues that may have a significant effect on the tertiary structure of V region domains, such as proline, glycine, and charged amino acids.

In this manner, the resultant "veneered" antigen-binding sites are thus designed to retain the rodent CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences that combine the CDRs of both the heavy and light chain of a antigen-binding site into human-appearing FRs that can be used to transfect mammalian cells for the expression of recombinant human antibodies that exhibit the antigen specificity of the rodent antibody molecule.

An additional method for selecting antibodies that specifically bind to a TGF-beta binding protein or variant or fragment thereof is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; William D. Huse et al., "Generation of a Large Combinational Library of the Immunoglobulin Repertoire in Phage Lambda," *Science* 246:1275-1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728-5732, August 1989; see also Michelle Alting-Mees et al., "Monoclonal Antibody Expression Libraries: A Rapid Alternative to Hybridomas," *Strategies in Molecular Biology* 3:1-9, January 1990; Kang et al., 1991 *Proc. Natl. Acad. Sci. USA* 88:4363-66; Hoogenboom et al., 1992 *J. Molec. Biol.* 227:381-388; Schlebusch et al., 1997 *Hybridoma* 16:47-52 and references cited therein). A commercial system is available from Stratagene (La Jolla, Calif.) which enables the production of antibodies through recombinant techniques. Briefly, mRNA is isolated from a B cell population, and utilized to create heavy and light chain immunoglobulin cDNA expression libraries in the λ ImmunoZap (H) and λImmunoZap(L) vectors. Positive plaques may subsequently be converted to a non-lytic plasmid which allows high level expression of monoclonal antibody fragments from *E. coli*. Alternatively, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426). These vectors may be screened individually or co-expressed to form Fab fragments or antibodies (see Huse et al., supra; see also Sastry et al., supra).

Similarly, portions or fragments, such as Fab and Fv fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratagene (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423-426, 1988). In addition, such techniques may be utilized to change a "murine" antibody to a "human" antibody, without altering the binding specificity of the antibody.

In certain particular embodiments of the invention, combinatorial phage libraries may also be used for humanization of non-human variable regions. See, e.g., Rosok et al., 1996 *J. Biol. Chem.* 271:22611-18; Rader et al., 1998 *Proc. Natl. Acad. Sci. USA* 95:8910-15. A phage library may be screened to select an Ig variable region fragment of interest by immunodetection methods known in the art and described herein, and the DNA sequence of the inserted immunoglobulin gene in the phage so selected may be determined by standard techniques. See, Sambrook et al., 2001 *Molecular Cloning: A Laboratory Manual*, Cold Spring Harbor Press. The selected Ig-encoding sequence may then be cloned into another suitable vector for expression of the Ig fragment or, optionally, may be cloned into a vector containing Ig constant regions, for expression of whole immunoglobulin chains.

In certain other embodiments, the invention contemplates SOST-specific antibodies that are multimeric antibody fragments. Useful methodologies are described generally, for example in Hayden et al. 1997, *Curr Opin. Immunol.* 9:201-12; Coloma et al., 1997 *Nat. Biotechnol.* 15:159-63). For example, multimeric antibody fragments may be created by phage techniques to form miniantibodies (U.S. Pat. No. 5,910,573) or diabodies (Holliger et al., 1997, *Cancer Immunol. Immunother.* 45:128-130).

In certain embodiments of the invention, an antibody specific for SOST may be an antibody that is expressed as an intracellular protein. Such intracellular antibodies are also referred to as intrabodies and may comprise an Fab fragment, or preferably comprise a scFv fragment (see, e.g., Lecerf et al., *Proc. Natl. Acad. Sci. USA* 98:4764-49 (2001). The framework regions flanking the CDR regions can be modified to improve expression levels and solubility of an intrabody in an intracellular reducing environment (see, e.g., Worn et al., *J. Biol. Chem.* 275:2795-803 (2000). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., *Mol. Cell Biol.* 15:1182-91 (1995); Lener et al., *Eur. J. Biochem.* 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

Introducing amino acid mutations into an immunoglobulin molecule specific for a TGF-beta binding protein may be useful to increase the specificity or affinity for TGF-beta binding protein or to alter an effector function. Immunoglobulins with higher affinity for TGF-beta binding protein may be generated by site-directed mutagenesis of particular residues. Computer assisted three-dimensional molecular modeling may be employed to identify the amino acid residues to be changed, in order to improve affinity for the TGF-beta binding protein. See, e.g., Mountain et al., 1992, *Biotechnol. Genet. Eng. Rev.* 10: 1-142. Alternatively, combinatorial libraries of CDRs may be generated in M13 phage and screened for immunoglobulin fragments with improved affinity. See, e.g., Glaser et al., 1992, *J. Immunol.* 149:3903-3913; Barbas et al., 1994 *Proc. Natl. Acad. Sci. USA* 91:3809-13; U.S. Pat. No. 5,792,456.

Effector functions may also be altered by site-directed mutagenesis. See, e.g., Duncan et al., 1988 *Nature* 332:563-64; Morgan et al., 1995 *Immunology* 86:319-24; Eghtedarze-deh-Kondri et al., 1997 *Biotechniques* 23:830-34. For example, mutation of the glycosylation site on the Fc portion of the immunoglobulin may alter the ability of the immunoglobulin to fix complement. See, e.g., Wright et al., 1997 *Trends Biotechnol.* 15:26-32. Other mutations in the constant region domains may alter the ability of the immunoglobulin to fix complement, or to effect antibody-dependent cellular cytotoxicity. See, e.g., Duncan et al., 1988 *Nature* 332:563-64; Morgan et al., 1995 *Immunology* 86:319-24; Sensel et al., 1997 *Mol. Immunol.* 34:1019-29.

According to certain embodiments, non-human, human, or humanized heavy chain and light chain variable regions of any of the Ig molecules described herein may be constructed as single chain Fv (scFv) polypeptide fragments (single chain antibodies). See, e.g., Bird et al., 1988 *Science* 242:423-426; Huston et al., 1988 *Proc. Natl. Acad. Sci. USA* 85:5879-5883. Multi-functional scFv fusion proteins may be generated by linking a polynucleotide sequence encoding an scFv polypeptide in-frame with at least one polynucleotide sequence encoding any of a variety of known effector proteins. These methods are known in the art, and are disclosed, for example, in EP-B1-0318554, U.S. Pat. No. 5,132,405, U.S. Pat. No. 5,091,513, and U.S. Pat. No. 5,476,786. By way of example, effector proteins may include immunoglobulin constant region sequences. See, e.g., Hollenbaugh et al., 1995 *J. Immunol. Methods* 188:1-7. Other examples of effector proteins are enzymes. As a non-limiting example, such an enzyme may provide a biological activity for therapeutic purposes (see, e.g., Siemers et al., 1997 *Bioconjug. Chem.* 8:510-19), or may provide a detectable activity, such as horseradish peroxidase-catalyzed conversion of any of a number of well-known substrates into a detectable product, for diagnostic uses. Still other examples of scFv fusion proteins include Ig-toxin fusions, or immunotoxins, wherein the scFv polypeptide is linked to a toxin.

The scFv or any antibody fragment described herein may, in certain embodiments, be fused to peptide or polypeptide domains that permits detection of specific binding between the fusion protein and antigen (e.g., a TGF-beta binding protein). For example, the fusion polypeptide domain may be an affinity tag polypeptide for detecting binding of the scFv fusion protein to a TGF-beta binding protein by any of a variety of techniques with which those skilled in the art will be familiar. Examples of a peptide tag, include avidin, streptavidin or His (e.g., polyhistidine). Detection techniques may also include, for example, binding of an avidin or streptavidin fusion protein to biotin or to a biotin mimetic sequence (see, e.g., Luo et al., 1998 *J. Biotechnol.* 65:225 and references cited therein), direct covalent modification of a fusion protein with a detectable moiety (e.g., a labeling moiety), non-covalent binding of the fusion protein to a specific labeled reporter molecule, enzymatic modification of a detectable substrate by a fusion protein that includes a portion having enzyme activity, or immobilization (covalent or non-covalent) of the fusion protein on a solid-phase support. Other useful affinity polypeptides for construction of scFv fusion proteins may include streptavidin fusion proteins, as disclosed, for example, in WO 89/03422, U.S. Pat. No. 5,489,528, U.S. Pat. No. 5,672,691, WO 93/24631, U.S. Pat. No. 5,168,049, U.S. Pat. No. 5,272,254; avidin fusion proteins (see, e.g., EP 511,747); an enzyme such as glutathione-S-transferase; and *Staphylococcus aureus* protein A polypeptide.

The polynucleotides encoding an antibody or fragment thereof that specifically bind a TGF-beta binding protein, as described herein, may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns (including use of anti-constant region antibodies attached to the column matrix), HPLC or RP-HPLC, purification on protein A or protein G columns, or any combination of these techniques.

c. Mutant TGF-beta Binding-proteins

As described herein and below in the Examples (e.g., Examples 8 and 9), altered versions of TGF-beta binding-protein which compete with native TGF-beta binding-protein's ability to block the activity of a particular TGF-beta family member should lead to increased bone density. Thus, mutants of TGF-beta binding-protein which bind to the TGF-beta family member but do not inhibit the function of the TGF-beta family member would meet the criteria. The mutant versions must effectively compete with the endogenous inhibitory functions of TGF-beta binding-protein.

d. Production of Proteins

Polypeptides described herein include the TGF binding protein sclerostin and variants thereof and antibodies or fragments thereof that specifically bind to sclerostin. The polynucleotides that encode these polypeptides include derivatives of the genes that are substantially similar to the genes and isolated nucleic acid molecules, and, when appropriate, the proteins (including peptides and polypeptides) that are encoded by the genes and their derivatives. As used herein, a nucleotide sequence is deemed to be "substantially similar" if (a) the nucleotide sequence is derived from the coding region of the above-described genes and nucleic acid molecules and includes, for example, portions of the sequence or allelic variations of the sequences discussed above, or alternatively, encodes a molecule which inhibits the binding of TGF-beta binding-protein to a member of the TGF-beta family; (b) the nucleotide sequence is capable of hybridization to nucleotide sequences of the present invention under moderate, high or very high stringency (see Sambrook et al., *Molecular Clon-* ing: *A Laboratory Manual*, 2nd ed., Cold Spring Harbor Laboratory Press, NY, 1989); and/or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent).

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157: 105-132, 1982).

Proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the proteins disclosed herein include conjugates of the proteins along with other proteins or polypeptides. This may be accomplished, for example, by the synthesis of N-terminal or C-terminal fusion proteins which may be added to facilitate purification or identification of proteins (see U.S. Pat. No. 4,851,341, see also, Hopp et al., *Bio/Technology* 6:1204, 1988.) Alternatively, fusion proteins such as Flag®/TGF-beta binding-protein be constructed in order to assist in the identification, expression, and analysis of the protein.

Proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene or nucleic acid molecule having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*Bio-Techniques*, January 1985, 12-19); Smith et al. (*Genetic Engineering: Principles and Methods*, Plenum Press, 1981); and Sambrook et al. (supra). Deletion or truncation derivatives of proteins (e.g., a soluble extracellular portion) may also be constructed by utilizing convenient restriction endonuclease sites adjacent to the desired deletion. Subsequent to restriction, overhangs may be filled in and the DNA religated. Exemplary methods of making the alterations set forth above are disclosed by Sambrook et al. (*Molecular Cloning: A Laboratory Manual*, 2d Ed., Cold Spring Harbor Laboratory Press, 1989).

Mutations which are made in the nucleic acid molecules of the present invention preferably preserve the reading frame of the coding sequences. Furthermore, the mutations will preferably not create complementary regions that when transcribed could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for gain or loss or retention of biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Nucleic acid molecules which encode proteins of the present invention may also be constructed utilizing techniques such as PCR mutagenesis, chemical mutagenesis (Drinkwater and Klinedinst, *PNAS* 83:3402-3406, 1986), by forced nucleotide misincorporation (e.g., Liao and Wise *Gene* 88:107-111, 1990), or by use of randomly mutagenized oligonucleotides (Horwitz et al., *Genome* 3:112-117, 1989).

The present invention also provides for the manipulation and expression of the above described genes and nucleic acid molecules by culturing host cells containing a vector capable of expressing the above-described genes. Such vectors or vector constructs include either synthetic or cDNA-derived nucleic acid molecules encoding the desired protein, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include a transcriptional promoter and enhancer or RNA polymerase binding sequence, a transcriptional terminator, and a ribosomal binding sequence, including a translation initiation signal.

Nucleic acid molecules that encode any of the proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc. Natl. Acad. Sci. USA* 75:1929-1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual*, 2nd ed., Cold Spring Harbor Laboratory Press, 1989; for plant cells see Czako and Marton, *Plant Physiol.* 104:1067-1071, 1994; and Paszkowski et al., *Biotech.* 24:387-392, 1992).

Bacterial host cells suitable for carrying out the present invention include *E. coli*, *B. subtilis*, *Salmonella typhimurium*, and various species within the genera *Pseudomonas*, *Streptomyces*, and *Staphylococcus*, as well as many other bacterial species well known to one of ordinary skill in the art and described herein. A representative example of a bacterial host cell includes *E. coli* DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155, 1983), and the tac promoter (Russell et al., *Gene* 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20-77, 1983 and Vieira and Messing, *Gene* 19:259-268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae*, the genera *Pichia* or *Kluyveromyces* and various species of the genus *Aspergillus* (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035-1039, 1978), YEp13 (Broach et al., *Gene* 8:121-133, 1979), pJDB249 and pJDB219 (Beggs, *Nature* 275:104-108, 1978) and derivatives thereof.

Preferred promoters for use in yeast include promoters from yeast glycolytic genes (Hitzeman et al., *J. Biol. Chem.* 255:12073-12080, 1980; Alber and Kawasaki, *J. Mol. Appl. Genet.* 1:419-434, 1982) or alcohol dehydrogenase genes (Young et al., in *Genetic Engineering of Microorganisms for Chemicals*, Hollaender et al. (eds.), p. 355, Plenum, New York, 1982; Ammerer, *Meth. Enzymol.* 101:192-201, 1983). Examples of useful promoters for fungi vectors include those derived from *Aspergillus nidulans* glycolytic genes, such as the adh3 promoter (McKnight et al., *EMBO J.* 4:2093-2099, 1985). The expression units may also include a transcriptional terminator. An example of a suitable terminator is the adh3 terminator (McKnight et al., supra, 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance, or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature and have been described, for instance, by Beggs (ibid.), Hinnen et al. (*Proc. Natl. Acad. Sci. USA* 75:1929-1933, 1978), Yelton et al. (*Proc. Natl. Acad. Sci. USA* 81:1740-1747, 1984), and Russell (*Nature* 301:167-169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983).

Transformation of fungi may also be carried out using polyethylene glycol as described by Cullen et al. (*Bio/Technology* 5:369, 1987).

Viral vectors include those that comprise a promoter that directs the expression of an isolated nucleic acid molecule that encodes a desired protein as described above. A wide variety of promoters may be utilized within the context of the present invention, including for example, promoters such as MoMLV LTR, RSV LTR, Friend MuLV LTR, adenoviral promoter (Ohno et al., *Science* 265:781-784, 1994), neomycin phosphotransferase promoter/enhancer, late parvovirus promoter (Koering et al., *Hum. Gene Therap.* 5:457-463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morphogenic protein promoter, human alpha1-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus, or parasite.

Mammalian cells suitable for carrying out the present invention include, among others COS, CHO, SaOS, osteosarcomas, KS483, MG-63, primary osteoblasts, and human or mammalian bone marrow stroma. Mammalian expression vectors for use in carrying out the present invention will include a promoter capable of directing the transcription of a cloned gene, nucleic acid molecule, or cDNA. Preferred promoters include viral promoters and cellular promoters. Bone specific promoters include the promoter for bone sialo-protein and the promoter for osteocalcin. Viral promoters include the cytomegalovirus immediate early promoter (Boshart et al., *Cell* 41:521-530, 1985), cytomegalovirus immediate late promoter, SV40 promoter (Subramani et al., *Mol. Cell. Biol.* 1:854-864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041-7045, 1983; Grant et al., *Nucleic Acids Res.* 15:5496, 1987) and a mouse $V_H$ promoter (Loh et al., *Cell* 33:85-93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nucleic Acids Res.* 9:3719-3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), or DEAE-dextran mediated transfection (Ausubel et al. (eds.), *Current Protocols in Molecular Biology*, John Wiley and Sons, Inc., NY, 1987). To identify cells that have stably transfected with the vector or have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference).

Mammalian cells containing a suitable vector are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable, selectable marker, the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals). Methods for using insect host cells and plant host cells for production of polypeptides are known in the art and described herein. Numerous insect host cells known in the art can also be useful within the present invention. For example, the use of baculoviruses as vectors for expressing heterologous DNA sequences in insect cells has been reviewed by Atkinson et al. (*Pestic. Sci.* 28:215-224, 1990). Numerous vectors and plant host cells known in the art can also be useful within the present invention, for example, the use of *Agrobacterium rhizogenes* as vectors for expressing genes and nucleic acid molecules in plant cells (see review by Sinkar et al., *J. Biosci.* (*Bangalore* 11:47-58, 1987).

Within related aspects of the present invention, proteins of the present invention may be expressed in a transgenic animal whose germ cells and somatic cells contain a gene which encodes the desired protein and which is operably linked to a promoter effective for the expression of the gene. Alternatively, in a similar manner transgenic animals may be prepared that lack the desired gene (e.g., "knock-out" mice). Such transgenics may be prepared in a variety of non-human animals, including mice, rats, rabbits, sheep, dogs, goats, and pigs (see Hammer et al., *Nature* 315:680-683, 1985, Palmiter et al., *Science* 222:809-814, 1983, Brinster et al., *Proc. Natl. Acad. Sci. USA* 82:4438-4442, 1985, Palmiter and Brinster, *Cell* 41:343-345, 1985, and U.S. Pat. Nos. 5,175,383, 5,087, 571, 4,736,866, 5,387,742, 5,347,075, 5,221,778, and 5,175, 384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, supra), which allows regulated expression of the transgene.

Proteins can be isolated by, among other methods, culturing suitable host and vector systems to produce the recombinant translation products as described herein. Supernatants from such cell lines, or protein inclusions, or whole cells from which the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody (e.g., an antibody that specifically binds to the polypeptide to be isolated) bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the art.

The purity of an isolated polypeptide may be determined by techniques known in the art and described herein, such as gel electrophoresis and chromatography methods. Preferably, such isolated polypeptides are at least about 90% pure, more preferably at least about 95% pure, and most preferably at least about 99% pure. Within certain specific embodiments, a protein is deemed to be "isolated" within the context of the present invention if no other undesired protein is detected pursuant to SDS-PAGE analysis followed by Coomassie blue staining. Within other embodiments, the desired protein can be isolated such that no other undesired protein is detected pursuant to SDS-PAGE analysis followed by silver staining.

3. Nucleic Acid Molecules

Within other aspects of the invention, nucleic acid molecules are provided which are capable of inhibiting TGF-beta binding-protein binding to a member of the TGF-beta family. For example, within one embodiment antisense oligonucleotide molecules are provided which specifically inhibit expression of TGF-beta binding-protein nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004-1012, 1993; WO 95/10607; U.S. Pat. No. 5,359,051; WO 92/06693; and EP-A2-612844). Briefly, such molecules are constructed such that they are complementary to, and able to form Watson-Crick base pairs with, a region of transcribed TGF-beta binding-protein mRNA sequence. The resultant double-stranded nucleic acid interferes with subsequent processing of the mRNA, thereby preventing protein synthesis (see Example 10).

Within other aspects of the invention, ribozymes are provided which are capable of inhibiting the TGF-beta binding-protein binding to a member of the TGF-beta family. As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211-220, 1987; Haseloff and Gerlach, *Nature* 328:596-600, 1988; Walbot and Bruening, *Nature* 334:196, 1988; Haseloff and Gerlach, *Nature* 334:585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and *Tetrahymena* ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

4. Labels

The gene product or any of the candidate molecules described above and below, may be labeled with a variety of compounds, including for example, fluorescent molecules, toxins, and radionuclides. Representative examples of fluorescent molecules include fluorescein, *Phycobili* proteins, such as phycoerythrin, rhodamine, Texas red and luciferase. Representative examples of toxins include ricin, abrin diphtheria toxin, cholera toxin, gelonin, pokeweed antiviral protein, tritin, *Shigella* toxin, and *Pseudomonas* exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, streptavidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1-32, 1988).

Pharmaceutical Compositions

As noted above, the present invention also provides a variety of pharmaceutical compositions, comprising one of the above-described molecules which inhibits the TGF-beta binding-protein binding to a member of the TGF-beta family along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The pharmaceutical compositions of the present invention may be prepared for administration by a variety of different routes. In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrastemal, intracavernous, intrameatal, or intraurethral injection or infusion. A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638).

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems, such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers or as controlled release matrices for the compositions of this invention. Exemplary calcium phosphate particles are disclosed, for example, in published patent application No. WO/0046147.

For pharmaceutical compositions comprising a polynucleotide encoding an anti-SOST antibody and/or modulating agent (such that the polypeptide and/or modulating agent is generated in situ), the polynucleotide may be present within any of a variety of delivery systems known to those of ordinary skill in the art, including nucleic acid, and bacterial, viral and mammalian expression systems. Techniques for incorporating DNA into such expression systems are well known to those of ordinary skill in the art. The DNA may also be "naked," as described, for example, in Ulmer et al., *Science* 259:1745-1749, 1993 and reviewed by Cohen, *Science* 259: 1691-1692, 1993. The uptake of naked DNA may be increased by coating the DNA onto biodegradable beads, which are efficiently transported into the cells.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399, 363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences,* 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3): 691-95, 1998; Chandran et al., *Indian J. Exp. Biol.* 35(8):801-09, 1997; Margalit, *Crit. Rev. Ther. Drug. Carrier Syst.* 12(2-3):233-61, 1995; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., *J. Biol. Chem.* 265(27):16337-42, 1990; Muller et al., *DNA Cell Biol.* 9(3): 221-29, 1990). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 µm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treatment

The present invention also provides methods for increasing the mineral content and mineral density of bone. Briefly, numerous conditions result in the loss of bone mineral content, including for example, disease, genetic predisposition, accidents which result in the lack of use of bone (e.g., due to fracture), therapeutics which effect bone resorption, or which kill bone forming cells and normal aging. Through use of the molecules described herein which inhibit the TGF-beta binding-protein binding to a TGF-beta family member such conditions may be treated or prevented. As utilized herein, it should be understood that bone mineral content has been increased if bone mineral content has been increased in a statistically significant manner (e.g. greater than one-half standard deviation), at a selected site.

A wide variety of conditions that result in loss of bone mineral content may be treated with the molecules described herein. Patients with such conditions may be identified through clinical diagnosis utilizing well known techniques (see, e.g., Harrison's Principles of Internal Medicine, McGraw-Hill, Inc.). Representative examples of diseases that may be treated included dysplasias, wherein there is abnormal growth or development of bone. Representative examples of such conditions include achondroplasia, cleidocranial dysostosis, enchondromatosis, fibrous dysplasia, Gaucher's Disease, hypophosphatemic rickets, Marfan's Syndrome, multiple hereditary exotoses, neurofibromatosis, osteogenesis imperfecta, osteopetrosis, osteopoikilosis, sclerotic lesions, fractures, periodontal disease, pseudoarthrosis, and pyogenic osteomyelitis.

Other conditions which may be treated or prevented include a wide variety of causes of osteopenia (i.e., a condition that causes greater than one standard deviation of bone mineral content or density below peak skeletal mineral content at youth). Representative examples of such conditions include anemic states, conditions caused by steroids, conditions caused by heparin, bone marrow disorders, scurvy, malnutrition, calcium deficiency, idiopathic osteoporosis, congenital osteopenia or osteoporosis, alcoholism, chronic liver disease, senility, postmenopausal state, oligomenorrhea, amenorrhea, pregnancy, diabetes mellitus, hyperthyroidism, Cushing's disease, acromegaly, hypogonadism, immobilization or disuse, reflex sympathetic dystrophy syndrome, transient regional osteoporosis, and osteomalacia.

Within one aspect of the present invention, bone mineral content or density may be increased by administering to a warm-blooded animal a therapeutically effective amount of a molecule that inhibits binding of the TGF-beta binding-protein to a TGF-beta family member. Examples of warm-blooded animals that may be treated include both vertebrates and mammals, including for example humans, horses, cows, pigs, sheep, dogs, cats, rats and mice. Representative examples of therapeutic molecules include ribozymes, ribozyme genes, antisense oligonucleotides, and antibodies (e.g., humanized antibodies or any other antibody described herein).

Within other aspects of the present invention, methods are provided for increasing bone density, comprising the steps of introducing into cells which home to bone, a vector that directs the expression of a molecule which inhibits binding of the TGF-beta binding-protein to a member of the TGF-beta family, and administering the vector-containing cells to a warm-blooded animal. Briefly, cells that home to bone may be obtained directly from the bone of patients (e.g., cells obtained from the bone marrow such as CD34+, osteoblasts, osteocytes, and the like), from peripheral blood, or from cultures.

A vector that directs the expression of a molecule that inhibits the binding of TGF-beta binding-protein to a member of the TGF-beta family may be introduced into cells. Representative examples of suitable vectors include viral vectors such as herpes viral vectors (e.g., U.S. Pat. No. 5,288,641), adenoviral vectors (e.g., WO 94/26914, WO 93/9191; Kolls et al., *PNAS* 91(1):215-219, 1994; Kass-Eisler et al., *PNAS* 90(24):11498-502, 1993; Guzman et al., *Circulation* 88(6): 2838-48, 1993; Guzman et al., *Cir. Res.* 73(6):1202-1207, 1993; Zabner et al., *Cell* 75(2):207-216, 1993; Li et al., *Hum Gene Ther.* 4(4):403-409, 1993; Caillaud et al., *Eur. J. Neurosci.* 5(10:1287-1291, 1993; Vincent et al., *Nat. Genet.* 5(2): 130-134, 1993; Jaffe et al., *Nat. Genet.* 1(5):372-378, 1992; and Levrero et al., *Gene* 101(2):195-202, 1991), adeno-associated viral vectors (WO 95/13365; Flotte et al., *PNAS* 90(22):10613-10617, 1993), baculovirus vectors, parvovirus vectors (Koering et al., *Hum. Gene Therap.* 5:457-463, 1994), pox virus vectors (Panicali and Paoletti, *PNAS* 79:4927-4931, 1982; and Ozaki et al., *Biochem. Biophys. Res. Comm.* 193 (2):653-660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218). Viral vectors may likewise be constructed which contain a mixture of different elements (e.g., promoters, envelope sequences, and the like) from different viruses, or non-viral sources. Within various embodiments, either the viral vector itself, or a viral particle which contains the viral vector may be utilized in the methods and compositions described below. Within other embodiments of the invention, nucleic acid molecules which encode a molecule which inhibits binding of the TGF-beta binding-protein to a member of the TGF-beta family may be administered by a variety of techniques; including, for example, administration of asialoosomucoid (ASOR) conjugated with poly-L-lysine DNA complexes (Cristano et al., *PNAS* 92122-92126, 1993), DNA linked to killed adenovirus (Curiel et al., *Hum. Gene Ther.* 3(2):147-154, 1992), cytofectin-mediated introduction (DM-RIE-DOPE, Vical, Calif.), direct DNA injection (Acsadi et al., *Nature* 352:815-818, 1991); DNA ligand (Wu et al., *J. of Biol. Chem.* 264:16985-16987, 1989); lipofection (Felgner et al., *Proc. Natl. Acad. Sci. USA* 84:7413-7417, 1989); liposomes (Pickering et al., *Circ.* 89(1):13-21, 1994; and Wang et al., *PNAS* 84:7851-7855, 1987); microprojectile bombardment (Williams et al., *PNAS* 88:2726-2730, 1991); and direct delivery of nucleic acids which encode the protein itself either alone (Vile and Hart, *Cancer Res.* 53: 3860-3864, 1993), or utilizing PEG-nucleic acid complexes. Representative examples of molecules that may be expressed by the vectors of present invention include ribozymes and antisense molecules, each of which are discussed in more detail above.

Determination of increased bone mineral content may be determined directly through the use of X-rays (e.g., Dual Energy X-ray Absorptometry or "DEXA"), or by inference through bone turnover markers (such as osteoblast specific alkaline phosphatase, osteocalcin, type 1 procollagen C' propeptide (PICP), and total alkaline phosphatase; see Comier, C., *Curr. Opin. in Rheu.* 7:243, 1995), or by markers of bone resorption (pyridinoline, deoxypryridinoline, N-telopeptide, urinary hydroxyproline, plasma tartrate-resistant acid phosphatases and galactosyl hydroxylysine; see Comier, supra). The amount of bone mass may also be calculated from body weights or by other methods known in the art (see Guinness-Hey, *Metab. Bone Dis. and Relat. Res.* 5:177-181, 1984).

As will be evident to one of skill in the art, the amount and frequency of administration will depend, of course, on such factors as the nature and severity of the indication being treated, the desired response, the condition of the patient, and so forth. Typically, the compositions may be administered by a variety of techniques, as noted above.

The following examples are offered by way of illustration and not by way of limitation.

EXAMPLES

Example 1

Sclerosteosis Maps to the Long Arm of Human Chromosome 17

Genetic mapping of the defect responsible for sclerosteosis in humans localized the gene responsible for this disorder to the region of human chromosome 17 that encodes a novel TGF-beta binding-protein family member. In sclerosteosis, skeletal bone displays a substantial increase in mineral density relative to that of unafflicted individuals. Bone in the head displays overgrowth as well. Sclerosteosis patients are generally healthy although they may exhibit variable degrees of syndactyly at birth and variable degrees of cranial compression and nerve compression in the skull.

Linkage analysis of the gene defect associated with sclerosteosis was conducted by applying the homozygosity mapping method to DNA samples collected from 24 South African Afrikaaner families in which the disease occurred. (Sheffield et al., 1994, *Human Molecular Genetics* 3:1331-1335. "Identification of a Bardet-Biedl syndrome locus on chromosome 3 and evaluation of an efficient approach to homozygosity mapping"). The Afrikaaner population of South Africa is genetically homogeneous; the population is descended from a small number of founders who colonized the area several centuries ago, and it has been isolated by geographic and social barriers since the founding. Sclerosteosis is rare everywhere in the world outside the Afrikaaner community, which suggests that a mutation in the gene was present in the founding population and has since increased in numbers along with the increase in the population. The use of homozygosity mapping is based on the assumption that DNA mapping markers adjacent to a recessive mutation are likely to be homozygous in affected individuals from consanguineous families and isolated populations.

A set of 371 microsatellite markers (Research Genetics, Set 6) from the autosomal chromosomes was selected to type pools of DNA from sclerosteosis patient samples. The DNA samples for this analysis came from 29 sclerosteosis patients in 24 families, 59 unaffected family members and a set of unrelated control individuals from the same population. The pools consisted of 4-6 individuals, either affected individuals, affected individuals from consanguineous families, parents and unaffected siblings, or unrelated controls. In the pools of unrelated individuals and in most of the pools with affected individuals or family members analysis of the markers showed several allele sizes for each marker. One marker, D17S1299, showed an indication of homozygosity: one band in several of the pools of affected individuals.

All 24 sclerosteosis families were typed with a total of 19 markers in the region of D17S1299 (at 17q12-q21). Affected individuals from every family were shown to be homozygous in this region, and 25 of the 29 individuals were homozygous for a core haplotype; they each had the same alleles between D17S1787 and D17S930. The other four individuals had one chromosome which matched this haplotype and a second which did not. In sum, the data compellingly suggested that this 3 megabase region contained the sclerosteosis mutation. Sequence analysis of most of the exons in this 3 megabase region identified a nonsense mutation in the novel TGF-beta binding-protein coding sequence (C>T mutation at position 117 of Sequence ID No. 1 results in a stop codon). This mutation was shown to be unique to sclerosteosis patients and carriers of Afrikaaner descent. The identity of the gene was further confirmed by identifying a mutation in its intron (A>T mutation at position +3 of the intron) which results in improper mRNA processing in a single, unrelated patient with diagnosed sclerosteosis.

Example 2

Tissue-Specificity of TGF-beta Binding-protein Gene Expression

A. Human Beer Gene Expression by RT-PCR:

First-strand cDNA was prepared from the following total RNA samples using a commercially available kit ("Superscript Preamplification System for First-Strand cDNA Synthesis", Life Technologies, Rockville, Md.): human brain, human liver, human spleen, human thymus, human placenta, human skeletal muscle, human thyroid, human pituitary, human osteoblast (NHOst from Clonetics Corp., San Diego, Calif.), human osteosarcoma cell line (Saos-2, ATCC# HTB-85), human bone, human bone marrow, human cartilage, vervet monkey bone, *saccharomyces cerevisiae*, and human peripheral blood monocytes. All RNA samples were purchased from a commercial source (Clontech, Palo Alto, Calif.), except the following which were prepared in-house: human osteoblast, human osteosarcoma cell line, human bone, human cartilage and vervet monkey bone. These in-house RNA samples were prepared using a commercially available kit ("TRI Reagent", Molecular Research Center, Inc., Cincinnati, Ohio).

PCR was performed on these samples, and additionally on a human genomic sample as a control. The sense Beer oligonucleotide primer had the sequence 5'-CCGGAGCTG-GAGAACAACAAG-3' (SEQ ID NO:19). The antisense Beer oligonucleotide primer had the sequence 5'-GCACTGGC-CGGAGCACACC-3' (SEQ ID NO:20). In addition, PCR was performed using primers for the human beta-actin gene, as a control. The sense beta-actin oligonucleotide primer had the sequence 5'-AGGCCAACCGCGAGAAGATGA CC-3' (SEQ ID NO:21). The antisense beta-actin oligonucleotide primer had the sequence 5'-GAAGT CCAGGGCGACG-TAGCA-3' (SEQ ID NO:22). PCR was performed using standard conditions in 25 ul reactions, with an annealing temperature of 61 degrees Celsius. Thirty-two cycles of PCR were performed with the Beer primers and twenty-four cycles were performed with the beta-actin primers.

Following amplification, 12 ul from each reaction were analyzed by agarose gel electrophoresis and ethidium bromide staining. See FIG. 2A.

B. RNA In-situ Hybridization of Mouse Embryo Sections:

The full length mouse Beer cDNA (Sequence ID No. 11) was cloned into the pCR2.1 vector (Invitrogen, Carlsbad, Calif.) in the antisense and sense direction using the manufacturer's protocol. $^{35}$S-alpha-GTP-labeled cRNA sense and antisense transcripts were synthesized using in-vitro transcription reagents supplied by Ambion, Inc (Austin, Tex.). In-situ hybridization was performed according to the protocols of Lyons et al. (*J. Cell Biol.* 111:2427-2436, 1990).

The mouse Beer cRNA probe detected a specific message expressed in the neural tube, limb buds, blood vessels and ossifying cartilages of developing mouse embryos. Panel A in FIG. 3 shows expression in the apical ectodermal ridge (aer) of the limb (l) bud, blood vessels (bv) and the neural tube (nt). Panel B shows expression in the 4$^{th}$ ventricle of the brain (4). Panel C shows expression in the mandible (ma) cervical vertebrae (cv), occipital bone (oc), palate (pa) and a blood vessel (bv). Panel D shows expression in the ribs (r) and a heart valve (va). Panel A is a transverse section of 10.5 dpc embryo. Panel B is a sagittal section of 12.5 dpc embryo and panels C and D are sagittal sections of 15.5 dpc embryos.

ba=branchial arch, h=heart, te=telencephalon (forebrain), b=brain, f=frontonasal mass, g=gut, h=heart, j=jaw, li=liver, lu=lung, ot=otic vesicle, ao=, sc=spinal cord, skm=skeletal muscle, ns=nasal sinus, th=thymus, to=tongue, fl=forelimb, di=diaphragm Example 3

Expression and Purification of Recombinant Beer Protein

A. Expression in COS-1 Cells:

The DNA sequence encoding the full length human Beer protein was amplified using the following PCR oligonucleotide primers: The 5' oligonucleotide primer had the sequence 5'-AAGCTTGGTACCATGCAGCTCCCAC-3' (SEQ ID NO:23) and contained a HindIII restriction enzyme site (in bold) followed by 19 nucleotides of the Beer gene starting 6 base pairs prior to the presumed amino terminal start codon (ATG). The 3' oligonucleotide primer had the sequence 5'-AAGCTTCTA<u>CTTGTCATCGTCGTCCTTGTAGTCGT</u> AGGCGTTCTCCAGCT-3' (SEQ ID NO:24) and contained a HindIII restriction enzyme site (in bold) followed by a reverse complement stop codon (CTA) followed by the reverse complement of the FLAG epitope (underlined, Sigma-Aldrich Co., St. Louis, Mo.) flanked by the reverse complement of nucleotides coding for the carboxy terminal 5 amino acids of the Beer. The PCR product was TA cloned ("Original TA Cloning Kit", Invitrogen, Carlsbad, Calif.) and individual clones were screened by DNA sequencing. A sequence-verified clone was then digested by HindIII and purified on a 1.5% agarose gel using a commercially available reagents ("QIAquick Gel Extraction Kit", Qiagen Inc., Valencia, Calif.). This fragment was then ligated to HindIII digested, phosphatase-treated pcDNA3.1 (Invitrogen, Carlsbad, Calif.) plasmid with T4 DNA ligase. DH10B *E. coli* were transformed and plated on LB, 100 µg/ml ampicillin plates. Colonies bearing the desired recombinant in the proper orientation were identified by a PCR-based screen, using a 5' primer corresponding to the T7 promoter/priming site in pcDNA3.1 and a 3' primer with the sequence 5'-GCACTGGCCGGAG-CACACC-3' (SEQ ID NO:25) that corresponds to the reverse complement of internal BEER sequence. The sequence of the cloned fragment was confirmed by DNA sequencing.

COS-1 cells (ATCC# CRL-1650) were used for transfection. 50 µg of the expression plasmid pcDNA-Beer-Flag was transfected using a commercially available kit following protocols supplied by the manufacturer ("DEAE-Dextran Transfection Kit", Sigma Chemical Co., St. Louis, Mo.). The final media following transfection was DMEM (Life Technologies, Rockville, Md.) containing 0.1% Fetal Bovine Serum. After 4 days in culture, the media was removed. Expression of recombinant BEER was analyzed by SDS-PAGE and Western Blot using anti-FLAG® M2 monoclonal antibody (Sigma-Aldrich Co., St. Louis, Mo.). Purification of recombinant BEER protein was performed using an anti-FLAG M2 affinity column ("Mammalian Transient Expression System", Sigma-Aldrich Co., St. Louis, Mo.). The column profile was analyzed via SDS-PAGE and Western Blot using anti-FLAG M2 monoclonal antibody.

B. Expression in SF9 Insect Cells:

The human Beer gene sequence was amplified using PCR with standard conditions and the following primers:

```
Sense primer:
                                         (SEQ ID NO:26)
5'-GTCGTCGGATCCATGGGGTGGCAGGCGTTCAAGAATGAT-3'

Antisense primer:
                                         (SEQ ID NO:27)
5'-GTCGTCAAGCTTCTACTTGTCATCGTCCTTGTAGTCGTAGGCGTTCT
CCAGCTCGGC-3'
```

The resulting cDNA contained the coding region of Beer with two modifications. The N-terminal secretion signal was removed and a FLAG epitope tag (Sigma) was fused in frame to the C-terminal end of the insert. BamHI and HindIII cloning sites were added and the gene was subcloned into pMelBac vector (Invitrogen) for transfer into a baculoviral expression vector using standard methods.

Recombinant baculoviruses expressing Beer protein were made using the Bac-N-Blue transfection kit (Invitrogen) and purified according to the manufacturers instructions.

SF9 cells (Invitrogen) were maintained in TNM_FH media (Invitrogen) containing 10% fetal calf serum. For protein expression, SF9 cultures in spinner flasks were infected at an MOI of greater than 10. Samples of the media and cells were taken daily for five days, and Beer expression monitored by western blot using an anti-FLAG M2 monoclonal antibody (Sigma) or an anti-Beer rabbit polyclonal antiserum.

After five days the baculovirus-infected SF9 cells were harvested by centrifugation and cell associated protein was extracted from the cell pellet using a high salt extraction buffer (1.5 M NaCl, 50 mM Tris pH 7.5). The extract (20 ml per 300 ml culture) was clarified by centrifugation, dialyzed three times against four liters of Tris buffered saline (150 mM NaCl, 50 mM Tris pH 7.5), and clarified by centrifugation again. This high salt fraction was applied to Hitrap Heparin (Pharmacia; 5 ml bed volume), washed extensively with HEPES buffered saline (25 mM HEPES 7.5, 150 mM Nacl) and bound proteins were eluted with a gradient from 150 mM NaCl to 1200 mM NaCl. Beer elution was observed at aproximately 800 mM NaCl. Beer containing fractions were supplemented to 10% glycerol and 1 mM DTT and frozen at −80 degrees C.

Example 4

Preparation and Testing of Polyclonal Antibodies to Beer, Gremlin, and Dan

A. Preparation of Antigen:

The DNA sequences of Human Beer, Human Gremlin, and Human Dan were amplified using standard PCR methods with the following oligonucleotide primers:

```
H. Beer
Sense:
                                  (SEQ ID NO:28)
5'-GACTTGGATCCCAGGGGTGGCAGGCGTTC-3'
Antisense
                                  (SEQ ID NO:29)
5'-AGCATAAGCTTCTAGTAGGCGTTCTCCAG-3'

H. Gremlin
Sense:
                                  (SEQ ID NO:30)
5'-GACTTGGATCCGAAGGGAAAAAGAAAGGG-3'
Antisense:
                                  (SEQ ID NO:31)
5'-AGCATAAGCTTTTAATCCAAATCGATGGA-3'

H. Dan
Sense:
                                  (SEQ ID NO:32)
5'-ACTACGAGCTCGGCCCCACCACCCATCAACAAG-3'
Antisense:
                                  (SEQ ID NO:33)
5'-ACTTAGAAGCTTTCAGTCCTCAGCCCCCTCTTCC-3'
```

In each case the listed primers amplified the entire coding region minus the secretion signal sequence. These include restriction sites for subcloning into the bacterial expression vector pQE-30 (Qiagen Inc., Valencia, Calif.) at sites BamHI/HindIII for Beer and Gremlin, and sites SacI/HindIII for Dan. pQE30 contains a coding sequence for a 6× His tag at the 5' end of the cloning region. The completed constructs were transformed into E. coli strain M-15/pRep (Qiagen Inc) and individual clones verified by sequencing. Protein expression in M-15/pRep and purification (6× His affinity tag binding to Ni—NTA coupled to Sepharose) were performed as described by the manufacturer (Qiagen, The QIAexpressionist).

The E. coli-derived Beer protein was recovered in significant quantity using solubilization in 6M guanidine and dialyzed to 2-4M to prevent precipitation during storage. Gremlin and Dan protein were recovered in higher quantity with solubilization in 6M guanidine and a post purification guanidine concentration of 0.5M.

B. Production and Testing of Polyclonal Antibodies:

Polyclonal antibodies to each of the three antigens were produced in rabbit and in chicken hosts using standard protocols (R & R Antibody, Stanwood, Wash.; standard protocol for rabbit immunization and antisera recovery; Short Protocols in Molecular Biology. 2nd edition. 1992. 11.37-11.41. Contributors Helen M. Cooper and Yvonne Paterson; chicken antisera was generated with Strategic Biosolutions, Ramona, Calif.).

Rabbit antisera and chicken egg IgY fraction were screened for activity via Western blot. Each of the three antigens was separated by PAGE and transferred to 0.45 um nitrocellulose (Novex, San Diego, Calif.). The membrane was cut into strips with each strip containing approximately 75 ng of antigen. The strips were blocked in 3% Blotting Grade Block (Bio-Rad Laboratories, Hercules, Calif.) and washed 3 times in 1× Tris buffer saline (TBS)/0.02% TWEEN buffer. The primary antibody (preimmunization bleeds, rabbit antisera or chicken egg IgY in dilutions ranging from 1:100 to 1:10,000 in blocking buffer) was incubated with the strips for one hour with gentle rocking. A second series of three washes 1× TBS/0.02% TWEEN was followed by an one hour incubation with the secondary antibody (peroxidase conjugated donkey anti-rabbit, Amersham Life Science, Piscataway, N.J.; or peroxidase conjugated donkey anti-chicken, Jackson ImmunoResearch, West Grove, Pa.). A final cycle of 3× washes of 1× TBS/0.02% TWEEN was performed and the strips were developed with Lumi-Light Western Blotting Substrate (Roche Molecular Biochemicals, Mannheim, Germany).

C. Antibody Cross-Reactivity Test:

Following the protocol described in the previous section, nitrocellulose strips of Beer, Gremlin or Dan were incubated with dilutions (1:5000 and 1:10,000) of their respective rabbit antisera or chicken egg IgY as well as to antisera or chicken egg IgY (dilutions 1:1000 and 1:5000) made to the remaining two antigens. The increased levels of nonmatching antibodies was performed to detect low affinity binding by those antibodies that may be seen only at increased concentration. The protocol and duration of development is the same for all three binding events using the protocol described above. There was no antigen cross-reactivity observed for any of the antigens tested.

Example 5

Interaction of Beer with TGF-Beta Super-Family Proteins

Figure 5:
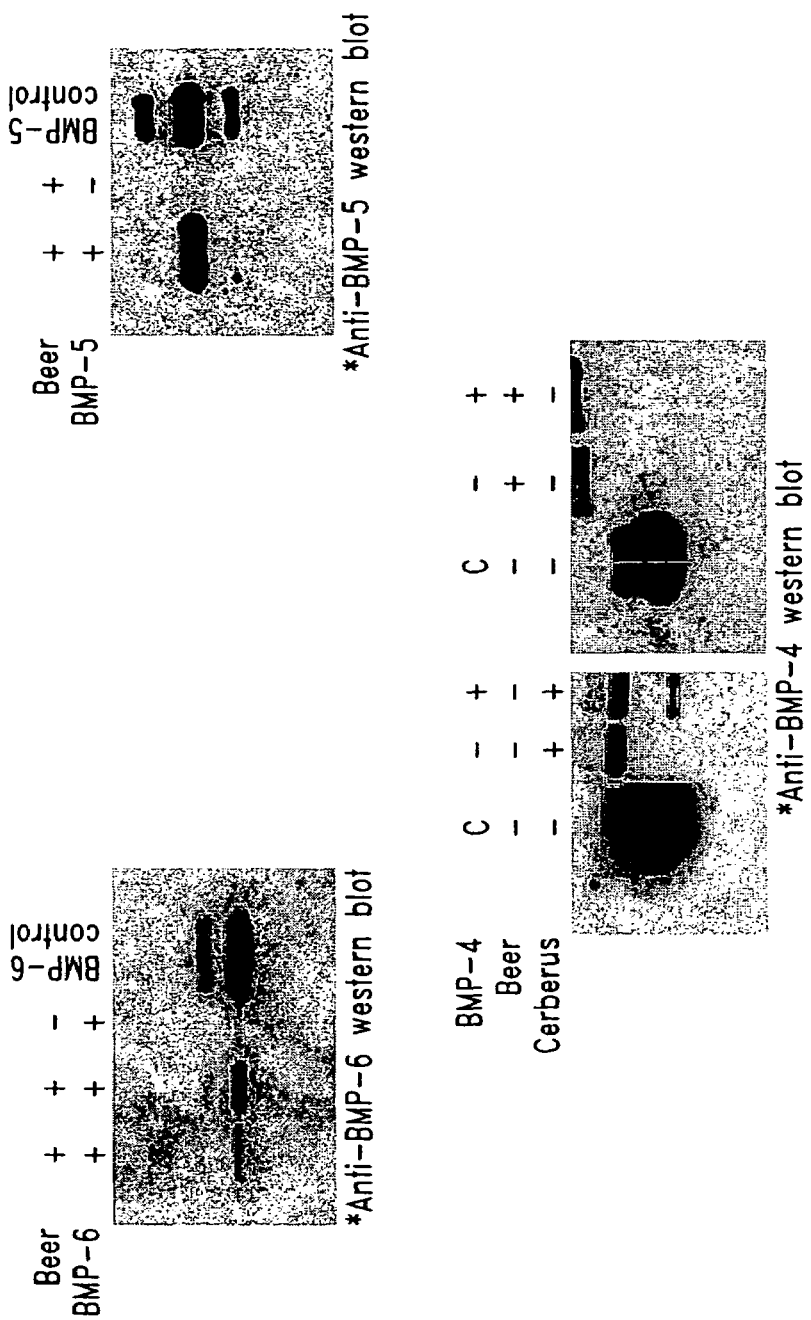
FIG. 5 illustrates, by western blot analysis, the selectivity of the TGF-beta binding-protein, Beer, for BMP-5 and BMP-6, but not BMP-4 (described in more detail in EXAMPLE 5).

The interaction of Beer with proteins from different phylogenetic arms of the TGF-β superfamily were studied using immunoprecipitation methods. Purified TGFβ-1, TGFβ-2, TGFβ-3, BMP-4, BMP-5, BMP-6 and GDNF were obtained from commerical sources (R&D systems; Minneapolis, Minn.). A representative protocol is as follows. Partially purified Beer was dialyzed into HEPES buffered saline (25 mM HEPES 7.5, 150 mM NaCl). Immunoprecipitations were done in 300 ul of IP buffer (150 mM NaCl, 25 mM Tris pH 7.5, 1 mM EDTA, 1.4 mM β-mercaptoethanol, 0.5% triton× 100, and 10% glycerol). 30 ng recombinant human BMP-5 protein (R&D systems) was applied to 15 ul of FLAG affinity matrix (Sigma; St Louis Mo.)) in the presence and absence of 500 ng FLAG epitope-tagged Beer. The proteins were incubated for 4 hours @ 4° C. and then the affinity matrix-associated proteins were washed 0.5 times in IP buffer (1 ml per wash). The bound proteins were eluted from the affinity matrix in 60 microliters of 1× SDS PAGE sample buffer. The proteins were resolved by SDS PAGE and Beer associated BMP-5 was detected by western blot using anti-BMP-5 antiserum (Research Diagnostics, Inc) (see FIG. 5).

BEER Ligand Binding Assay:

FLAG-Beer protein (20 ng) is added to 100 ul PBS/0.2% BSA and adsorbed into each well of 96 well microtiter plate previously coated with anti-FLAG monoclonal antibody (Sigma; St Louis Mo.) and blocked with 10% BSA in PBS. This is conducted at room temperature for 60 minutes. This protein solution is removed and the wells are washed to remove unbound protein. BMP-5 is added to each well in concentrations ranging from 10 pM to 500 nM in PBS/0.2% BSA and incubated for 2 hours at room temperature. The binding solution is removed and the plate washed with three times with 200 ul volumes of PBS/0.2% BSA. BMP-5 levels are then detected using BMP-5 antiserum via ELISA (F. M. Ausubel et al (1998) Current Protocols in Mol. Biol. Vol 2 11.2.1-11.2.22). Specific binding is calculated by subtracting non-specific binding from total binding and analyzed by the LIGAND program (Munson and Podbard, Anal. Biochem., 107, p220-239, (1980).

In a variation of this method, Beer is engineered and expressed as a human Fc fusion protein. Likewise the ligand BMP is engineered and expressed as mouse Fc fusion. These proteins are incubated together and the assay conducted as described by Mellor et al using homogeneous time resolved fluorescence detection (G. W. Mellor et al., *J. of Biomol Screening,* 3(2) 91-99, 1998).

Example 6

Screening Assay for Inhibition of TGF-Beta Binding-Protein Binding to TGF-Beta Family Members The assay described above is replicated with two exceptions. First, BMP concentration is held fixed at the Kd determined previously. Second, a collection of antagonist candidates is added at a fixed concentration (20 uM in the case of the small organic molecule collections and 1 uM in antibody studies). These candidate molecules (antagonists) of TGF-beta binding-protein binding include organic compounds derived from commercial or internal collections representing diverse chemical structures. These compounds are prepared as stock solutions in DMSO and are added to assay wells at ≦1% of final volume under the standard assay conditions. These are incubated for 2 hours at room temperature with the BMP and Beer, the solution removed and the bound BMP is quantitated as described. Agents that inhibit 40% of the BMP binding observed in the absence of compound or antibody are considered antagonists of this interaction. These are further evaluated as potential inhibitors based on titration studies to determine their inhibition constants and their influence on TGF-beta binding-protein binding affinity. Comparable specificity control assays may also be conducted to establish the selectivity profile for the identified antagonist through studies using assays dependent on the BMP ligand action (e.g. BMP/BMP receptor competition study).

Example 7

Inhibition of TGF-Beta Binding-Protein Localization to Bone Matrix

Evaluation of inhibition of localization to bone matrix (hydroxyapatite) is conducted using modifications to the method of Nicolas (Nicolas, V. *Calcif Tissue Int* 57:206, 1995). Briefly, $^{125}$I-labelled TGF-beta binding-protein is prepared as described by Nicolas (supra). Hydroxyapatite is added to each well of a 96 well microtiter plate equipped with a polypropylene filtration membrane (Polyfiltroninc, Weymouth Mass.). TGF-beta binding-protein is added to 0.2% albumin in PBS buffer. The wells containing matrix are washed 3 times with this buffer. Adsorbed TGF-beta binding-protein is eluted using 0.3M NaOH and quantitated.

Inhibitor identification is conducted via incubation of TGF-beta binding-protein with test molecules and applying the mixture to the matrix as described above. The matrix is washed 3 times with 0.2% albumin in PBS buffer. Adsorbed TGF-beta binding-protein is eluted using 0.3 M NaOH and quantitated. Agents that inhibit 40% of the TGF-beta binding-protein binding observed in the absence of compound or antibody are considered bone localization inhibitors. These inhibitors are further characterized through dose response studies to determine their inhibition constants and their influence on TGF-beta binding-protein binding affinity.

Example 8

Construction of TGF-Beta Binding-Protein Mutant

A. Mutagenesis:

A full-length TGF-beta binding-protein cDNA in pBluescript SK serves as a template for mutagenesis. Briefly, appropriate primers (see the discussion provided above) are utilized to generate the DNA fragment by polymerase chain reaction using Vent DNA polymerase (New England Biolabs, Beverly, Mass.). The polymerase chain reaction is run for 23 cycles in buffers provided by the manufacturer using a 57° C. annealing temperature. The product is then exposed to two restriction enzymes and after isolation using agarose gel electrophoresis, ligated back into pRBP4-503 from which the matching sequence has been removed by enzymatic digestion. Integrity of the mutant is verified by DNA sequencing.

B. Mammalian Cell Expression and Isolation of Mutant TGF-beta Binding-Protein:

The mutant TGF-beta binding-protein cDNAs are transferred into the pcDNA3.1 mammalian expression vector described in EXAMPLE 3. After verifying the sequence, the resultant constructs are transfected into COS-1 cells, and secreted protein is purified as described in EXAMPLE 3.

Example 9

Animal Models-I Generation of Transgenic Mice Overexpressing the Beer Gene

The ~200 kilobase (kb) BAC clone 15G5, isolated from the CITB mouse genomic DNA library (distributed by Research Genetics, Huntsville, Ala.) was used to determine the complete sequence of the mouse Beer gene and its 5' and 3' flanking regions. A 41 kb SalI fragment, containing the entire gene body, plus ~17 kb of 5' flanking and ~20 kb of 3' flanking sequence was sub-cloned into the BamHI site of the Super-CosI cosmid vector (Stratagene, La Jolla, Calif.) and propagated in the *E. coli* strain DH10B. From this cosmid construct, a 35 kb MluI-AvilI restriction fragment (Sequence No. 6), including the entire mouse Beer gene, as well as 17 kb and 14 kb of 5' and 3' flanking sequence, respectively, was then gel purified, using conventional means, and used for microinjection of mouse zygotes (DNX Transgenics; U.S. Pat. No. 4,873,191). Founder animals in which the cloned DNA fragment was integrated randomly into the genome were obtained at a frequency of 5-30% of live-born pups. The presence of the transgene was ascertained by performing Southern blot analysis of genomic DNA extracted from a small amount of mouse tissue, such as the tip of a tail. DNA was extracted using the following protocol: tissue was digested overnight at 55° C. in a lysis buffer containing 200 mM NaCl, 100 mM Tris pH8.5, 5 mM EDTA, 0.2% SDS and 0.5 mg/ml Proteinase K. The following day, the DNA was extracted once with phenol/chloroform (50:50), once with chloroform/isoamylalcohol (24:1) and precipitated with ethanol. Upon resuspension in TE (10 mM Tris pH7.5, 1 mM EDTA) 8-10 ug of each DNA sample were digested with a restriction endonuclease, such as EcoRI, subjected to gel electrophoresis and transferred to a charged nylon membrane, such as HyBondN+ (Amersham, Arlington Heights, Ill.). The resulting filter was then hybridized with a radioactively labelled fragment of DNA deriving from the mouse Beer gene locus, and able to recognize both a fragment from the endogenous gene locus and a fragment of a different size deriving from the transgene. Founder animals were bred to normal non-transgenic mice to generate sufficient numbers of transgenic and non-transgenic progeny in which to determine the effects of Beer gene overexpression. For these studies, animals at various ages (for example, 1 day, 3 weeks, 6 weeks, 4 months) are subjected to a number of different assays designed to ascertain gross skeletal formation, bone mineral density, bone mineral content, osteoclast and osteoblast activity, extent of endochondral ossification, cartilage formation, etc. The transcriptional activity from the transgene may be determined by extracting RNA from various tissues, and using an RT-PCR assay which takes advantage of single nucleotide polymorphisms between the mouse strain from which the transgene is derived (129Sv/J) and the strain of mice used for DNA microinjection [(C57BL5/J×SJL/J)F2].

Animal Models-II

Disruption of the Mouse Beer Gene by Homologous Recombination

Homologous recombination in embryonic stem (ES) cells can be used to inactivate the endogenous mouse Beer gene and subsequently generate animals carrying the loss-of-function mutation. A reporter gene, such as the *E. coli* β-galactosidase gene, was engineered into the targeting vector so that its expression is controlled by the endogenous Beer gene's promoter and translational initiation signal. In this way, the spatial and temporal patterns of Beer gene expression can be determined in animals carrying a targeted allele.

The targeting vector was constructed by first cloning the drug-selectable phosphoglycerate kinase (PGK) promoter driven neomycin-resistance gene (neo) cassette from pGT-N29 (New England Biolabs, Beverly, Mass.) into the cloning vector pSP72 (Promega, Madson, Wis.). PCR was used to flank the PGKneo cassette with bacteriophage P1 loxP sites, which are recognition sites for the P1 Cre recombinase (Hoess et al., PNAS USA, 79:3398, 1982). This allows subsequent removal of the neo-resistance marker in targeted ES cells or ES cell-derived animals (U.S. Pat. No. 4,959,317). The PCR primers were comprised of the 34 nucleotide (ntd) loxP sequence, 15-25 ntd complementary to the 5' and 3' ends of the PGKneo cassette, as well as restriction enzyme recognition sites (BamHI in the sense primer and EcoRI in the anti-sense primer) for cloning into pSP72. The sequence of the sense primer was 5'-AATCTGGATCCATAACTTCG-TATAGCATACATTATACGAAGTTATCTGCAG GATTC-GAGGGCCCCT-3' (SEQ ID NO:34); sequence of the anti-sense primer was 5'-AATCTGAATTCCACCGGTGTT AATTAAATAACTTCGTATAATGTATGCTATACGAAGT TATAGATCTAGAG TCAGCTTCTGA-3' (SEQ ID NO:35).

The next step was to clone a 3.6 kb XhoI-HindIII fragment, containing the *E. coli* β-galactosidase gene and SV40 polyadenylation signal from pSVβ (Clontech, Palo Alto, Calif.) into the pSP72-PGKneo plasmid. The "short arm" of homology from the mouse Beer gene locus was generated by amplifying a 2.4 kb fragment from the BAC clone 15G5. The 3' end of the fragment coincided with the translational initiation site of the Beer gene, and the anti-sense primer used in the PCR also included 30 ntd complementary to the 5' end of the β-galactosidase gene so that its coding region could be fused to the Beer initiation site in-frame. The approach taken for introducing the "short arm" into the pSP72-βgal-PGKneo plasmid was to linearize the plasmid at a site upstream of the β-gal gene and then to co-transform this fragment with the "short arm" PCR product and to select for plasmids in which the PCR product was integrated by homologous recombination. The sense primer for the "short arm" amplification included 30 ntd complementary to the pSP72 vector to allow for this recombination event. The sequence of the sense primer was 5'-ATTTAGGTGACACT ATAGAACTCGAG-CAGCTGAAGCTTAACCACATGGTGGCT-CACAACCAT-3' (SEQ ID NO:36) and the sequence of the anti-sense primer was 5'-AACGACGGCCAGTGAATC-CGTA ATCATGGTCATGCTGCCAGGTGGAG-GAGGGCA-3' (SEQ ID NO:37).

The "long arm" from the Beer gene locus was generated by amplifying a 6.1 kb fragment from BAC clone 15G5 with primers which also introduce the rare-cutting restriction enzyme sites SgrAI, FseI, AscI and PacI. Specifically, the sequence of the sense primer was 5'-ATTACCACCGGTGA-CACCCGCTTCCTGACAG-3' (SEQ ID NO:38); the sequence of the anti-sense primer was 5'-ATTACTTAAT-TAAACATGGCGCGCCAT ATGGCCGGCCCCTAAT-TGCGGCGCATCGTTAATT-3' (SEQ ID NO:39). The resulting PCR product was cloned into the TA vector (Invitrogen, Carlsbad, Calif.) as an intermediate step.

The mouse Beer gene targeting construct also included a second selectable marker, the herpes simplex virus I thymidine kinase gene (HSVTK) under the control of rous sarcoma virus long terminal repeat element (RSV LTR). Expression of this gene renders mammalian cells sensitive (and inviable) to gancyclovir; it is therefore a convenient way to select against neomycin-resistant cells in which the construct has integrated by a non-homologous event (U.S. Pat. No. 5,464,764). The RSVLTR-HSVTK cassette was amplified from pPS1337 using primers that allow subsequent cloning into the FseI and AscI sites of the "long arm"-TA vector plasmid. For this PCR, the sequence of the sense primer was 5'-ATTACGGCCGGC-CGCAAAGGAATTCAAGA TCTGA-3' (SEQ ID NO:40); the sequence of the anti-sense primer was 5'-ATTACG-GCGCGCCCTC ACAGGCCGCACCCAGCT-3' (SEQ ID NO:41).

The final step in the construction of the targeting vector involved cloning the 8.8 kb SgrAI-AscI fragment containing the "long arm" and RSVLTR-HSVTK gene into the SgrAI and AscI sites of the pSP72-"short arm"-βgal-PGKneo plasmid. This targeting vector was linearized by digestion with either AscI or PacI before electroporation into ES cells.

Example 10

Antisense-Mediated Beer Inactivation 17-nucleotide antisense oligonucleotides are prepared in an overlapping format, in such a way that the 5' end of the first oligonucleotide overlaps the translation initiating AUG of the Beer transcript, and the 5' ends of successive oligonucleotides occur in 5 nucleotide increments moving in the 5' direction (up to 50 nucleotides away), relative to the Beer AUG. Corresponding control oligonucleotides are designed and prepared using equivalent base composition but redistributed in sequence to inhibit any significant hybridization to the coding mRNA. Reagent delivery to the test cellular system is conducted through cationic lipid delivery (P. L. Felgner, *Proc. Natl. Acad. Sci. USA* 84:7413, 1987). 2 ug of antisense oligonucleotide is added to 100 ul of reduced serum media (Opti-MEM I reduced serum media; Life Technologies, Gaithersburg Md.) and this is mixed with Lipofectin reagent (6 ul) (Life Technologies, Gaithersburg Md.) in the 100 ul of reduced serum media. These are mixed, allowed to complex for 30 minutes at room temperature and the mixture is added to previously seeded MC3T3E21 or KS483-cells. These cells are cultured and the mRNA recovered. Beer mRNA is monitored using RT-PCR in conjunction with Beer specific primers. In addition, separate experimental wells are collected and protein levels characterized through western blot methods described in Example 4. The cells are harvested, resuspended in lysis buffer (50 mM Tris pH 7.5, 20 mM NaCl, 1 mM EDTA, 1% SDS) and the soluble protein collected. This material is applied to 10-20% gradient denaturing SDS PAGE. The separated proteins are transferred to nitrocellulose and the western blot conducted as above using the antibody reagents described. In parallel, the control oligonucleotides are added to identical cultures and experimental operations are repeated. Decrease in Beer mRNA or protein levels are considered significant if the treatment with the antisense oligonucleotide results in a 50% change in either instance compared to the control scrambled oligonucleotide. This methodology enables selective gene inactivation and subsequent phenotype characterization of the mineralized nodules in the tissue culture model.

Example 11

Modeling of Sclerostin Core Region

Homology recognition techniques (e.g., PSI-BLAST (Altschul et al., *Nucleic Acids Res.* 25:3389402 (1997)), FUGUE (Shi et al., *J. Mol. Biol.* 310:243-57 (2001)) suggested that the core region of SOST (SOST_Core) adopts a cystine-knot fold. FUGUE is a sensitive method for detecting homology between sequences and structures. Human Chorionic Gonadotropin β (hCG-β), for which an experimentally determined 3D structure is known, was identified by FUGUE (Shi et al., supra) as the closest homologue of SOST_Core. Therefore, hCG-β was used as the structural template to build 3D models for SOST_Core.

Figure 7:
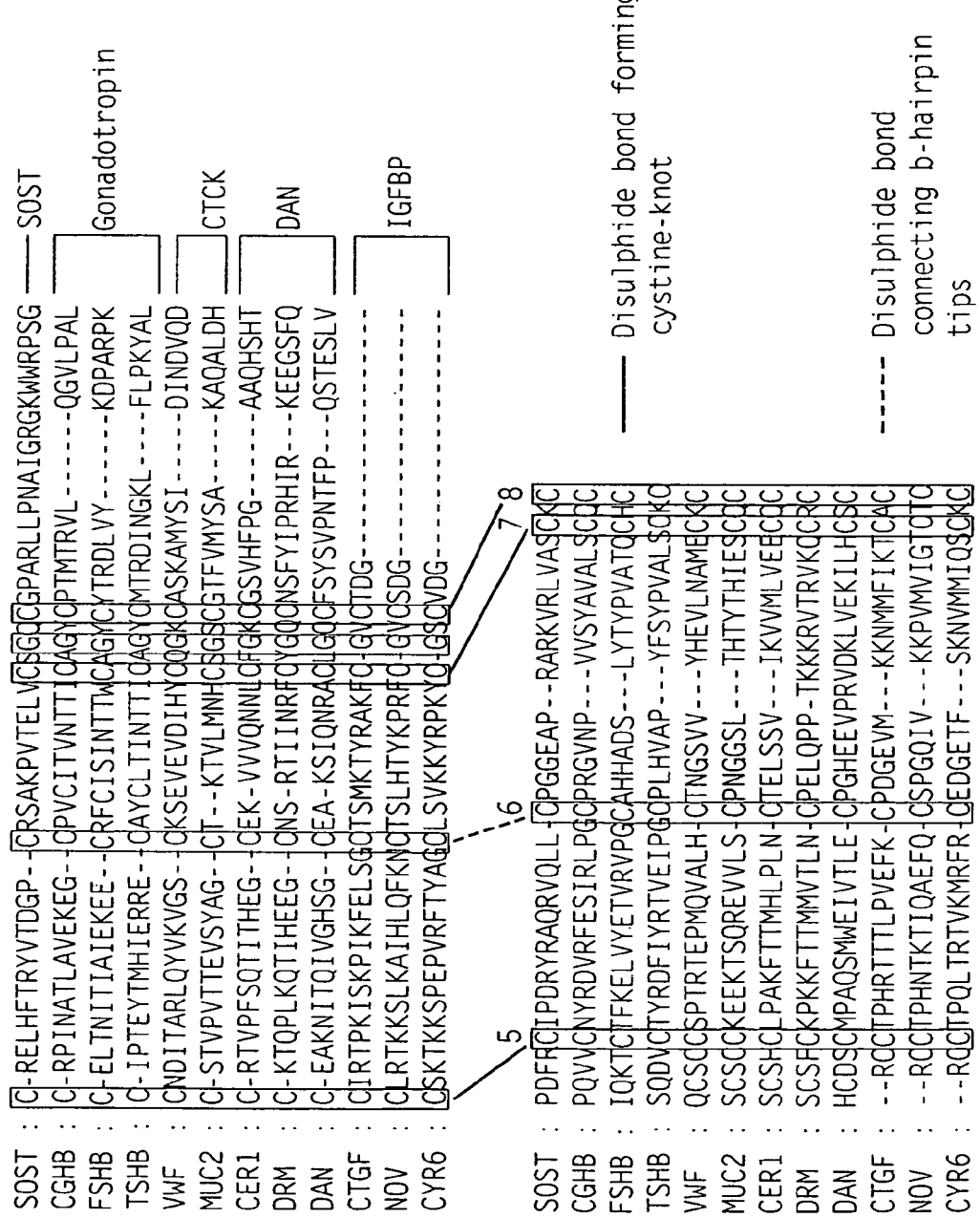
FIG. 7 presents an alignment of the region containing the characteristic cystine-knot of a SOST (sclerostin) polypeptide and its closest homologues. Three disulphide bonds that form the cystine-knot are illustrated as solid lines. An extra disulphide bond, shown by a dotted line, is unique to this family, which connects two β-hairpin tips in the 3D structure. The polypeptides depicted are SOST: sclerostin (SEQ ID NO:126); CGHB: Human Chorionic Gonadotropin β (SEQ ID NO:127); FSHB: follicle-stimulating hormone beta subunit (SEQ ID NO:128); TSHB: thyrotropin beta chain precursor (SEQ ID NO:129); VWF: Von Willebrand factor (SEQ ID NO:130); MUC2: human mucin 2 precursor (SEQ ID NO:131); CER1: Cerberus 1 (*Xenopus laevis* homolog) (SEQ ID NO:132); DRM: gremlin (SEQ ID NO:133); DAN: (SEQ ID NO:134); CTGF: connective tissue growth factor precursor (SEQ ID NO:135); NOV: NovH (nephroblastoma overexpressed gene protein homolog) (SEQ ID NO:136); CYR6: (SEQ ID NO:137).

An alignment of SOST_Core and its close homologues is shown in FIG. 7. Among the homologues shown in the alignment, only hCG-β (CGHB) had known 3D structure. The sequence identity between SOST_Core and hCG-β was approximately 25%. Eight CYS residues were conserved throughout the family, emphasizing the overall structural similarity between SOST_Core and hCG-β. Three pairs of cystines (1-5, 3-7, 4-8) formed disulfide bonds (shown with solid lines in FIG. 7) in a "knot" configuration, which was characteristic to the cystine-knot fold. An extra disulfide bond (2-6), shown as a dotted line in FIG. 7, was unique to this family and distinguished the family of proteins from other cystine-knot families (e.g., TGF-β, BMP).

Figure 8:
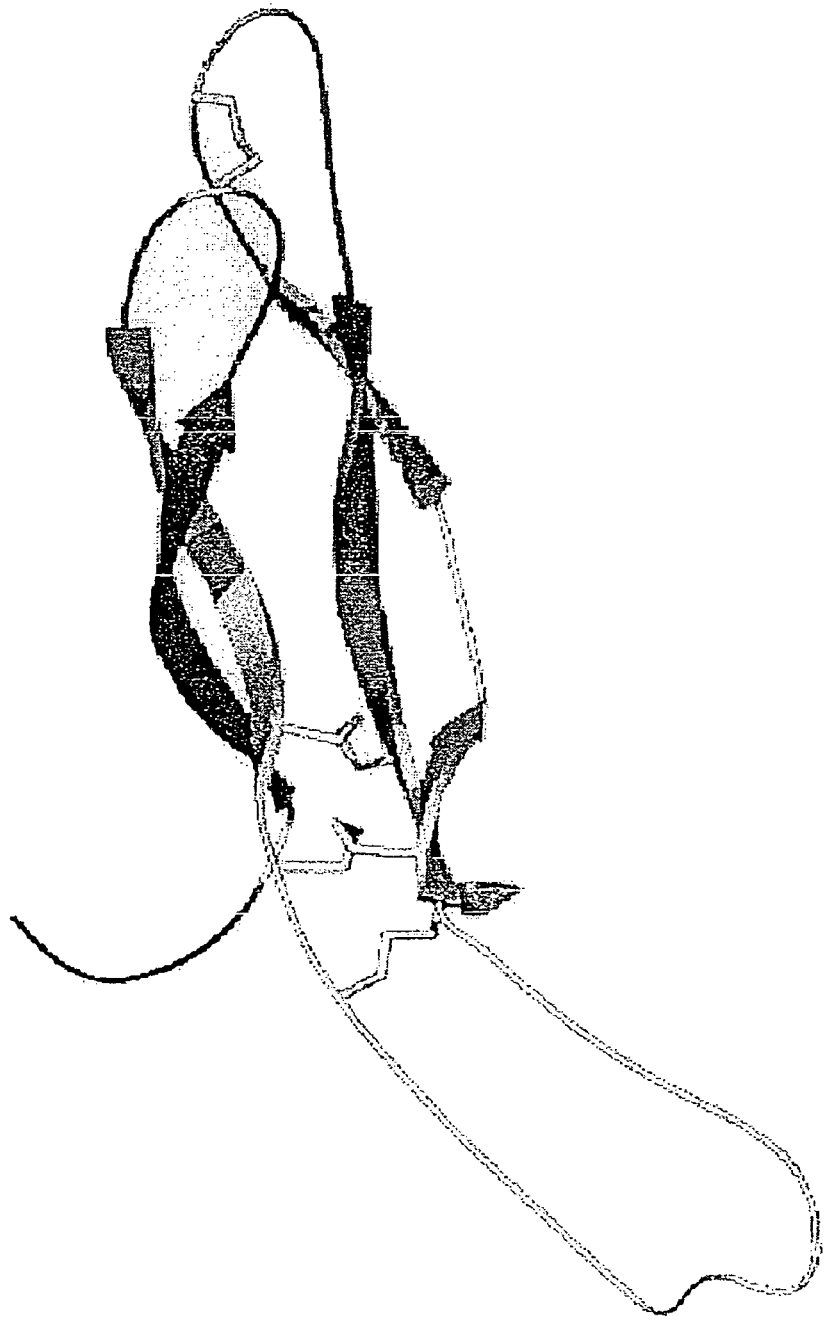
FIG. 8 illustrates a 3D model of the core region of SOST (SOST_Core).

SOST_Core was modeled using PDB (Berman et al., *Acta Crystallogr. D. Biol. Crystallogr.* 58(Pt 6 Pt1):899-907 (2002)) entry 1HCN, the 3D structure of hCG-β (Wu et al., *Structure* 2:545-58 (1994)), as the structural template. Models were calculated with MODELER (Sali & Blundell, *J. Mol. Biol.* 234:779-815 (1993)). A snapshot of the best model is shown in FIG. 8.

Figure 9:
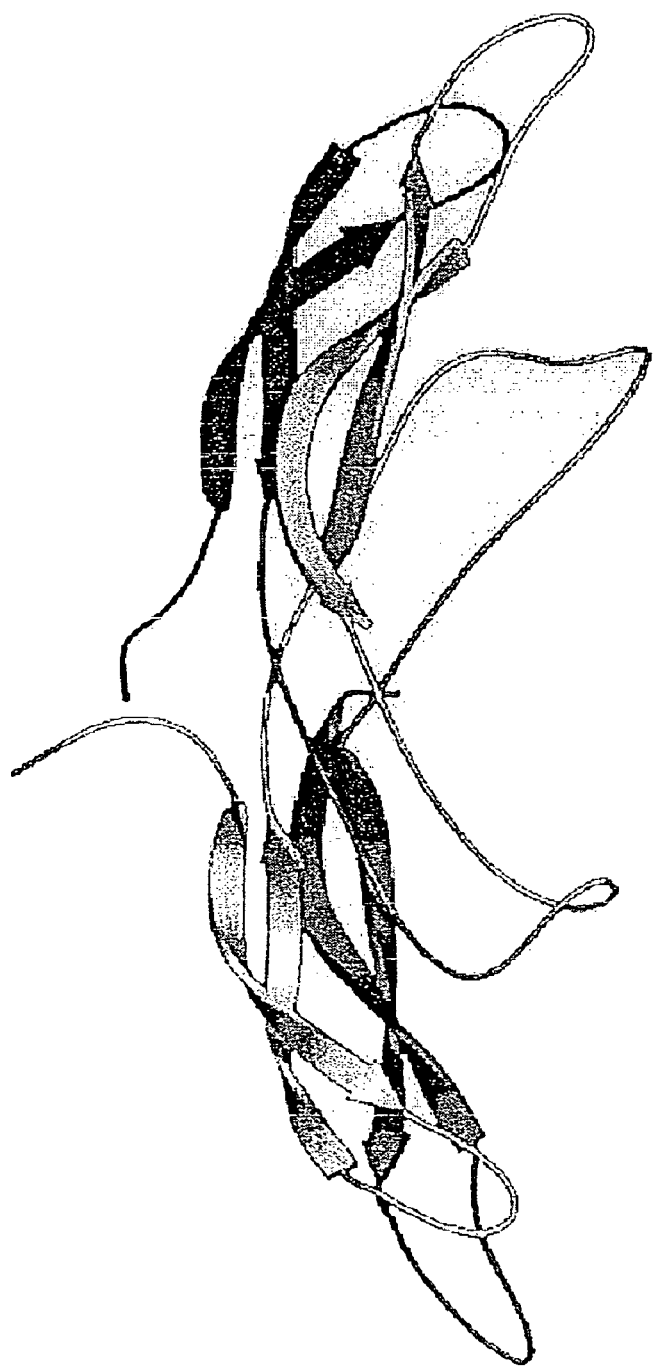
FIG. 9 presents a 3D model of the core region of SOST homodimer.

Most of the cystine-knot proteins form dimers because of the lack of hydrophobic core in a monomer (Scheufler et al., supra; Schlunegger and Grutter, *J. Mol. Biol.* 231:445-58 (1993)); Wu et al., supra). SOST likely follows the same rule and forms a homodimer to increase its stability. Constructing a model for the dimerized SOST_Core region presented several challenges because (1) the sequence similarity between SOST_Core and hCG-β was low (25%); (2) instead of a homodimer, hCG-β formed a heterodimer with hCG-α; and (3) a number of different relative conformations of monomers have been observed in dimerized cystine-knot proteins from different families (e.g., PDGF, TGF-β, Neurotrophin, IL-17F, Gonadotropin), which suggested that the dimer conformation of SOST could deviate significantly from the hCG-α/β heterodimer conformation. In constructing the model, hCG-α was replaced with hCG-β from the heterodimer structure (1HCN) using structure superimposition techniques combined with manual adjustment, and then a SOST_Core homodimer model was built according to the pseudo hCG-β homodimer structure. The final model is shown in FIG. 9.

Example 12

Modeling SOST-BMP Interaction

This example describes protein modeling of type I and type II receptor binding sites on BMP that are involved with interaction between BMP and SOST.

Competition studies demonstrated that SOST competed with both type I and type II receptors for binding to BMP. In an ELISA-based competition assay, BMP-6 selectively interacted with the sclerostin-coated surface (300 ng/well) with high affinity ($K_D$=3.4 nM). Increasing amounts of BMP receptor IA (FC fusion construct) competed with sclerostin for binding to BMP-6 (11 nM) ($IC_{50}$=114 nM). A 10-fold molar excess of the BMP receptor was sufficient to reduce binding of sclerostin to BMP-6 by approximately 50%. This competition was also observed with a BMP receptor II-FC fusion protein ($IC_{50}$=36 nM) and DAN ($IC_{50}$=43 nM). Specificity of the assay was shown by lack of competition for binding to BMP-6 between sclerostin and a rActivin R1B-FC fusion protein, a TGF-β receptor family member that did not bind BMP.

The type I and type II receptor binding sites on a BMP polypeptide have been mapped and were spatially separated (Scheufler et al., supra; Innis et al., supra; Nickel et al., supra; Hart et al. supra). Noggin, another BMP antagonist that binds to BMP with high affinity, contacts BMP at both type I and type II receptor binding sites via the N-terminal portion of Noggin (Groppe et al., supra). The two β-strands in the core region near the C-terminal also contact BMP at the type II receptor binding site.

A manually tuned alignment of Noggin and SOST indicated that the two polypeptides shared sequence similarity between the N-terminal portions of the proteins and between the core regions. An amino acid sequence alignment is presented in FIG. 10. The cysteine residues that form the characteristic cys-knot were conserved between Noggin and SOST. The overall sequence identity was 24%, and the sequence identity within the N-terminal binding region (alignment positions 1-45) was 33%. Two residues in the Noggin N-terminal binding region, namely Leu (L) at alignment position 21 and Glu (E) at position 23, were reported to play important roles in BMP binding (Groppe et al., supra). Both residues were conserved in SOST as well. The sequence similarity within the core region (alignment positions 131-228) was about 20%, but the cys-knot scaffold was maintained and a sufficient number of key residues was conserved, supporting homology between Noggin and SOST.

Figure 11:
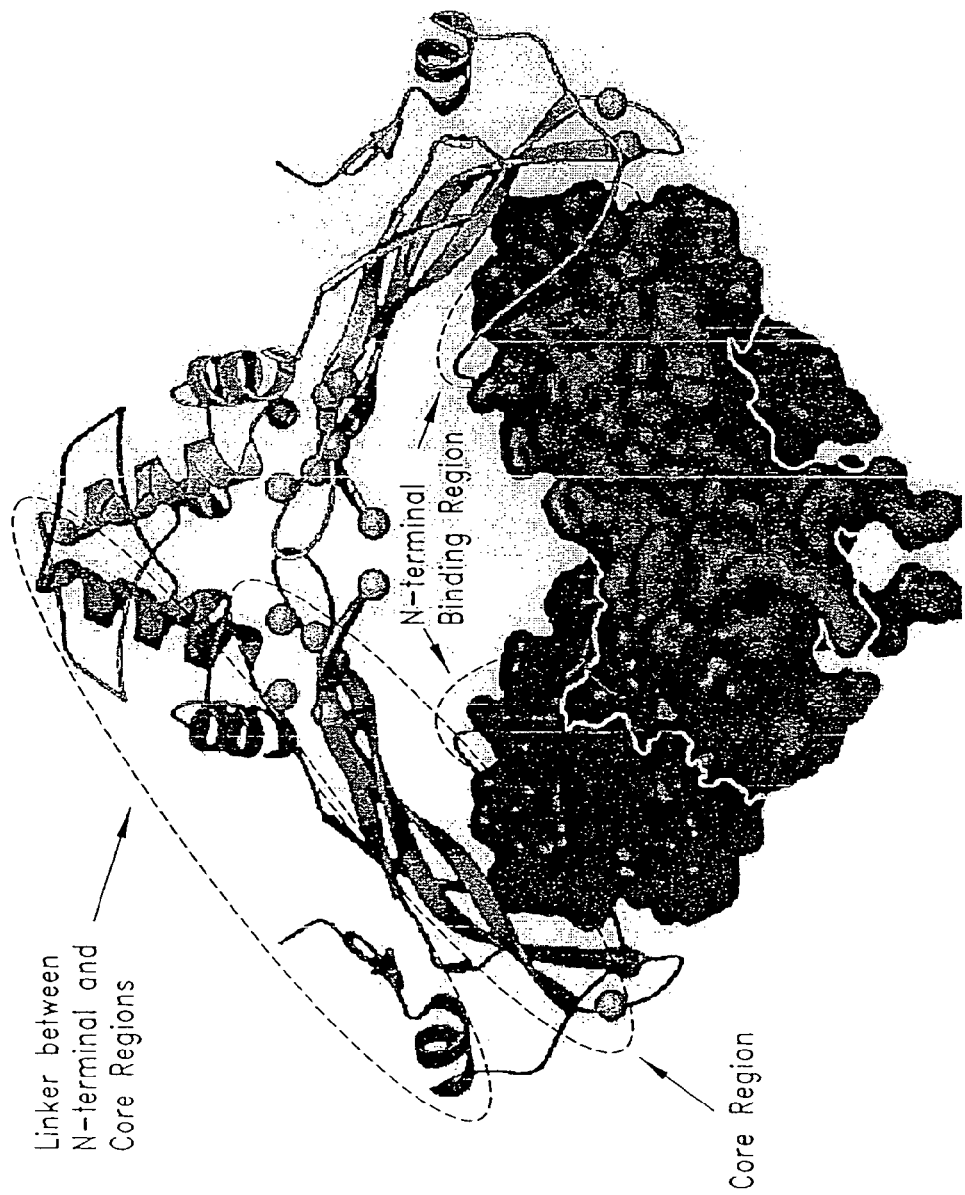
FIG. 11 illustrates the Noggin/BMP-7 complex structure. The BMP homodimer is shown on the bottom portion of the figure in surface mode. The Noggin homodimer is shown on top of the BMP dimer in cartoon mode. The circles outline the N-terminal binding region, the core region, and the linker between the N-terminal and core regions.

The Noggin structure was compared to SOST also to understand how two SOST monomers dimerize. As shown in FIG. 11, the Noggin structure suggested that the linker between the N-terminal region and the core region not only played a role in connecting the two regions, but also formed part of the dimerization interface between two Noggin monomers. One major difference between Noggin and SOST was that the linker between the N-terminal region and the core region was much shorter in SOST.

The C-terminal region of SOST may play a role in SOST dimerization. The sequence of Noggin ended with the core region, while SOST had an extra C-terminal region. In the Noggin structure a disulfide bond connected the C-termini of two Noggin monomers. Thus, the C-terminal region of SOST started close to the interface of two monomers and could contribute to dimerization. In addition, secondary structure prediction showed that some portions of the C-terminal region of SOST had a tendency to form helices. This region in SOST may be responsible for the dimerization activity, possibly through helix-helix packing, which mimicked the function of the longer linker in Noggin. Another difference between the structure of Noggin and SOST was the amino acid insertion in the SOST core region at alignment positions 169-185 (see FIG. 10). This insertion extended a β-hairpin, which pointed towards the dimerization interface in the Noggin structure (shown in FIG. 11 as a loop region in the middle of the monomers and above the C-terminal Cys residue). This elongated β-hairpin could also contribute to SOST dimerization.

Example 13

Design and Preparation of SOST Peptide Immunogens

This Example describes the design of SOST peptide immunogens that are used for immunizing animals and generating antibodies that block interactions between BMP and SOST and prevent dimer formation of SOST monomers.

BMP Binding Fragments

The overall similarity between SOST and Noggin and the similarity between the N-terminal regions of the two polypeptides suggest that SOST may interact with BMP in a similar manner to Noggin. That is, the N-terminal region of SOST may interact with both the type I and type II receptor binding sites on BMP, and a portion of the core region (amino acid alignment positions 190-220 in FIG. 10) may interact with the type II receptor binding site such that antibodies specific for these SOST regions may block or impair binding of BMP to SOST.

The amino acid sequences of these SOST polypeptide fragments for rat and human SOST are provided as follows.

SOST_N_Linker: The N-terminal region (includes the short linker that connects to the core region)

```
Human:
QGWQAFKNDATEIIPELGEYPEPPPELENNKTMNRAE    (SEQ ID
                                          NO:92)
NGGRPPHHPFETKDVSEYS Rat:
QGWQAFKNDATEIIPGLREYPEPPQELENNQTMNRAE    (SEQ ID
                                          NO:93)
NGGRPPHHPYDTKDVSEYS
```

SOST_Core_Bind: Portion of the core region that is likely to contact BMP at its type II receptor binding site (extended slightly at both termini to include the CYS residue anchors):

```
Human:
CIPDRYRAQRVQLLCPGGEAPRARKVRLVASC    (SEQ ID NO:94)

Rat:
CIPDRYRAQRVQLLCPGGAAPRSRKVRLVASC    (SEQ ID NO:95)
```

SOST Dimerization Fragments

The C-terminal region of SOST is likely to be involved in the formation of SOST homodimers (see Example 12). The elongated β-hairpin may also play a role in homodimer formation. Antibodies that specifically bind to such regions may prevent or impair dimerization of SOST monomers, which may in turn interfere with interaction between SOST and BMP. Polypeptide fragments in rat and human SOST corresponding to these regions are as follows.

SOST_C: the C-Terminal Region

```
                                              (SEQ ID NO:96)
Human:    LTRFHNQSELKDFGTEAARPQKGRKPRPRARSAKANQA
          ELENAY (SEQ ID NO:97)
Rat:      LTRFHNQSELKDFGPETARPQKGRKPRPRARGAKANQAE
          LENAY
```

SOST_Core_Dimer: Portion of the core region that is likely involved in SOST dimerization (extended slightly at both termini to include the Cys residue anchors):

```
Human:  CGPARLLPNAIGRGKWWRPSGPDFRC    (SEQ ID NO:98)

Rat:    CGPARLLPNAIGRVKWWRPNGPDFRC    (SEQ ID NO:99)
```

BMP Binding Fragment at SOST N-Terminus

Figure 12:
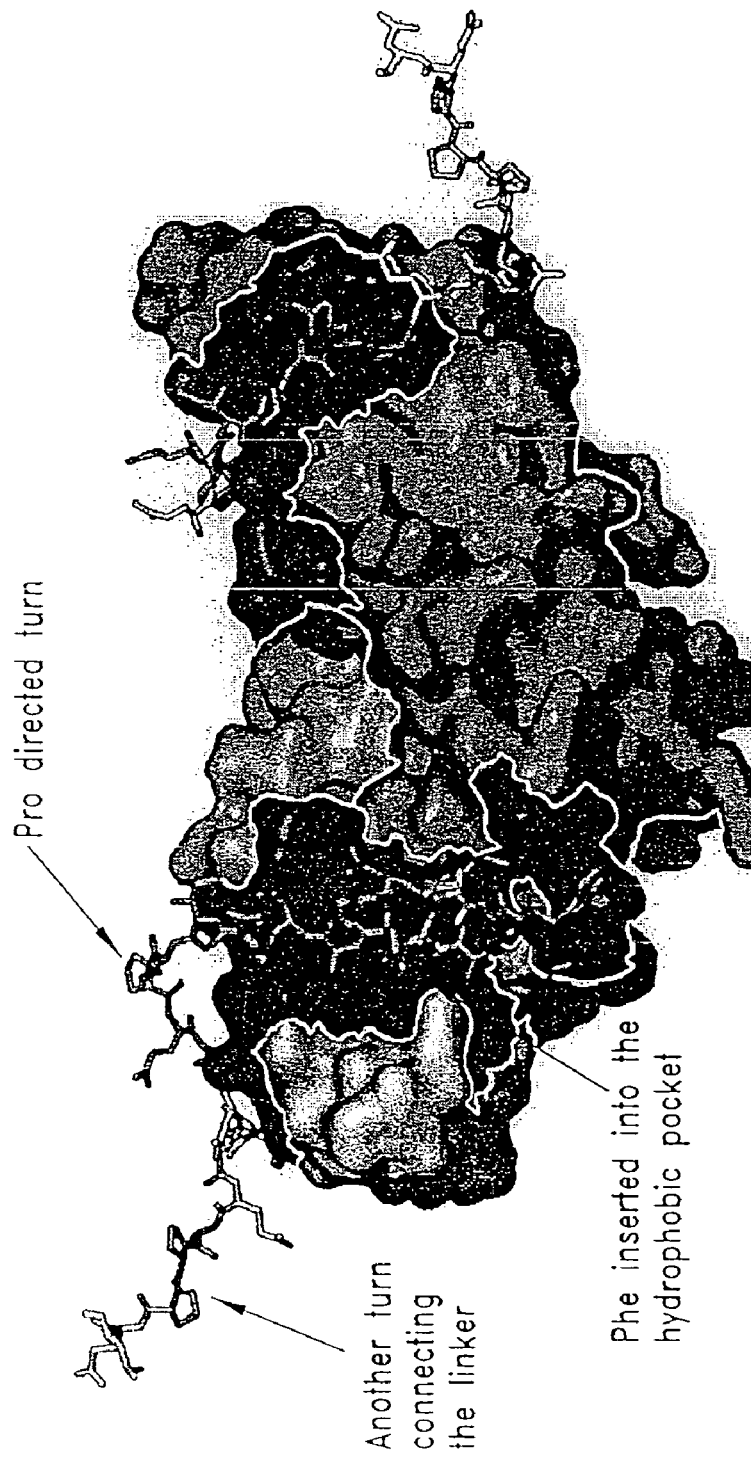
FIG. 12 depicts a 3D model of the potential BMP-binding fragment located at the SOST N-terminal region. A BMP dimer is shown in surface mode, and the potential BMP-binding fragment is shown in stick mode. A phenylalanine residue fitting into a hydrophobic pocket on the BMP surface is noted.

The key N-terminal binding region of SOST (alignment positions 1-35 in FIG. 10) was modeled on the basis of the Noggin/BMP-7 complex structure (Protein Data Bank Entry No: 1M4U) and the amino acid sequence alignment (see FIG. 10) to identify amino acid residues of the SOST N-terminus that likely interact with BMP. The model of SOST is presented in FIG. 12. In the comparative model, phenylalanine (Phe, F) at alignment position 8 (see arrow and accompanying text) in the SOST sequence projects into a hydrophobic pocket on the surface of the BMP dimer. The same "knob-into-hole" feature has been observed in the BMP and type I receptor complex structure (Nickel et al., supra), where Phe85 of the receptor fits into the same pocket, which is a key feature in ligand-type I receptor recognition for TGF-β superfamily members (including, for example, TGF-β family, BMP family, and the like). According to the model, a proline (Pro) directed turn is also conserved, which allows the N-terminal binding fragment to thread along the BMP dimer surface, traveling from type I receptor binding site to type II receptor binding site on the other side of the complex. Also conserved is another Pro-directed turn near the carboxy end of the binding fragment, which then connects to the linker region. Extensive contacts between SOST and BMP are evident in FIG. 12.

Peptide Immunogens

Peptides were designed to encompass the SOST N-terminal region predicted to make contact with BMP proteins. The peptide sequences are presented below. For immunizing animals, the peptide sequences were designed to overlap, and an additional cysteine was added to the C-terminal end to facilitate crosslinking to KLH. The peptides were then used for immunization. The peptide sequences of the immunogens are as follows.

```
Human SOST:
QGWQAFKNDATEIIPELGEY           (SEQ ID NO:47)
TEIIPELGEYPEPPPELENN           (SEQ ID NO:48)
PEPPPELENNKTMNRAENGG           (SEQ ID NO:49)
KTMNRAENGGRPPHHPFETK           (SEQ ID NO:50)
RPPHHPFETKDVSEYS               (SEQ ID NO:51)

Human SOST Peptides with Additional
Cys:
QGWQAFKNDATEIIPELGEY-C         (SEQ ID NO:52)
TEIIPELGEYPEPPPELENN-C         (SEQ ID NO:53)
PEPPPELENNKTMNRAENGG-C         (SEQ ID NO:54)
KTMNRAENGGRPPHHPFETK-C         (SEQ ID NO:55)
RPPHHPFETKDVSEYS-C             (SEQ ID NO:56)

Rat SOST:
QGWQAFKNDATEIIPGLREYPEPP       (SEQ ID NO:57)
PEPPQELENNQTMNRAENGG           (SEQ ID NO:58)
ENGGRPPHHPYDTKDVSEYS           (SEQ ID NO:59)
TEIIPGLREYPEPPQELENN           (SEQ ID NO:60)

Rat SOST Peptides with Additional
Cys:
QGWQAFKNDATEIIPGLREYPEPP-C     (SEQ ID NO:61)
PEPPQELENNQTMNRAENGG-C         (SEQ ID NO:62)
ENGGRPPHHPYDTKDVSEYS-C         (SEQ ID NO:63)
TEIIPGLREYPEPPQELENN-C         (SEQ ID NO:64)
```

The following peptides were designed to contain the amino acid portion of core region that was predicted to make contact with BMP proteins. Cysteine was added at the C-terminal end of each peptide for conjugation to KLH, and the conjugated peptides were used for immunization. In the Docking Core N-terminal Peptide an internal cysteine was changed to a serine to avoid double conjugation to KLH.

```
For Human SOST:
Amino acid sequence without Cys
residues added:
Docking_Core_N-terminal_Peptide:  IPDRYRAQRVQLLCPGGEAP    (SEQ ID NO:66)
Docking_Core_Cterm_Peptide:       QLLCPGGEAPRARKVRLVAS    (SEQ ID NO:67)
Docking_Core_N-terminal_Peptide:  IPDRYRAQRVQLLCPGGEAP-C  (SEQ ID NO:68)
Docking_Core_Cterm_Peptide:       QLLCPGGEAPRARKVRLVAS-C  (SEQ ID NO:69)

For Rat SOST:
Amino acid sequence without Cys
residues added or substituted:
Docking_Core_N-terminal_Peptide:  IPDRYRAQRVQLLSPGG       (SEQ ID NO:70)
Docking_Core_Cterm_Peptide:       PGGAAPRSRKVRLVAS        (SEQ ID NO:71)

Peptide immunogens with Cys
added and substituted:
Docking_Core_N-terminal_Peptide:  IPDRYRAQRVQLLSPGG-C     (SEQ ID NO:72)
Docking_Core_Cterm_Peptide:       PGGAAPRSRKVRLVAS-C      (SEQ ID NO:73)
```

Two regions within SOST that potentially interact to form SOST homodimers include the amino acids with the SOST core region that are not present in Noggin. Human SOST peptides designed to contain this sequence had a C-terminal or N-terminal Cys that was conjugated to KLH. For the rat SOST peptide, a cysteine was added to the carboxy terminus of the sequence (SEQ ID NO:76). The KLH conjugated peptides were used for immunization.

```
For Human SOST:
CGPARLLPNAIGRGKWWRPS           (SEQ ID NO:74)
IGRGKWWRPSGPDFRC               (SEQ ID NO:75)

For Rat SOST:
PNAIGRVKWWRPNGPDFR             (SEQ ID NO:76)

Rat SOST peptide
with cysteine added
PNAIGRVKWWRPNGPDFR-C           (SEQ ID NO:77)
```

The second region within SOST that potentially interacts to form SOST homodimers includes the C-terminal region. Peptide immunogens were designed to include amino acid sequences within this region (see below). For conjugation to KLH, a cysteine residue was added to the C-terminal end, and the conjugated peptides were used for immunization.

```
For Human SOST:
KRLTRFHNQS ELKDFGTEAA          (SEQ ID NO:78)
ELKDFGTEAA RPQKGRKPRP          (SEQ ID NO:79)
RPQKGRKPRP RARSAKANQA          (SEQ ID NO:80)
RARSAKANQA ELENAY              (SEQ ID NO:81)

Peptide immunogens with
Cys added at C-terminus:
KRLTRFHNQS ELKDFGTEAA-C        (SEQ ID NO:82)
ELKDFGTEAA RPQKGRKPRP-C        (SEQ ID NO:83)
RPQKGRKPRP RARSAKANQA-C        (SEQ ID NO:84)
RARSAKANQA ELENAY-C            (SEQ ID NO:85)

For Rat SOST:
KRLTRFHNQSELKDFGPETARPQ        (SEQ ID NO:86)
KGRKPRPRARGAKANQAELENAY        (SEQ ID NO:87)
SELKDFGPETARPQKGRKPRPRAR       (SEQ ID NO:88)

Peptide immunogens with
Cys added at C-terminus:
KRLTRFHNQSELKDFGPETARPQ-C      (SEQ ID NO:89)
KGRKPRPRARGAKANQAELENAY-C      (SEQ ID NO:90)
SELKDFGPETARPQKGRKPRPRAR-C     (SEQ ID NO:91)
```

Example 14

Assay for Detecting Binding of Antibodies to a TGF-Beta Binding-Protein

This example describes an assay for detecting binding of a ligand, for example, an antibody or antibody fragment thereof, to sclerostin.

A FLAG®-sclerostin fusion protein was prepared according to protocols provided by the manufacturer (Sigma Aldrich, St. Louis, Mo.) and as described in U.S. Pat. No. 6,395, 511. Each well of a 96 well microtiter plate is coated with anti-FLAG® monoclonal antibody (Sigma Aldrich) and then blocked with 10% BSA in PBS. The fusion protein (20 ng) is added to 100 µl PBS/0.2% BSA and adsorbed onto the 96-well plate for 60 minutes at room temperature. This protein solution is removed and the wells are washed to remove unbound fusion protein. A BMP, for example, BMP-4, BMP-5, BMP-6, or BMP-7, is diluted in PBS/0.2% BSA and added to each well at concentrations ranging from 10 pM to 500 nM. After an incubation for 2 hours at room temperature, the binding solution is removed and the plate is washed three times with 200 µl volumes of PBS/0.2% BSA. Binding of the BMP to sclerostin is detected using polyclonal antiserum or monoclonal antibody specific for the BMP and an appropriate enzyme-conjugated second step reagent according to standard ELISA techniques (see, e.g., Ausubel et al., *Current Protocols in Mol. Biol. Vol* 2 11.2.1-11.2.22 (1998)). Specific binding is calculated by subtracting non-specific binding from total binding and analyzed using the LIGAND program (Munson and Podbard, *Anal. Biochem.* 107:220-39 (1980)).

Binding of sclerostin to a BMP is also detected by homogeneous time resolved fluorescence detection (Mellor et al., *J Biomol. Screening,* 3:91-99 (1998)). A polynucleotide sequence encoding sclerostin is operatively linked to a human immunoglobulin constant region in a recombinant nucleic acid construct and expressed as a human Fc-sclerostin fusion protein according to methods known in the art and described herein. Similarly, a BMP ligand is engineered and expressed as a BMP-mouse Fc fusion protein. These two fusion proteins are incubated together and the assay conducted as described by Mellor et al.

Example 15

Screening Assay for Antibodies that Inhibit Binding of TGF-Beta Family Members to TGF-Beta Binding Protein This example describes a method for detecting an antibody that inhibits binding of a TGF-beta family member to sclerostin. An ELISA is performed essentially as described in Example 14 except that the BMP concentration is held fixed at its Kd (determined, for example, by BIAcore analysis). In addition, an antibody or a library or collection of antibodies is added to the wells to a concentration of 1 µM. Antibodies are incubated for 2 hours at room temperature with the BMP and sclerostin, the solution removed, and the bound BMP is quantified as described (see Example 14). Antibodies that inhibit 40% of the BMP binding observed in the absence of antibody are considered antagonists of this interaction. These antibodies are further evaluated as potential inhibitors by performing titration studies to determine their inhibition constants and their effect on TGF-beta binding-protein binding affinity. Comparable specificity control assays may also be conducted to establish the selectivity profile for the identified antagonist using assays dependent on the BMP ligand action (e.g., a BMP/BMP receptor competition study).

Example 16

Inhibition of TGF-Beta Binding-Protein Localization to Bone Matrix

Evaluation of inhibition of localization to bone matrix (hydroxyapatite) is conducted using modifications to the method of Nicolas (Calcif. Tissue Int. 57:206-12 (1995)). Briefly, $^{125}$I-labelled TGF-beta binding-protein is prepared as described by Nicolas (supra). Hydroxyapatite is added to each well of a 96-well microtiter plate equipped with a polypropylene filtration membrane (Polyfiltroninc, Weymouth Mass.). TGF-beta binding-protein diluted in 0.2% albumin in PBS buffer is then added to the wells. The wells containing matrix are washed 3 times with 0.2% albumin in PBS buffer. Adsorbed TGF-beta binding-protein is eluted using 0.3 M NaOH and then quantified.

An antibody that inhibits or impairs binding of the sclerostin TGF-beta binding protein to the hydroxyapatite is identified by incubating the TGF-beta binding protein with the antibody and applying the mixture to the matrix as described above. The matrix is washed 3 times with 0.2% albumin in PBS buffer. Adsorbed sclerostin is eluted with 0.3 M NaOH and then quantified. An antibody that inhibits the level of binding of sclerostin to the hydroxyapatite by at least 40% compared to the level of binding observed in the absence of antibody is considered a bone localization inhibitor. Such an antibody is further characterized in dose response studies to determine its inhibition constant and its effect on TGF-beta binding-protein binding affinity.

From the foregoing, although specific embodiments of the invention have been described herein for purposes of illustration, various modifications may be made without deviating from the spirit and scope of the invention. Accordingly, the invention is not limited except as by the appended claims.

We claim the following:

1. An isolated antibody, or an antigen-binding fragment thereof, that specifically binds to an epitope within amino acids 86-111 of SEQ ID NO: 46.

2. The antibody of claim 1, wherein the antibody, or an antigen-binding fragment thereof, specifically binds to an epitope within amino acids 86-105 of SEQ ID NO: 46.

3. The antibody of claim 1, wherein the antibody, or an antigen-binding fragment thereof, specifically binds to an epitope within amino acids 96-111 of SEQ ID NO: 46.

4. An isolated antibody, or antigen binding fragment thereof, that binds to a peptide consisting of amino acids 86-111 of SEQ ID NO: 46 with an affinity $K_D$ of less than or equal to about $10^{-7}$ M.

5. The antibody of any one of claims 1-3 and 4, wherein the antibody is a monoclonal antibody.

6. The antibody of claim 5, wherein the monoclonal antibody is a human antibody, a humanized antibody or a chimeric antibody.

7. The antibody of claim 5, wherein the monoclonal antibody is selected from the group consisting of a mouse monoclonal antibody, a rat monoclonal antibody, and a hamster monoclonal antibody.

8. The antibody of any one of claims 1-3 and 4, wherein the antibody is an antigen-binding fragment.

9. The antibody of claim 8, wherein the antigen-binding fragment is selected from the group consisting of F(ab')$_2$, Fab, Fab, Fd, and Fv.

10. The antibody of claim 9, wherein the antibody comprises an Fv fragment.

11. The antibody of any one of claims 1-3 and 4, wherein the antibody comprises a single chain antibody.

12. The antibody of any one of claims 1-3 and 4, wherein the antibody comprises at least one heavy chain and at least one light chain.

13. A hybridoma cell producing the antibody of claim 12.

14. A composition comprising the antibody or antigen-binding fragment thereof of any one of claims 1-3 and 4-12 and a pharmaceutically acceptable carrier.

15. A method of increasing bone mineral content or bone density in a warm-blooded animal, comprising administering an effective amount of the composition according to claim 14 to said animal.

16. The method of claim 15, wherein bone mineral content is increased.

17. The method of claim 15 wherein bone density is increased.

18. The method of claim 15 wherein said animal suffers from a condition selected from the group consisting of achondroplasia, cleidrocranial dysostosise, echondromatosis, fibrous dysplasia, Gaucher's hypophosphatemic rickets, Marfan's, multiple hereditary exostoses, neurofibromastosis, osteogenesis imperfecta, osteopetrosis, osteopoikilosis sclerotic lesions, fractures, periodontal disease, pseudoarthosis, and pyogenic osteomyelitis.

19. The method of claim 15 wherein said animal suffers from a bone fracture.

20. The method of claim 15 wherein said animal suffers from a dysplasia associated with abnormal growth or development of bone.

21. The method of claim 15 wherein said animal suffers from osteoporosis.

22. The method of claim 15 wherein said animal suffers from osteopenia.

23. The method of claim 22 wherein said osteopenia is caused by an anaemic state, steroids, heparin, a bone marrow disorder, scurvy, malnutrition, calcium deficiency, idiopathic osteoporosis, congenital osteopenia or osteoporosis, alcoholism, chronic liver disease, senility, post menstrual state, oligomenorrhea, amenorrhea, pregnancy, diabetes mellitus, hyperthyroidism, Gushing's disease, acromegaly, hypogonadism, immobilization or disuse, reflex sympathetic dystrophy syndrome, transient regional osteoporosis, or osteomalacia.

\* \* \* \* \*

UNITED STATES PATENT AND TRADEMARK OFFICE
CERTIFICATE OF CORRECTION

PATENT NO. : 7,578,999 B2
APPLICATION NO. : 11/399210
DATED : August 25, 2009
INVENTOR(S) : David G. Winkler et al.

It is certified that error appears in the above-identified patent and that said Letters Patent is hereby corrected as shown below:

In the Specification:

At Column 3, line 45, please delete "molecules," and insert --molecules--.

At Column 5, line 42, please delete "provied" and insert --provided--.

At Column 6, line 49, please delete "are" and insert --is--.

At Column 6, line 50, please delete "are" and insert --is--.

At Column 8, line 6, please delete "scierostin" and insert --sclerostin--.

At Column 15, line 22, please delete "proteolyically" and insert --proteolytically--.

At Column 18, line 48, please delete "art." and insert --art--.

At Column 24, line 34, please delete "is" and insert --are--.

At Column 25, line 40, please delete "occuring" and insert --occurring--.

At Column 29, line 33, please delete "á-halocarboxylic" and insert --α-halocarboxylic--.

At Column 32, line 6, please delete "scierostin" and insert --sclerostin--.

At Column 32, line 7, please delete "scierostin" and insert --sclerostin--.

At Column 32, line 35, please delete "settins" and insert --settings--.

At Column 33, line 8, please delete "Indentification" and insert --Identification--.

UNITED STATES PATENT AND TRADEMARK OFFICE
CERTIFICATE OF CORRECTION

PATENT NO. : 7,578,999 B2
APPLICATION NO. : 11/399210
DATED : August 25, 2009
INVENTOR(S) : David G. Winkler et al.

It is certified that error appears in the above-identified patent and that said Letters Patent is hereby corrected as shown below:

At Column 33, line 64, please delete "scierostin" and insert --sclerostin--.

At Column 34, line 38, please delete "scierostin" and insert --sclerostin--.

At Column 36, line 46, please delete "immunoglobulings" and insert --immunoglobulins--.

At Column 38, line 59, please delete "an known" and insert --and known--.

At Column 45, line 14, please delete "a" and insert --an--.

At Column 47, line 53, please delete "permits" and insert --permit--.

At Column 49, line 36, please delete "be" and insert --can be--.

At Column 57, line 6, please delete "responses" and insert --response--.

At Column 59, line 20, please delete "he" and insert --the--.

At Column 65, line 3, please delete "manufacturers" and insert --manufacturer's--.

At Column 65, lines 22-23, please delete "aproximately" and insert --approximately--.

At Column 66, line 48, please delete "was" and insert --were--.

At Column 66, line 61, please delete "were" and insert --was--.

At Column 66, line 64, please delete "commerical" and insert --commercial--.

UNITED STATES PATENT AND TRADEMARK OFFICE
CERTIFICATE OF CORRECTION

PATENT NO.        : 7,578,999 B2
APPLICATION NO.   : 11/399210
DATED             : August 25, 2009
INVENTOR(S)       : David G. Winkler et al.

It is certified that error appears in the above-identified patent and that said Letters Patent is hereby corrected as shown below:

<u>In the Sequence Listing:</u>

At Column 249, line 67, SEQ ID NO: 135, field <213>, please delete "sapies" and insert --sapiens--.

<u>In the Claims:</u>

In claim 9, at Column 259, lines 53-54, please delete "Fab, Fab" and insert --Fab, Fab'--.

In claim 23, at Column 260, line 59, please delete "Gushing's" and insert --Cushing's--.

Signed and Sealed this

Seventeenth Day of November, 2009

David J. Kappos
*Director of the United States Patent and Trademark Office*